US006017734A

United States Patent [19]

Summers et al.

[11] Patent Number: 6,017,734
[45] Date of Patent: Jan. 25, 2000

[54] UNIQUE NUCLEOTIDE AND AMINO ACID SEQUENCE AND USES THEREOF

[75] Inventors: Max D. Summers; Sharon C. Braunagel; Tao Hong, all of Bryan, Tex.

[73] Assignee: The Texas A & M University System, College Station, Tex.

[21] Appl. No.: 08/792,832

[22] Filed: Jan. 30, 1997

Related U.S. Application Data

[63] Continuation-in-part of application No. 08/678,435, Jul. 3, 1996, abandoned
[60] Provisional application No. 60/000,955, Jul. 7, 1995.

[51] Int. Cl.[7] .............................. C07H 21/00; C12N 5/10; C12N 15/33; C12N 15/63

[52] U.S. Cl. .................... 435/69.7; 435/91.4; 435/320.1; 435/348; 435/365; 536/23.1; 536/23.72; 536/24.1
[58] Field of Search .................................. 435/69.1, 69.7, 435/69.8, 172.1, 320.1, 325, 348, 365, 410, 91.4; 514/44; 536/23.1, 23.72, 24.1

[56] References Cited

FOREIGN PATENT DOCUMENTS

| | | |
|---|---|---|
| 0 362 526 | 4/1990 | European Pat. Off. . |
| 0 505 207 A1 | 3/1992 | European Pat. Off. . |

OTHER PUBLICATIONS

Harvey et al. (1983) Biochemical and biological variation of Cydia pomenella (Coding Moth) granulosis virus. (Virology 124:21–34.

Kuzio et al. (1984) Regions of repeated DNA in the genome of Choristoneura fumiferana nuclear polyhedrosis virus. Virology 139:185–188.

Ma et al. (Jan. 1993) Cloning and sequence analysis of a p40 structural protein gene of Helicoverpa zea nuclear polyhedrosis virus. Virology 192:224–233.

Kondo et al. (Jul. 1991) Host range expansion by recombination of the baculoviruses Bombyx mori nuclear polyhedrosis virus and Autographa californica nuclear polyhedrosis virus. J. Virol. 65:3625–3632.

Leisy et al. (Nov. 1984) Conservation of genome organization in two multicapsid nuclear polyhedrosis viruses. J. Virol. 52:699–702.

Camacho et al. (1991) Protein p22 of African Swine Fever Virus: an early structural protein that is incorporated into the membrane of infected cells. Virology 181:251–257.

Friedmann (Jun. 1997) Overcoming the obstacles to gene therapy. Scientific Amer. Jun.:96–101.

Adams, J.R., and McClintock, J. T.; Baculoviridae. Nuclear Polyhedrosis Virus, In "Atlas of Invertebrate Viruses" (J.R. Adams and J. R. Bonami, Eds.). CRC Press, Boca Raton, FL. (1991) 87–204.

Ahmad, S., Bassiri, M., Banerjee, AK., Yilma, T. (1993). Immunological Characterization of the VSV Nucleocapsid (N) Protein Expressed by Recombinant Baculovirus in *Spodoptera exigua* Larva: Use in Differential Diagnosis Between Vaccinated and Infected Animals. *Virology*.192:207–216.

Arvinte T., Schulz B., Cudd A. Nicolau C. (1989). Low pH association of proteins with the membranes of intact red blood cells. I. Exogenous glycophorin and the CD4 molecule. *Biochim. Biophys. Acta* 981:51–60.

Ayres, M. D., Howard, S. C., Kuzio, J., Lopez–Ferber, M., and Possee, R. D. (1994). The Complete DNA Sequence of *Autographa californica* Nuclear Polyhedrosis Virus. *Virology.* 202:586–605.

Belyaev, A. S., and Roy, P. (1993). Development of baculovirus triple and quadruple expression vectors: co–expression of three or four bluetongue virus proteins and the synthesis of bluetongue virus–like particles in insect cells. *Nucleic Acids Res.* 21:1219–1223.

Blissard, G. W., and Rohrmann, G. F. (1989). Location, Sequence, Transcriptional Mapping, and Temporal Expression of the gp64 Envelope Glycoprotein Gene of the *Orgyia pseudotsugata* Multicapsid Nuclear Polyhedrosis Virus. *Virology*.170:537–555.

Blissard, G.W., and Rohrmann, G. F., (1990). Baculovirus Diversity and Molecular Biology. *Annu. Rev. Entomol.* 35:127–155.

Bozzola, J. J., and Russell, L. D. (1992). Electron Microscopy. Jones and Bartlett Publishers, Boston, MA.

Bradford, M. M. (1976). A Rapid and Sensitive Method for the Quantitation of Microgram Quantities of Protein Utilizing the Principle of Protein–Dye Binding. *Anal. Biochem.* 72:248–254.

Braunagel, S. C., et al. (1992). Sequence, Genomic Organization of the EcoR1–A Fragment *Autographa californica* Nuclear Polyhedrosis Virus, and Identification of a Viral Encoded Protein Resembling the Outer Capsid Protein VPS of Rotavirus, *Virology.* 191:1003–1008.

Braunagel, S. C., et al. (1996). Identification and Anaylsis of an *Autographa californica* Nuclear Polyhedrosis Virus Structural Protein of the Occlusion–Derived Virus Envelope ODV–E35, and ODV–EC27, *Virology.* 222:(in press).

Braunagel, S. C., et al. (1996). Transcription, Translation and Cellular Localization of Three *Autographa californica* Nuclear Polyhedrosis Virus Structural Proteins: ODV–E18, ODV–E35, and ODV–EC27, *Virology.* 222:100–114.

(List continued on next page.)

*Primary Examiner*—George C. Elliott
*Assistant Examiner*—Robert Schwartzman
*Attorney, Agent, or Firm*—Arnold, White & Durkee

[57] ABSTRACT

Provided are hydrophobic targeting sequences, which may serve to target heterologous proteins to a variety of cellular membranes. In particular, the structural components of the nuclear envelope, or those components which become nucleus-associated, may be targeted with the sequences provided. Also provided are methods of targeting heterologous proteins to particular membranes, and the use of these targeted proteins in therapeutic, diagnostic and insecticidal applications.

56 Claims, 24 Drawing Sheets

OTHER PUBLICATIONS

Braunagel, S. C., et al. (1994). *Autographa californica* Nuclear Polyhedrosis Virus, PDV, and ECV Viral Envelopes and Nucleocapsids: Structural Proteins, Antigens, Lipid and Fatty Acid Profiles. *Virology.* 202:315–328.

Carrington, J. C., and Freed, D. D. (1990). Cap–Independent Enhancement of Translation by a Plant Potyvirus 5' Non-translated Region. *J. Virol.* 64:1590–1597.

Carson, D. D., Guarino, L. A., and Summers, M. D. (1988). Functional Mapping of an AcMNPV Immediate Early Gene Which Augments Expression of the IE–1 trans–Activated 39K Gene. *Virology.* 162:444–451.

Carson, D.D., Summers, M. D., and Guarino, L. A. (1991). Transient Expression of the *Autographa californica* Nuclear Polyhedrosis Virus Immediate Early Gene, IE–N, Is Regulated by Three Viral Elements. *J. Virol.* 65:945–951.

Charlton, C. A., and Volkman, L. E. (1993). Penetration of *Autographa californica* Nuclear Polyhedrosis Virus Nucleocapsids into IPLB Sf21 Cells Induces Actin Cable Formation. *Virology.* 197:245–254.

Choi, J., and Guarino, L. A. (1995). A Temperature–Sensitive IE1 Transactivation and DNA Binding Activities. *Virology.* 209:90–98.

Choi, J., and Guarino, L. A. (1995). Expression of the IE1 Transactivator of *Autographa californica* Nuclear Polyhedrosis Virus During Viral Infection. *Virology.* 209:99–107.

Choi, J., and Guarino, L. A. (1995). The Baculoviruses Transactivator IE1 Binds to Viral Enhancer Elements in the Absence of Insect Cell Factors. *J. Virol.* 69:4548–4551.

Cory, J. S., and Bishop, D. H. L. (1995). Use of Baculoviruses as Biological Insecticides, In "Methods in Molecular Biology". vol.39, pp. 277–294, (C. D. Richardson, ed.). Humana Press, Inc., Totowa, N.J.

Devereux, J., Haeberli, P., and Smithies, O. (1984). A comprehensive set of sequence analysis programs for the VAX. *Nucl. Acids Res.* 12:389–395.

Dewey, R. E., Levings, C. S., III, and Timothy, D. H. (1986). Novel Recombinations in the Maize Mitochondrial Genome Produce a Unique Transcriptional Unit in the Texas Male–Sterile Cytoplasm. *Cell.* 44:439–449.

Funk, C. J., and Consigli, R. A. (1993). Temporal expression and immunogold localization of *Plodia interpunctella* granulosis virus structural proteins. *Virus Res.* 28:57–66.

Furukawa, K., Pante, N., Aebi, U., and Gerace, L. (1995). Cloning of a cDNA for lamina associated polypeptide 2 (LAP2) and identification of regions that specify targeting to the nuclear envelope. *EMBO J.* 14:1626–1636.

Gilbert, R., Ghosh, K., Rasile, L., and Ghosh, H. P. (1994). Membrane Anchoring Domain of Herpes Simplex Virus Glycoprotein gB Is Sufficient for Nuclear Envelope Localization. *J. Virol.* 68:2272–2285.

Gluzman, Y. (1981). SV40–Transformed Simian Cells Support the Replication of Early SV40 Mutants. *Cell.* 23:175–182.

Groner, A. (1986). Specificity and safety of baculoviruses. In "The Biology of Baculoviruses." pp. 177–202, (R. R. Granados and B. A. Federici, eds.). CRC Press, Boca Raton, FL.

Guarino, L. A., Smith, G., and Dong, W. (1995). Ubiquitin is Attached to Membranes of Baculovirus Particles by a Novel Type of Phospholipid Anchor. *Cell.* 80:301–309.

Harel, A., Zlotkin, E., Nainudel–Epszteyn, S., Feinstein, N., Fisher, P. A., and Gruenbaum, Y. (1989). Persistence of major nuclear envelope antigens in an envelope–like structure during mitosis in *Drosophila melanogaster* embryos. *J. Cell Sci.* 94:463–470.

Harlow, E., and Lane D. (1988). Antibodies: A Laboratory Manual. Cold Spring Harbor Laboratory Press, Cold Spring Harbor, New York, pp. 92–115.

Hershberger, P. A., LaCount, D. J., and Friesen, P. D. (1994). The Apoptotic Suppressor P35 Is Required Early During Baculovirus Replication And Is Targeted to the Cytosol of Infected Cells. *J. Virol.* 68:3467–3477.

Hill, J. E., and Faulkner, P. (1994). Identification of the gp67 gene of a baculovirus pathogenic to the spruce budworm, *Choristoneura fumiferana* multinucleocapsid nuclear polyhedrosis virus. *J. Gen. Virol.* 75:1811–1813.

Hong, T. (1995). Studies on a PDV Envelope Protein of *Autographa californica* Nuclear Polyhedrosis Virus. Ph.D dissertation, Department of Biology, Texas A&M University, College Station, Texas.

Hong, T., Braunagel, S. C., and Summers, M. D. (1994). Transcription, Translation, and Cellular Localization of PDV–E66: A Structural Protein of the PDV Envelope of *Autographa californica* Nuclear Polyhedrosis Virus. *Virology.* 204:210–222.

Hong, T., Braunagel, S. C., and Summers, M. D. (1996). A Baculovirus Envelope Protein Sequence Mediates Protein Transport to Membranes Within the Cytoplasm, Nuclear Envelope, Baculovirus–Induced Intranuclear Microvesicles and the Envelope of Occlusion Derived Virus. *Mole. Cell Biol.* (Submitted).

Hooft van Iddekinge, B. J. L., Smith, G. E., and Summers, M. D. (1983). Nucleotide Sequence of the Polyhedrin Gene of *Autographa califonica* Nuclear Polyhedrosis Virus. *Virology.* 131:561–565.

Hunter, T. (1993). Braking the Cycle. *Cell.* 75:839–841.

Ignoffo, C. M. (1971). Intraperitoneal Injection of White Mice with Nucleopolyhedrosis Virus of the Beet Armyworm, *Spodoptera exigua. J. Invert Pathol.* 17:453–454.

Ignoffo, C. M., Anderson, R. F., and Woodward, G. (1972). Teratogenic Potential in Rats Fed the Nuclear Polyhedrosis Virus of Heliothis. *Environmental Entomology.* 2:337–338.

Ignoffo, C. M., and Heimpel, A. M. (1965). The Nuclear–Polyhedrosis Virus of *Heliothis zea* (Boddie) and *Heliothis virescens* (Fabricius) V. Toxicity–Pathogenicity of Virus to White Mice and Guinea Pigs. *J. Invert. Pathol.* 7:329–340.

Ignoffo, C. M., and Rafajko, R. R. (1972). In vitro Attempts to Infect Primate Cells with the Nucleopolyhedrosis Virus of Heliothis. *J. Invet. Pathol.* 20:321–325.

Ismail, T., Ahmad, S., D'Souza–Ault, M., Bassiri, M., Saliki, J., Mebus, C., Yilma, T. (1994). Cloning and Expression of the Nucleocapsid Gene of Virulent Kabete O Strain of Rinderpest Virus in Baculovirus: Use in Differential Diagnosis Between Vaccinated and Infected Animals. *Virology.* 198:138–147.

Jackson, A. O., Francki, R. I. B., and Zuidema, D. (1987). Biology, Structure and Replication of Plant Rhabdoviruses. In "The Rhabdoviruses" (R. R. Wagner, Ed.). Plenum Press, New York, pp. 427–508.

Jarvis, D. L., Bohlmeyer, D. A., and Gracia, A., Jr. (1991). Requirements for Nuclear Localization and Supramolecular Assembly of a Baculovirus Polyhedrin Protein. *Virology.* 185:795–810.

Jarvis, D. L., Weinkauf, C., and Guarino, L. A. (1996). Immediate Early Baculovirus Vectors for Foreign Gene Expression in Transformed of Infected Insect Cells. *Protein Expression and Purification.* 8:191–203.

Jha, P. K., Nakhai, B., Sridhar, P., Talwar, G. P., Hasnain, S. E. (1990). Firefly luciferase, synthesized to very high levels in caterpillars infected with a recombinant baculovirus, can also be used as an efficient reported enzyme in vivo. *FEBS Letters.* 274:23–26.

Kawanishi, C. Y., Summers, M. D., Stoltz, D. B., and Arnott, H. J. (1972). Entry of an Insect Virus in Vivo by Fusion of Viral Envelope and Microvillus Membrane. *J. Invert. Pathol.* 20:104–108.

Keddie, B. A., and Volkman, L. E. (1985). Infectivity Differences Between the Two Phenotypes of *Autographa califonica* Nuclear Polyhedrosis Virus: Importance of the 64K Envelope Glycoprotein. *J. Gen. Virol.* 66:1195–1200.

Kennedy, et al. (1976). Protein–Protein Coupling Reactions and the Applications of Protein Conjgates. *Clin. Chim. Acta.* 70:1–31.

Kool, M., Ahrens, C. H., Goldbach, R. W., Rohrmann, G. F., and Vlak, J. M. (1994). Identification of genes involved in DNA replication of the *Autographa califirnica* baculovirus *Proc. Natl. Acad. Sci. USA.* 90:11212–11216.

Korth, K. L., and Levings, C. S., III. (1993). Baculovirus expression of the maize mitochondrial protein URF13 confers insecticidal activity in cell cultures and larvae. *Proc. Natl. Acad. Sci. USA.* 90:3388–3392.

Kovacs, G. R., Guarino, L. A., Graham, B. L., and Summers, M. D. (1991). Identification of Spliced Baculovirus RNAs Expressed Late in Infection. *Virology.* 185:633–643.

Kovacs, G. R., Guarino, L. A., and Summers, M. D. (1991b). Novel regulatory properties of the IE1 and IE0 transactivators encoded by the baculovirus *Autographa californica* multi–capsid nuclear polyhedrosis virus. *J. Virol.* 65:5281–5288.

Kozuma, K., and Hukuhara, T. (1994). Fusion characteristics of a nuclear polyhedrosis virus in cultured cells: time course and effect of a synergistic factor and pH. *J. Invert. Pathol.* 63:63–67.

Krappa, R., Behn–Krappa, A., Jahnel, F., Doerfler, W., and Knebel–Morsdorf, D. (1992). Differential Factor Binding at the Promoter of Early Baculovirus Gene PE38 During Viral Infection: GATA Motif Is Recognized by an Insect Protein. *J. Virol.* 66:3494–3503.

Kuzio, J., Jaques, R., and Faulkner, P. (1989). Identification of p74, a Gene Essential for Virulence of Baculovirus Occlusion Bodies. *Virology.* 173:759–763.

Kuzio, J., Rohel, D. Z., Curry, C. J., Krebs, A., Carstens, E. B., and Faulkner, P. (1984). Nucleotide Sequence of the p10 Polypeptide Gene of *Autographa californica* Nuclear Polyhedrosis Virus. *Virology.* 139:414–418.

Laukkanen, M–L., Oker–Blom, C., and Keinanen, K. (1996). Secretion of green fluorescent protein from recombinant baculovirus–infected cells. *Biochim. Biophys. Res. Comm.* 226:755–761.

Lu, A., and Carstens, E. B. (1992). Nucleotide Sequence and Transcriptional Analysis of the p80 Gene of *Autographa californica* Nuclear Polyhedrosis Virus: A Homologue of the *Orgyia pseudotsugata* Nuclear Polyhedrosis Virus Capsid–Associated Protein. *Virology.* 190:201–209.

Luckow, V. A., and Summers, M. D. (1989). High Level Expression of Nonfused Foreign Genes with *Autographa californica* Nuclear Polyhedrosis Virus Expression Vectors. *Virology.* 170:31–39.

Maddon, P. J., Dalgleish, A. G., McDougal, J. S., Clapham, P. E., Weiss, R. A., and Axel R. (1986). The T4 Gene Encodes the AIDS Virus Receptor and Is Expressed in the Immune System and the Brain. *Cell.* 47:333–348.

Maeda, S., Kawai, T., Obinata, M., Fujiwara, H., Horiuchi, T., Saeki, Y., Sato, Y., and Furusawa, M. (1985). Production of human alpha–interferon in silkwork using a baculovirus vector. *Nature.* 315:592–594.

Martens, J. (1994). Development of a Baculovirus Insecticide Exploiting the *Bacillus thuringiensis* Insecticidal Crystal Protein. Ph.D. dissertation, Department of Virology, Agricultural University in Wageningen, Netherlands. pp. 9–125, 133.

Martignoni, M. E., Stelzer, M. J., and Iwai, P. J. (1982). Baculovirus of *Autographa californica* (Lepidoptera: Noctuidae): a Candidate Biological Control Agent for Douglas–Fir Tussock Moth (Lepidoptera: Lymantriidae). *J. Econ. Entomol.* 75:1120–1124.

Martin, L., Crimaudo, C., and Gerace, L. (1995). cDNA Cloning and Characterization of Lamina–Associated Polypeptide 1C(LAP1C), an Integral Protein of the Inner Nuclear Membrane. *J. Biol. Chem.* 270:8822–8828.

Marutoto, Y., Sato, Y., Fujiwara, H., Saeki, Y., Agata, M., Furusawa, M., and Maeda, S. (1987). Hyperproduction of Polyhedrin–IGF II Fusion Protein in Silkworm Larvae Infected with Recombinant *Bombyx mori* Nuclear Polyhedrosis Virus. *J. Gen. Virol.* 68:2599–2606.

Matsubara, T., Beeman, R. W., Shike, H., Besansky, N. J., Mukabayire, O., Higgs, S., James, A. A., and Burns, J. C. (1996). Pantropic retroviral vectors integrate and express in cells of the malaria mosquito, *Anopheles gambiae. Proc. Natl. Acad. Sci. USA* 93:6181–6185.

Knebel–Morsdorf, D., Kremer, A., and Jahnel, F. (1993). Baculovirus Gene ME53, Which Contains a Putative Zinc Finger Mofif, Is One of the Major Early–Transcribed Genes. *J. Virol.* 67:753–758.

Murphy, F. A., Fauquet, C. M., Bishop, D. H. L., Ghabrial, S. A., Jarvis, A. W., Martelli, G. P., Mayo, M. A., and Summers, M. D. (1995). Virus Taxonomy. Sixth Report of the International Committee on Taxonomy of Viruses. Springer–Verlag Wien, New York, pp. 104–113.

Nicolau, C., Tosi, P. F., Arvinte, T., Mouneimme, Y., Cudd, A., Sneed, L., Madoulet, C., Schulz, B., Barhoumi, R. (1990). CD4 Inserted in Red Blood Cell Membranes or Reconstituted in Liposome Bilayers as a Potential Therapeutic Agent Against AIDS. *Horizons in Mem. Biotech.* 343:147–177.

Ogawa, H., Inouye, S., Tsuji, F. I., Yasuda, K., and Umesono, K. (1995). Localization, trafficking, and temperature––dependence of the Aequorea green fluorescent protein in cultured vertebrate cells. *Proc. Natl. Acad. Sci.* 92:11899–11903.

Oker–Blom, C., Orellana, A., and Keinanen, K. (1996). Highly efficient production of GFP and its derivatives in insect cells for visual in vitro applications *FEBS Letters* 389:238–243.

Padan, R., Nainudel–Epszteyn, S., Goitein, R., Fainsod, A., and Gruenbaum, Y. (1990). Isolation and Characterization of the Drosophila Nuclear Enveolpe Otefin cDNA. *J. Biol. Chem.* 265:7808–7813.

Reis, U., Blum, B., von Specht, B. U., Domdy, H., and Collins, J. (1992). Antibody Production in Silkworm Cells and Silkworm Larvae Infected With a Dual Recombinant *Bombyx mori* Nuclear Polyhedrosis Virus. *Bio/Technology* 10:910–912.

Richardson, C. D., Banville, M., Lalumiere, M., Vialard, J., Meighan, E. A. (1992). Bacterial Luciferase Produced with Rapid–Screening Baculovirus Vectors Is a Sensitive Reporter for Infection of Insect Cells and Larvae. *Intervirology* 34:213–227.

Roder, A., and Punter, J. (1977). Interacations Between Nuclear Polyhedrosis Viruses and Vertebrate Cells. *Zbl. Bakt. Hyg. I. Abt. Orig. A.* 239:459–464.

Rohrmann, G. F. (1992). Baculovirus structural proteins. *J. Gen. Virol.* 73:749–761.

Roizman, B., and Sears, A. E. (1990). Herpes Simplex Viruses and Their Replication. In "Virology." (B. N. Fields and D. M. Knipe, Eds.) pp. 1795–1841, vol. 2. Raven Press, New york.

Ross, T. K., Prahl, J. M., Herzberg, I. M., and DeLuca, H. F. (1992). Baculovirus–mediated expression of retinoic acid receptor type gamma in cultured insect cells reveals a difference in specific DNA–binding behavior with the 1,25–dihydroxyvitamin D3 receptor. *Proc. Natl. Acad. Sci. USA* 89:10282–10286.

Runge, V. M., et al., (1984). Paramagnetic NMR Contrast Agents Development and Evaluation. *Invest. Radiol.* 19:408–415.

Russell, R. L. Q., and Rohrmann, G. F. (1993). A 25–kDa Protein Is Associated with the Envelopes of Occluded Baculovirus Virions. *Virology.* 195:532–540.

Sambrook, J., Fritsch, E. F., and Maniatis, T. (1989). Molecular cloning: A Laboratory Manual. Cold Spring Harbor Laboratory Press, Cold Spring Harbor, New York.

Schaefer, S., et al., (1989). In Vivo Nuclear Magnetic Resonance Imaging of Myocarial Perfusion Using the Paramagnetic Contrast Agent Manganese Gluconate. *JACC* 14:472–480.

Schuurs, A. H. W. M., et al., (1977). Enzyme–Immunoassay. *Clin. Chim. Acta* 81:1–40.

Senior, A., and Gerace, L. (1988). Integral Membrane Proteins Specific to the Inne Nuclear Membrane and Associated with the Nuclear Lamina. *J. Cell Biol.* 107:2029–2036.

Shreve, P., et al., (1986). Monoclonal Antibodies Labeled with Polymeric Paramagnetic Ion Chelates. *Magn. Reson. Med.* 3:336–340.

Simos, G., Maison, C., and Georgatos, S. D. (1996). Characterization of p18, a Coimponent of the Lamin B Receptor Complex and a New Integral Membrane Protein of the Avian Erythrocyte Nuclear Envelope. *J. Biol. Chem.* 271:12617–12625.

Smith, S., and Blobel, G. (1993). The First Membrane Spanning Region of the Lamin B Receptor Is Sufficient For Sorting to the Inner Nuclear Membrane. *J. Cell Biol.* , 120:631–637.

Soullam, B., and Worman, H. J. (1993). The Amino–Terminal Domain of the Lamin B Receptor Is a Nuclear Envelope Targeting Signal. *J. Cell Biol.* 120:1093–1100.

Summers, M. D., and Smith, G. E. (1987). A Manual of Methods for Baculovirus Vectors and Insect Cell Culture Procedures. *Tex. Agric. Exp. Stn. Bull.* No. 1555.

Theilmann, D. A., Chantler, J. K., Stewart, S., Flipsen, H. T. M., Vlak, J. M., Crook, N. E. (1996). Characterization of a Highly Conserved Baculovirus Structural Protein That Is Specific for Occlusion–Derived Virus. *Virology.* 218:148–158.

Thiem, S. M., and Miller, L. K. (1989). Identification, Sequence, and Transcriptional Mapping of the Major Capsid Protein Gene of the Baculovirus, *Autographa califonica* Nuclear Polyhedrosis Virus. *J. Virol.* 63:2008–2017.

Tweeten, K. A., Bulla, Jr., L. A., and Consigli, R. A. (1980). Characterization of an Extremely Basic Protein Derived from Granulosis Virus Nucleocapsides. *J. Virol.* 33:866–876.

Vandenbosch, K. A. (1991). Immunogold Labeling. In "*Electron Microscopy pf Plant Cells.*" (J. L. Hall and C. Hawes, Eds.), pp. 181–218.

Venable, J.H., and Coggeshall, R. (1965). A simplified Lead Citrate Strain for Use in Electron Microscopy. *J. Cell Biol.* 25:407–408.

Volkman, L. E. (1986). The 64K Envelope Protein of Budded *Autographa californica* Nuclear Polyhedrosis Virus. *Curr. Top. Microbiol. Immunol.* 131:103–118.

Volkman, L. E., Goldsmith, P. A., and Hess, R. T. (1986). Alternate Pathway of Entry of Budded *Autographa californica* Nuclear Polyhedrosis Virus: Fusion at the Plasma Membrane. *Virology.* 148:288–297.

Volkman, L. E., Summers, M. D. (1977). *Autographica californica* Nuclear Polyhedrosis Virus: Comparative Infectivity of the Occluded, Alkali–Liberated and Nonoccluded Forms. *J. Invert. Pathol.* 30:102–103.

Volkman, L. E., Summers, M. D., and Hsieh, C. H. (1976). Occluded and Nonoccluded Nuclear Polyhedrosis Virus Grown in *Trichoplusia ni*: Comparative Neutralization, Comparative Infectivity, and In Vitro Growth Studies. *J. Virtol.* 19:820–832.

von Heijne, G. (1990). The Signal Peptide. *J. Membr. Biol.* 115:195–201.

Webb, N. R., Madoulet, C., Tosi, P. F., Broussard, D. R., Sneed, L., Nicolau, C., and Summers, M. D. (1989). Cell–surface expression and purification of human CD4 produced in baculovirus–infected cells. *Proc. Natl. Acad. Sci. USA* 86:7731–7735.

Webb, N. R., and Summers, M. D. (1990). Expression of Proteins Using Recombinant Baculoviruses. *Technique.* 2:173–188.

Wesbey, G., et al. (1984). Paramagnetic Pharmaceuticals for Magnetic Resonance Imaging. *Physiol. Chem. Phys. Med. NMR* 16:145–155.

White, J. M. (1990). Viral and Cellular Membrane Fusion Proteins. *Annu. Rev. Physiol.* 52:675–697.

Whitford, M., and Faulkner, P. (1992). A structural Polypeptide of the Baculovirus *Autographa californica* Nuclear Polyhedrosis Virus Contains O–Linked N–Acetylglucosamine. *J. Virol.* 66:3324–3329.

Whitford, M., and Faulkner, P. (1992). Nucleotide Sequence and Transcriptional Analysis of a Gene Encoding gp41, a Structural Glycoprotein of the Baculovirus *Autographa californica* Nuclear Polyhedrosis Virus. *J. Virol.* 66:4763–4768, 2447.

Whitford, M., Stewart, S., Kuzio, J., and Faulkner, P. (1989). Identification and Sequence Analysis of a Gene Encoding gp67, an Abundant Envelope Glycoprotein of the Baculovirus *Autographa californica* Nuclear Polyhedrosis Virus. J. Virol. 63:1393–1399.

Whitt, M. A., and Manning, J. S. (1987). Role of Chelating Agents, Monocalent Anion and Cation in the Dissociation of *Autographa californica* Nuclear Polyhedrosis Virus Occlusion Body. *J. Invert. Pathol.* 49:61–69.

Wilson, M. E. (1988). A Synthetic Peptide to the Predicted 6.9K Translation Product of the Hind III–H/EcoRI–D Region of the AcNPV Genome Induces Antibodies to the Basic DNA–Binding Protein. *Virus Res.* 9:21–31.

Wilson, M. E., Mainprize, T. H., Friesen, P. D., and Miller, L. K. (1987).. Location, Transcription, and Sequence of a Baculovirus Gene Encoding a Small Arginine–Rich Polypeptide. *J. Virol.* 61:661–666.

Wolf, G. L. (1984). Contrast Enhancement in Biomedical NMR. *Physiol. Chem. Phys. Med. NMR* 16:93–95.

Wolgamot, G. M., Gross, C. H., Russell, R. L. Q., and Rohrmann, G. F. (1993). Immunocytochemical characterization of p24, a baculovirus capsid–associated protein. *J. Gen. Virol.* 74:103–107.

Wozniak, R. W., and Blobel, G. (1992). The Single Transmembrane Segment of gp210 Is Sufficient for Sorting to the Pore Membrane Domain of the Nuclear Envelope. *J. Cell Biol.* 119:1441–1449.

Chisholm, G. E., et al. (1988). Multiple Early Transcripts and Splicing of the *Autographa californica Nuclear Poluhedrosis Virus IE–1 Gene. J. Virol.* 62:3193–3200.

TAMK:176; Serial No. 08/678,435, filed Jul. 3, 1996; Parent of TAMK:190 (Present case).

Oomens, et al. (1995). The Baculovirus GP64 Envelope Fusion Protein: Synthesis, Oligomerization and Processing. *Virology* 209:592–603.

FIG. 1A-1

```
701  ATGAACATTACCATTGTGCTAAACGAAAACGCAGCATTACGACGAAGCTGCGTCCCTCACGGGTTACTGGC
194   M  N  I  T  I  V  L  N  E  T  Q  H  Y  D  E  A  A  S  L  T  R  Y  W  L
771  TCGGCTTGTATCTGCCCACGGCCGTCAACTCGATGGGCTGGCACCGGACGGCAGGCAACTCAATGCGCAT
217   G  L  Y  L  P  T  A  V  N  S  M  G  W  H  R  T  A  G  N  S  M  R  M
841  GGGTGTGCCCTACAGTACGGCGTTTCGTACGGACTCAAGGCAAGGCTTGCACGTCGATTCGA
241   G  V  P  Y  T  S  Q  M  L  R  G  Y  S  L  A  Q  I  R  Q  E  Q  G
911  ATACAAGAAATCCTAAACACGATCGCTTCCGTACGGACTCAAGGCAAGGCTTGCACGTCGATTCGA
264   I  Q  E  L  N  T  I  A  F  P  Y  V  T  Q  G  N  G  L  H  V  D  S  I
981  TATACATCGATCACATTGACGTTGCCGCGCTTACGGCGTAATCAACACGGTTGGGTTTGACGAGAGCCATCGAAAACGTGGGCAGT
288   Y  D  H  I  D  V  R  A  Y  G  Y  L  I  N  S  Y  F  T  F  A  Y  Y
1051 CACGTACTATTTGGAGACGAGGTAATCAACACGGTTGGGTTTGACGAGAGCCATCGAAAACGTGGGCAGT
311   T  Y  F  G  D  E  V  I  N  T  V  G  L  T  R  A  I  E  N  V  G  S
1121 CCCGAGGGAGTTGTGGTGCCAGGCGTCATGTCTCGAAACGGCACGTTGTACTCTAACGTGATAGGCAACT
334   P  E  G  V  V  P  G  V  M  S  R  N  G  T  L  Y  S  N  V  I  G  N  F
1191 TTATTACGTATCCGTTGGCCGTCCATTCGGCCGATTACTCCAAAGTGTTGACCAAACTTTCAAAAACATA
358   I  T  Y  P  L  A  V  H  S  A  D  Y  S  K  V  L  T  K  L  S  K  T  Y
1261 TTACGGTTCGGTTGTGTGGGCGTAACGAATAGGTTGGCTTACTAGGCTTACTATACGAATCCAACAACATTCAA
381   Y  G  S  V  G  V  T  N  R  L  A  Y  E  S  D  P  T  N  I  Q
1331 GCGCCCCTGTGGACCATGGCGCGCCCGATTGGAATCGGCGCGCAGAATTATCAACTATAATGCCAACA
404   A  P  L  W  T  M  A  R  I  W  N  R  R  G  R  I  I  N  Y  N  A  N  T
1401 CGGTGTCGTTGAGTCGGGTATTTTGCAAAGTTTGAACGGAATCATGCGGAATCATGCGGCCATCCCGTCGGGCACCAC
428   V  S  F  E  S  G  I  I  L  Q  S  L  N  G  I  M  R  I  P  S  G  T  T
1471 GTCCACGCAGTCGTTCAGACCGGATAGCCAAAACCGACGGCCGGCCATT
451   S  T  G  S  F  R  P  T  I  G  Q  T  A  I  A  K  T  D  T  A  G  A  I
```

FIG. 1A-2

```
1541  TTGGTGTACGGCCAAGTTTGCGGAAATGAACAATTTGCAATTTAAATCGTTGCACGTTGTTCTACGATCACG
 474   L  V  Y  G  Q  V  C  G  E  M  N  N  L  Q  F  K  S  C  T  L  F  Y  D  H  G
1611  GCATGTTCCAGCTATATTACAACACATTGGGCGTGGAACCAAACTCGCTCAACAACACAACGGGCGGGTGAT
 498   M  F  Q  L  Y  Y  N  T  L  G  V  E  P  N  S  L  N  N  T  N  G  R  V  I
1681  TGTGCTAAGAGAGACACGTCGGTCAACACCAAGATTGTCATTTGAAGGCAAAGAATTAACAACAAC
 521   V  L  S  R  D  T  S  V  N  T  N  D  L  S  F  E  A  Q  R  I  N  N  N
1751  AACTCGTCGGAAGGCACCACGTTCAACGGTCTGTGTCATGCGTTCCTATCACAAACATCAACGTGC
 544   N  S  S  E  G  T  T  F  N  G  V  V  C  H  R  V  P  I  T  N  I  N  V  P
1821  CTTCTCTGACCGTTCGAAGTCCCAATTCTAGCGTCGAACTAGTCGAGCAGATAATTAGTTTTCAAACAAT
 568   L  L  T  V  R  S  P  N  S  S  V  E  L  V  E  Q  I  I  S  F  Q  T  M
1891  GTACACGGCCACGCTTCGGCCTGTTACAAATTAAACGTCGAAGGTCATTCGGATTCCTGAGAGCTTTT
 591   Y  T  A  T  S  A  C  Y  K  L  N  V  E  G  H  S  D  S  L  R  A  F
1961  AGAGTTAATTCCGACGAAAACATTTATGTAACGTGGGCAACGGTTAAAGCCCTGTTAATTATCCT
 614   R  V  N  S  D  E  N  I  Y  V  N  V  G  N  G  V  K  A  L  F  N  Y  P  W
2031  GGGTAATGGTCAAAGAAAAATAACAAAAGTGTCTTCATGTCGGCTAACGAAGACACTACTATACCATTTAG
 638   V  M  V  K  E  N  K  V  S  F  M  S  A  N  E  D  T  T  I  P  F  S
2101  CGTTATAATGAATTCCTTCACCTCTATCGGCGAACCAGCTTTGCAATACTCTCCATCAAATTGCTTTGTG
                EcoRI
 661       V  I  M  N  S  F  T  S  I  G  E  P  A  L  Q  Y  S  P  S  N  C  F  V
2171  TATGGAAACGGTTTCAAATTGAACAACAGCACGTTGATTTACAATTTATTTTTGAAATTGTGTAATTAT
 684   Y  G  N  G  F  K  L  N  N  S  T  F  D  L  Q  F  I  F  E  I  V  *
2241  ATTTAGGAGAATGTGAATATTCAAAAGACTGACTGTTAACACAAAAGACTGATATTGTTGTGTTACAAA
2311  ATAGATAATAAAACAAACAATTAAATAAATATTATTTATTTAAACTGTTAATTTAATGCTAACGC
2381  GTACAAATCACGCTGTTCCGACGTGGACATGGAATTGCGCAGAAAAGTCTTGATAGTGTCGATTTCTTCG
2451  CCGTTCATCCACCACTTCCATATATTTGATTTCTTCCTGATTGCATTTGCGTATTCTTGCAAAT
2521  AATAATCTAG   (SEQ ID NO:1)
```

FIG. 1A-3

NUCLEOTIDE AND AMINO ACID SEQUENCE FOR 23AA:

```
ATG TCT ATC GTA TTG ATT ATT GTC
 M   S   I   V   L   I   I   V

ATA GTT GTA ATA TTT TTA ATA TGT
 I   V   V   I   F   L   I   C

TTT TTG TAC CTA TCA AAT AGC
 F   L   Y   L   S   N   S
```

AMINO ACID SEQUENCE FOR 23AA:

M S I V L I I V V I F L I C F L Y L S N S  (SEQ ID NO:3)

FIG. 1B

| Name | Structure | Promoter | Gene Locus | Production of Viral Occlusion | Protein Location |
|---|---|---|---|---|---|
| 1. ODV-E66 | 1 23  125 704 | ODV-E66 | ODV-E66 | Yes | ODV-Env, M, NE |
| 2. 125β-gal | 1 23  125 1140 β-gal | ODV-E66 | ODV-E66 | Yes | ODV-Env, M, NE |
| 3. Δ2-23β-gal | β-gal | ODV-E66 | ODV-E66 | Yes | — |
| 4. 23β-gal | 1 23  β-gal | ODV-E66 | ODV-E66 | Yes | ODV-Env, M, NE |
| 5. pAcUW21-23GFP | 1 23  261 GFP | p10 | polyhedrin | Yes | ODV-Env, M, NE, CM |
| 6. pVL1393-23GFP | 1 23  GFP | polyhedrin | polyhedrin | No | ODV-Env, M, NE, CM |
| 7. pVL1393-E66F | 1 23  125 704 | polyhedrin | polyhedrin | No | ODV-Env, M, NE |
| 8. pAcUW21-23URF13 | 1 23  138 URF13 | p10 | polyhedrin | Yes | ODV-Env, M, NE, CM |
| 9. pIE1HR4-23GFP (uninfected Sf9 cells) | GFP | IE1 | N/A | N/A | Cell cycle regulation to NE |
| 10. pCMV-23GFP (uninfected COS-1 cells) | GFP | CMV-IE | N/A | N/A | Cell cycle regulation to NE |
| 11. pRTL2-23GFP (Plant cells) | GFP | 35S | N/A | N/A | ? |
| 12. pVL1392-24GFP (ODV-E25) | GFP | polyhedrin | polyhedrin | ? | ? |

ODV-Env — ODV envelope
M — Intranuclear microvesicles and membrane
CM — Cytoplasmic membranes
CMV-IE — Major immediate early promoter of cytomegalovirus
N/A — Not applicable
NE — Nuclear envelope ▨ N-terminal 23 amino acid hydrophobic sequence derived from ODV-E66

▩ N-terminal 24 amino acid hydrophobic sequence derived from ODV-E25

FIG. 2

FIG. 3A
FIG. 3B
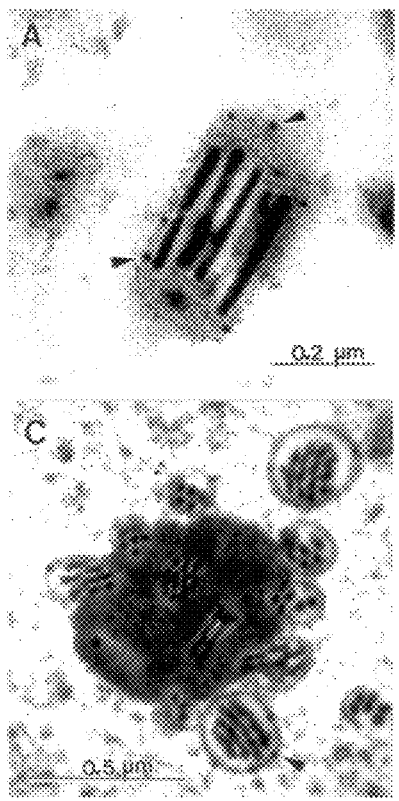
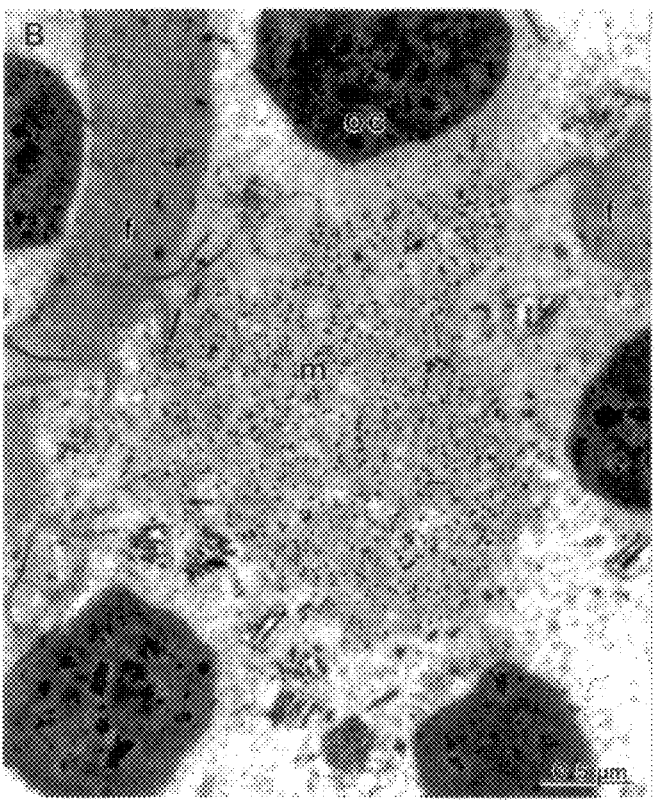
FIG. 3C

FIG. 4A
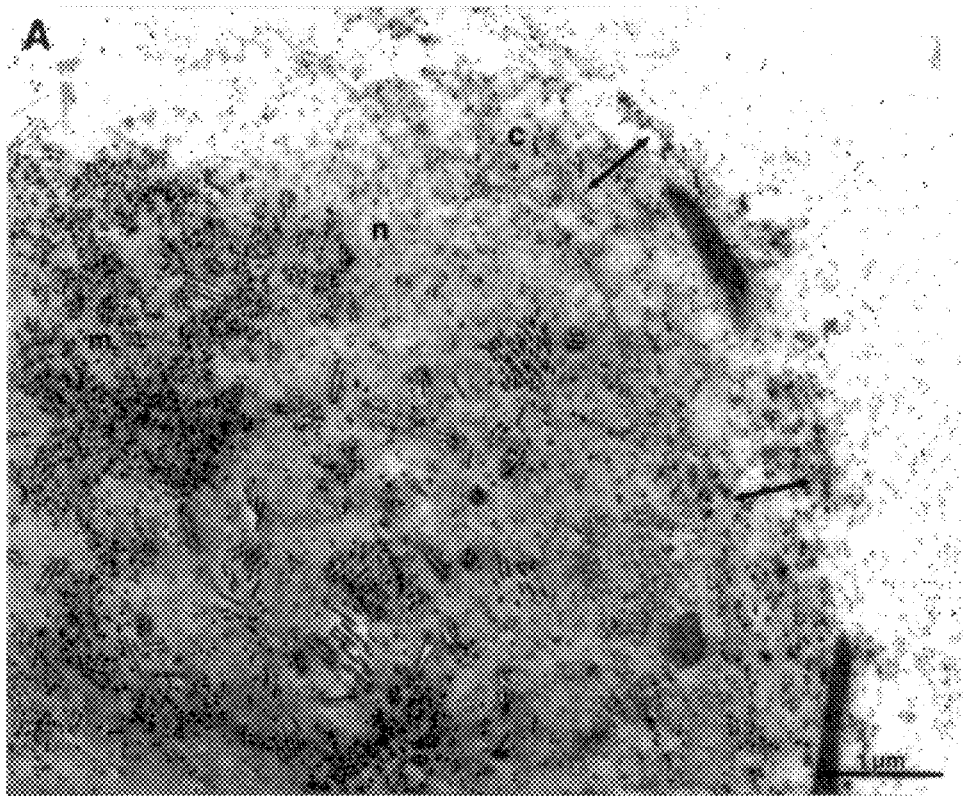
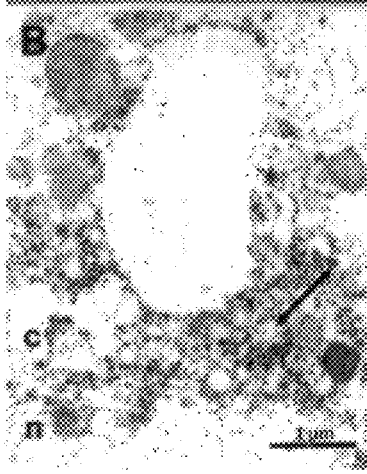
FIG. 4B
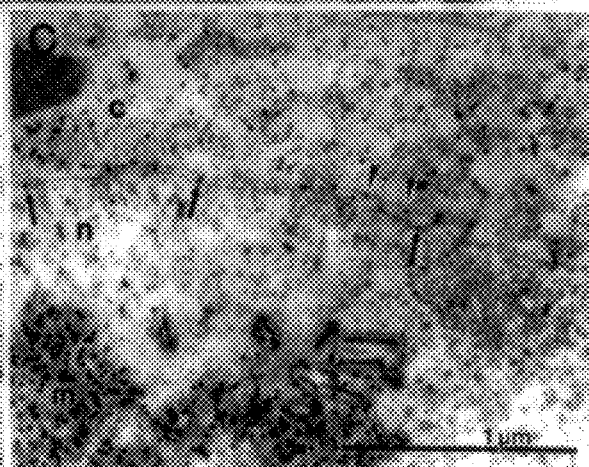
FIG. 4C

FIG. 6A
FIG. 6B
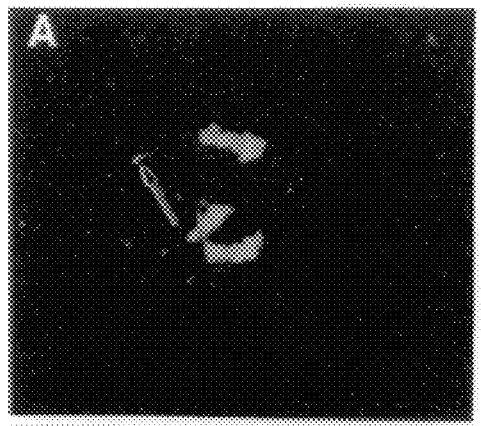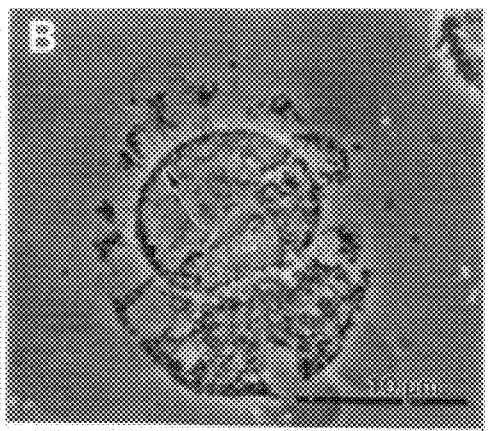
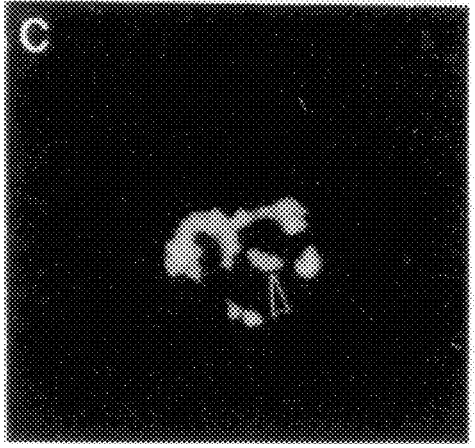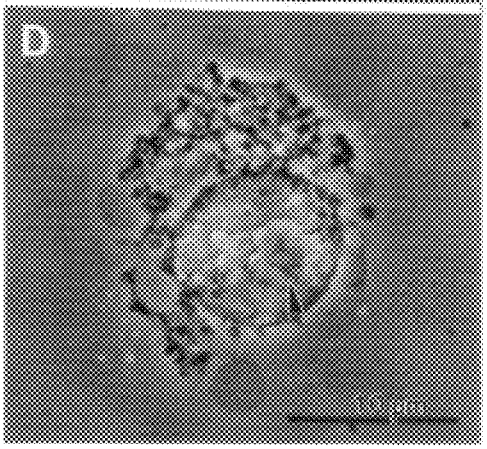
FIG. 6C
FIG. 6D

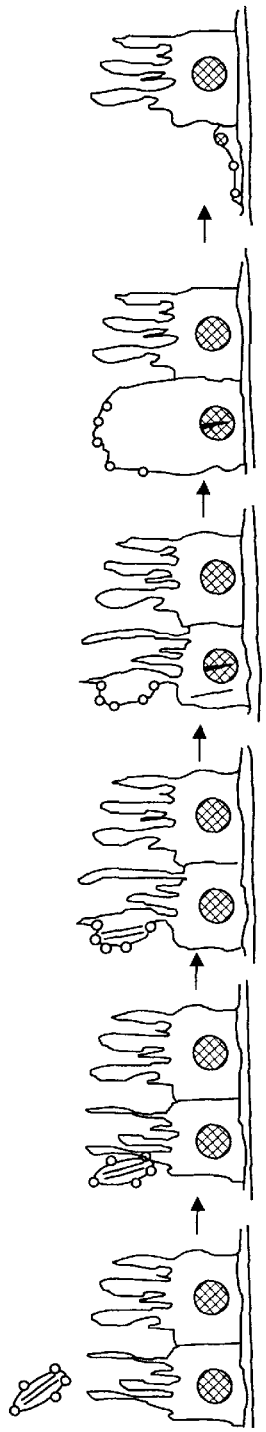
FIG. 10A
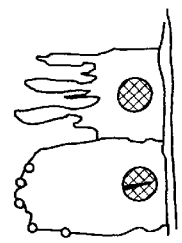
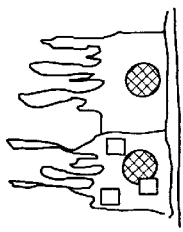
FIG. 10B

LARVAL-TISSUE CULTURE EXPRESSION LEVELS

| | Tissue Culture | Larval | References |
|---|---|---|---|
| Firefly luciferase | *S. littoralis*<br>>25% total protein | *T. ni*<br>15% total protein | Jha *et al.*, 1990 |
| IgG2A | *T. ni*<br>6.4 μg/ml supernatant | *T. ni*<br>800 μg/larva/7 dpi | Reis *et al.*, 1992 |
| Murine retinoic acid receptor | Sf9 cells<br>300 pmol/mg protein | *Manduca sexta*<br>100 pmol/mg protein | Ross *et al.*, 1992 |
| VSV-N protein | Sf9 cells<br>41-60% total protein | *Spodoptera exigua*<br>68% total protein<br>larva = 30,000 ELISAS | Ahmad *et al.*, 1993 |
| Rinderpest virus N protein | | *Spodoptera frugiperda*<br>larva = 15,000 sera tests | Ismail *et al.*, 1994 |
| Insulin-like growth factor II | | silkworm larva<br>3.6 mg/larva | Marumoto *et al.*, 1987 |
| Human α interferon | | silkworm larva<br>50 μg/hemolymph/larva | Maeda *et al.*, 1985 |
| Bacterial luciferase | | *E. acrea*<br>195 μg/larva | Richardson *et al.*, 1992 |

FIG. 11

```
23β-Gal    MSIVLIIVIVVIFLICFLYLSNSGTKDPVVLQ → βGALACTOSIDASE (SEQ ID NO:48)
                                  **  ***
23-GFP     MSIVLIIVIVVIFLICFLYLSNSKDPRVPVELM → GFP (SEQ ID NO:49)
                                  *
AcNPV
ODV-E66    MSIVLIIVIVVIFLICFLYLSNSNNKNDANKNNAFI (SEQ ID NO:50)
                              *  *
OpNPV
ODV-E66    MGLITLILALIVVLFVFASNSSKPANNASFADNGAQRT (SEQ ID NO:51)
                              * ** ***
Bm NPV
ODV-E66    MSTVLIIVVVVIFLICFWCLLNSSNNSNNKNDANRNNVFV (SEQ ID NO:52)
                                *
AcNPV
ODV-E25    MWGIVLLIVLLILFYLYWTNALNFNSLTESSPSLGQSSD (SEQ ID NO:53)
                                *
OpNPV
ODV-E25    MWGALILLILLVFLFYLWYNGKLNLNSLTESSPSLAQSSD (SEQ ID NO:54)
                                *
BmNPV
ODV-E25    MWKIVLLIVLLVLTYLYWTNALNLNSLTEASPSLGQSSE (SEQ ID NO:55)
                                ** *
24-GFP     MWGIVLLIVLLILFYLYWTNALNFKDPRVPVELM → GFP (SEQ ID NO:56)
```

FIG. 16

SEQUENCE LISTING (1) GENERAL INFORMATION:

(iii) NUMBER OF SEQUENCES: 56

(2) INFORMATION FOR SEQ ID NO:1:

(i) SEQUENCE CHARACTERISTICS:
      (A) LENGTH: 2530 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 122..2233

(xi) SEQUENCE DESCRIPTION: SEQ ID NO:1:

```
CGGTGTTGGC GTCTATTTGT TTAAAACACT CGTTCGGCAA ATGCGAGTGG TTGGACAAAA        60

ATATAAAAAC TGTGTGTTTA CAATTAAGAA AAATTTGTAT CAATAATAAG CAACATTCGA       120

C ATG TCT ATC GTA TTG ATT ATT GTC ATA GTT GTA ATA TTT TTA ATA          166
  Met Ser Ile Val Leu Ile Ile Val Ile Val Val Ile Phe Leu Ile
  1               5                   10                  15
```

```
TGT TTT TTG TAC CTA TCA AAT AGC AAT AAT AAA AAT GAT GCC AAT AAA      214
Cys Phe Leu Tyr Leu Ser Asn Ser Asn Asn Lys Asn Asp Ala Asn Lys
             20                  25                  30

AAC AAT GCT TTT ATT GAT CTC AAT CCC TTG CCG CTC AAT GCT ACA ACC      262
Asn Asn Ala Phe Ile Asp Leu Asn Pro Leu Pro Leu Asn Ala Thr Thr
             35                  40                  45

GCT ACT ACT ACC ACT GCC GTT GCT ACC ACC ACT ACC AAC AAC AAC AAC      310
Ala Thr Thr Thr Thr Ala Val Ala Thr Thr Thr Thr Asn Asn Asn Asn
             50                  55                  60

AGC ATA GTG GCC TTT CGG CAA AAC AAC ATT CAA GAA CTA CAA AAC TTT      358
Ser Ile Val Ala Phe Arg Gln Asn Asn Ile Gln Glu Leu Gln Asn Phe
             65                  70                  75

GAA CGA TGG TTC AAA AAT AAT CTC TCA TAT TCG TTT AGC CAA AAA GCT      406
Glu Arg Trp Phe Lys Asn Asn Leu Ser Tyr Ser Phe Ser Gln Lys Ala
 80              85                  90                  95

GAA AAG GTG GTA AAT CCC AAT AGA AAT TGG AAC GAC AAC ACG GTA TTT      454
Glu Lys Val Val Asn Pro Asn Arg Asn Trp Asn Asp Asn Thr Val Phe
                100                 105                 110

GAC AAT TTG AGT CCG TGG ACA AGC GTT CCG GAC TTT GGT ACC GTG TGC      502
Asp Asn Leu Ser Pro Trp Thr Ser Val Pro Asp Phe Gly Thr Val Cys
            115                 120                 125

CAC ACG CTC ATA GGG TAT TGC GTA CGC TAC AAC AAC ACC AGC GAC ACG      550
His Thr Leu Ile Gly Tyr Cys Val Arg Tyr Asn Asn Thr Ser Asp Thr
            130                 135                 140

TTA TAC CAG AAC CCT GAA TTG GCT TAC AAT CTC ATT AAC GGG CTG CGC      598
Leu Tyr Gln Asn Pro Glu Leu Ala Tyr Asn Leu Ile Asn Gly Leu Arg
145                 150                 155

ATC ATT TGC AGC AAA CTG CCC GAT CCG CCG CCG CAC CAA CAA GCG CCC      646
Ile Ile Cys Ser Lys Leu Pro Asp Pro Pro Pro His Gln Gln Ala Pro
160                 165                 170                 175

TGG GGC CCG GTC GCC GAT TGG TAC CAT TTC ACA ATC ACA ATG CCC GAG      694
Trp Gly Pro Val Ala Asp Trp Tyr His Phe Thr Ile Thr Met Pro Glu
            180                 185                 190

GTG TTT ATG AAC ATT ACC ATT GTG CTA AAC GAA ACG CAG CAT TAC GAC      742
Val Phe Met Asn Ile Thr Ile Val Leu Asn Glu Thr Gln His Tyr Asp
            195                 200                 205

GAA GCT GCG TCC CTC ACG CGT TAC TGG CTC GGC TTG TAT CTG CCC ACG      790
Glu Ala Ala Ser Leu Thr Arg Tyr Trp Leu Gly Leu Tyr Leu Pro Thr
            210                 215                 220

GCC GTC AAC TCG ATG GGC TGG CAC CGG ACG GCA GGC AAC TCA ATG CGC      838
Ala Val Asn Ser Met Gly Trp His Arg Thr Ala Gly Asn Ser Met Arg
225                 230                 235

ATG GGT GTG CCC TAC ACG TAC AGT CAA ATG TTG CGC GGA TAT TCA TTG      886
Met Gly Val Pro Tyr Thr Tyr Ser Gln Met Leu Arg Gly Tyr Ser Leu
240                 245                 250                 255

GCG CAA ATT AGG CAA GAG CAG GGA ATA CAA GAA ATC CTA AAC ACG ATC      934
Ala Gln Ile Arg Gln Glu Gln Gly Ile Gln Glu Ile Leu Asn Thr Ile
                260                 265                 270

GCG TTT CCG TAC GTG ACT CAA GGC AAC GGC TTG CAC GTC GAT TCG ATA      982
Ala Phe Pro Tyr Val Thr Gln Gly Asn Gly Leu His Val Asp Ser Ile
            275                 280                 285

TAC ATC GAT CAC ATT GAC GTG CGC GCT TAC GGC TAT TTG ATA AAT TCA     1030
Tyr Ile Asp His Ile Asp Val Arg Ala Tyr Gly Tyr Leu Ile Asn Ser
            290                 295                 300

TAC TTT ACG TTT GCC TAT TAC ACG TAC TAT TTT GGA GAC GAG GTA ATC     1078
Tyr Phe Thr Phe Ala Tyr Tyr Thr Tyr Tyr Phe Gly Asp Glu Val Ile
305                 310                 315

AAC ACG GTG GGT TTG ACG AGA GCC ATC GAA AAC GTG GGC AGT CCC GAG     1126
Asn Thr Val Gly Leu Thr Arg Ala Ile Glu Asn Val Gly Ser Pro Glu
320                 325                 330                 335
```

-continued

```
GGA GTT GTG GTG CCA GGC GTC ATG TCT CGA AAC GGC ACG TTG TAC TCT    1174
Gly Val Val Val Pro Gly Val Met Ser Arg Asn Gly Thr Leu Tyr Ser
            340                 345                 350

AAC GTG ATA GGC AAC TTT ATT ACG TAT CCG TTG GCC GTC CAT TCG GCC    1222
Asn Val Ile Gly Asn Phe Ile Thr Tyr Pro Leu Ala Val His Ser Ala
            355                 360                 365

GAT TAC TCC AAA GTG TTG ACC AAA CTT TCA AAA ACA TAT TAC GGT TCG    1270
Asp Tyr Ser Lys Val Leu Thr Lys Leu Ser Lys Thr Tyr Tyr Gly Ser
        370                 375                 380

GTT GTG GGC GTA ACG AAT AGG TTG GCT TAC TAC GAA TCC GAT CCC ACA    1318
Val Val Gly Val Thr Asn Arg Leu Ala Tyr Tyr Glu Ser Asp Pro Thr
        385                 390                 395

AAC AAC ATT CAA GCG CCC CTG TGG ACC ATG GCG CGG CGC ATT TGG AAT    1366
Asn Asn Ile Gln Ala Pro Leu Trp Thr Met Ala Arg Arg Ile Trp Asn
400                 405                 410                 415

CGG CGC GGC AGA ATT ATC AAC TAT AAT GCC AAC ACG GTG TCG TTT GAG    1414
Arg Arg Gly Arg Ile Ile Asn Tyr Asn Ala Asn Thr Val Ser Phe Glu
                420                 425                 430

TCG GGT ATT ATT TTG CAA AGT TTG AAC GGA ATC ATG CGC ATC CCG TCG    1462
Ser Gly Ile Ile Leu Gln Ser Leu Asn Gly Ile Met Arg Ile Pro Ser
            435                 440                 445

GGC ACC ACG TCC ACG CAG TCG TTC AGA CCG ACC ATT GGC CAA ACG GCT    1510
Gly Thr Thr Ser Thr Gln Ser Phe Arg Pro Thr Ile Gly Gln Thr Ala
            450                 455                 460

ATA GCC AAA ACC GAC ACG GCC GGC GCC ATT TTG GTG TAC GCC AAG TTT    1558
Ile Ala Lys Thr Asp Thr Ala Gly Ala Ile Leu Val Tyr Ala Lys Phe
        465                 470                 475

GCG GAA ATG AAC AAT TTG CAA TTT AAA TCG TGC ACG TTG TTC TAC GAT    1606
Ala Glu Met Asn Asn Leu Gln Phe Lys Ser Cys Thr Leu Phe Tyr Asp
480                 485                 490                 495

CAC GGC ATG TTC CAG CTA TAT TAC AAC ATT GGC GTG GAA CCA AAC TCG    1654
His Gly Met Phe Gln Leu Tyr Tyr Asn Ile Gly Val Glu Pro Asn Ser
                500                 505                 510

CTC AAC AAC ACA AAC GGG CGG GTG ATT GTG CTA AGC AGA GAC ACG TCG    1702
Leu Asn Asn Thr Asn Gly Arg Val Ile Val Leu Ser Arg Asp Thr Ser
            515                 520                 525

GTC AAC ACC AAC GAT TTG TCA TTT GAA GCG CAA AGA ATT AAC AAC AAC    1750
Val Asn Thr Asn Asp Leu Ser Phe Glu Ala Gln Arg Ile Asn Asn Asn
            530                 535                 540

AAC TCG TCG GAA GGC ACC ACG TTC AAC GGT GTG GTC TGT CAT CGC GTT    1798
Asn Ser Ser Glu Gly Thr Thr Phe Asn Gly Val Val Cys His Arg Val
545                 550                 555

CCT ATC ACA AAC ATC AAC GTG CCT TCT CTG ACC GTT CGA AGT CCC AAT    1846
Pro Ile Thr Asn Ile Asn Val Pro Ser Leu Thr Val Arg Ser Pro Asn
560                 565                 570                 575

TCT AGC GTC GAA CTA GTC GAG CAG ATA ATT AGT TTT CAA ACA ATG TAC    1894
Ser Ser Val Glu Leu Val Glu Gln Ile Ile Ser Phe Gln Thr Met Tyr
                580                 585                 590

ACG GCC ACG GCT TCG GCC TGT TAC AAA TTA AAC GTC GAA GGT CAT TCG    1942
Thr Ala Thr Ala Ser Ala Cys Tyr Lys Leu Asn Val Glu Gly His Ser
            595                 600                 605

GAT TCC CTG AGA GCT TTT AGA GTT AAT TCC GAC GAA AAC ATT TAT GTA    1990
Asp Ser Leu Arg Ala Phe Arg Val Asn Ser Asp Glu Asn Ile Tyr Val
        610                 615                 620

AAC GTG GGC AAC GGC GTT AAA GCC CTG TTT AAT TAT CCC TGG GTA ATG    2038
Asn Val Gly Asn Gly Val Lys Ala Leu Phe Asn Tyr Pro Trp Val Met
        625                 630                 635

GTC AAA GAA AAT AAC AAA GTG TCT TTC ATG TCG GCT AAC GAA GAC ACT    2086
Val Lys Glu Asn Asn Lys Val Ser Phe Met Ser Ala Asn Glu Asp Thr
640                 645                 650                 655
```

```
ACT ATA CCA TTT AGC GTT ATA ATG AAT TCC TTC ACC TCT ATC GGC GAA    2134
Thr Ile Pro Phe Ser Val Ile Met Asn Ser Phe Thr Ser Ile Gly Glu
            660                 665                 670

CCA GCT TTG CAA TAC TCT CCA TCA AAT TGC TTT GTG TAT GGA AAC GGT    2182
Pro Ala Leu Gln Tyr Ser Pro Ser Asn Cys Phe Val Tyr Gly Asn Gly
            675                 680                 685

TTC AAA TTG AAC AAC AGC ACG TTT GAT TTA CAA TTT ATT TTT GAA ATT    2230
Phe Lys Leu Asn Asn Ser Thr Phe Asp Leu Gln Phe Ile Phe Glu Ile
            690                 695                 700

GTG TAATTATATT TAGGGAGAAT GTGATATTCA AAAGACTGAC TGTTAACACA         2283
Val

AAAGACTGAT ATTGTTGTTG TTACAAAATA GATAATAAAA CAAAAAATAA ATTAAATATT  2343

ATTTATTTAT TAAACTGTTT AATTTTAATG CTAACGCGTA CAAATCACGC TGTTCCGACG  2403

TGGACATGGA ATTGCGCAGA AAAGTCTTGA TAGTGTCGAT TCTTCGCCG TCATCCACTT   2463

CCATATATTT GATTTCTTCC TCGATTTGCA TTTCCAAGTT TGCGTATTCT TGCAAATAAT  2523

AATCTAG                                                            2530
```

(2) INFORMATION FOR SEQ ID NO:2:

(i) SEQUENCE CHARACTERISTICS:
        (A) LENGTH: 704 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Ile Val Leu Ile Ile Val Ile Val Ile Phe Leu Ile Cys
 1               5                  10                  15

Phe Leu Tyr Leu Ser Asn Ser Asn Asn Lys Asn Asp Ala Asn Lys Asn
                20                  25                  30

Asn Ala Phe Ile Asp Leu Asn Pro Leu Pro Leu Asn Ala Thr Thr Ala
            35                  40                  45

Thr Thr Thr Thr Ala Val Ala Thr Thr Thr Asn Asn Asn Asn Ser
    50                  55                  60

Ile Val Ala Phe Arg Gln Asn Asn Ile Gln Glu Leu Gln Asn Phe Glu
65              70                  75                  80

Arg Trp Phe Lys Asn Asn Leu Ser Tyr Ser Phe Ser Gln Lys Ala Glu
                85                  90                  95

Lys Val Val Asn Pro Asn Arg Asn Trp Asn Asp Asn Thr Val Phe Asp
                100                 105                 110

Asn Leu Ser Pro Trp Thr Ser Val Pro Asp Phe Gly Thr Val Cys His
            115                 120                 125

Thr Leu Ile Gly Tyr Cys Val Arg Tyr Asn Asn Thr Ser Asp Thr Leu
    130                 135                 140

Tyr Gln Asn Pro Glu Leu Ala Tyr Asn Leu Ile Asn Gly Leu Arg Ile
145                 150                 155                 160

Ile Cys Ser Lys Leu Pro Asp Pro Pro His Gln Gln Ala Pro Trp
                165                 170                 175

Gly Pro Val Ala Asp Trp Tyr His Phe Thr Ile Thr Met Pro Glu Val
            180                 185                 190

Phe Met Asn Ile Thr Ile Val Leu Asn Glu Thr Gln His Tyr Asp Glu
                195                 200                 205

Ala Ala Ser Leu Thr Arg Tyr Trp Leu Gly Leu Tyr Leu Pro Thr Ala
            210                 215                 220
```

-continued

| | | | | | | | | | | | | | | |
|---|---|---|---|---|---|---|---|---|---|---|---|---|---|---|
Val Asn Ser Met Gly Trp His Arg Thr Ala Gly Asn Ser Met Arg Met
225                     230                     235                     240

Gly Val Pro Tyr Thr Tyr Ser Gln Met Leu Arg Gly Tyr Ser Leu Ala
            245                     250                     255

Gln Ile Arg Gln Glu Gln Gly Ile Gln Glu Ile Leu Asn Thr Ile Ala
        260                     265                     270

Phe Pro Tyr Val Thr Gln Gly Asn Gly Leu His Val Asp Ser Ile Tyr
    275                     280                     285

Ile Asp His Ile Asp Val Arg Ala Tyr Gly Tyr Leu Ile Asn Ser Tyr
290                     295                     300

Phe Thr Phe Ala Tyr Tyr Thr Tyr Tyr Phe Gly Asp Glu Val Ile Asn
305                     310                     315                     320

Thr Val Gly Leu Thr Arg Ala Ile Glu Asn Val Gly Ser Pro Glu Gly
                325                     330                     335

Val Val Val Pro Gly Val Met Ser Arg Asn Gly Thr Leu Tyr Ser Asn
            340                     345                     350

Val Ile Gly Asn Phe Ile Thr Tyr Pro Leu Ala Val His Ser Ala Asp
        355                     360                     365

Tyr Ser Lys Val Leu Thr Lys Leu Ser Lys Thr Tyr Tyr Gly Ser Val
    370                     375                     380

Val Gly Val Thr Asn Arg Leu Ala Tyr Tyr Glu Ser Asp Pro Thr Asn
385                     390                     395                     400

Asn Ile Gln Ala Pro Leu Trp Thr Met Ala Arg Arg Ile Trp Asn Arg
                405                     410                     415

Arg Gly Arg Ile Ile Asn Tyr Asn Ala Asn Thr Val Ser Phe Glu Ser
            420                     425                     430

Gly Ile Ile Leu Gln Ser Leu Asn Gly Ile Met Arg Ile Pro Ser Gly
        435                     440                     445

Thr Thr Ser Thr Gln Ser Phe Arg Pro Thr Ile Gly Gln Thr Ala Ile
    450                     455                     460

Ala Lys Thr Asp Thr Ala Gly Ala Ile Leu Val Tyr Ala Lys Phe Ala
465                     470                     475                     480

Glu Met Asn Asn Leu Gln Phe Lys Ser Cys Thr Leu Phe Tyr Asp His
                485                     490                     495

Gly Met Phe Gln Leu Tyr Tyr Asn Ile Gly Val Glu Pro Asn Ser Leu
            500                     505                     510

Asn Asn Thr Asn Gly Arg Val Ile Val Leu Ser Arg Asp Thr Ser Val
        515                     520                     525

Asn Thr Asn Asp Leu Ser Phe Glu Ala Gln Arg Ile Asn Asn Asn Asn
    530                     535                     540

Ser Ser Glu Gly Thr Thr Phe Asn Gly Val Val Cys His Arg Val Pro
545                     550                     555                     560

Ile Thr Asn Ile Asn Val Pro Ser Leu Thr Val Arg Ser Pro Asn Ser
                565                     570                     575

Ser Val Glu Leu Val Glu Gln Ile Ile Ser Phe Gln Thr Met Tyr Thr
            580                     585                     590

Ala Thr Ala Ser Ala Cys Tyr Lys Leu Asn Val Glu Gly His Ser Asp
        595                     600                     605

Ser Leu Arg Ala Phe Arg Val Asn Ser Asp Glu Asn Ile Tyr Val Asn
    610                     615                     620

Val Gly Asn Gly Val Lys Ala Leu Phe Asn Tyr Pro Trp Val Met Val
625                     630                     635                     640

Lys Glu Asn Asn Lys Val Ser Phe Met Ser Ala Asn Glu Asp Thr Thr
                645                     650                     655

```
Ile Pro Phe Ser Val Ile Met Asn Ser Phe Thr Ser Ile Gly Glu Pro
            660                 665                 670

Ala Leu Gln Tyr Ser Pro Ser Asn Cys Phe Val Tyr Gly Asn Gly Phe
            675                 680                 685

Lys Leu Asn Asn Ser Thr Phe Asp Leu Gln Phe Ile Phe Glu Ile Val
            690                 695                 700
```

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:3:

```
Met Ser Ile Val Leu Ile Ile Val Ile Val Ile Phe Leu Ile Cys
1               5                   10                  15

Phe Leu Tyr Leu Ser Asn Ser
            20
```

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:4:

```
Met Ser Ile Val Leu Ile Ile Val Ile
1               5
```

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:5:

AAAAAAGCTT GTTAACAATA AAAATGATGC C          31

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

AAAAGGATCC TTACACAATT TCAAA          25

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:7:

```
Asp Tyr Lys Asp Asp Asp Asp Lys
1               5
```

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:8:

AAGCTTCATA TGGACTACAA AGACGACGAC GACAAGCTT            39

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:9:

Met Asp Tyr Lys Asp Asp Asp Asp Lys Leu Val Asn
1             5                 10

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:10:

GGTACCAAGG ATCCTTGGTA CC                          22

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:11:

GCAACATTCG ACATGAGCAA TAATAAAAAT GATGCC              36

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:12:

CTCTAGAGGA ACCCCGGGAA CCGAGCTCG                   29

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:13:

CCTATCAAAT AGCGGTACCA AAAATGATGC CAAT                34

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:14:

TTTTTTAAGC TTATGTCTAT CGTATTG                        27

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:15:

TTTTTTGGAT CCTTGCTATT TGATAGGTA                      29

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:16:

TTTTTGGATC CACCATGTCT ATCGTATTG                      29

(2) INFORMATION FOR SEQ ID NO:17:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO:17:

TTTTTCTGCA GTTACTTGTC GTCGTCGTCT TTGTAGTCCA CAATTTCAAA AAT      53

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:18:

TTTTCGGGAT CCATGTCTAT CGTATTG                        27

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:19:

TAAGAAAGTA GTGATGCTAT TTGATAGGTA                    30

(2) INFORMATION FOR SEQ ID NO:20:

```
        (i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:20:

TACCTATCAA ATAGCATCAC TACTTTCTTA                                        30

(2) INFORMATION FOR SEQ ID NO:21:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:21:

AAAAAGGAAT TCTCACGGTA CTTGTAC                                           27

(2) INFORMATION FOR SEQ ID NO:22:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:22:

TTTTCGGGGG ATCCATGTCT ATCGTATTG                                         29

(2) INFORMATION FOR SEQ ID NO:23:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:23:

TTTTTTCCAT GGCATCTATC GTATTGATT                                         29

(2) INFORMATION FOR SEQ ID NO:24:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:24:

GACAAGTGTT GGCCAGGGAA CAGGTAGTTT TCC                                    33

(2) INFORMATION FOR SEQ ID NO:25:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:25:

GGAAAACTAC CTGTTCCCTG GCCAACACTT GTC                                    33

(2) INFORMATION FOR SEQ ID NO:26:

(i) SEQUENCE CHARACTERISTICS:
```

-continued

```
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:26:

TTTTTTTCTA GACTATTTGT ATAGTTC                                27

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:27:

TTTTTTCTGC AGATGTGGGG AATCGTG                                27

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:28:

TTTTTTGGAT CCTTGAAATT TAATGCATT                              29

(2) INFORMATION FOR SEQ ID NO:29:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:29:

Phe Gly Thr Phe Met Leu Met Phe Phe Leu Pro Ala Thr Val Leu Tyr
1               5                   10                  15

Leu Val Leu Met Cys
            20

(2) INFORMATION FOR SEQ ID NO:30:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:30:

Val Pro Met Trp Ile Lys Met Leu Leu Phe Ala Leu Val Ala Gly Phe
1               5                   10                  15

Leu Phe Leu Tyr Gln Ala Met
            20

(2) INFORMATION FOR SEQ ID NO:31:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:31:
```

```
Ser Tyr Gln Val Met Phe Phe Thr Phe Phe Ala Leu Leu Ala Gly Thr
1               5                   10                  15

Ala Val Thr Ile Ile Ala Tyr
            20
```

(2) INFORMATION FOR SEQ ID NO:32:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:32:

```
Met Ser Ile Val Leu Ile Ile Val Ile Val Val Ile Phe Leu Ile Cys
1               5                   10                  15

Phe Leu Tyr Leu Ser Asn Ser
            20
```

(2) INFORMATION FOR SEQ ID NO:33:

(i) SEQUENCE CHARACTERISTICS:
        (A) LENGTH: 24 amino acids
        (B) TYPE: amino acid
        (C) STRANDEDNESS:
        (D) TOPOLOGY: linear (xi) SEQUENCE DESCRIPTION: SEQ ID NO:33:

```
Met Trp Gly Ile Val Leu Leu Ile Val Leu Leu Ile Leu Phe Tyr Leu
1               5                   10                  15

Tyr Trp Thr Asn Ala Leu Asn Phe
            20
```

(2) INFORMATION FOR SEQ ID NO:34:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:34:

```
Ile Ile Leu Leu Ile Gly Ala Val Leu Phe Leu Gly Leu Ile Phe Tyr
1               5                   10                  15

Phe Ile Tyr
```

(2) INFORMATION FOR SEQ ID NO:35:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:35:

```
Met Phe Leu Thr Ile Leu Ala Val Val Val Ile Ile Ala Leu Ile Ile
1               5                   10                  15

Ile Phe Val
```

(2) INFORMATION FOR SEQ ID NO:36:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:36:

Met Trp Gly Ala Leu Ile Leu Leu Ile Leu Leu Val Phe Leu Phe Tyr
1               5                   10                  15

Leu Trp Tyr (2) INFORMATION FOR SEQ ID NO:37:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:37:

Leu Ile Trp Leu Ile Gly Ala Val Leu Phe Leu Ala Leu Val Val Tyr
1               5                   10                  15

Leu Ile Tyr (2) INFORMATION FOR SEQ ID NO:38:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:38:

Met Ser Thr Val Leu Ile Ile Val Val Val Ile Phe Leu Ile Cys
1               5                   10                  15

Phe Trp Cys Leu Leu
            20

(2) INFORMATION FOR SEQ ID NO:39:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:39:

Met Trp Lys Ile Val Leu Leu Ile Val Leu Leu Val Leu Ile Tyr Leu
1               5                   10                  15

Tyr Trp (2) INFORMATION FOR SEQ ID NO:40:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:40:

Ile Ile Met Met Ile Gly Ala Val Leu Phe Leu Gly Leu Ile Leu Tyr
1               5                   10                  15

Phe Ile Tyr (2) INFORMATION FOR SEQ ID NO:41:

(i) SEQUENCE CHARACTERISTICS:
        (A) LENGTH: 19 amino acids
        (B) TYPE: amino acid
        (C) STRANDEDNESS:

(D) TOPOLOGY: linear (xi) SEQUENCE DESCRIPTION: SEQ ID NO:41:

Met Phe Leu Thr Ile Leu Ala Val Val Ile Ile Ala Leu Ile Ile
1               5                  10                  15

Met Phe Val (2) INFORMATION FOR SEQ ID NO:42:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:42:

Ile Ile Val Val Leu Gly Ile Val Leu Leu Ile Ile Phe Ile Gly Tyr
1               5                  10                  15

Ile Val Ile (2) INFORMATION FOR SEQ ID NO:43:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:43:

Met Leu Met Thr Ile Leu Ile Ala Leu Val Ile Ile Leu Leu Ile
1               5                  10                  15

Met Leu Phe (2) INFORMATION FOR SEQ ID NO:44:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:44:

Leu Ile Trp Leu Ile Gly Ala Val Leu Phe Leu Gly Leu Ile Ile Tyr
1               5                  10                  15

Leu Ile Tyr (2) INFORMATION FOR SEQ ID NO:45:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:45:

Ile Leu Leu Val Ile Gly Gly Ile Leu Leu Leu Thr Phe Ile Gly Phe
1               5                  10                  15

Val Ile Phe (2) INFORMATION FOR SEQ ID NO:46:

(i) SEQUENCE CHARACTERISTICS:
        (A) LENGTH: 23 amino acids
        (B) TYPE: amino acid
        (C) STRANDEDNESS:

143

-continued (D) TOPOLOGY: linear (xi) SEQUENCE DESCRIPTION: SEQ ID NO:46:

Met Gly Leu Ile Thr Leu Ile Leu Ala Leu Ile Val Val Leu Phe Val
1               5                   10                  15

Phe Ala Ser Asn Ser Ser Lys
            20

(2) INFORMATION FOR SEQ ID NO:47:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (xi) SEQUENCE DESCRIPTION: SEQ ID NO:47:

```
ATGTGGGGAA TCGTGTTACT TATCGTTTTG CTCATACTGT TTTATCTTTA TTGGACGAAT      60
GCATTAAATT TCAATTCCTT AACCGAGTCG TCGCCCAGTT TAGGGCAGAG CAGCGACTCG     120
GTGGAATTAG ACGAGAACAA ACAATTAAAC GTAAAGCTGA ATAACGGCCG GGTGGCCAAC     180
TTGCGCATCG CACACGGCGA TAATAAATTG AGCCAAGTGT ATATTGCCGA AAAACCGCTA     240
TCTATAGACG ACATAGTCAA AGAGGGCTCC AACAAGGTGG GCACTAACAG CGTTTTTCTG     300
GGCACCGTAT ACGACTATGG AATCAAATCA CCAAACGCGG CCAGCACATC TAGTAATGTA     360
ACCATGACGC GCGGCGCCGC AAACTTTGAT ATCAAGGAAT TCAAGTCCAT GTTTATCGTA     420
TTCAAGGGTG TGACGCCCAC TAAAACTGTA GAGGACAATG GCATGTTGCG ATTCGAAGTC     480
GACAACATGA TTGTGTGTTT GATCGACCCC AACACGGCGC CGCTGTCCGA ACGAGAGGTG     540
CGCGAATTGC GCAAATCTAA TTGCACTTTG GTGTACACAA GAAACGCGGC AGCTCAGCAA     600
GTTTTATTGG AAAATAACTT TACCGTCATT AATGCTGAAC AAACCGCCTA TCTCAAAAAC     660
TATAAATCAT ACAGAGAAAT GAATT                                          685
```

(2) INFORMATION FOR SEQ ID NO:48:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:48:

Met Ser Ile Val Leu Ile Ile Val Ile Val Val Ile Phe Leu Ile Cys
1               5                   10                  15

Phe Leu Tyr Leu Ser Asn Ser Gly Thr Lys Asp Pro Val Val Leu Gln
            20                  25                  30

(2) INFORMATION FOR SEQ ID NO:49:

(i) SEQUENCE CHARACTERISTICS:
        (A) LENGTH: 33 amino acids
        (B) TYPE: amino acid
        (C) STRANDEDNESS:
        (D) TOPOLOGY: linear (xi) SEQUENCE DESCRIPTION: SEQ ID NO:49:

Met Ser Ile Val Leu Ile Ile Val Ile Val Val Ile Phe Leu Ile Cys
1               5                   10                  15

Phe Leu Tyr Leu Ser Asn Ser Lys Asp Pro Arg Val Pro Val Glu Leu
            20                  25                  30

Met (2) INFORMATION FOR SEQ ID NO:50:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:50:

```
Met Ser Ile Val Leu Ile Ile Val Ile Val Val Ile Phe Leu Ile Cys
1               5                   10                  15

Phe Leu Tyr Leu Ser Asn Ser Asn Asn Lys Asn Asp Ala Asn Lys Asn
                20                  25                  30

Asn Ala Phe Ile
            35
```

(2) INFORMATION FOR SEQ ID NO:51:

(i) SEQUENCE CHARACTERISTICS:
        (A) LENGTH: 38 amino acids
        (B) TYPE: amino acid
        (C) STRANDEDNESS:
        (D) TOPOLOGY: linear (xi) SEQUENCE DESCRIPTION: SEQ ID NO:51:

```
Met Gly Leu Ile Thr Leu Ile Leu Ala Leu Ile Val Val Leu Phe Val
1               5                   10                  15

Phe Ala Ser Asn Ser Ser Lys Pro Ala Asn Asn Ala Ser Phe Ala Asp
                20                  25                  30

Asn Gly Ala Gln Arg Thr
            35
```

(2) INFORMATION FOR SEQ ID NO:52:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:52:

```
Met Ser Thr Val Leu Ile Ile Val Val Val Ile Phe Leu Ile Cys
1               5                   10                  15

Phe Trp Cys Leu Leu Asn Ser Ser Asn Asn Ser Asn Asn Lys Asn Asp
                20                  25                  30

Ala Asn Arg Asn Asn Val Phe Val
            35                  40
```

(2) INFORMATION FOR SEQ ID NO:53:

(i) SEQUENCE CHARACTERISTICS:
        (A) LENGTH: 39 amino acids
        (B) TYPE: amino acid
        (C) STRANDEDNESS:
        (D) TOPOLOGY: linear (xi) SEQUENCE DESCRIPTION: SEQ ID NO:53:

```
Met Trp Gly Ile Val Leu Leu Ile Val Leu Leu Ile Leu Phe Tyr Leu
1               5                   10                  15

Tyr Trp Thr Asn Ala Leu Asn Phe Asn Ser Leu Thr Glu Ser Ser Pro
                20                  25                  30

Ser Leu Gly Gln Ser Ser Asp
            35
```

-continued (2) INFORMATION FOR SEQ ID NO:54:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:54:

```
Met Trp Gly Ala Leu Ile Leu Leu Ile Leu Leu Val Phe Leu Phe Tyr
1               5                   10                  15

Leu Trp Tyr Asn Gly Lys Leu Asn Leu Asn Ser Leu Thr Glu Ser Ser
                20                  25                  30

Pro Ser Leu Ala Gln Ser Ser Asp
            35                  40
```

(2) INFORMATION FOR SEQ ID NO:55:

(i) SEQUENCE CHARACTERISTICS:
        (A) LENGTH: 39 amino acids
        (B) TYPE: amino acid
        (C) STRANDEDNESS:
        (D) TOPOLOGY: linear (xi) SEQUENCE DESCRIPTION: SEQ ID NO:55:

```
Met Trp Lys Ile Val Leu Leu Ile Val Leu Leu Val Leu Ile Tyr Leu
1               5                   10                  15

Tyr Trp Thr Asn Ala Leu Asn Leu Asn Ser Leu Thr Glu Ala Ser Pro
                20                  25                  30

Ser Leu Gly Gln Ser Ser Glu
            35
```

(2) INFORMATION FOR SEQ ID NO:56:

(i) SEQUENCE CHARACTERISTICS:
        (A) LENGTH: 34 amino acids
        (B) TYPE: amino acid
        (C) STRANDEDNESS:
        (D) TOPOLOGY: linear (xi) SEQUENCE DESCRIPTION: SEQ ID NO:56:

```
Met Trp Gly Ile Val Leu Leu Ile Val Leu Leu Ile Leu Phe Tyr Leu
1               5                   10                  15

Tyr Trp Thr Asn Ala Leu Asn Phe Lys Asp Pro Arg Val Pro Val Glu
                20                  25                  30

Leu Met
```

UNIQUE NUCLEOTIDE AND AMINO ACID SEQUENCE AND USES THEREOF

The present application is a continuation-in-part of U.S. patent application Ser. No. 08/678,435 filed Jul. 3, 1996, abandoned, which claims the priority date of U.S. Provisional patent application Ser. No. 60/000,955 filed Jul. 7, 1995. The entire text of each of the above-referenced disclosures is specifically incorporated by reference herein without disclaimer.

The government may own rights in the present invention pursuant to grant number 2RO1 GM 47552 from the National Institutes of Health, Texas Agricultural Experiment Station project TEXO 8078, and grant number 999902-011 from the Texas Higher Education Coordinating Board ARP/ATP.

BACKGROUND OF THE INVENTION

1. Field of the Invention

The present invention relates generally to peptide and nucleic acid compositions. More particularly, it concerns peptide and nucleic acid sequences which may serve to target host and/or foreign proteins to a membrane of a host cell. Additionally, the invention concerns methods of using the peptide and nucleic acid sequences.

2. Description of Related Art

Naturally occurring insect baculoviruses have received considerable attention for their potential to be used as non-chemical, environmentally safe control agents for insect pests. They infect only arthropods, and each virus strain infects only one or a limited number of species. Many of the virus hosts are commercially important agricultural insect pests. Examples include infestation of cotton, sorghum and corn by the bollworm/budworm complex, and infestation of garden crops by the cabbage looper and tomato hornworm. As important, beneficial insects that are natural predators of insect pests are not hosts for baculoviruses. Baculovirus AcMNPV has undergone five controlled release trials and these trials indicate that when the virus is genetically modified by deletion of a single gene, it does not persist in the environment (Cory and Bishop, 1995). Thus, genetically engineered baculoviruses can be used safely as a "one pass" insecticide that will kill the insect pest and not persist in the environment.

The host range of insect baculoviruses has been extensively studied and no evidence of infection or pathogenic responses have been identified in non-host insects, plants, vertebrates and man (Groner, 1986). This feature may make baculoviruses as ideal agent to be modified and used for the delivery of drugs, genes, or therapeutics.

The occlusion derived virus (ODV) is the primary infectious agent to the insect host. The ODV envelope fuses with the plasma membrane of the gut cell, thus releasing the nucleocapsid and viral DNA into the cell (Kawanishi et al., 1972). In this process, viral envelope proteins are incorporated into the gut cell plasma membrane. Elucidation of the mechanism by which virus expressed genes are targeted to the viral envelope would represent a significant advance in the art.

Directed insertion of proteins into cellular membranes would have a number of therapeutic, diagnostic and insecticidal applications. A method leading to the insertion of heterologous proteins not normally associated with membranes into the membranes of a cell would thus be a tremendous benefit to the art.

SUMMARY OF THE INVENTION

The present invention overcomes the need present in the art by disclosing a variety of amino acid sequences which can target proteins to membranes of a cell, for use as treatment delivery agents in animal and human diseases (therapeutic and diagnostic applications), as well as in insecticidal compositions.

Baculovirus envelope proteins are inserted into the membranes of host cells in a unique manner specific to the viral maturation strategy late in infection for the induction, synthesis and assembly of intranuclear membrane structures. No other virus matures in a similar manner; as a result of this unique process, this invention teaches the targeting and insertion of heterologous proteins into cellular membranes for potential therapeutic, diagnostic or insecticidal uses through this unique pathway of membrane targeting and assembly. The invention fills a need in the art for directed genetic manipulation/alteration of the nuclear envelope and/or nuclear induced membranes for the human health and agricultural applications proposed.

The invention provides a polypeptide comprising a hydrophobic targeting region of between about 8 and about 20 amino acids, wherein at least about 75% of the amino acids of the hydrophobic targeting region are independently valine, leucine, isoleucine, alanine or phenylalanine. In one embodiment of the invention at least about 90% of the amino acids of the hydrophobic targeting region are independently valine, leucine, isoleucine, alanine or phenylalanine. In another embodiment of the invention each of the amino acids of the hydrophobic targeting region are independently valine, leucine, isoleucine, alanine or phenylalanine. In a further embodiment of the invention the hydrophobic targeting region further comprises at least one tyrosine residue.

The invention additionally provides a polypeptide comprising an introduced hydrophobic targeting region of between about 8 and about 20 amino acids, wherein at least about 75% of the amino acids of the hydrophobic targeting region are independently valine, leucine, isoleucine, alanine or phenylalanine. In certain aspects of the present invention, the hydrophobic targeting region preferably functions to target a heterologous polypeptide to a membrane. The term "heterologous polypeptide", when used in this context, preferably refers to a polypeptide that is not ordinarily targeted to a membrane, or destined for membrane localization.

For this invention, the phrase "transport polypeptide" can also be described as a "retention polypeptide," as a "target polypeptide," or as a "signal polypeptide." In this respect, "transport polypeptide" is meant to include a "retention polypeptide," a "target polypeptide" and a "signal polypeptide."

For the purposes of the present invention, it will be understood that the term "between about 8 and about 20 amino acids" includes ranges such as between about 8 and about 15 amino acids, between about 10 and about 20 amino acids, between about 10 and about 15 amino acids, between about 12 and about 20 amino acids and between about 12 and about 15 amino acids, as well as values within the range, such as about 8 amino acids, about 10 amino acids, about 12 amino acids, about 15 amino acids and about 17 amino acids, and the like.

In an additional embodiment of the invention the hydrophobic targeting region is at least about 8 amino acids in length. In another embodiment of the invention the hydrophobic targeting region is at least about 12 amino acids in length. In another embodiment of the invention the hydrophobic targeting region is at least about 15 amino acids in length. In a further aspect of the invention the hydrophobic targeting region is at least about 20 amino acids in length.

It will be understood that the term "about 8 amino acids" is also intended to include about 7 amino acids, about 6 amino acids, about 9 amino acids or about 10 amino acids. Further, the term "about 12 amino acids" is intended to include about 11 amino acids or about 13 amino acids. The term "about 15 amino acids" is intended to include about 14 amino acids, about 16 amino acids or about 17 amino acids. Additionally, the term "about 20 amino acids" will be understood to include about 18 amino acids, about 19 amino acids, about 21 amino acids, about 22 amino acids and the like.

In another embodiment of the invention the hydrophobic targeting region comprises the contiguous amino acid sequence from between amino acid 4 and amino acid 15 of SEQ ID NO:3. In a further aspect of the invention the hydrophobic targeting region comprises the contiguous amino acid sequence from between amino acid 4 and amino acid 15 of SEQ ID NO:33.

An additional embodiment of the invention comprises an interaction region of between about 8 and about 20 amino acids, the interaction region being substantially adjacent to the hydrophobic targeting region and comprising at least one of the following interaction elements: (a) at least three amino acids being independently asparagine or serine; (b) at least one charged amino acid; (c) at least one tyrosine residue; or (d) at least one amino acid capable of participating in hydrogen or disulfide bond formation.

In the context of positioning amino acid segments in combination, exemplified by, but not limited to, hydrophobic targeting regions and interaction regions, the term "substantially adjacent" will be understood to mean either directly connected to each other such that a contiguous amino acid segment is produced, or separated from each other by a relatively short distance, for example about 1, about 2, about 3, about 5, about 10 or about 20 amino acids, such that a contiguous amino acid segment is still generated. The term proximal will be understood to have the same meaning as "substantially adjacent".

In an additional aspect of the invention the interaction region comprises at least three amino acids being independently asparagine or serine. In a further embodiment of the invention the interaction region comprises at least one charged amino acid. In another embodiment of the invention the interaction region comprises at least one tyrosine residue. In another aspect of the invention the interaction region comprises at least one amino acid capable of participating in hydrogen or disulfide bond formation. In another embodiment of the invention the interaction region comprises a threonine or cysteine residue.

In a further aspect of the invention the interaction region comprises at least two of the interaction elements. In an additional embodiment of the invention the interaction region comprises at least three of the interaction elements. In another aspect of the invention the interaction region comprises each of the interaction elements.

In one embodiment of the invention the interaction region is separated from the hydrophobic targeting region by a maximum of about 5, about 10, about 15, about 20, about 25, about 30 or about 50 amino acids. In one embodiment of the invention the interaction region contiguous with the hydrophobic targeting region. In one aspect of the invention the interaction region is located towards the C-terminus of the hydrophobic targeting region. In other aspects, the interaction region is located towards the N-terminus of the hydrophobic targeting region. In certain aspects of the present invention, more than one interaction region is combined with a hydrophobic targeting region. In these aspects, the interaction regions may both be located towards the C-terminus of the hydrophobic targeting region, both be located towards the N-terminus of the hydrophobic targeting region, or be located on both sides of the hydrophobic targeting region.

In another aspect of the invention the interaction region comprises the contiguous amino acid sequence from between amino acid 16 and amino acid 23 of SEQ ID NO:3. In a further aspect of the invention the interaction region comprises the contiguous amino acid sequence from between amino acid 16 and amino acid 24 of SEQ ID NO:33. An additional aspect of the invention comprises the contiguous amino acid sequence of SEQ ID NO:3. Yet another aspect of the invention comprises the contiguous amino acid sequence of SEQ ID NO:33.

In another embodiment of the invention the hydrophobic targeting region is located towards the N-terminus of the polypeptide. In a further embodiment of the invention the hydrophobic targeting region is located within a central portion of the polypeptide. In a further aspect of the invention the hydrophobic targeting region is located towards the C-terminus of the polypeptide.

In certain aspects of the present invention, the polypeptide comprises multiple hydrophobic targeting regions. In additional embodiments, the polypeptide comprises about 2, about 3, about 4, about 5 or about 10 hydrophobic targeting regions.

An additional aspect of the invention comprises a heterologous polypeptide sequence region. In another embodiment of the invention the heterologous polypeptide sequence region may comprise a protein selected from Table 9. In a further embodiment of the invention the heterologous polypeptide sequence region is located towards the C-terminus of the hydrophobic targeting region. In other embodiments of the invention, the heterologous polypeptide sequence region is located towards the N-terminus of the hydrophobic targeting region. In particular aspects, the heterologous polypeptide sequence region may comprise a hydrophobic targeting region at both its N-terminus and C-terminus. In further embodiments, there may be multiple hydrophobic targeting region-heterologous polypeptide sequence region fusions.

In an additional aspect of the invention the heterologous polypeptide sequence region comprises a biologically active protein. In another aspect of the invention the polypeptide is dispersed in a biologically appropriate buffer. In a further embodiment of the invention the heterologous polypeptide sequence region comprises a pharmaceutically active protein. In another embodiment of the invention the polypeptide is dispersed in a pharmaceutically acceptable diluent.

In a further aspect of the invention the heterologous polypeptide sequence region comprises an insecticidal protein. In an additional embodiment of the invention the polypeptide is formulated for administration to an insect.

The invention further provides a polypeptide comprising a hydrophobic targeting region of between about 8 and about 20 amino acids, wherein at least 75% of the amino acids of the hydrophobic targeting region are independently valine, leucine, isoleucine, alanine or phenylalanine, or an amino acid having a hydropathic index value within ±2.0 units of the hydropathic index value of valine, leucine, isoleucine, alanine or phenylalanine. In one embodiment of the invention between about 4 and about 10 of the amino acids of the hydrophobic targeting region are independently valine, leucine, isoleucine, alanine or phenylalanine. It will be understood that in this context the term "between about 4 and about 10 of the amino acids of the hydrophobic targeting region are independently valine, leucine, isoleucine, alanine or phenylalanine" refers to 4 to 10 amino acids of the 75% of the amino acids of the hydrophobic targeting region are independently valine, leucine, isoleucine, alanine or phenylalanine, or an amino acid having a hydropathic index value within ±2.0 units of the hydropathic index value of valine, leucine, isoleucine, alanine or phenylalanine.

For example, for hydrophobic targeting regions comprising 8 amino acids, at least 6 amino acids of the hydrophobic targeting region are independently valine, leucine, isoleucine, alanine or phenylalanine, or an amino acid having a hydropathic index value within ±2.0 units of the hydropathic index value of valine, leucine, isoleucine, alanine or phenylalanine. Of these six, for example, 4 may be independently valine, leucine, isoleucine, alanine or phenylalanine.

The invention further provides an isolated polypeptide of between about 8 and about 30 amino acids in length, comprising a hydrophobic targeting region, wherein at least 75% of the amino acids of the hydrophobic targeting region are independently valine, leucine, isoleucine, alanine or phenylalanine.

The invention further provides an isolated polypeptide of between about 16 and about 50 amino acids in length, comprising a hydrophobic targeting region comprising between about 8 and about 20 amino acids, wherein at least 75% of the amino acids of the hydrophobic targeting region are independently valine, leucine, isoleucine, alanine or phenylalanine, and an interaction region comprising between about 8 and about 20 amino acids, the interaction region being substantially adjacent to the hydrophobic targeting region and comprising at least one of the following interaction elements: (a) at least three amino acids being independently asparagine or serine; (b) at least one charged amino acid; (c) at least one tyrosine residue; or (d) at least one amino acid capable of participating in hydrogen or disulfide bond formation.

The invention further provides a fusion protein comprising an operatively linked series of polypeptide regions characterized as: (a) a hydrophobic targeting region comprising between about 8 and about 20 amino acids, wherein at least 75% of the amino acids of the hydrophobic targeting region are independently valine, leucine, isoleucine, alanine or phenylalanine; (b) an interaction region comprising between about 8 and about 20 amino acids, the interaction region being substantially adjacent to the hydrophobic targeting region and comprising at least one of the following interaction elements: (i) at least three amino acids being independently asparagine or serine; (ii) at least one charged amino acid; (iii) at least one tyrosine residue; or (iv) at least one amino acid capable of participating in hydrogen or disulfide bond formation; and (c) a heterologous polypeptide sequence region.

The invention further provides an isolated nucleic acid segment comprising at least a first sequence region, the first sequence region encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine. In a further embodiment of the invention, the nucleic acid segment further comprises at least a second sequence region, the second sequence region operatively linked to the first sequence region, the second sequence region encoding an interaction region of between about 8 and about 20 amino acids, the interaction region comprising at least one of the following interaction elements: (a) at least three amino acids being independently asparagine or serine; (b) at least one charged amino acid; (c) at least one tyrosine residue; or (d) at least one amino acid capable of participating in hydrogen or disulfide bond formation.

In another embodiment of the invention the nucleic acid segment encodes a peptide that comprises a contiguous amino acid sequence from SEQ ID NO:3. An additional embodiment of the invention comprises a contiguous nucleic acid sequence from between about position 122 and about position 190 of SEQ ID NO: 1. In another aspect of the invention the nucleic acid segment encodes a peptide that comprises a contiguous amino acid sequence from SEQ ID NO:33.

An additional embodiment of the invention comprises a contiguous nucleic acid sequence from between position 1 and position 72 of SEQ ID NO:47. In another aspect of the invention the nucleic acid segment is positioned under the control of a heterologous promoter. The term "heterologous promoter" is understood to include naturally occurring promoters which are not normally associated with the nucleic acid segment they are being linked to, including naturally occurring promoters obtained from a different organism than the "isolated nucleic acid segment". This term also includes engineered promoters which combine different promoter elements, or fragments thereof, and synthetic promoters.

In an additional embodiment of the invention, the nucleic acid segment further comprises a cloning site. In a further aspect of the invention the cloning site is a multiple cloning site. In a further embodiment of the invention the multiple cloning site is operationally positioned downstream from the first sequence region. An additional embodiment of the invention comprises a multiple cloning site, the multiple cloning site operationally positioned downstream from the first sequence region and the second sequence region.

Yet another embodiment of the invention comprises at least a first selected coding region encoding a selected protein, the first selected coding region operably linked to the first sequence region. In the context of positioning nucleic acid segments and sequence regions in combination, the term "operably linked" will be understood to mean connected so as to form a single, contiguous coding region. In certain aspects of the present invention, the first selected coding region may be selected from Table 8 below.

The amino acid segments comprising hydrophobic targeting regions, interaction regions, heterologous polypeptide sequences or the nucleic acid segments encoding them, may be combined in a variety of different ways. In certain aspects, the heterologous polypeptide sequences may be combined with a hydrophobic targeting region, or both a hydrophobic targeting region and an interaction region. In alternative aspects, the hydrophobic targeting region, or combination of a hydrophobic targeting region and an interaction region may be present at the N-terminus, the C-terminus, or at both the N-terminus and the C-terminus of a heterologous polypeptide sequence.

In another aspect of the invention, the nucleic acid segment is further defined as a recombinant vector. In an additional embodiment of the invention the vector of the nucleic acid segment is a mammalian expression vector. In another aspect of the invention the vector of the nucleic acid segment is a viral vector. In yet another aspect of the invention the vector of the nucleic acid segment is a retroviral vector. In still another aspect of the invention the vector of the nucleic acid segment is an adenoviral vector. In another embodiment of the invention the vector of the nucleic acid segment is a baculoviral vector.

In another aspect of the invention, the nucleic acid segment is comprised within a virus. In yet another aspect of the invention, the nucleic acid segment is comprised within a host cell. In still another aspect of the invention, the host cell is a prokaryotic host cell. In another aspect of the invention, the host cell is a eukaryotic host cell.

The invention further provides a recombinant host cell comprising a nucleic acid segment comprising at least a first sequence region, the first sequence region encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine. In one embodiment of the invention the nucleic acid segment further comprises at least a second sequence region, the second sequence region operatively linked to the first sequence region, the second sequence region encoding an interaction region of between about 8 and about 20 amino acids, the interaction region comprising at least one of the following interaction elements: (a) at least three amino acids being independently asparagine or serine; (b) at least one charged amino acid; (c) at least one tyrosine residue; or (d) at least one amino acid capable of participating in hydrogen or disulfide bond formation.

In another embodiment of the invention the host cell comprises at least a first selected coding region encoding a selected protein, the first selected coding region operably linked to the first sequence region, thereby forming a fusion protein coding region. In another embodiment of the invention the host cell contains a nucleic acid segment which is introduced into the cell by means of a recombinant vector. In still another embodiment of the invention the host cell expresses the nucleic acid segment to produce the encoded fusion protein comprising the hydrophobic targeting region encoded by the first sequence region and the selected protein encoded by the first coding region. In another embodiment of the invention the host cell contains an expressed fusion protein which includes a contiguous amino acid sequence from SEQ ID NO:3. In another embodiment of the invention the host cell contains an expressed fusion protein which includes a contiguous amino acid sequence from SEQ ID NO:33.

The invention further provides a nucleic acid segment comprising an isolated ODV-E66 gene from an *Autographa californica* nuclear polyhedrosis virus that encodes an ODV-E66 envelope protein. In one embodiment of the invention the nucleic acid segment comprises an isolated ODV-E66 gene that encodes an ODV-E66 protein comprising a contiguous amino acid sequence of at least about 8 amino acids from SEQ ID NO:2. In another embodiment of the invention the nucleic acid segment comprises an isolated ODV-E66 gene comprising a contiguous nucleic acid sequence from between about position 122 and about position 2233 of SEQ ID NO:1. In still another embodiment of the invention the nucleic acid segment comprises an isolated ODV-E66 gene that encodes an ODV-E66 peptide of from between about 8, about 10, about 12, about 15, about 20, about 25, about 40 or about 50 amino acids in length. In another aspect of the invention the nucleic acid segment comprises an isolated ODV-E66 gene that encodes an ODV-E66 peptide of from between about 15 and about 30 amino acids in length.

The invention further provides a pharmaceutical composition comprising (a) a polypeptide comprising: (i) a hydrophobic targeting region of between about 8 and about 20 amino acids, wherein at least 75% of the amino acids of the hydrophobic targeting region are independently valine, leucine, isoleucine, alanine or phenylalanine; and (ii) at least a first heterologous polypeptide sequence region comprising a pharmaceutically active protein, the first heterologous polypeptide sequence region substantially adjacent to the hydrophobic targeting region; or (b) a recombinant nucleic acid vector encoding the polypeptide.

In another aspect of the invention the pharmaceutical composition includes a polypeptide comprising a hydrophobic targeting region of between about 8 and about 20 amino acids, wherein at least 75% of the amino acids of the hydrophobic targeting region are independently valine, leucine, isoleucine, alanine or phenylalanine, and at least a first heterologous polypeptide sequence region comprising a pharmaceutically active protein, the first heterologous polypeptide sequence region substantially adjacent to the hydrophobic targeting region.

In another aspect of the invention the pharmaceutical composition includes a recombinant nucleic acid vector encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine, and at least a first heterologous polypeptide sequence region comprising a pharmaceutically active protein, the first heterologous polypeptide sequence region substantially adjacent to the hydrophobic targeting region.

In another aspect of the invention the pharmaceutical composition further comprises an interaction region comprising between about 8 and about 20 amino acids, the interaction region being substantially adjacent to the hydrophobic targeting region and comprising at least one of the following interaction elements: (a) at least three amino acids being independently asparagine or serine; (b) at least one charged amino acid; (c) at least one tyrosine residue; or (d) at least one amino acid capable of participating in hydrogen or disulfide bond formation. In another aspect of the pharmaceutical compositions of the present invention, the polypeptide is associated with an artificial membrane.

The invention further provides an insecticidal composition comprising: (a) a polypeptide comprising: (i) a hydrophobic targeting region of between about 8 and about 20 amino acids, wherein at least 75% of the amino acids of the hydrophobic targeting region are independently valine, leucine, isoleucine, alanine or phenylalanine; and (ii) at least a first heterologous polypeptide sequence region comprising an insecticidal protein, the first heterologous polypeptide sequence region substantially adjacent to the hydrophobic targeting region; or (b) a recombinant nucleic acid vector encoding the polypeptide.

In a particular aspect of the invention, the insecticidal composition includes a polypeptide comprising a hydrophobic targeting region of between about 8 and about 20 amino acids, wherein at least 75% of the amino acids of the hydrophobic targeting region are independently valine, leucine, isoleucine, alanine or phenylalanine; and at least a first heterologous polypeptide sequence region comprising an insecticidal protein, the first heterologous polypeptide sequence region substantially adjacent to the hydrophobic targeting region.

In another aspect of the invention, the insecticidal composition includes a recombinant nucleic acid vector encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine, and at least a first heterologous polypeptide sequence region comprising an insecticidal protein, the first heterologous polypeptide sequence region substantially adjacent to the hydrophobic targeting region.

In a further aspect of the invention the polypeptide of the insecticidal composition further comprises an interaction region comprising between about 8 and about 20 amino acids, the interaction region being substantially adjacent to the hydrophobic targeting region and comprising at least one of the following interaction elements: (a) at least three amino acids being independently asparagine and serine; (b) at least one charged amino acid; (c) at least one tyrosine residue; or (d) at least one amino acid capable of participating in hydrogen or disulfide bond formation.

The invention further provides a method for producing a recombinant nucleic acid vector, comprising the steps of obtaining at least a first nucleic acid segment encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine, operatively linking the first nucleic acid segment to a second nucleic acid segment encoding a selected protein to prepare a coding region, and positioning the coding region under the control of a promoter operative in a cell.

Another aspect of the invention provides a method for producing a recombinant nucleic acid vector, further comprising the steps of: (a) obtaining at least a third nucleic acid segment, the third nucleic acid segment encoding an interaction region of between about 8 and about 20 amino acids and comprising at least one of the following interaction elements: (i) at least three amino acids being independently asparagine and serine; (ii) at least one charged amino acid; (iii) at least one tyrosine residue; or (iv) at least one amino acid capable of participating in hydrogen or disulfide bond formation; and (b) operatively linking the third nucleic acid segment to the first nucleic acid segment.

The invention further provides a method of producing a fusion protein in a cell, comprising expressing in the cell a recombinant nucleic acid vector, the vector comprising an isolated targeting sequence comprising at least a first nucleic acid segment encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine, and at least a second nucleic acid segment encoding a selected protein, operatively linked to the first nucleic acid segment to prepare a coding region encoding a fusion protein, the coding region under the control of a promoter operative in the cell, thereby producing the fusion protein.

The invention further provides a method of targeting a fusion protein to a membrane of a cell, comprising expressing in the cell a recombinant nucleic acid vector, the vector comprising an isolated membrane targeting sequence comprising at least a first nucleic acid segment encoding a polypeptide comprising a hydrophobic targeting region of between about 8 and about 20 amino acids, wherein at least 75% of the amino acids of the hydrophobic targeting region are independently valine, leucine, isoleucine, alanine or phenylalanine and at least a second nucleic acid segment encoding a selected protein, operatively linked to the first nucleic acid segment to prepare a coding region encoding a fusion protein, the coding region under the control of a promoter operative in the cell, thereby producing the fusion protein, the hydrophobic targeting region targeting the fusion protein to the membrane of the cell.

In certain aspects of the present invention, the membrane is an intranuclear membrane, endoplasmic reticulum, Golgi apparatus, nuclear envelope, inner nuclear membrane, outer nuclear membrane, microvessicle, viral envelope, cytoplasmic membrane or induced nuclear membrane. In a further embodiment of the invention the membrane is a nuclear envelope or an intranuclear membrane.

In an additional embodiment of the invention the cell is a prokaryotic cell. In a further aspect of the invention the cell is comprised within a prokaryote. In another embodiment of the invention the cell is a eukaryotic cell. In an additional aspect of the invention the cell is comprised within a eukaryote. In a further aspect of the invention the cell is a vertebrate cell. In another embodiment of the invention the cell is comprised within a vertebrate animal. In another aspect of the invention the cell is a invertebrate cell. In an additional aspect of the invention the cell is comprised within an invertebrate animal. In a further aspect of the invention the cell is a insect cell. In an additional embodiment of the invention the cell is comprised within an insect. In an additional aspect of the invention the cell is a plant cell. In another aspect of the invention the cell is comprised within a plant.

In another embodiment of the invention the vector is introduced into the cell by transformation or transfection. In another aspect of the invention the vector is a viral vector. In a further aspect of the invention the viral vector is comprised within a virus.

In one embodiment of the invention the vector is introduced into the cell by infection. In another embodiment of the invention the fusion protein is targeted to the membrane during a specific stage of the infection.

The invention further provides a method of killing an insect, comprising providing to the insect a polypeptide comprising a hydrophobic targeting region of between about 8 and about 20 amino acids, wherein at least 75% of the amino acids of the hydrophobic targeting region are independently valine, leucine, isoleucine, alanine or phenylalanine, and at least a first heterologous polypeptide sequence region comprising an insecticidal protein, the first heterologous polypeptide sequence region substantially adjacent to the hydrophobic targeting region, or a recombinant nucleic acid vector encoding the polypeptide. In a particular aspect of the invention, the nucleic acid vector encoding the polypeptide is provided to the insect by infecting the insect with a virus comprising the vector. In a preferred embodiment of the invention, the virus is a baculovirus.

The invention further provides a method of providing a fusion protein to an animal, comprising providing to the animal a recombinant nucleic acid vector comprising an isolated targeting sequence comprising at least a first nucleic acid segment encoding a polypeptide comprising a hydrophobic targeting region of between about 8 and about 20 amino acids, wherein at least 75% of the amino acids of said hydrophobic targeting region are independently valine, leucine, isoleucine, alanine or phenylalanine, and at least a second nucleic acid segment encoding a selected protein, operatively linked to said first nucleic acid segment to prepare a coding region encoding a fusion protein, said coding region under the control of a promoter operative in a cell of said animal, thereby providing said fusion protein. In one aspect of the invention, the recombinant nucleic acid vector is comprised within a virus. In a particular embodiment of the invention, the virus is an adenovirus. In an alternative embodiment of the invention, the virus is an retrovirus. In certain aspects of the present invention, the animal is a human subject.

The invention also provides a virus comprising at least a first fusion protein of the present invention within the viral coat of the virus. In certain aspects, the fusion protein may be targeted to the viral coat of the virus by a hydrophobic targeting region of the instant invention. In other aspects, the fusion protein may be a pharmaceutically active fusion protein, a biologically active fusion protein or an insecticidal fusion protein.

In certain embodiments of the present invention, fusion proteins may be delivered to an animal comprised within a liposome, or comprised within the liposomal membrane.

The invention also provides nucleic acid probes, to which the DNA of the invention hybridizes, consisting of a sequence of at least 17, at least 20, at least 25, at least 30, at least 40 or at least 50 consecutive nucleotides of the coding sequence of the nucleotides listed in SEQ ID NO:1 or the complement thereof. Such a probe is useful for detecting expression of hydrophobic transport polypeptide in a biological sample by a method including the steps of (a) contacting a biological sample with an antibody or antibody fragment made against hydrophobic transport polypeptide, and (b) determining whether the antibody or antibody fragment binds to a component of the sample, such binding being an indication that the sample contains hydrophobic transport polypeptide.

This invention also provides a substantially pure DNA containing a sequence of at least 15, at least 20, at least 30, at least 50, or all of the region from nucleotides 122 to 190 of the nucleotides listed in SEQ ID NO:1.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO:1 which encodes an alternative splice variant of the hydrophobic targeting region.

The DNA may have at least about 70%, 75%, 80% or preferably 90% sequence identity to the coding sequence of the nucleotides listed in SEQ ID NO:1. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 30 nucleotides, and most preferably at least 50 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The invention also provides vectors containing a DNA encoding a polypeptide which may include the full length amino acid sequence of SEQ ID NO:2 or a contiguous portion thereof, e.g., a construct in which the coding sequence is operably linked to a suitable promoter or other regulatory sequences for expression of the polypeptide, and a cell containing such a vector. This vector includes a suitable promoter that is compatible to the system used and directs the expression of the desired protein. The cell may be procaryotic or eukaryotic and preferably expresses a recombinant polypeptide encoded by the nucleotides listed in SEQ ID NO:1.

A "vector" is defined as a replicable nucleic acid construct, e.g., a plasmid or viral nucleic acid. Vectors may be used to amplify and/or express nucleic acid encoding a fusion protein comprising a hydrophobic targeting domain of the present invention. An expression vector is a replicable construct in which a nucleic acid sequence encoding a polypeptide is operably linked to suitable control sequences (promoters) capable of effecting expression of the polypeptide, e.g., a fusion protein comprising a hydrophobic targeting domain, in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional/translational control signals. See for example, the techniques described in Sambrook et al., 1989, Molecular Cloning: A Laboratory Manual (2nd Edition), Cold Spring Harbor Press, N.Y., which are incorporated by reference.

A gene and its transcription control sequences are defined as being "operably linked" if the transcription control sequences effectively control the transcription of the gene. Vectors of the invention include, but are not limited to, baculovirus expression vectors and other viral vectors. Preferred viral vectors of the invention are those derived from retroviruses, adenovirus, adeno-associated virus, SV40 virus, or herpes viruses.

As stated above, the invention features a cell expressing a recombinant polypeptide, for example encoded by the nucleotides listed in SEQ ID NO:1. This cell can be a prokaryotic cell, e.g., an *Escherichia coli* cell, or a eukaryotic cell. Eukaryotic cells that can be used in the invention include, but are not limited to, COS, CHO, HeLa, *TN*368, *Sf*21, and *Sf*9 cells. In the case of a eukaryotic cell, the gene may or may not be integrated into the genome of the cell. Also included in the invention is an essentially homogeneous population of prokaryotic or eukaryotic cells, each of which contains (i.e., is infected, transfected or transformed with) a recombinant hydrophobic targeting region containing nucleic acid segment. Transfection or transformation can be transient or stable, and if desired can be carried out in vivo or ex vivo, using the patient's own cells.

By "polypeptide" is meant any chain of amino acids, regardless of length or post-translational modification (e.g., glycosylation or phosphorylation). The amino acid sequence of a transport polypeptide may differ from the amino acid sequence of SEQ ID NO:3 by conservative amino acid substitutions, e.g., substitution of one amino acid for another of the same class (e.g., valine for alanine, arginine for lysine, etc.) or by one or more non-conservative substitutions, deletions, or insertions located at positions of the amino acid sequence where the changes do not destroy the function of the transport polypeptide (e.g., to direct the localization of fused or hybrid proteins to membranes).

By a "substantially pure transport polypeptide" is meant a polypeptide which has been separated from at least some of those components which naturally accompany it. Typically, the polypeptide is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure transport polypeptide may be obtained, for example, by extraction from a natural source (e.g., baculovirus ODV-E66); by expression of a recombinant nucleic acid encoding a transport polypeptide; or by chemically synthesizing the polypeptide.

Purity can be measured by any appropriate method, e.g., column chromatography such as immunoaffinity chromatography using an antibody specific for the hydrophobic transport polypeptide, polyacrylamide gel electrophoresis, or HPLC analysis. A protein or polypeptide is substantially free of naturally associated components when it is separated from at least some of those contaminants which accompany it in its natural state. Thus, a polypeptide which is chemically synthesized or produced in a cellular system different from the cell from which it naturally originates will be, by definition, substantially free from its naturally associated components. Accordingly, substantially pure proteins or polypeptides include eukaryotic proteins synthesized in *E. Coli*, other prokaryotes, or any other organism in which they do not naturally occur.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1A-1, FIG. 1A-2, FIG. 1A-3 and FIG. 1B are diagrams showing the nucleotide (SEQ ID NO:1) and amino acid (SEQ ID NO:2) sequences of ODV-E66. FIG. 1A is a diagram showing the full length nucleotide and amino acid sequences of ODV-E66. FIG. 1B is a diagram showing the nucleotide and amino acid sequences of the N-terminal 23 amino acids of ODV-E66 (nucleotide numbers 122 to 190).

FIG. 2 is an outline summarizing the different constructs used in this invention.

FIG. 3A, FIG. 3B and FIG. 3C are photographs showing immunogold labeling of the ODV-E66 protein. FIG. 3A is a photograph of purified ODV, showing immunogold labeling of the ODV-E66 protein. FIG. 3B is a photograph of wild type AcMNPV infected Sf9 cells at 48 h.p.i., showing immunogold labeling of the ODV-E66 protein in the intranuclear microvesicles. FIG. 3C is also a photograph of wild type AcMNPV infected Sf9 cells at 48 h.p.i., showing immunogold labeling of the ODV-E66 protein in the ODV envelope that is maturing into the occluded form.

FIG. 4A, FIG. 4B, and FIG. 4C are photographs showing immunogold labeling of Sf9 cells infected with pVL1393-E66F at 48 h.p.i. FIG. 4A: Labeling of ODV-E66 in the intranuclear microvesicles and cytoplasmic membranes close to the nuclear envelope (dual arrow). FIG. 4B: Labeling of ODV in the cytoplasmic membranes (dual arrow). FIG. 4C: Labeling of ODV-E66 in the outer (arrowhead) and inner (arrow) nuclear membranes. The following abbreviations are used in this figure: m, microvesicles; n, nucleus; c, cytoplasm.

FIG. 5A: 23 β-gal fusion protein was localized to the intranuclear microvesicles (arrowhead) and ODV envelope (arrow) in infected Sf9 cells. FIG. 5B: 23 β-gal fusion protein was localized to the intranuclear microvesicles (arrowhead) and ODV envelope (arrow) in infected IFN368 cells. The following abbreviations are used in this figure: m, microvesicles; n, nucleus; c, cytoplasm.

FIG. 6A, FIG. 6B, FIG. 6C, FIG. 6D, FIG. 6E, FIG. 6F, FIG. 6G, FIG. 6H, FIG. 6I are photographs showing localization of 23GFP in pVL1393-23GFP infected Sf9 cells. FIG. 6A: 48 h.p.i., GFP autofluorescence. FIG. 6B: 48 h.p.i., GFP autofluorescence and phase contrast. Arrows in FIG. 6A and FIG. 6B point to the fluorescence at the periphery of the nucleus. FIG. 6C: 72 h.p.i., GFP autofluorescence. FIG. 6D: 72 h.p.i., GFP autofluorescence and phase contrast. Arrowheads in FIG. 6C and FIG. 6D point to the fluorescence in the interior of the nucleus. FIG. 6E, FIG. 6F, FIG. 6G, FIG. 6H, FIG. 6I: Immunogold labeling of Sf9 cells infected with pVL1393-23GFP at 48 h.p.i. using rabbit GFP antiserum and anti-rabbit IgG 30 nm gold-conjugate. FIG. 6E: Note the labeling of cytoplasmic membranes at the periphery of the nucleus and foci of intranuclear microvesicles. FIG. 6F: Labeling of cytoplasmic membranes (dual arrow), outer (arrow) and inner (arrowhead) nuclear membranes. FIG. 6G: Labeling of large cytoplasmic vesicles (open-arrow). FIG. 6H: Labeling of outer (arrow) and inner (arrowhead) nuclear membranes. FIG. 6I: Labeling of the ODV envelope (arrow). The following abbreviations are used in these figures: c, cytoplasm; n, nucleus; v, virogenic stroma; m, microvesicles.

FIG. 7A: Labeling of the ODV envelope (arrow) and intranuclear vesicles (open arrow). FIG. 7B: Labeling of cytoplasmic membranes (arrowhead). The following abbreviations are used in this figure: c, cytoplasm; n, nucleus.

FIG. 8A, FIG. 8C, FIG. 8E: Fluorescence microscopy at 24 hr post-transfection. FIG. 8B, FIG. 8D, FIG. 8F: Matched fluorescence and phase contrast image double exposure to fluorescence images in FIG. 8A, FIG. 8C, FIG. 8E, respectively. FIG. 8G and FIG. 8H: Immunogold labeling of binucleated cells at 48 hr post-transfection using rabbit GFP antiserum and anti-rabbit IgG 30 nm gold-conjugate. FIG. 8G: Note small vesicles in the nucleoplasm (arrowhead) and cytoplasmic vesicles juxtaposed to the nuclear envelope (dual arrow in insert). FIG. 8H: Labeling of cytoplasmic vesicles (open arrow), outer and inner nuclear membranes (arrow). Also note the invagination of the inner nuclear membrane into the nucleoplasm (arrowhead). The following abbreviations are used in this figure: c, cytoplasm; n, nucleus; ne, nuclear envelope.

FIG. 9A: Note the ring of fluorescence (arrowhead) in a cell with two nuclei that is likely in mitosis. FIG. 9B: The ring of fluorescence is not obvious. This cells is possibly not in the mitosis due to the presence of a single nucleus and intact nuclear envelope (arrowhead).

FIG. 10A and FIG. 10B are diagrams showing an overview of directed delivery to target cell and subsequent gene delivery. FIG. 10A is a diagram showing targeting and delivery to target cell via membrane fusion with the purified microvesicles or ODV envelope (I-V). If the delivered protein has toxic activity after being incorporated into the cell membrane, then this protein may have an insecticidal application (VI). FIG. 10B is an extension of the delivery shown in FIG. 10A to include gene delivery and expression.

FIG. 11 is a diagram showing levels of protein production utilizing BEVS technology and comparing amounts of foreign protein produced in tissue culture and larva.

FIG. 13A shows the contemplated applications of the invention using baculovirus expression of the instant constructs. FIG. 13B shows the contemplated applications of the invention independent of baculovirus expression.

FIG. 15A shows the results with cells infected with the 23 β-gal recombinant virus (anti-β-gal antibody); FIG. 15B shows the results with cells infected with AcMNPV (E2 strain; anti-ODV-E25 antibody, 1:1000 dilution). FIG. 15C shows the results with cells infected with the 23GFP recombinant virus (anti-GFP antibody). FIG. 15D shows the results with cells infected with the 24GFP recombinant virus (anti-GFP antibody). FIG. 15E and FIG. 15F show the results with cells infected with the pVL-E66 recombinant virus. (anti-ODV-E66 antibody; Hong et al., 1994). N, nucleus, C, cytoplasm, m, microvesicles, open arrows, labeling of ODV envelope, arrowheads, labeling of the nuclear envelope, arrows, labeling of cytoplasmic membranes, dual arrows, condensation of cytoplasmic membranes to the periphery of the nucleus. Bar=1 μm.

FIG. 16. Comparison of N-terminal domains of ODV-E66, ODV-E25 from three different baculoviruses, and some of the fusion constructs used in the Examples. Shown are 23β-Gal (SEQ ID NO:48), 23-GFP (SEQ ID NO:49), AcNPV ODV-E66 (SEQ ID NO:50), OpNPV ODV-E66 (SEQ ID NO:51), BmNPV ODV-E66 (SEQ ID NO:52), AcNPV ODV-E25 (SEQ ID NO:53), OpNPV ODV-E25 (SEQ ID NO:54), BmNPV ODV-E25 (SEQ ID NO:55) and 24-GFP (SEQ ID NO:56). Blocked and shaded amino acids indicate hydrophobic domain, Underlined (dashed) amino acids were directly N-terminal sequenced, Underlined (solid) amino acids indicate N, S rich region, boxed amino acids indicate amino acids added by cloning strategy, *indicates charged amino acids. AcMNPV=*Autographa californica* multinucleocapsid nuclear polyhedrosis virus, OpMNPV=*Orgyia pseudotsugata* nuclear polyhedrosis virus; BmMNPV=*Bombyx mori* nuclear polyhedrosis virus.

DESCRIPTION OF ILLUSTRATIVE EMBODIMENTS

Figure 5A:
FIG. 5A and FIG. 5B are photographs showing immunogold labeling of *Spodoptera frugiperda* (Sf9) and *Trichoplusia ni* (TN368) cells infected with 23 β-gal virus at 48 h.p.i.

Infection by AcMNPV and other baculoviruses induce extensive elaboration and proliferation of intranuclear membranes that appear as microvesicles and unit membranes within the nucleoplasm (Fraser, 1986; Hong et al., 1994). Previous results using occlusion derived virus (ODV) envelope proteins as markers to study trafficking and assembly of intranuclear microvesicles and the ODV envelope, suggest that movement of these proteins could be mediated through cytoplasmic membranes and the nuclear envelope (Braunagel et al., 1996a). This model predicts that ODV envelope proteins are incorporated into the ER, transported to the outer and inner nuclear membrane (ONM, INM), with subsequent proliferation of INM into the nucleus in the form of membrane fragments or microvesicles (Braunagel et al., 1996a).

Based on this model, one might expect ODV envelope proteins to contain similar targeting/retention signals as other INM proteins. The molecular signals necessary for transport or retention of proteins into the INM are largely uncharacterized, however for certain proteins a hydrophobic domain has been identified to play a role in this process. Transmembrane domains from lamin B receptor, gp210, and herpes simplex virus glycoprotein B (gB) can direct proteins to the nuclear envelope (Gilbert et al., 1994; Smith and Blobel, 1993; Wozniak and Blobel, 1992). It is unknown why these domains are sufficient to direct proteins to the nuclear envelope while other, apparently similar transmembrane domains do not function as such.

As described herein, this invention provides hydrophobic targeting sequences, capable of targeting desired proteins to the membranes of both infected and uninfected cells. The present invention thus provides a number of uses, and advantages over the current art.

The use of the claimed hydrophobic targeting sequences for directing the location of an engineered protein product in a desired cell would include, but is not limited to, the delivery of proteins, peptides or derivatives thereof for (a) insecticidal effects—insect pest control; (b) therapeutic applications (for example, but not limited to, the localization of a protein, peptide or derivative into the nuclear envelope which will alter the cell cycle); and (c) diagnostics (for example, but not limited to, insertion of a marker specific for a disease or abnormality into a cell tissue manifesting such abnormalities).

For example, the hydrophobic targeting sequences can be used to target desired proteins, with known properties or desired characteristics, to the ODV envelope. The hydrophobic targeting sequences may also be used to locate potentially any protein, peptide, or derivative to the nuclear envelope or other nuclear membranes. Additionally, the targeting sequences of this invention can be used to locate a protein, peptide or derivative of such to cytoplasmic membranes, the nuclear envelope, the inner nuclear membrane or intranuclear membranes induced during viral infection or during specific stage(s) of cell cycle.

The hydrophobic targeting sequence may be incorporated into a viral vector for delivering preferred targeted constructs into a cell via infection. Any eukaryotic or prokaryotic cell capable of infection by a virus or phage is contemplated for use with the targeting sequences of the present invention. Examples of insect infected cells, include, but are not limited to (a) Sf9 cells, Sf21 cells or related strains, (b) TN368 cells or related strains or (c) any insect cell (or invertebrate cell) infected by a baculovirus (e.g., AcMNPV) or other virus capable of infecting an insect, which has been constructed to express a structural or functional protein cognate containing a hydrophobic targeting sequence or its structural/functional equivalent.

Examples of viral infection of insects include, but are not limited to (a) *Heliothis virescens* larvae or related susceptible strains; (b) *Trichoplusia ni* larvae or related susceptible strains; or (c) any insect larvae species susceptible to infection by a baculovirus or other virus capable of infecting insects.

The hydrophobic targeting sequences of the present invention can be expressed in infected cells as a single copy, multiple copies of the same protein or in variable combinations with other proteins (for example, but not limited to, targeting sequence-protein A, targeting sequence-protein B, . . . targeting sequence-protein X). The hydrophobic targeting sequences of this invention can also be expressed in the infected cell at any time during the infection process by expression from promoter classes representing immediate early (0–4 h.p.i.), delayed early (4–6 h.p.i.), late (6–24 h.p.i.) or very late (24 h.p.i. to 5 days or more).

Also, the targeted protein products can be directed to locate to the desired locations in vertebrate, plant or other cell types during viral infection of that organism or cell. This can be done by placing the hydrophobic targeting sequences under the expression of any viral gene of any viral promoter class engineered for expression during infection of vertebrate, plant or microbial cells. This could therefor introduce protein products comprising the hydrophobic targeting sequences into the cell during the infection cycle to deliver the desired protein into, for example, cytoplasmic or nuclear membranes.

Additionally, the hydrophobic targeting sequences of the present invention can be expressed in uninfected cells by using gene promoters that function in cells in the absence of or during viral infection. For example, the desired targeted protein product construct can be expressed in uninfected insect cells by the AcMNPV-IE1 or other immediate early gene promoters regulated by the cell DNA-dependent RNA polymerase; or, expressed from a baculovirus (or other) gene promoter transactivated by an immediate early gene; or, a host cell gene promoter which is, for example, constitutively expressed or cell cycle or developmentally regulated.

Examples of transfected, but uninfected cells, include, but are not limited to, (a) Sf9 cells or related strains (Sf21, etc.); (b) TN368 cells or related strains; and (c) any insect or invertebrate cells, vertebrate cells, plant cells, or microbial cells capable of transfection. Examples of transformed, but uninfected cells, include, but are not limited to, (a) Sf9 cells or related strains (Sf21, etc.); (b) TN368 cells or related strains; and (c) any insect cells, invertebrate cells, vertebrate cells, plant, or microbial cells capable of transformation.

Additionally, the hydrophobic targeting sequences, and heterologous protein constructs thereof, provided in the present invention may be delivered to insect cells, insects, vertebrates, plant and microbial cells or organisms for targeting to a number of different membrane structures, including, but not limited to, the endoplasmic reticulum, nuclear envelope and intranuclear membranes, by a variety of artificially developed or genetically engineered strategies. For example, artificial membranes (for example, liposomes) may be used to deliver the targeted-protein product to the surface of a cell which could be then targeted to the ER and nuclear envelope by the cellular endocytic and vesicular retrograde transport pathways. Alternatively, a retrovirus engineered to target a specific cell or tissue type, could carry in the viral envelope a specific hydrophobic targeting sequence-protein product, or have incorporated in the viral genome sequence information specific for expression, translation and targeting of the derived hydrophobic targeting sequence-protein product during or after genetic transformation of the cell. Further, the nucleotide sequence for a derived hydrophobic targeting sequence-protein product could be incorporated into a protein or polyprotein which would be processed at a specific time in the cellular or viral protein processing pathway for incorporation into cytoplasmic membranes, nuclear envelope, or induced nuclear membranes.

Also, there are many possibilities for deriving or obtaining a hydrophobic targeting sequence or its structural and functional cognate for any of the uses as described above. For example, the hydrophobic targeting sequence may be derived from, for example, but not limited to: (1) the ODV-E66 gene sequence; (2) a synthetic DNA sequence with codon usage for a particular cell species or organism optimized for the hydrophobic targeting sequence. This would include the use of codons not preferred by the baculovirus nucleotide sequence which would translate the same amino acid because of degeneracy in the genetic code; (3) a synthetic hydrophobic targeting peptide or a structural and functional cognate of amino acids made synthetically or derived in part or whole from another naturally occurring protein sequence; (4) the ODV-E66 genes or proteins of other baculoviruses; and (5) the ODV-E25 protein from any baculovirus with a similar hydrophobic sequence.

A. General Properties of Baculovirus

The family Baculoviridae consists of viruses with an enveloped rod-shaped virion containing a circular double-stranded DNA genome ranging from 88 to 153 kb (Murphy et al., 1995). Baculoviruses have been isolated only from arthropods; primarily from insects of the order Lepidoptera, but also from Hymenoptera, Diptera, Coleoptera, Neuroptera, Thysanura, and Trichoptera as well as from the crustacean order Decapoda (shrimp). Individual baculovirus may infect one species or multiple species within the same order (e.g., AcMNPV infection of Lepidoptera). However, none of the baculoviruses infects a large number of insects, or members of different orders of the class Insecta. *Autographa californica* multinucleocapsid nuclear polyhedrosis virus (AcMNPV) is unusual among baculoviruses because it displays a wider host range than most baculoviruses, which includes 32 species in 12 families (Martignoni et al., 1982).

AcMNPV is the most extensively studied baculovirus and its genome sequence is known (Ayres et al, 1994). It is distinguished by a unique biphasic life cycle in its lepidopteran host insect (reviewed in Blissard and Rohrrmann, 1990). Infection produces high titers of two forms of progeny virus, budded virus (BV) and occlusion derived virus (ODV). Both forms are essential for natural propagation of the virus. Infection initiates when the insect feeds on a food source contaminated by viral occlusions. The alkaline midgut fluids dissolve the viral occlusion, and release ODV to infect the midgut epithelium. Early in infection nucleocapsids assemble in the nucleus, migrate to the cell surface, and obtain an envelope by budding through the plasma membrane into the insect hemolymph. This form of virus is named BV and is responsible for secondary or systemic infection of a variety of tissues in the insect. Late in infection the production of BV decreases. Instead of budding from the cell surface, the nucleocapsids remain within the nucleoplasm where they are enveloped and occluded within the viral occlusion. This form of virus is named occlusion derived virus or ODV. The insect midgut epithelium is generally believed to be the site of primary infection in vivo (Adams and McClintock, 1991).

ODV and BV contain the same genome, yet exhibit significant differences in morphology, timing and cellular site of maturation, structural proteins, source of viral envelopes, antigenicity, and infectivity (Blissard and Rohrmann, 1990; Braunagel and Summers, 1994). The differences between the envelopes of ODV and BV may function to regulate important aspects of the role of these two viral forms in infectivity, host range, and tissue specificity.

1. Regulation of Viral Gene Expression

AcMNPV gene expression is temporally regulated. AcMNPV genes are classified into two phases (early and late) which are further subdivided into four classes: immediate early or "IE", delayed early, late, and very late (Blissard and Rohrmann, 1990). Promoters of immediate early genes are active in uninfected insect cells and are expressed very early in infection, thus making them ideal promoters for the expression of proteins with insecticidal properties to compromise infected insects at a very early stage or for the expression of genes with therapeutic or diagnostic properties in transiently transfected or stably transformed cells.

Five immediate early (IE) genes have been identified; IE-0 (Chisholm and Henner, 1988), IE-1 (Kovacs et al., 1991a, b; Choi and Guarino, 1995a, b, c), IE-2 (Carson et al., 1988, 1991), PE-38 (Krappa et al., 1992), and ME53 (Morsdorf et al., 1993). Very late genes are highly expressed very late during infection and their promoters have been utilized to express a variety of proteins using the baculovirus expression vector system. Two very late genes are known: polyhedrin (Hooft van Iddekinge et al., 1983) and p10 (Kuzio et al., 1984). The identity and nucleotide sequence of promoters representing all classes of genes are known and can be used for the expression of chimeric genes attached to them or simultaneous expression of multiple genes at controlled times.

2. Virion Structure a. Nucleocapsid

The differences in nucleocapsid protein composition between ODV and BV of AcMNPV have been investigated (Braunagel and Summers, 1994). Several proteins have been identified as common nucleocapsid components in both phenotypes of AcMNPV (Blissard and Rohrmann, 1990; Rohrmann, 1992), including: p39 (Thiem and Miller, 1989); p80 (Lu and Carstens, 1992); p6.9 (Wilson et al., 1987; Wilson, 1988); p24 (Wolgamot et al., 1993). Homologs of these nucleocapsid proteins have also been identified in other baculoviruses.

b. Viral envelope

Generally, the ODV envelope is closely associated with the nucleocapsid and has no apparent specialized morphology, whereas the BV envelope is loose-fitting and has a specialized region (peplomer) at one end of the virion which is enriched with the viral envelope glycoprotein gp64 (Adams and McClintock, 1991).

The biochemical composition of both viral envelopes is fairly well defined. A recent study shows major differences between BV and ODV in envelope protein SDS-PAGE profiles, major antigens, lipid, and fatty acid compositions (Braunagel and Summers, 1994).

i. BV envelope proteins

So far, only one BV envelope protein (gp64) has been mapped in the genomes of AcMNPV (Whitford et al., 1989), OpMNPV (Orgyia pseudotsugata multinucleocapsid nuclear polyhedrosis virus; Blissard and Rohrmann, 1989), and CfMNPV (Christoneura fumiferana multinucleocapsid nuclear polyhedrosis virus; Hill and Faulkner, 1994). Gp64 is a type I transmembrane protein which is N-glycosylated (Rohrmann, 1992).

AcMNPV encodes a ubiquitin-like protein which is integrated into the BV envelope through a novel type of phospholipid anchor (Guarino et al., 1995). The baculovirus apoptotic inhibitor p35 is also detected in purified BV by Western-blot analysis; however, the exact location of p35 in the virion is unknown. It is not known whether p35 is present in ODV (Hershberger et al., 1994).

ii. ODV envelope proteins

Several ODV envelope proteins of AcMNPV have been identified, including ODV-E66 (Hong et al., 1994), ODV-E56 (Braunagel et al., 1996a), and ODV-E18/E35 (Braunagel et al., 1996b). Other candidate ODV envelope proteins have also been identified. A fatty acylated protein of 26.4 kDa (p26.4) is associated with AcMNPV ODV (Rohrmann, 1992). The p74 protein is known to play a role in ODV infectivity (Kuzio et al., 1989) and is believed to be a ODV structural protein; however, its location within the virus has not been determined. Two ODV envelope proteins have been identified in other baculoviruses: Vp17 of Plodia interpunctella granulosis virus (Funk and Consigli, 1993) and ODV-E25 (or p25) of Orygia pseudotsugata multinucleocapsid nuclear polyhedrosis virus (Russell and Rohrmann, 1993).

iii. Tegument

An ODV-specific structural O-linked glycoprotein, gp41, is suggested to reside between the envelope and nucleocapsid, i.e. in the tegument (Whitford and Faulkner, 1992a, b).

3. Replication Pathway of AcMNPV

The replication pathway of AcMNPV is briefly discussed below. A more extensive review can be found in Adams and McClintock (1991).

a. Virion attachment and penetration

Two routes, adsorptive endocytosis (or viropexis) and direct fusion of BV envelope with plasma membrane, are initially proposed for entry of BV into cultured cells. Although BV may enter cells by fusion (Volkman et al., 1986; Kozuma and Hukuhara, 1994), the majority of data indicates that the primary route is by adsorptive endocytosis (Charlton and Volkman, 1993).

By extrapolation with other enveloped animal viruses, especially orthomyxoviruses (White, 1990), a model is proposed to explain the BV entry process in cultured insect cells (reviewed in Volkman, 1986). According to this model, BV virions enter cells via the endocytic pathway during which virions are invaginated into the cytoplasm as clathrincoated vesicles. In the cytoplasm, the clathrin coat dissociates and the uncoated vesicles containing virions fuse with cellular vesicles to form endosomes. Following the decrease of pH in the endosome, presumably by an ATP-driven proton pump, the BV envelope fuses with the endosomal membrane through the function of gp64, and release the nucleocapsid into the cytoplasm.

ODV is the primary infectious agent to the insect host. The ODV envelope fuses with the plasma membrane of the midgut cell, thus releasing the nucleocapsid and viral DNA into the cell (Kawanishi et al, 1972; reviewed in Adams and McClintock, 1991). In this process, viral envelope proteins are incorporated into the gut cell plasma membrane.

b. Nucleocapsid uncoating

After nucleocapsids are released into the cytoplasm, they are transported to the nucleus for uncoating.

c. Progeny nucleocapsid assembly

Progeny nucleocapsids are assembled within the nucleoplasm of infected cells.

d. Envelopment of progeny viruses

The envelopes of ODV and BV are derived from distinct cellular sources and appear to exhibit marked tissue specificity (Adams and McClintock, 1991). ODV appears to be specialized both for interaction with polyhedrin and for infection of the epithelial cells in the insect midgut. BV is specialized for interaction with other cell types and tissues in the insect. ODV is responsible for spreading infection among the natural insect hosts, whereas BV is responsible for the secondary infection within the infected host and in cultured insect cells. There are dramatic differences in the infectivity of ODV and BV both in vivo and in vitro as well as in their ability to be neutralized by homologous and heterologous antisera (Volkman et al., 1976; Volkman and Summers, 1977; Keddie and Volkman, 1985). Differences in infectivity correlate with the different roles of these two viral forms in the virus life cycle (Blissard and Rohrmann, 1990).

In the early phase, nucleocapsids destined for BV escape the nucleus, possibly by budding through both outer and inner nuclear membranes, and reach the plasma membrane in an unenveloped state. Then, nucleocapsids bud through the plasma membrane to become BV virions. Budding appears to occur at gp64-containing plasma membrane regions with a "spiny coat" appearance. BV also contains a "spiny coat" structure called peplomer at one end of the virion. In the mature BV, gp64 is distributed throughout the envelope, but appears more concentrated in the peplomer, thus constituting the major protein component of the peplomer.

In the late phase, ODV are enveloped from membrane structures, microvesicles, induced within the nucleoplasm of infected cells. Intranuclear morphogenesis of microvesicles begins at approximately 12 hours post-infection (h.p.i.). The microvesicles have a unit membrane structure and they normally appear as open-ended membranes as well as thin tubular membranes. ODV nucleocapsids display polarity in their association with microvesicles. In many cases, before the completion of envelopment, they are seen lined with each other with the capped end attached to the membrane. After ODV obtains its envelope, it is further occluded into the viral occlusion which is released after cell lysis and is very stable in the environment for many years.

Maturation of the ODV envelope within the nucleus is very unique compared to herpes simplex virus (HSV) and plant nucleohabdovirus (Jackson et al., 1987; Roizman and Sears, 1990). Maturation of HSV results in initial envelopment of nucleocapsids in the perinuclear space, but the progeny viruses are further transported through the cytoplasm to the exterior of the cell (Roizman and Sears, 1990). In contrast, there is no evidence that ODV ever leaves the nucleus for ODV envelope proteins to be further modified in the cytoplasm after their incorporation into the ODV envelope. During HSV infection, the inner nuclear membrane is modified in regions where nucleocapsids bud, but unit-membranes are not observed in the nucleoplasm. In contrast, baculoviruses induce extensive elaboration of unit-membranes within the nucleoplasm and budding of nucleocapsids through unit-membranes occurs at the intranuclear membranes.

B. Biological Functional Equivalents

As mentioned above, modification and changes may be made in the structure of the hydrophobic targeting sequences and still obtain a molecule having like or otherwise desirable characteristics. For example, certain amino acids may be substituted for other amino acids in the hydrophobic targeting sequences without appreciable loss of membrane targeting activity. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of hydrophobic targeting proteins or peptides (or underlying DNA) without appreciable loss of their biological utility or activity.

In terms of functional equivalents, It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged.

Conservative substitutions well known in the art include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent, or in certain embodiments, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

In addition to the "standard" twenty amino acids in the genetic code, modified and "unusual" amino acids are also contemplated for use in the present invention, in that certain modified or unusual amino acids can be substituted for another having a similar hydrophilicity value and still obtain a biologically equivalent peptide or protein. Table 1 below is an exemplary, although certainly not exhaustive, list of modified and unusual amino acids.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| bAad | 3-Aminoadipic acid | Hyl | Hydroxylysine |
| bAla | beta-alanine, beta-Amino-propionic acid | aHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | aIle | allo-Isoleucine |
| Aib | 2-Aminoisobutyric acid | MeGly | N-Methylglycine, sarcosine |
| bAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like. Exemplary of these changes, Table 2 shows the preferred DNA codons, and Table 3 shows the preferred RNA codons, for use in humans. Table 4 shows the preferred DNA codons, and Table 5 shows the preferred RNA codons, for use in insects such as *Bombyx mori*, exemplary of insects that are infected by baculoviruses (Wada et al., 1990).

TABLE 2

Preferred Human DNA Codons

| Amino Acids | | | Codons | | | |
|---|---|---|---|---|---|---|
| Alanine | Ala | A | GCC | GCT | GCA | GCG |
| Cysteine | Cys | C | TGC | TGT | | |
| Aspartic acid | Asp | D | GAC | GAT | | |
| Glutamic acid | Glu | E | GAG | GAA | | |
| Phenylalanine | Phe | F | TTC | TTT | | |
| Glycine | Gly | G | GGC | GGG | GGA | GGT |
| Histidine | His | H | CAC | CAT | | |
| Isoleucine | Ile | I | ATC | ATT | ATA | |
| Lysine | Lys | K | AAG | AAA | | |
| Leucine | Leu | L | CTG | CTC | TTG | CTT | CTA | TTA |
| Methionine | Met | M | ATG | | | |
| Asparagine | Asn | N | AAC | AAT | | |
| Proline | Pro | P | CCC | CCT | CCA | CCG |
| Glutamine | Gln | Q | CAG | CAA | | |
| Arginine | Arg | R | CGC | AGG | CGG | AGA | CGA | <u>CGT</u> |
| Serine | Ser | S | AGC | TCC | TCT | AGT | TCA | <u>TCG</u> |
| Threonine | Thr | T | ACC | ACA | ACT | ACG |
| Valine | Val | V | GTG | GTC | GTT | GTA |
| Tryptophan | Trp | W | TGG | | | |
| Tyrosine | Tyr | Y | TAC | TAT | | |

Codon prevalence shown as decreasing from left (most prevalent) to right (least prevalent). Underlined codons are those used less than 5 times per one thousand codons.

TABLE 3

Preferred Human RNA Codons

| Amino Acids | | | Codons | | | |
|---|---|---|---|---|---|---|
| Alanine | Ala | A | GCC | GCU | GCA | GCG |
| Cysteine | Cys | C | UGC | UGU | | |
| Aspartic acid | Asp | D | GAC | GAU | | |
| Glutamic acid | Glu | E | GAG | GAA | | |
| Phenylalanine | Phe | F | UUC | UUU | | |
| Glycine | Gly | G | GGC | GGG | GGA | GGU |
| Histidine | His | H | CAC | CAU | | |
| Isoleucine | Ile | I | AUC | AUU | AUA | |
| Lysine | Lys | K | AAG | AAA | | |
| Leucine | Leu | L | CUG | CUC | UUG | CUU | CUA | UUA |
| Methionine | Met | M | AUG | | | |
| Asparagine | Asn | N | AAC | AAU | | |
| Proline | Pro | P | CCC | CCU | CCA | CCG |
| Glutamine | Gln | Q | CAG | CAA | | |
| Arginine | Arg | R | CGC | AGG | CGG | AGA | CGA | <u>CGU</u> |
| Serine | Ser | S | AGC | UCC | UCU | AGU | UCA | <u>UCG</u> |
| Threonine | Thr | T | ACC | ACA | ACU | ACG |
| Valine | Val | V | GUG | GUC | GUU | GUA |
| Tryptophan | Trp | W | UGG | | | |
| Tyrosine | Tyr | Y | UAC | UAU | | |

Codon prevalence shown as decreasing from left (most prevalent) to right (least prevalent). Underlined codons are those used less than 5 times per one thousand codons.

TABLE 4

Preferred DNA Codons For *Bombyx mori*

| Amino Acids | | | Codons | | | | | |
|---|---|---|---|---|---|---|---|---|
| Alanine | Ala | A | GCC | GCT | GCG | GCA | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGT | GGC | GGA | GGG | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTC | CTG | TTG | CTT | TTA | CTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGA | CGT | AGG | CGA | CGG |
| Serine | Ser | S | AGC | TCC | TCG | TCT | AGT | TCA |
| Threonine | Thr | T | ACC | ACT | ACA | ACG | | |
| Valine | Val | V | GTC | GTG | GTT | GTA | | |
| Tryptophan | Trp | W | TGG | | | | | |
| Tyrosine | Tyr | Y | TAC | TAT | | | | |

Codon prevalence shown as decreasing from left (most prevalent) to right (least prevalent). Underlined codons are those used less than 5 times per one thousand codons.

TABLE 5

Preferred RNA Codons For *Bombyx mori*

| Amino Acids | | | Codons | | | | | |
|---|---|---|---|---|---|---|---|---|
| Alanine | Ala | A | GCC | GCU | GCG | GCA | | |
| Cysteine | Cys | C | UGC | UGU | | | | |
| Aspartic acid | Asp | D | GAC | GAU | | | | |
| Glutamic acid | Glu | E | GAG | GAA | | | | |
| Phenylalanine | Phe | F | UUC | UUU | | | | |
| Glycine | Gly | G | GGU | GGC | GGA | GGG | | |
| Histidine | His | H | CAC | CAU | | | | |
| Isoleucine | Ile | I | AUC | AUU | AUA | | | |
| Lysine | Lys | K | AAG | AAA | | | | |
| Leucine | Leu | L | CUC | CUG | UUG | CUU | UUA | CUA |
| Methionine | Met | M | AUG | | | | | |
| Asparagine | Asn | N | AAC | AAU | | | | |
| Proline | Pro | P | CCC | CCU | CCA | CCG | | |
| Glutamine | Gln | Q | CAG | CAA | | | | |
| Arginine | Arg | R | CGC | AGA | CGU | AGG | CGA | CGG |
| Serine | Ser | S | AGC | UCC | UCG | UCU | AGU | UCA |
| Threonine | Thr | T | ACC | ACU | ACA | ACG | | |
| Valine | Val | V | GUC | GUG | GUU | GUA | | |
| Tryptophan | Trp | W | UGG | | | | | |
| Tyrosine | Tyr | Y | UAC | UAU | | | | |

Codon prevalence shown as decreasing from left (most prevalent) to right (least prevalent). Underlined codons are those used less than 5 times per one thousand codons.

C. Promoters and Enhancers

In certain aspects of the present invention, vectors which are designed for the expression of a desired gene or genes are required. Thus, particular embodiments may require a selected nucleic acid segment to be operatively positioned relative to control sequences, such as promoters and enhancers.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

There are at least three basic procedures for expressing cloned genes from promoters, which are both useful with the present invention. In transient systems, the gene of interest is introduced into the cell by infection with a recombinant virus, for example baculovirus. In the most widely used baculovirus systems, the gene of interest is under the control of the polyhedrin promoter. The polyhedrin promoter is a very late promoter, which means that the expression of the gene of interest does not start until the late phase of the baculovirus infection. The expression levels are high, but transient as the baculovirus infection eventually leads to cell death.

The second method for expressing cloned genes from control regions is stable transfection. Stable transfection may allow for moderate expression levels from a transfected gene to be obtained in a long term continuous culture. In this method the recombinant DNA molecule and promoter/enhancer combination is introduced via transfection, with a gene encoding a selectable marker protein either on the same vector (transfection), or on a separate vector (co-transfection). After selection for clones which express the marker protein, the cells are assayed for the presence of the gene of interest (for example by Southern analysis of the genomic DNA, northern analysis of the RNA or western analysis of the protein product). Cells which have the gene of interest incorporated into the genomic DNA of the host cell will stably express the gene.

The third method for expressing cloned genes from control regions is transformation. Transformation can be either transient or stable, depending on the absence or presence, respectively, of a selectable marker gene. Methods for transforming cells are discussed in greater detail below.

In any event, it will be understood that promoters are DNA elements which when positioned functionally upstream of a gene leads to the expression of that gene. Each heterologous gene in the vector of the present invention is functionally positioned downstream of a promoter element.

1. Baculoviral Promoters and Enhancers

There are four distinct phases of a baculovirus infection, termed immediate-early, delayed-early, late and very late. Therefore, different baculovirus genes may be classified according to the phase of the viral infection during which they are expressed. Also there are a class of genes which have been defined as early genes, which have not been subcatagorized as either immediate-early or delayed-early. Different classes of promoters control each class of gene.

a. Immediate-Early Promoters

This class of promoters are distinguished by needing only host cell factors to drive expression. Examples are the ie1 (Guarino and Summers, 1987), ieN (ie2; Carson et al., 1991) and ie0 promoters.

b. Delayed-Early Promoters

This class of promoters are distinguished by needing only products of the immediate-early genes, in addition to host cell factors to drive expression. Examples are the 39K (Guarino and Smith, 1991) and gp64 (Blissard and Rohrmann, 1989; Whitford et al., 1989) promoters.

c. Early Promoters

This class of promoters have not been placed into the specific immediate-early of delayed-early class. Examples include the DA26, ETL and 35K promoters.

d. Late Promoters

This class of promoters requires products of the delayed-early and immediate-early genes, as well as other host cell factors, to drive expression. Examples are the gp64 (Blissard and Rohrmann, 1989; Whitford et al., 1989) and capsid (p39; Thiem and Miller, 1989) promoters.

e. Very Late Promoters

This class of promoters requires a number of baculovirus gene products, in addition to other host cell factors, to drive expression. Examples of promoters from this class are the polyhedrin (Hooft van Iddekinge et al., 1983) and the p10 (Kuzio et al., 1984) promoters. The best characterized and most often used baculoviral promoter is the polyhedrin promoter. The use of the polyhedrin promoter is a preferred embodiment of the present invention.

f. Baculovirus Enhancers

As mentioned, enhancers are DNA elements which can be positionally located to enhance transcription from a given promoter. Enhancers which are active in insect cells to drive transcription are preferred in the present invention. Preferred are viral enhancers, and most preferred are baculoviral enhancers. Examples of baculoviral enhancers include hr1, hr2, hr3, hr4 and hr5 (Guarino et al., 1986).

2. Other Viral and Cellular Promoters and Enhancers

Below are a list of viral promoters, cellular promoters/enhancers and inducible promoters/enhancers that could be used in combination with the present invention. Additionally any promoter/enhancer combination (as per the Eukaryotic Promoter Data Base, EPDB) could also be used to drive expression of exemplary constructs. Table 6 lists exemplary enhancer elements, while Table 7 lists examples of promoters.

TABLE 6

| ENHANCER | REFERENCES |
| --- | --- |
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene el al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al, 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_{1\text{-}Antitrypain}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al. 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; |

TABLE 6-continued

| ENHANCER | REFERENCES |
|---|---|
| Retroviruses | de Villiers et al., 1984; Hen et al., 1986; Satake et al., 1988; Campbell and Villarreal, 1988 Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al, 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immuno-deficiency Virus | Muesing et al., 1987; Hauber and Cullan, 1988; Jakobovits et al., 1988; Feng and Holland, 1988; Takebe et al, 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 7

| Promoter Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | poly(rI)x poly(rc) | Tavernier et al, 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2Kb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

D. Infection with Viral Vectors

In certain embodiments of the invention, the nucleic acid encoding a selected gene may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

1. Baculoviral Vectors

Baculovirus expression vectors are useful tools for the production of proteins for a variety of applications (Summers and Smith, 1987; O'Reilly et al., 1992; also U.S. Pat. Nos., 4,745,051 (Smith and Summers), 4,879,236 (Smith and Summers), 5,077,214 (Guarino and Jarvis), 5,155,037 (Summers), 5,162,222, (Guarino and Jarvis), 5,169,784 (Summers and Oker-Blom) and 5,278,050 (Summers), each incorporated herein by reference). Baculovirus expression vectors are recombinant insect vectors in which the coding region of a particular gene of interest is placed behind a promoter in place of a nonessential baculoviral gene. The classic approach used to isolate a recombinant baculovirus expression vector is to construct a plasmid in which the foreign gene of interest is positioned downstream of the polyhedrin promoter. Then, via homologous recombination, that plasmid can be used to transfer the new gene into the viral genome in place of the wild-type polyhedrin gene (Summers and Smith, 1987; O'Reilly et al., 1992).

The resulting recombinant virus can infect cultured lepidopteran insect cells or larvae and express the foreign gene under the control of the polyhedrin promoter, which is strong and provides very high levels of transcription during the very late phase of infection. The strength of the polyhedrin promoter is an advantage of the use of recombinant baculoviruses as expression vectors because it usually leads to the synthesis of large amounts of the foreign gene product during infection.

2. Adenoviral Vectors

Another method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue-specific transforming construct that has been cloned therein.

The expression vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1991; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993). Recombinant adenovirus and adeno-associated virus (see below) can both infect and transduce non-dividing human primary cells.

3. AAV Vectors

Adeno-associated virus (AAV) is an attractive vector system for use in the cell transduction of the present invention as it has a high frequency of integration and it can infect nondividing cells, thus making it useful for delivery of genes into mammalian cells for example, in tissue culture (Muzyczka, 1992) or in vivo. AAV has a broad host range for infectivity (Tratschin, et al., 1984; Laughlin, et al, 1986; Lebkowski, et al., 1988; McLaughlin, et al., 1988). Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt, et al., 1994; Lebkowski, et al., 1988; Samulski, et al., 1989; Yoder, et al., 1994; Zhou, et al., 1994; Hermonat and Muzyczka, 1984; Tratschin, et al., 1985; McLaughlin, et al., 1988) and genes involved in human diseases (Flotte, et al., 1992; Luo, et al., 1994; Ohi, et al., 1990; Walsh, et al., 1994; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski, et al., 1989; McLaughlin, et al., 1988; Kotin, et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

4. Retroviral Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

5. Other viral vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al, 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

6. Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

E. Other Methods of DNA Delivery

As well as the viral mediated methods of DNA delivery via infection of cells described above, other methods of introducing the nucleic acid constructs of the present invention into a cell are contemplated. In certain embodiments of the invention, the nucleic acid construct may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

1. Transfection and Transformation

In order to effect expression of a gene construct, the expression construct must be delivered into a cell. As described herein, a preferred mechanism for delivery is via viral infection, where the expression construct is encapsidated in an infectious viral particle. However, several non-viral methods for the transfer of expression constructs into eukaryotic and prokaryotic cells also are contemplated by the present invention. In one embodiment of the present invention, the expression construct may consist only of naked recombinant DNA or plasmids. Transfer of the construct may be performed by any of the methods mentioned which physically or chemically permeabilize the cell membrane.

a. Liposome-Mediated Transfection and Transformation

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

b. Electroporation

In certain embodiments of the present invention, the expression construct is introduced into the cell via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

c. Calcium Phosphate Precipitation or DEAE-Dextran Treatment

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

d. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

e. Direct Microinjection or Sonication Loading

Further embodiments of the present invention include the introduction of the expression construct by direct microinjection or sonication loading. Direct microinjection has been used to introduce nucleic acid constructs into Xenopus oocytes (Harland and Weintraub, 1985), and LTK$^-$ fibroblasts have been transfected with the thymidine kinase gene by sonication loading (Fechheimer et al., 1987).

f. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

g. Receptor Mediated Transfection

Still further expression constructs that may be employed to deliver the construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds a degree of specificity to the present invention. Specific delivery in the context of another mammalian cell type is described by Wu and Wu (1993; incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. In the context of the present invention, the ligand will be chosen to correspond to a receptor specifically expressed on the neuroendocrine target cell population.

In other embodiments, the DNA delivery vehicle component of a cell-specific gene targeting vehicle may comprise a specific binding ligand in combination with a liposome.

The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialoganglioside, incorporated into liposomes and observed an increase in the uptake of the insulin gene by hepatocytes. It is contemplated that the tissue-specific transforming constructs of the present invention can be specifically delivered into the target cells in a similar manner.

F. Heterologous Genes and Proteins

A number of heterologous genes and proteins are contemplated for use in the therapeutic, diagnostic and insecticidal embodiments of the present invention. Below is a list of selected cloned structural genes that are contemplated for use in the present invention (Table 8). The list is not in any way meant to be interpreted as limiting, only as exemplary of the types of structural genes contemplated for use in the present invention. In addition, Table 9 below is an exemplary, but in no means limiting, list of proteins that may be used in the present invention.

TABLE 8

Selected Cloned Structural Genes

| Gene | Clone Type* | Reference |
|---|---|---|
| activin | porcine-cDNA | Mason AJ, Nat, 318:659, 1985 |
| adenosine deaminase | h-cDNA | Wiginton DA, PNAS, 80:7481, 1983 |
| angiotensinogen I | r-cDNA | Ohkubo H, PNAS, 80:2196, 1983 |
|  | r-gDNA | Tanaka T, JBC, 259:8063, 1984 |
| antithrombin III | H-cDNA | Bock SC, NAR 10:8113, 1982 |
|  | h-cDNA and gDNA | Prochownik EV, JBC, 258:8389, 1983 |
| antitrypsin, alpha I | h-cDNA | Kurachi K, PNAS, 78:6826, 1981 |
|  | h-gDNA | Leicht M, Nat, 297:655, 1982 |
|  | RFLP | Cox DW, AJHG, 36:134S, 1984 |
| apolipoprotein A-I | h-cDNA, h-gDNA | Shoulders CC, NAR, 10:4873, 1982 |
|  | RFLP | Karathanasis SK, Nat, 301:718, 1983 Kranthanasis SK, PNAS, 80:6147, 1983 |
|  | h-gDNA |  |
| apolipoprotein A-II | h-cDNA | Sharpe CR, NAR, 12:3917, 1984 Sakaguchi, AY, AJHB, 36:207S, 1984 Knott TJ, BBRC, 120:734, 1984 |
|  | Chr |  |
|  | h-cDNA |  |
| apolipoprotein C-I | h-cDNA | Knott TJ, NAR, 12:3909, 1984 |
| apolipoprotein C-II | h-cDNA | Jackson CL, PNAS, 81:2945, 1984 Mykelbost O, JBC, 249:4401, 1984 Fojo SS, PNAS, 81:6354, 1984 Humphries SE, C Gen, 26:389, 1984 |
|  | h-cDNA |  |
|  | h-cDNA |  |
|  | RFLP |  |
| apolipoprotein C-III | h-cDNA and gDNA | Karanthanasis SK, Nat, 304:371, 1983 Sharpe CR, NAR, 12:3917, 1984 |
|  | h-cDNA |  |
| apolipoprotein E | h-cDNA | Brewslow JL, JBC, 257:14639, 1982 |
| atrial natriuretic factor | h-cDNA | Oikawa S, Nat, 309:724, 1984 |
|  | h-cDNA | Nakayama K, Nat, 310:699, 1984 |
|  | h-cDNA | 1984 Zivin RA, PNAS, 81:6325, |

TABLE 8-continued

Selected Cloned Structural Genes

| Gene | Clone Type* | Reference |
|---|---|---|
|  | h-gDNA | 1984 Seidman CE, Sci, |
|  | h-gDNA | 226:1206, 1984 Nemer M, Nat, |
|  | h-gDNA | 312:654, 1984 Greenberg BI, Nat, 312:665, 1984 |
| chorionic gonadotropin, alpha chain | h-cDNA | Fiddes JC, Nat, 281:351, 1981 |
|  | RFLP | Boethby M, JBC, 256:5121, 1981 |
| chorionic gonadotropin, beta chain | h-cDNA | Fiddes JC, Nat, 286:684, 1980 |
|  | h-gDNA | Boorstein WR, Nat, 300:419, 1982 Talmadge K, Nat, 307:37, 1984 |
|  | h-gDNA |  |
| chymosin, pro (rennin) | bovine-cDNA | Harris TJR, NAR, 10:2177, 1982 |
| complement, factor B | h-cDNA | Woods DE, PNAS, 79:5661, 1982 Duncan R, PNAS, 80:4464, 1983 |
|  | h-cDNA and gDNA |  |
| complement C2 | h-cDNA | Bentley DR, PNAS, 81:1212, 1984 Carroll MC, Nat, 307:237, 1984 |
|  | h-gDNA (C2, C4, and B) |  |
| complement C3 | m-cDNA | Domdey H, PNAS, 79:7619, 1983 Whitehead AS, PNAS, 79:5021, 1982 |
|  | h-gDNA |  |
| complement C4 | h-cDNA and gDNA | Carroll MC, PNAS, 80:264, 1983 Whitehead AS, PNAS, 80:5387, 1983 |
|  | h-cDNA |  |
| complement C9 | h-cDNA | DiScipio RC, PNAS, 81:7298, 1984 |
| corticotropin releasing factor | sheep-cDNA | Furutani Y, Nat, 301:537, 1983 |
|  | h-gDNA | Shibahara S, EMBO J, 2:775, 1983 |
| epidermal growth factor | m-cDNA | Gray A, Nat, 303:722, 1983 |
|  | m-cDNA | Scott J, Sci, 21:236, 1983 |
|  | h-gDNA | Brissenden JE, Nat, 310:781, 1984 |
| epidermal growth factor receptor, oncogene c-erb B | h-cDNA and Chr | Lan CR, Sci, 224:843, 1984 |
| epoxide dehydratase | r-cDNA | Gonzlalez FJ, JBC, 256:4697, 1981 |
| erythropoietin | h-cDNA | Lee-Huang S, PNAS, 81:2708, 1984 |
| esterase inhibitor, dehydratase | h-cDNA | Stanley KK, EMBO J, 3:1429, 1984 |
| factor VIII | h-cDNA and gDNA | Gitschier J, Nat, 312:326, 1984 |
|  | h-cDNA | Toole JJ, Nat, 312:342, 1984 |
| factor IX, Christmas factor | h-cDNA | Kutachi K, PNAS, 79:6461, 1982 Choo KH, Nat, 299:178, 1982 Camerino G, PNAS, 81:498, 1984 Anson DS, EMBO J, 3:1053, 1984 |
|  | h-cDNA |  |
|  | RFLP |  |
|  | h-gDNA |  |
| factor X | h-cDNA | Leytus SP, PNAS, 81:3699, 1984 |
| fibrinogen A alpha, B beta, gamma | h-cDNA | Kant JA, PNAS, 80:3953, 1983 |
|  | h-gDNA (gamma) | Fornace AJ, Sci, 224:161, 1984 |
|  | h-cDNA (alpha gamma) | Imam AMA, NAR, 11:7427, 1983 Fornace AJ, JBC, 259:12826, 1984 |
|  | h-gDNA (gamma) |  |
| gastrin releasing peptide | h-cDNA | Spindel ER, PNAS, 81:5699, 1984 |
| glucagon, prepro | hamster c-DNA | Bell GI, Nat, 302:716, 1983 |
|  | h-gDNA | Bell GI, Nat, 304:368, 1983 |
| growth hormone | h-cDNA | Martial JA, Sci, 205:602, 1979 |
|  | h-gDNA | DeNoto FM, NAR, 9:3719, 1981 Owerbach, D, Sci, 209:289, 1980 |
|  | GH-like gene |  |
| growth hormone, RF, somatocrinin | h-cDNA | Gubler V, PNAS, 80:3411, 1983 |
|  | h-cDNA | Mayo KE, Nat, 306:86:1983 |

TABLE 8-continued

Selected Cloned Structural Genes

| Gene | Clone Type* | Reference |
|---|---|---|
| hemopexin | h-cDNA | Stanley KK, BMBO J, 3:1429, 1984 |
| inhibin | porcine-cDNA | Mason AJ, Nat, 318:659, 1985 |
| insulin, prepro | h-gDNA | Ullrich a, Sci, 209:612, 1980 |
| insulin-like growth factor I | h-cDNA h-cDNA Chr | Jansen M, Nat, 306:609, 1983 Bell GI, Nat, 3 10:775, 1984 Brissenden JE, Nat, 310:781, 1984 |
| insulin-like growth factor II | h-cDNA h-gDNA Chr | Bell GI, Nat, 310:775, 1984 Dull TJ, Nat, 310:777, 1984 Brissenden JE, Nat, 310:781, 1984 |
| interferon, alpha (leukocyte), multiple | h-cDNA h-cDNA (8 distinct) h-gDNA h-gDNA h-gDNA | Maeda S, PNAS, 77:7010, 1980 Goeddel DV, nat, 290:20, 1981 Lawn RM, PNAS, 78:5435, 1981 Todokoro K, EMBO J, 3:1809, 1984 Torczynski RM, PNAS, 81:6451, 1984 |
| interferon, beta (fibroblast) | h-cDNA h-gDNA h-gDNA (related) h-gDNA (related) | Taniguchi T, Gene; 10:11, 1980 Lawn RM, NAR, 9:1045, 1981 Sehgal P, PNAS, 80:3632, 1983 Sagar AD, Sci, 223:1312, 1984 |
| interferon, gamma (immune) | h-cDNA h-gDNA | Gray PW, Nat, 295:503, 1982 Gray PW, Nat, 298:859, 1982 |
| interleukin-1 | m-cDNA | Lomedico PT, Nat, 312:458, 1984 |
| interleukin-2, T-cell growth factor | h-cDNA h-gDNA Chr | Devos R, NAR, 11:4307, 1983 Taniguchi T, Nat, 302:305, 1983 Hollbrook NJ, PNAS, 81:1634, 1984 Siegel LF, Sci, 223:175, 1984 |
| interleukin-3 | m-cDNA | Fung MC, Nat, 307:233, 1984 |
| kininogen, two forms | bovine-cDNA bovine,-cDNA and gDNA | Nawa H, PNAS, 80:90, 1983 Kitamura N, Nat, 305:545, 1983 |
| leuteinizing hormone, beta subunit | h-gDNA and Chr | Talmadge K, Nat, 207:37, 1984 |
| leuteinizing hornone releasing hormone | h-cDNA and gDNA | Seeburg PH, Nat, 311:666, 1984 |
| lymphotoxin | h-cDNA and gDNA | Gray PW, Nat, 312:721, 1984 |
| mast cell growth factor | m-cDNA | Yokoya T, PNAS, 81:1070, 1984 |
| nerve growth factor, beta subunit | m-cDNA h-gDNA Chr | Scott J, Nat, 302:538, 1983 Ullrich A, Nat, 303:821, 1983 Franke C, Sci, 222:1248, 1983 |
| oncogene, c-sis, PGDF chain A | h-gDNA h-cDNA | Dalla-Favera R, Nat, 295:31, 1981 Clarke MF, Nat, 208:464, 1984 |
| pancreatic polypeptide and icosapeptide | h-cDNA | Boel E, EMBO J, 3:909, 1984 |
| parathyroid hormone, prepro | h-cDNA h-gDNA | Hendy GN, PNAS, 78:7365, 1981 Vasicek TJ, PNAS, 80:2127, 1983 |
| plasminogen | h-cDNA and gDNA | Malinowski DP, Fed P, 42:1761, 1983 |
| plasminogen activator | h-cDNA h-cDNA h-gDNA | Edlund T, PNAS, 80:349, 1983 Pennica D, Nat, 301:214, 1983 Ny T, PNAS, 81:5355, 1984 |
| prolactin | h-cDNA r-gDNA | Cook NE, JBC, 256:4007, 1981 Cooke NE, Nat, 297:603, 1982 |
| proopio-melanocortin | h-cDNA h-gDNA | DeBold CR, Sci, 220:721, 1983 Cochet M, Nat, 297:335, 1982 |
| protein C | h-cDNA | Foster D, PNAS, 81:4766, 1984 |
| prothrombin | bovine-cDNA | MacGillivray RTA, PNAS, 77:5153, 1980 |
| relaxin | h-gDNA h-cDNA (2 genes) Chr | Hudson P, Nat, 301:628, 1983 Hudson P, EMBO J, 3:2333, 1984 Crawford, RJ, EMBO J, 3:2341, 1984 |
| renin, prepro | h-cDNA h-gDNA h-gDNA Chr | Imai T, PNAS, 80:7405, 1983 Hobart PM, PNAS 81:5026, 1984 Miyazaki H, PNAS, 81:5999, 1984 Chirgwin JM, SCMG, 10:415, 1984 |
| somatostatin | h-cDNA h-gDNA and Ri-IP | Shen IP, PNAS, 79:4575, 1982 Naylot SI, PNAS, 80:2686, 1983 |
| tachykinin, prepro, substances P & K | bovine-cDNA bovine-gDNA | Nawa H, Nat, 306:32, 1983 Nawa H, Nat, 312:729, 1984 |
| urokinase | h-cDNA | Verde P, PNAS, 81:4727, 1984 |
| vasoactive intestinal peptide, prepro | h-cDNA | Itoh N, Nat, 304:547, 1983 |
| vasopressin | r-cDNA | Schmale H, EMBO J, 2:763, 1983 |

Key to Table 8:
*cDNA - complementary DNA;
Chr - chromosome;
gDNA - genomic DNA; RFLP - restriction fragment polymorphism;
h - human;
m - mouse;
r - rat

TABLE 9

Heterologous Proteins for Use in the Present Invention

| Heterologous Protein | Reference |
|---|---|
| AcMNPV p10 | Weyer et al. 1988 |
| adeno-associated virus Rep 78 | Owens et al. 1991 |
| adenovirus: | |
| E3/19K protein | Levy and Kvist 1990 |
| preterminal protein (pTP) | Zhao et al. 1991 |
| types 5 and 12 12S, 13S | Peeper et al. 1992 |
| EIA | Patel and Jones 1990 |
| type 2 DNA polymerase | Watson et al. 1990 |
| type 2 fiber | Novelli et al. 1991 |
| type 2 fiber | Novelli and Boulanger 1991 |
| type 2-penton base | Karayan et al. 1994 |
| type 2 protease | Keyvani-Amineh et al. 1995 |
| African horsesickness: | |
| reovirus type 4-VP7 | Chuma et al. 1992 |
| virus - VP2 | Martinez-Torrecuadrada et al. 1994 |
| virus - VP5 | Martinez-Torrecuadrada et al. 1994 |
| virus - VP7 | Basak et al. 1996 |
| virus - Serotype 3 NS2, VP7 | Bremer et al. 1994 |
| African swine fever virus p12 | Angulo et al. 1993 |
| altacin | Hellers and Steiner 1992 |
| Amyloid precursor protein (APP) | Bhasu et al. 1991 |
| *Androctonus australis*: | |
| AaIT | Maeda et al. 1991 |
| Hector neurotoxin | Stewart et al. 1991 |
| *Antheraea pernyi* pheromone-binding protein | Krieger et al. 1992 |
| antibodies: | |
| bovine anti-lipoprotein I of (lgb) | Reis et al. 1992 |
| *Pseudomonas aeruginosa* apoprotein of L-gulono-g-lactone oxidase | Nishikimi et al. 1994 |
| Arabis mosaic virus (ARMV) coat protein | Bertoili et al. 1991 |

TABLE 9-continued

Heterologous Proteins for Use in the Present Invention

| Heterologous Protein | Reference |
|---|---|
| Avian erythroblastosis virus v-erbb | Morishita et al. 1992 |
| Avian myeloblastosis virus - v-myb | Vranosvsky et al. 1992 |
| $b_2$-microglobulin | Levy and Kvist 1990 |
| BTV VP2 | Urakawa et al. 1994 |
| *B. pertussis* tetanus toxin | Peakman et al. 1992 |
| *B-thuringiensis* delta endotoxin | Pan et al. 1992 |
| *Bacillus thuringiensis* | Martens 1994 |
| *Bacillus thuringensis* subsp *kurstaki* HD-1 cry1A | Ribeiro and Crook 1993 |
| *Bacillus thuringensis* subsp *kurstaki* HD-73 cry1A | Ribeiro and Crook 1993 |
| *Bacillus anthracis* protective antigen | Iacono-Conners et al. 1990 |
| *Bacillus thuringienesis* CryIVD | Pang et al. 1992 |
| barley (1—>3,1—>4)-b-glucanase (EC3.2.1.73) | |
| isoenzyme EI | Doan et al. 1993 |
| isoenzyme EII | Doan et al. 1993 |
| bat plasminogen activator DSPAa1 | Petri et al. 1995 |
| bluetongue virus: | |
| chimeric VP3 | Tanaka et al. 1995 |
| Type 10 group specific antigen VP3 | Inumaru et al. 1987 |
| Type 10 NS1 structural gene product | Urakawa et al. 1988 |
| Type 10; NS3 and NS3A | French et al. 1989 |
| Type 10 VP3; VP7 | Hewat et al. 1992 |
| Type 10 neutralization antigen VP2 | Inumaru et al. 1987 |
| Type 10 VP1 protein | Urakawa et al. 1989 |
| Type 10 VP6 | Roy et al. 1990 |
| Type 10 VP5 | Loudon et al. 1991 |
| Type 10 VP7 | Basak et al. 1992 |
| VP1, VP2, VP3, VP5, VP7 | Loudon et al. 1991 |
| VP2, VP3, VP5, VP7 | Belyaev and Roy 1993 |
| VP3, VP7 | LeBlois and Roy 1993 |
| VP7 | Belyaev and Roy 1992 |
| virus-10 NS1 | Monastyrskaya 1994 |
| virus 10 NS1 | Zhao et al. 1994 |
| *Bombyx mori* chorion genes HcA.12 - HcB.12 | Iatrou and Meidinger 1990 |
| *Boophilus microphis* BM86 | Richardson et al. 1993 |
| Borna Disease Virus p24, p38/40 | Hsu et al. 1994 |
| bovine: | |
| ADP-ribosylation factors | Kunz et al. 1993 |
| b-adrenergic receptor kinase | Kim et al. 1993 |
| calcineurin | Fan et al. 1996 |
| cation-dependent mannose 6-phosphate receptors | Dahms & Brzycki-Wessell 1995 |
| cytochrome P-450 precursor inactive | Takagi et al. 1992 |
| cytochrome P-450 | Takagi et al. 1992 |
| endothelial nitric oxide synthase | Busconi & Michel 1995 |
| GABA receptor a1,b1 subunits | Atkinson et al. 1992 |
| herpes virus type 1 glycoprotein GI | van den Hurk et al. 1992 |
| herpes virus 1-glycoprotein III | Okazaki et al. 1994 |
| immunodeficiency-like virus gp145, gp100, gp45 | Rasmissen et al. 1992 |
| liver carboxylase vitamin K-dependent | Roth et al. 1993 |
| nicotinic acetylcholine receptor - a subunit | Iizuka and Fukuda 1993 |
| opsin | Jansen et al. 1991 |
| p450 c17 | Barnes et al. 1994 |
| Ras GTPase-activating protein (GAP) | Park et al. 1992 |
| rhodopsi | DeCaluwe et al. 1993 |
| rod cGMP-gated cation channel subunit 1 | Marheineke et al. 1995 |
| rotavirus (RF strain) genomic segment 5 | Brottier et al. 1992 |
| rotovirus NsP2, NsP3 | Aponte et al. 1993 |
| type-1 CGMP-dependent protein kinase | Boerth and Lincoln 1994 |
| UDP-GalNAc:polypeptide, N-acetylgalactosaminyltransferase | Homa et al. 1995 |
| viral diarrhoea virus - nonstructural proteins | Petric et al. 1992 |
| bovine respiratory syncytial virus: | |
| nucleocapsid protein | Samal et al. 1993 |
| fusion protein | Hines and Gershins 1992 |
| bread wheat LMW glutenin | Thompson et al. 1994 |
| Broadhaven virus VP2, VP7 | Moss and Nuttall 1994 |
| c-abl IV proto-oncogene | Peakman et al. 1992 |
| cGMP-dependent protein kinases Ib and II | Pohler et al. 1995 |
| cabbage histidinol dehydrogenase | Nagai et al. 1992 |
| *Caenorhabditis elegans* a subunit of prolyl 4-hydroxylase | Veijola et al. 1994 |
| *Campoletis sonorensis* segment w | Blissard et al. 1989 |
| canine parvovirus VP2 | Lopez de Turiso et al. 1992 |
| carp gonadotropin a1, a2 | Huang et al. 1991 |
| Cauliflower mosaic virus: | |
| aphid transmission factor | Blanc et al. 1993 |
| | Espinazo et al. 1992 |
| gene 1 | Vlak et al. 1990 |
| P1 | Maule et al. 1992 |
| cecropin | Andersons et al. 1991 |
| | Hellers and Steiner 1992 |
| cecropin A | Andersons et al. 1991 |
| cell-CAM105 isoform | Cheung et al. 1993 |
| chicken: | |
| anaemia virus VP1 | Koch et al. 1995 |
| anaemia virus VP2 | Koch et al. 1995 |
| anaemia virus VP3 | Koch et al. 1995 |
| caldesmon | Wang et al. 1994 |
| erythroid-specific transcription factor cGATA-1 | Pikaart & Felsenfeld 1996 |
| gizzard heavy meromyosin | Onishi et al. 1995 |
| liver gluthione S-transferase | Chang et al. 1992 |
| c-myb | Vranovsky et al. 1992 |
| myosin II-B | Pato et al. 1996 |
| $P60^{c-src}$ | Morgan et al. 1991 |
| poly(ADP-ribose) polymerase | Jung et al. 1994 |
| progesterone receptor (A form) | Elliston et al. 1992 |
| c-Src | Park et al. 1992 |
| chimeric plasminogen activator (scu-PA) | Devlin et al. 1989 |
| chloramphenicol acetyltransferase (CAT) | Zhang et al. 1993 |
| chronic myelongenous leukemia associated P210 | Pedergast et al. 1989 |
| coronavirus: | |
| bovine hemagglutinin-esterase | Yoo et al. 1991 |
| bovine spike protein S, S1 | Yoo et al. 1991 |
| mouse hepatitis virus JHM E2 peplomer glycoprotein | Yoden et al. 1989 |
| cowpea mosaic virus 200k polyprotein | Bokhoven et al. 1992 |
| cystic fibrosis gene product (CFTR) | Kartner et al. 1991 |
| cytochrome P450 CYP2D6 | Paine et al. 1996 |
| cytochrome P450 2C11 | Biagini & Celier 1996 |
| cytochrome P450 | |
| 2A1 | Grogan et al. 1995 |
| 2E1 | Grogan et al. 1995 |
| 2C9 | Grogan et al. 1995 |
| dengue virus: | |
| envelope glycoprotein | Staropoli et al. 1996 |
| 1 envelope glycoprotein | Putnak et al. 1991 |
| 1 envelope proteins | Johnson et al. 1994 |
| 2 envelope proteins | Johnson et al. 1994 |
| 2 glycoproteins | Delenda et al. 1994 |
| 2 NS1 protein | Leblois & Young 1995 |
| 2 virus envelope protein | Delenda et al. 1994 |
| 3 glycoproteins | Delenda et al. 1994 |
| 4 virus core protein | Makino et al. 1989 |

TABLE 9-continued

Heterologous Proteins for Use in the Present Invention

| Heterologous Protein | Reference |
|---|---|
| 4 virus C, preM, E, NS1 and NS2a | Rothan et al. 1989 |
| 4 E protein | Makino et al. 1992 |
| type-2 envelope protein | Feighny et al. 1994 |
| virus C, preM, E, NS1 and NS2 | Zhang et al. 1988 |
| virus envelope glycoprotein | Men et al. 1991; Deubel et al. 1991 |
| dihydroxyvitamin $D_3$ receptor | Ross et al. 1991 |
| $D_2$ dopamine receptor | Sanderson & Strange 1995 |
| Drosophila: | |
| cation channel trp1 | Harteneck et al. 1995 Dong et al. 1995 |
| GABA receptor | Lee et al. 1993 |
| *melanogaster* acetylcholinesterase | Chaabihi et al. 1994 |
| *melanogaster* Kr protein | Ollo et al. 1987 |
| *melanogaster* casein kinase II a and b subunits | Birnbaum et al. 1992 |
| protein trp | Vaca et al. 1994 |
| shaker potassium channel protein | Santacruz-Toloza et al. 1994 |
| trpL protein, $M_5$ muscarinic receptor | Hu et al. 1994 |
| *Eimeria acervulina merozoite* antigen | Jenkins et al. 1991 |
| ENV | Yamshchikov et al. 1995 |
| $ENV_t$ | Yamshchikov et al. 1995 |
| epidermal growth factor receptor extracellular domain | Tom et al. 1995 |
| epizootic haemorrhagic disease virus capsid protein | Nagesha et al. 1996 |
| epizootic hemorrhagic disease virus (EHDV) VP3 | Le Blois et al. 1991 |
| epoxide hydrolase | Wang et al. 1993 |
| Epstein-Barr virus: | |
| alkaline deoxyribonuclease | Baylis et al. 1991 |
| DNA polymerase accessory protein | Tsurumi 1993 |
| gp85 | Pulford et al. 1995 |
| gp125 | Sanchez-Martinez et al. 1995 |
| gp350 | Zhang and Marcus-Sekura 1993 |
| latent membrane protein | Chen et al. 1992 |
| membrane antigen gp350/220 | Nuebling et al. 1992 |
| nuclear antigen 2 | Schubach et al. 1991 |
| nuclear antigen 1, 2A and 2B | Hille et al. 1993 |
| latent membrane protein | Chen et al. 1992 |
| pp58 and DNase | Chen et al. 19?? |
| TP1 | French et al. 1990 |
| virus envelope fusion glycoprotein gp85 | Pulford et al. 1994 |
| equine herpesviridae: | |
| glycoprotein D | Love et al. 1993 |
| 1-glycoprotein C | Whalley et al. 1995 |
| 1-glycoprotein D | Whalley et al. 1995 Flowers et al. 1995 |
| 1-glycoprotein H | Whalley et al. 1995 |
| 1-glycoprotein L | Whalley et al. 1995 |
| type 1-gp14 | Osterrieder et al. 1994 |
| infectious anemia virus gp90 | Wang et al. 1994 |
| *Escherichia-coli* B-galactosidase | Pennock et al. 1984 |
| *Escherichia coli* b-galactosidase | Hara et al. 1993 |
| feline: | |
| immunodeficiency virus envelope glycoprotein | Lutz et al. 1996 |
| leukaemia virus, gag, gp85 | Thomsen et al. 1992 |
| leukaemia virus, gag, env | Wardley et al. 1992 |
| firefly luciferase | Jha et al. 1990 Hasnain and Nakhai 1990 Hasnain et al. 1994 Palhan et al. 1995 |
| flock house virus coat protein | Fisher et al. 1993 |
| flock house virus - RNA2 | Schneedmann et al. 1993 |
| foot and mouth disease virus: | |
| capsid protein | Belsham et al. 1991 |
| P1 | Saiz et al. 1994 |
| peptide 2A | Saiz et al. 1994 |

TABLE 9-continued

Heterologous Proteins for Use in the Present Invention

| Heterologous Protein | Reference |
|---|---|
| structural protein precursor (P1) | Lewis et al. 1991 |
| truncated 2B | Saiz et al. 1994 |
| G-protein a subunits | Graber et al. 1994 |
| G-protein-coupled receptors | Zastawny et al. 1994 |
| $G_q$ family G proteins | |
| $G_{L1}a(G_{14}a)$ | Nakamura et al. 1995 |
| $G_{L2}a(G_{11}a)$ | Nakamura et al. 1995 |
| $G_qa$ | Nakamura et al. 1995 |
| GluR-D glutamate receptor | Kuusinen et al. 1995 |
| GTP binding protein Ra66 | Yang et al. 1992 |
| GTPase-activating protein | Settleman & Foster 1995 |
| $a_{i-2}$ subunit of GTP-binding protein | Inoue et al. 1995 |
| b-Galactosidase | Licari et al. 1992 |
| genetically engineered immuno-globulins | Coloma & Morrison 1993 |
| Gravis disease thyrotrophin hormone receptor | Huang et al. 1993 |
| guanine nucleotide-binding proteins | Graber et al. 1992 |
| Ha-ras p21 | Page et al. 1989 |
| HRab1A | Drummond & McCaffrey 1995 |
| hamster B2-adrenergic receptor | Reilander et al. 1991 |
| hamster prion protein | Scott et al. 1988 |
| Hantaan virus: | |
| N and Env proteins | Yoshimatsu et al. 1993 |
| nucleocapsid protein | Schmaljohn et al. 1988 Rossie et al. 1990 |
| hantavirus nucleocapsid protein | Yoshimatsu et al. 1995 |
| *Heliothis virescens* juvenile hormone esterase | Booth et al. 1992 |
| hematopoietic necrosis virus glycoprotein | Koener et al. 1990 |
| heme-regulated eIF-2a kinase | Chefalo et al. 1994 |
| hepatitis virus: | |
| A virus VP1, VP3 and P2 | Harmon et al. 1988 |
| A virus ORF | Rosen et al. 1993 |
| B virus M envelope protein | Price et al. 1988 |
| B virus capsid | Beames et al. 1991 |
| B virus polymerase | Lanford et al. 1995 |
| B surface antigen | Higashihashi et al. 1991 |
| B surface and core antigens | Lanford et al. 1990 |
| B virus X protein | Spandau et al. 1991 |
| C capsid, E1, E2/NS1 | Hsu et al. 1993 |
| C virus capsid - E1, E2, NS1 | Lanford et al. 1993 |
| C virus core protein | Chiba et al. 1991 |
| C virus E1 glycoprotein | Matsuura et al. 1994 |
| C virus E2 glycoprotein | Matsuura et al. 1994 |
| C virus envelope protein | Matsuura et al. 1992 |
| C virus NS3 proteinase | Overton et al. 1995 |
| C virus protease NS3 | Steinkuhler et al. 1996 |
| C virus serine proteinase | Suzuki et al. 1995 |
| delta antigen | Kos et al. 1991 |
| E ORF2 | Tsarev et al. 1993 |
| human hepatitis delta virus - large and small delta antigen | Huang et al. 1992 |
| herpes virus: | |
| DNA polymerase | Marcy et al. 1990 |
| simplex type 2 - glycoprotein D | Landolfi et al. 1993 |
| type 1 glycoprotein | Krishan et al. 1989 |
| type 1 glycoprotein | Ghiasi et al. 1992 |
| type 1 glycoprotein D | Damhof et al. 1994 |
| type 1 glycoprotein I | Ghiasi et al. 1992 |
| type 1 glycoprotein C | Ghiasi et al. 1992 |
| type 1 glycoprotein G | Sanchez-Martinez et al. 1991 |
| type 1 glycoprotein H | Ghiasi et al. 1991 |
| type 1 glycoprotein L | Ghiasi et al. 1994 |
| type 1, origin binding protein | Olico et al. 1988 |
| type 1 UL30 | Stow 1992 |
| type 1 UL42 | Stow 1992 |
| type 1 UL29 | Stow 1992 |
| type 1 UL9 | Stow 1992 |
| type 1 UL5 | Stow 1992 |

TABLE 9-continued

Heterologous Proteins for Use in the Present Invention

| Heterologous Protein | Reference |
| --- | --- |
| type 1 UL8 | Stow 1992 |
| type 1 UL52 | Stow 1992 |
| type 1–2 gG1 and gG2 | Sanchez-Martinez et al. 1991 |
| type 2 glycoprotein D | Damhof et al. 1994 |
| type 2 glycoprotein G | Sanchez-Martinez et al. 1991 |
| type 1 glycoprotein gIV | van Drunen et al. 1991 |
| type 1 glycoprotein gD | Sisk et al. 1994 |
| type 1 thymidine-thymidylate kinase | Godeau et al. 1992 |
| bovine herpesvirus I glycoprotein gIV | Lutel-van den Hurk et al. 1991 |
| thymidine kinase | Wang et al. 1992 |
| simplex virus - type 1 - glycoprotein B | Ghiasi et al. 1991 |
| simplex virus - glycoprotein G | Ghiasi et al. 1992 |
| simplex virus type 1 - glycoprotein C | Ghiasi et al. 1992 |
| simplex virus type 1 - gk | Ghiasi et al. 1994 |
| simplex virus vp5, vp19c, vp21, vp22a, vp23, vp24 and vp26 | Thomsen et al. 1994 |
| hirudin | Benette et al. 1991 |
| hog cholera virus E1 | Hulst et al. 1993 |
| human: | |
| 2AP-70 protein-tyrosine kinase | Isakov et al. 1996 |
| ABC transporter tap1 processing (TAP) | Meyer et al. 1994 |
| ABC transporter tap2 processing (TAP) | Meyer et al. 1994 |
| a$_2$ C$_2$ adrenoceptor | Marjamaki et al. 1994 |
| a-galactosidase A | Coppola et al. 1994 |
| a and b globins | Groebe et al. 1992 |
| a$_1$ glycine receptor | Cascio et al. 1993 |
| a-macroglobulins (aM) | Rompaey & Marynen 1992 |
| a and b platelet-derived growth factor receptors | Jensen et al. 1992 |
| adenosine deaminase | Medin et al. 1990 |
| aldase reductase | Nishimura et al. 1991 |
| a-interferon | Maeda et al. 1985 |
| 5-a reductase (type 1) | Delos et al. 1994 |
| Ah receptor and Ah receptor nuclear translocater | Chan et al. 1994 |
| alzheimer amyloid precursor protein | Ramakrishna et al. 1991 |
| alzheimer b-amyloid peptide precursor | Currie et al. 1991 |
| amyloid peptide precursor | Essalmani et al. 1996 |
| amyloid precursor protein | Bhasin et al. 1991 |
| amyloid b protein precursor | Bhasin et al. 1991 |
| amyloid precursor protein | Lowery et al. 1991 |
| androgen receptor | Beitel et al. 1995 |
| angiotensin | Williams et al. 1994 |
| androgen receptor | Chang et al. 1992 |
| antithrombin III | Gillespie et al. 1991 |
| apolipoprotein E | Gretch et al. 1991 |
| aromatase P450 | Amarneh & Simpson 1995 |
| autoantigen of Wegener's granulomatrosis (PR3) | Szymkowiak et al. 1996 |
| b1,2-N-acetylglucosaminyl-transferase I (hGNT-I) | Wagner et al. 1996 |
| b$_1$g$_2$ dimers of G-protein | Dietrich et al. 1992 |
| b$_1$,b$_2$,g$_2$ subunits of hetertrimeric guanine nucleotide-binding protein | Graber et al. 1992 |
| b$_1$-adrenergic receptor | Ravet et al. 1992 |
| b$_2$-adrenergic receptor | Kleymann et al. 1993 |
| b-adrenergic receptor kinase | Sohlemann et al. 1993 |
| b galactosidase | Itoh et al. 1990 |
| b interferon | Smith et al. 1983 |
| b$_2$-glycoprotein I | Igarashi et al. 1996 |
| BCl2 | Alnemri et al. 1992 |
| BCl-2 oncoprotein | Reid et al. 1992 |
| bone morphogenetic protein-2 | Maruoka et al. 1995 |
| Cc gene | Poul et al. 1995 |
| Cg1 sequence | Poul et al. 1995 |
| C-reactive protein | Marnell et al. 1995 |
| cAMP-specific phosphodiesterase | Amegadzie et al. 1995 |
| CD95/APO-1/Fas ligand | Mariani et al. 1996 |
| CD4 | Murphy et al. 1990 |
|  | Lazarte et al. 1992 |
| Cdc42 GTP-binding protein | Cerione et al. 1995 |
| c-fos protein | Tratner et al. 1990 |
| CYP2A6 | Nanji et al. 1994 |
| calpain I | Meyer et al. 1996 |
| carcinoembryonic antigen | Bei et al. 1994 |
| carcinoemryonic antigen CD 66b | Yamamaka et al. 1996 |
| carcinoembryonic antigen CD66c | Yamamaka et al. 1996 |
| cholecystokinin B (CCK$_B$) | Gimpl et al. 1996 |
| choriogonadotropin a subunit | Nakhai et al. 1991 |
| choriogonadotropin β-subunit | Chen et al. 1991 |
| choriogonadotropin β-subunit descarboxyl-terminal peptide | Chen and Bahl 1991 |
| chorionic gonadotropin hormone precursor | Nakhai et al. 1991 |
| chorionic gonadotropin hormone (b-subunit) | Hasnain et al. 1994 |
| chorionic gonadotropin hormone b subunit | Nakhai et al. 1992 |
| complement C1r | Sass et al. 19?? |
| complement C1r proenzyme | Gal et al. 1989 |
| complement protein C9 | Tomlinson et al. 1993 |
| corticosteroid binding globulin | Ghose Dastidar et al. 1991 |
| c-myc protein | Miyamoto et al. 1985 |
| complement protein C9 | Tomlinson et al. 1993 |
| corticosteroid binding globulin (hCBG) | Ghose-Dastidar et al. 1991 |
| creatine kinase B (B-CK) | de Kok et al. 1995 |
| cyclooxygenase-2 | Cromlish et al. 1994 |
| cytochrome b$_5$ | Patten & Koch 1995 |
| cytochrome B$_{558}$ | Katkin et al. 1992 |
| cytochrome CYP3A4 | Lee et al. 1995 |
| cytochrome P450 CYP3A4 | Buters et al. 1994 |
| cytochrome P-450 isoform(s) | Clair et al. 1994 |
| cytomegalovirus 65K tegument phosphoprotein | La Fauci et al. 1994 |
| cytomegalovirus IE1, IE1 exon 4 | Davrinche et al. 1993 |
| cytosolic phospholipase A$_2$ | Abdullah et al. 1995 |
| D4 dopamine receptor | Mills et al. 1993 |
| DNA ligase I | Gallina et al. 1995 |
| DNA polymerase a subunit | Copeland and Wang 1991 |
| DNA polymerase d catalytic subunit | Zhou et al. 1996 |
| DNA topoisomerase 1 | Zhelkovsky & Moore 1994 |
| dopamine D$_2$ receptor | Javitch et al. 1994 |
| EGF receptor | Greenfield et al. 1988 |
| EGF receptor-tyrosine kinase domain | Wedegaertner et al. 1989 |
| endothelial nitric-oide synthase | Chen et al. 1996 |
| epidermal growth factor receptor | Waterfield & Greenfield 1991 |
| epidermal-growth-factor receptor protein-tyrosine kinase | McGlynn et al. 1992 |
| epidermal growth factors IX and XIIa | Astermark et al. 1994 |
| erythrocyte anion exchanger | Dale et al. 1996 |
| erythropoietin | Quelle et al. 1992 |
| estrogen receptor | Beekman et al. 1994 |
| factor VIII - B domain deleted | Webb et al. 1993 |
| fibroblast growth factor receptor subtype ligand binding domain | Sisk et al. 1992 |
| follicle-stimulating hormone receptor | Christophe et al. 1993 |
| furin | Bravo et al. 1994 |
| GABA$_A$ receptor a1 subunits | Birnir et al. 1995 |
| GABA$_A$ receptor b1 subunits | Birnir et al. 1995 |
| ga773 - 2 antigen | Strassburg et al. 1992 |
| GMP synthetase | Lou et al. 1995 |
| glucocerebrosidase | Martin et al. 1988 |
| glucocorticoid receptor | Srinivasan et al. 1990 |
| glutamic acid decarboxylase | Mauch et al. 1993 |
| glycine receptor a1 | Morr et al. 1995 |
| group b rotavirus ADRV, VP4 | Mackow et al. 1993 |
| group II Phospholipase A$_2$ | Tremblay et al. 1993 |
| growth hormone | Sumathy et al. 1996 |
| growth hormone receptor - extracellular domain | Ota et al. 1991 |
| 5-HT$_{1A}$ receptor | Mulheron et al. 1994 |
| hst-1 transforming protein | Miyagawa et al. 1988 |
| heart (R)-3-hydroxybutyrate dehydrogenase | Green et al. 1996 |

TABLE 9-continued

Heterologous Proteins for Use in the Present Invention

| Heterologous Protein | Reference |
| --- | --- |
| hematopoietic glycopeptide erythropoietin | Quelle et al. 1992 |
| hemopexin | Satoh et al. 1994 |
| heparin cofactor II | Ciaccia et al. 1995 |
| hepatitis b virus X protein | Klein et al. 1992 |
| hepatocyte growth factor | Yee et al. 1993 |
| hepatocyte growth factor | Lee et al. 1993 |
| high-affinity IgE receptor-a chain | Yagi et al. 1994 |
| 17b-hydroxysteriod dehydrogenase | Breton et al. 1994 |
| 5-hydroxytryptamine$_{1A}$ | Butkerait et al. 1995 |
| 5-hydroxytryptamine receptors (5-HT$_{1A}$, 5-HT$_{1Da}$, 5-HT$_{1Db}$, 5-HT$_{1E}$) | Parker et al. 1994 |
| IgA | Carayannopoulos et al. 1994 |
| IL2 receptor a & b chains | Lindqvist et al. 1993 |
| immunodeficiency virus-type 1 gag precursor | Chazal et al. 1994 |
| immunodeficiency virus-1 gp41 | Lu et al. 1993 |
| immunodeficiency virus-1 gp120 | Yeh et al. 1993 |
| insulin holoreceptor | Paul et al. 1990 |
| insulin receptor substrate-1 | Siemeister et al. 1995 |
| insulin receptor b-subunit | Herrera et al. 1988 |
| insulin receptor b subunit transmembrane/cytoplasmic domain | Li et al. 1992 |
| insulin receptor ectodomain | Sissom et al. 1989; 1991 |
| insulin receptor protein-tryosine kinase domain | Ellis et al. 1988 |
| insulin receptor cytoplasmic domain of b subunit | Herrera et al. 1988 |
| insulin receptor protein tyrosine-kinase-cytoplasmic domain | Ellis and Levine 1991 |
| insulin-like growth factor II | Congote and Li, 1994 |
| insulin-like growth factor II | Marumoto et al. 1992 |
| intercellular adhesion molecule 1 (1CAM-1) | Cobb et al. 1992 |
| interferon-g glycoforms | Ogonah et al. 1995 |
| interleukin 2 | Smith et al. 1985 |
| interleukin 2 glycoprotein variants | Grabenhorst et al. 1993 |
| interleukin-2 receptor gamma chain | Raivio et al. 1995 |
| interleukin 5 | Brown et al. 1995 |
| interleukin 6 | Matsuura et al. 1991 |
| interleukin-6 receptor | Weiergraber et al. 1995 |
| intrinsic factor | Gordon et al. 1992 |
| iron regulatory factor | Emery-Goodman et al. 1993 |
| isoforms (neuronal, inducible, endothelial) nitric oxide synthase | Nakane et al. 1995 |
| Ku autoantigen | Allaway et al. 1990 |
| lecithin-cholesterol acyltransferase | Chawla & Owen 1995 |
| Leukotriene A$_4$ hydrolase | Gierse et al. 1993 |
| link protein | Grover & Roughley 1994 |
| liver carboxylesterase | Kroetz et al. 1993 |
| lymphocytic activation gene (LAG-1) | Baizleras et al. 1990 |
| lysyl hydroxylase | Krol et al. 1996 |
|  | Pirskanen et al. 1996 |
| lysosomal b-galactosidase | Itoh et al. 1991 |
| 5'lipoxygenase | Dunk et al. 1989 |
| m1 muscarinic acetylcholine receptors | Haga et al. 1996 |
| m2 muscarinic cholinergic receptor | Debburman et al. 1995 |
| m3 (hm3) muscarinic cholinergic receptors | Debburman et al. 1995 |
| MHC class I HLA-b27 antigen | Levy and Kvist 1990 |
| MHC class II DR4a, DR4b, extra-cellular domain | Scheerle et al. 1992 |
| macrophage colony stimulating factor | Qiu et al. 1995 |
| matrilysin | Lopez de Turiso et al. 1996 |
| metallothionein-II | Schmiel et al. 1985 |
| mineralocorticosteriod receptor | Binart et al. 1991 |
| monocyte chemoattractant protein-1 | Ueda et al. 1994 |
|  | Ishii et al. 1995 |
| multidrug resistance 1 | Germann et al. 1990 |
| multidrug resistance P-glycoprotein | Rao et al. 1994 |
| muscarine receptor m2 | Kameyama et al. 1994 |
| myeloperoxidase | Taylor et al. 1992 |
| myogenic factors myf4, myf5 | Braun et al. 1991 |
| N-formyl peptide receptor | Quehenberger et al. 1992 |
| Na$^+$/H$^+$ antiporter | Fafournoux et al. 1991 |
| NADPH-P450 oxidoreductase | Tamura et al. 1992 |
| nerve growth factor | Buxser et al. 1991 |
| nerve growth factor receptor | Vissavajjhala et al. 1990 |
| neutrophil NADPH oxidase factors p47-[phox], p67[phox] | Leto et al. 1991 |
| nuclear hormone receptor H-2R11BP | Marks et al. 1992 |
| nucleolar protein p120 | Ren et al. 1996 |
| oxytocin receptor | Gimpl et al. 1995 |
| p53 | Patterson et al. 1996 |
| P450 2E1 | Patten & Koch 1995 |
| pancreatic lipase | Thirstrup et al. 1993 |
| pancreatic procolipase | Lowe 1994 |
| papillmoavirus type 11 E1, E2 | Bream et al. 1993 |
| papillomavirus type 11-L1 protein | Rose et al. 1993 |
| papillomavirus type 16 E2 | Sanders et al. 1995 |
| papillomavirus type 16 E2 protein | Sanders et al. 1995 |
| papillomovirus type 16 L1, L2 | Xi and Banks, 1991 |
| papillomavirus type 45 L1 major capsid protein | Touze et al. 1996 |
| parainfluenza virus type 3, 7, HN, 7HN | Lehman et al. 1993 |
| parathyroid hormone | Mathavan et al. 1995 |
| parvovirus B19 vp1, vp2 | Cubie et al. 1993 |
| phospholipase A$_2$ | Abdullah et al. 1995 |
| placental aromatase (CYP19A1) | Sigle et al. 1994 |
| plasma plasminogen | Whitefleet-Smith et al. 1989 |
| plasminogen | Davidson et al. 1991 |
| plasminogen (HPg) | Castellino et al. 1993 |
| plasminogen activator inhibitor-2 | Pei et al. 1995 |
| platelet glycoprotein IBb | Finch et al. 1996 |
| platelet 12-lipoxygenase | Chen et al. 1993 |
| poly(ADP-ribose) polymerase | Giner et al. 1992 |
| pre-pro endothelin-1 | Benatti et al. 1992 |
| pre-pro gastrin releasing peptide | Lebacq-verheyden et al. 1988 |
| pro-al(III) chains | Tomita et al. 1995 |
| proapoA-I | Sorci-Thomas et al. 1996 |
| progesterone receptor (A form) | Elliston et al. 1992 |
| progesterone receptors A&B forms | Christensen et al. 1991 |
| prolyl 4-hydroxylase a, b subunits | Vuori et al. 1992 |
| prolyl 4-hydroxylae a subunit with BiP polypeptide | Veijola et al. 1996 |
| prosaposin | Leonova et al. 1996 |
| prostaglandin G/H synthase | George et al. 1996 |
| prostaglandin G/H synthase 1 | Barnett et al. 1994 |
| prostaglandin G/H synthase 2 | Barnett et al. 1994 |
| protein disulphide isomerase | Vuori et al. 1992 |
| protein kinase c-d | Rankl et al. 1994 |
| protein kinase Cm | Dieterich et al. 1996 |
| pro-urokinase | Gao and Hu 1994 |
| rab 6 | Yang et al. 1992 |
| rap1A | Quilliam et al. 1990 |
| recombinant IL-8 | Kang et al. 1992 |
| recombinant p56[1ck] | Flotow et al. 1996 |
| renin | Mathews et al. 1996 |
| respiratory syncytial virus F and G glycoproteins | Wathen et al. 1989 |
| retinoblastoma pp110[RB] | Wang et al. 1990 |
| retinoic acid receptor a1 | Quick et al. 1994 |
| retinoic acid receptor - g1 | Reddy et al. 1992 |
| ssDNA-binding protein | Stigger et al. 1994 |
| sex steroid-binding protein (hSBP/hABP, hSHBG) | Sui et al. 1995 |
| soluble human insulin receptor - ectodomain | Sissom and Ellis 1992 |
| soluble human insulin receptor tyrosine kinase | Ahn et al. 1993 |
| Sos1 protein | Frech et al. 1995 |
| steroid 5a-reductase | Iehle et al. 1993 |
| synthetic basic fibroblast growth factor | Hills & Crane-Robinson 1995 |
| TII (CD2) t-lymphocyte surface glycoprotein | Richardson et al. 1988 |
| TII (CD2) | Alcover et al. 1988 |
| T-cell leukemia virus type I p40 | Nyunoya et al. 1988 |

TABLE 9-continued

Heterologous Proteins for Use in the Present Invention

| Heterologous Protein | Reference |
|---|---|
| T-cell protein tyrosine kinase | Lehr et al. 1996 |
| T-cell protein-tyrosine-phosphatase | Zander et al. 1991 |
| T-lymphotropic virus type 1 envelope protein | Yamashita et al. 1992 |
| terminal transferase | Chang et al. 1988 |
| terminal deoxynucleotidyl transferase | di Primio et al. 1992 |
| thrombomodulin | Marumoto et al. 1993 |
| thromboxane synthase | Yokoyama et al. 1993 |
| thyroid hormone $B_1$ receptor | Putlitz et al. 1991 |
| thyroid peroxidase | Kendler et al. 1993 |
| thyrotropin receptor extracellular domain | Seetharamaiah et al. 1993 |
| thyrotropin hormone receptor-extracellular domain | Huang et al. 1993 |
| tissue inhibitor of metallo-proteinases-1 | Gomez et al. 1994 |
| tissue plasminogen activator | Jarvis et al. 1993 |
| tissue-type plasminogen activator | Steiner et al. 1988 |
| trancobalamin II isoproteins | Quadros et al. 1993 |
| tyrosine hydroxylase | Ginns et al. 1988 |
| tryptase | Sakai et al. 1996 |
| tumor necrosis factor-b | Chai et al. 1996 |
| type II collagen | Lamberg et al. 1996 |
| urokinase | Laurie et al. 1995 |
| urokinase-type plasminogen activator | King et al. 1991 |
| vascular cell adhesion molecule-1 | Stoltenborg et al. 1993 |
| vascular cell adhesion molecule-1 (VCAM1) | Stoltenborg et al. 1994 |
| vascular endothelial growth factor $VEGF_{121}$, $VEGF_{165}$ | Fiebich et al. 1993 |
| vitamin D receptor | Nakajima et al. 1993 |
| Vitronectin | Zhao and Sane, 1993 |
| Y1 neuropeptide Y receptor | Munoz et al. 1995 |
| yoked chorionic gonadotropin | Narayan et al. 1995 |
| *Hyalophora cecropia* pupae attacin | Gunn et al. 1990 |
| immunodeficiency virus: | |
| bovine immunodeficiency-like virus-env 20 kDa; gp145; gp100; gp45 | Rasmussen et al. 1992 |
| bovine immunodeficiency-like virus gag | Rasmussen et al. 1990 |
| feline immunodeficiency virus gag | Morikawa et al. 1991 |
| feline immunodeficiency virus gag, env | Verschoor et al. 1993 |
| human envelope glycoprotein | Rusche et al. 1987 |
| human gag | Royer et al. 1991 |
| | Nermut et al. 1994 |
| human gag and gag-pol | Hughes et al. 1993 |
| human gag precursors | Royer et al. 1992 |
| human gag-related proteins | Madisen et al. 1987 |
| human gp120, gp160 | Murphy et al. 1990 |
| human gp160, envelope PB1 | Dolin et al. 1991 |
| human type 1 envelope glycoproteins | Bristow et al. 1994 |
| human type 1 integrase protein | Rodner et al. 1993 |
| human type 1 matrix protein | Chazal et al. 1995 |
| human P55 gag | Gheysen et al. 1989 |
| human p55 gag and protease | Overton et al. 1989 |
| human pol gene, reverse transcriptase and integrase | Manns and Grosse 1991 |
| human type 1 reverse transcriptase | Kawa et al. 1993 |
| human tat protein | Jeang et al. 1988 |
| human type 1 gag precursor | Hong and Boulanger 1993 |
| human Type 1 Nef | Matsuura et al. 1991 |
| human type 1 recombinant glycoprotein 160 | Keefer et al. 1994 |
| human type 1 reverse transcriptase | Kaua et al. 1993 |
| human - 1 integrase | Peakman et al. 1992 |
| human type 2 gag | Luo et al. 1994 |
| infectious bursal disease virus - VP2, VP3, VP4 (GLS-5 strain) | Vakharia et al. 1993 |
| influenza virus: | |
| A virus M2 | Black et al. 1993 |
| A virus N2 euramiidase | Johansson et al. 1995 |
| A virus RNA polymerase $PB_2$ subunit | Shi et al. 1996 |

TABLE 9-continued

Heterologous Proteins for Use in the Present Invention

| Heterologous Protein | Reference |
|---|---|
| A/Ann Arbor nucleoprotein | Rota et al. 1990 |
| B/Ann Arbor nucleoprotein | Rota et al. 1990 |
| fowl plague hemagglutinin | Kuroda et al. 1990 |
| haemagglutinin | Kuroda et al. 1991 |
| | Weyer & Possee, 1991 |
| haemagglutinin epitope | McLinden et al. 1992 |
| neuraminidase | Weyer & Possee, 1991 |
| | Price et al. 1989 |
| | Mather et al. 1992 |
| polymerase proteins | St. Angelo et al. 1987 |
| RNA polymerase | Kobayashi et al. |
| RNA polymerase - PB1; PB2; PA | Kobayashi et al. 1992 |
| virus M2 | Schroeder et al. 1994 |
| virus recombinant hemagglutinin | Treanor et al. 1996 |
| insect: | |
| g-aminobutyric acid (GABA) receptor | Shotkoski et al. 1996 |
| *Bombyx mori* prothor acicotropic hormone | O'Reilly et al. 1995 |
| ecdysteroid UDP-glucosyl transferase | O'Reilly 1995 |
| fungal protease inhibitor F(FPI-F) | Pham et al. 1996 |
| juvenile hormone esterase | Bonning et al. 1995 |
| synthetic pheromone biosynthesis activating neuropeptide | Vakharia et al. 1995 |
| transferrin | Winzerling et al. 1996 |
| invertebrate $GABA_A$ receptor b-subunit | Smith et al. 1995 |
| JC virus T antigen | Bollag et al. 1996 |
| Japanese encephalitis virus: | |
| envelope glycoprotein E | Aira 1987 |
| glycoprotein NS1 | Flamand et al. 1995 |
| nonstructural protein NS1 | Flamand et al. 1992 |
| viral structural proteins | Matsuura et al. 1989 |
| Japanese type hepatitis C virus: | |
| p70(NS3) | Hirowatari et al. 1995 |
| p4(NS4A) | Hirowatari et al. 1995 |
| p27(NS4B) | Hirowatari et al. 1995 |
| p58/56(NS5A) | Hirowatari et al. 1995 |
| p66(NS5B) | Hirowatari et al. 1995 |
| jellyfish green fluorescet protein | Eriksson et al. 1996 |
| Johnson grass mosaic virus coat protein | Edwards et al. 1994 |
| juvenile hormone esterase | Booth et al. 1992 |
| LaCrosse virus: | |
| G1 | Pekosz et al. 1995 |
| G2 | Pekosz et al. 1995 |
| Lassa virus N protein | Barber et al. 1990 |
| Lassa virus glycoprotein | Hummel et al. 1992 |
| Leishmania virus - capsid | Cadd and Patterson 1994 |
| Leishmania gp63 | Button et al. 1993 |
| locust ion transport peptide | Meredith et al. 1996 |
| Louping ill virus - envelope, core and membrane proteins | Shiu et al. 1992 |
| luciferase-streptavidin fusion protein | Karp et al. 1996 |
| lutropin/choriogonadotropin receptor | Narayan et al. 1996 |
| lymphocyte-specific protein-tyrosyl kinase $p56^{lck}$ | Watts et al. 1992 |
| lymphocytic choriomeningitis virus nucleocapsid protein | Min and Bishop 1991 |
| lymphocytic choriomeningitis virus nucleoprotein and glycoprotein precursor | Matsuura et al. 1986 |
| lymphoid-cell protein tyrosine kinase $p56^{lck}$ | Ramen et al. 1991 |
| maize: | |
| AcTPase | Kunze et al. 1995 |
| auxin-binding protein | Henderson et al. 1995 |
| mitochondrial protein URF13 | Korth and Levings 1993 |
| transposable element Ac protein | Hauser et al. 1988 |
| *Manduca sexta* diuretic hormone | Maeda 1989 |

TABLE 9-continued

Heterologous Proteins for Use in the Present Invention

| Heterologous Protein | Reference |
|---|---|
| *Manduca sexta* juvenile hormone binding protein | Touhara et al. 1993 |
| Marburg virus surface protein | Becker et al. 1996 |
| Marek's disease virus: | |
| 88; 110; 49; 58 | Niikura et al. 1992 |
| A antigen | Niikura et al. 1991 |
| B antigen | Niikura et al. 1992 |
| disease virus type 1 (mDV1)-specific protein p40 | Urakawa et al. 1994 |
| virus glycoprotein D | Ono et al. 1995 |
| measles virus: | |
| AIK-C strain hemaggluten and fusion glycoproteins | Takehara et al. 1992 |
| hemagglutinin | Vialard et al. 1990 |
| N protein | Fooks et al. 1993 |
| nucleoprotein | Hummel et al. 1992 |
| melanocortin 1 receptors | Schioth et al. 1996 |
| mink enteritis parvovirus VP-2 | Christensen et al. 1994 |
| minute virus of mice NS-1 | Wilson et al. 1991 |
| mite allergen der fI | Shoji et al. 1996 |
| Mokola virus glycoprotein | Tordo et al. 1993 |
| mouse: | |
| CD95/APO1/Fas ligand | Mariani et al. 1996 |
| c-fos | Corvello et al. 1994 |
| cFos protein | Corvello et al. 1995 |
| focal adhesion kinase | Withers et al. 1996 |
| glutamate receptor subunits a1, a2 | Kawamoto et al. 1993 |
| growth hormone | Thordarson et al. 1996 |
| immunophilin FKBP-52 | Alnemri et al. 1993 |
| interleukin-3 | Hogeland et al. 1992<br>Knepper et al. 1992 |
| perforin | Liu et al. 1994 |
| phosphorylase kinase 1 subunit | Lanciotte and Bender, 1994 |
| prolyl 4-hydroxylase a-subunit isoform | Helaakoski et al. 1995 |
| thrombospodin 2 | Chen et al. 1994 |
| multifunctional mammalian transcription factor, YY1 | Momoeda et al. 1995 |
| murine: | |
| a1-subunit of AMPA-selective glutamate receptor channel | Kawamoto et al. 1993 |
| b2 - microglobulin | Godeau et al. 1992 |
| bip | Hsu et al. 1994 |
| acetylcholinesterase | Radic et al. 1992 |
| C-5 cytosine DNA methyl transferase | Glickman & Reich 1994 |
| c-kit extracellular ligand binding domain | Liu et al. 1993 |
| c-abl Type IV | Peakman et al. 1992 |
| c-ets-1 | Chen 1990 |
| $Ca^{2+}$/calmodulin-dependent protein kinase II - a subunit | Brickey et al. 1990 |
| Class I histocompatability complex molecule | Godeau et al. 1992 |
| egr-1 | Ragona et al. 1991 |
| entactin | Tsao et al. 1990 |
| erythropoietin receptor | Spivak et al. 1996 |
| gastrin-releasing peptide receptor | Kusui et al. 1995 |
| -human chimeric antibody | Jin et al. 1995 |
| interferon - 8 receptor | Fountoulakis et al. 1991 |
| interleukin-3 | Miyajima et al. 1987<br>Knepper et al. 1992 |
| interleukin 4 | Rodewald et al. 1990 |
| interleukin 5 | Rodewald et al. 1990 |
| a-lactalbumin | Soulier et al. 1995 |
| osteoblast-specific factor 2 | Sugiura et al. 1995 |
| p53 | O'Reilly et al. 1988 |
| PAC1 | Abrams et al. 1994 |
| platelet derived growth factor receptor | Morrisson et al. 1989 |
| protein tyrosyl kinase $p56^{lck}$ | Watts et al. 1993 |
| recombinant p53 | Delphin et al. 1994 |

TABLE 9-continued

Heterologous Proteins for Use in the Present Invention

| Heterologous Protein | Reference |
|---|---|
| retinoic acid receptor Type g | Ross et al. 1992 |
| retinoic acid receptor | Ross et al. 1992 |
| soluble CD4 | Kupsch et al. 1992 |
| tissue inhibitor | Kurschat et al. 1995 |
| tyrosine protein kinase $P56^{lck}$ | Spana et al. 1993 |
| muscarinic: | |
| acetylcholine receptor subtype (m1–m5) | Dong et al. 1995 |
| acetylcholine receptor subtype m1–m4 | Rinken 1995 |
| *Mycobacterium bovis* (BCG strain) Protein A lipoprotein | Stover et al. 1993 |
| Na, K-ATPase | DeTomaso & Mercer 1992 |
| $Na^+/K^+$-ATPase: | |
| $\alpha_1$ isoform | Xie et al. 1995 |
| $\alpha_2$ isoform | Xie et al. 1995 |
| neomycin phosphotransferase | Hartig and Cardon 1992 |
| nerve growth factor receptor - low affinity | Hempstead et al. 1993 |
| neuronal nitric oxide synthase | Watanabe et al. 1996 |
| neutral endopeptidase | Fossiez et al. 1992 |
| Newcastle Disease Virus: | |
| fusion glycoprotein | Murakami et al. 1994 |
| fusion and hemagglutinin-neuraminidase | Kamiya et al. 1994 |
| haemagglutinin-neuraminidase | Murakami et al. 1994 |
| nucleocapsid protein | Errington et al. 1995 |
| Norwalk virus: | |
| capsid | Jiang et al. 1992 |
| capsid antigen | Gray et al. 1993<br>Green et al. 1993 |
| capsid protein | Jiang et al. 1992<br>Hardy et al. 1996 |
| nuclear pore protein p62 | Bailer et al. 1995 |
| Nudaurelia virus capid protein | Agrawal & Johnson 1995 |
| ovine: | |
| lenti virus envelope glycoprotein gp40 | Kwang et al. 1995 |
| lenti virus envelope glycoprotein gp70 | Kwang et al. 1995 |
| P68 protein kinase | Barber et al. 1992 |
| pancreatic necrosis virus, polyprotein and VP1 | Magyar and Dobos 1994 |
| papillomavirus: | |
| bovine BVP1 - E2 | Tada et al. 1988 |
| human HPV6b | Tada et al. 1988 |
| human type 6b early gene product | Sekine et al. 1988 |
| human type 16 capsid | Xi and Banles 1991 |
| human type 16, E7 | Stacey et al. 1993 |
| human type 16 - L1, L2 | Kirnbauer et al. 1993 |
| human type 18 E6 protein | Grossman et al. 1989 |
| -like particles | Benincasa et al. 1996 |
| parvovirus: | |
| (B19) VP1, VP2 | Kajigaya et al. 1991 |
| B19 vaccine | Tsao et al. 1996 |
| VP1 and VP2 | Brown et al. 1991 |
| aleutian mink disease NS-1, NS-2, NS-3, VP1, VP2 | Christensen et al. 1993 |
| canine capsid-VP2 | Lopey et al. 1992 |
| human B19 structural proteins | Brown et al. 1991 |
| human B19 - VP1 | Gray et al. 1993 |
| parainfluenza virus: | |
| human Type 3 virus hemagglutinin-neuroaminidase | Van Wyke Coelingh et al. 1987 |
| human virus Type 3 fusion glycoprotein | Hall et al. 1991 |
| 3 fusion glycoprotein | Hall et al. 1991 |

TABLE 9-continued

Heterologous Proteins for Use in the Present Invention

| Heterologous Protein | Reference |
|---|---|
| perforin | Liu et al. 1996 |
| *Phanerochaete chrysosporium*: | |
| lignin peroxidase | Johnson and Li 1991 |
| lignin peroxidase isozyem H2 | Johnson et al. 1992 |
| manganese peroxidase (isozyme H4) | Pease et al. 1991 |
| *Phaseolus vulgaris* B-phaseolin | Buston et al. 1988 |
| *Photinus pyralis* luciferase | Mori et al. 1992 |
| | Kopylova-Sviridova et al. 1992 |
| pheromone-binding proteins | Krieger et al. 1992 |
| pig: | |
| pancreatic lipase CoPL | Thirstrup et al. 1995 |
| pancreatic lipase CoPL-RP2 | Thirstrup et al. 1995 |
| procolipaes | Thirstrup et al. 1995 |
| testicular 3a/b(20b)-hydroxysteroid-dehyrogenase | Nakajin et al. 1995 |
| placental alkaline phosphatase | Davis et al. 1992 |
| propapain | Tessier et al. 1991 |
| plant: | |
| auxin-binding protein At-ERabp1 | Massotte et al. 1995 |
| immidazoleglycerolphosphate dehydratase | Tada et al. 1995 |
| $K^+$ channel KAT1 | Marten et al. 1996 |
| pectate lyase-like LAT56 | Dircks et al. 1996 |
| pectate lyase-like LAT59 | Dircks et al. 1996 |
| propapain | Tessier et al. 1991 |
| ricin B chain | Afrin et al. 1994 |
| Plasmodium: | |
| *berghei* ookinete surface antigen | Matsuoka et al. 1996 |
| *falciparum* | |
| apical membrane antigen | Thomas et al. 1994 |
| C-terminal 19 KDa fragment | Hui et al. 1994 |
| major merzoite antigen gp195 | Chang et al. 1992 |
| merozoite surface protein-1 | Chang et al. 1996 |
| *vivax* merozoite surface protein 1 | Longacre et al. 1994 |
| poly(hydroxyalkanoate) synthase | Williams et al. 1996 |
| polyoma virus: | |
| large T antigen | Rice et al. 1987 |
| middle T antigen | Forstova et al. 1989 |
| middle t antigen and pp60(c-src) | Piwnica-Worms et al. 1990 |
| VP1 | Li et al. 1995 |
| VP2 | Li et al. 1995 |
| VP1 protein | Delos et al. 1993 |
| VP2 protein | Delos et al. 1993 |
| VP3 protein | Delos et al. 1993 |
| polio virus: | |
| $3B^{VPg}$, $3C^{pro}$, $3D^{pol}$ | Neufeld et al. 1991 |
| P3/Leon/37 | Urakawa et al. 1989 |
| (P3/LEON/37) NPO, VP3, VP1 | Brautigam et al. 1993 |
| receptor | Kaplan et al. 1990 |
| poplar phenylalanine ammonia-lyase | McKegney et al. 1996 |
| porcine: | |
| leukocyte 12-lipoxygenase | Reddy et al. 1994 |
| parvovirus - VP2 | Martinez et al. 1992 |
| rotavirus OSU strain - VP4 | Juarbe-Osorio et al. 1993 |
| type I interferon | Niu et al. 1995 |
| potato leafroll virus coat protein P3 | Lamb et al. 1996 |
| potato tuber protein, patatin | Andrews et al. 1988 |
| proapolipoprotein A-1 | Pyle et al. 1995 |
| protein disulfide isomerase (PDI) | Hsu et al. 1996 |
| protein Kinase C | Burns and Beel 1991 |
| protein kinase C - a, $-B_1$, $-B_2$, $-Y_1$-E | Stabel et al. 1991 |
| protozoan piroplasm surface protein | Matsuba et al. 1995 |
| *Pseudomonas diminuta* organophosphate degrading gene | Dave et al. 1994 |
| pseudorabies virus: | |
| gD | Garnier et al. 1995 |
| glycoprotein gII | Xuan et al. 1995 |
| gIII | Inumaru & Yamada 1991 |
| immediate-early regulatory protein IE180 | Yamada & Shimizu 1994 |
| neutralization antigen gIII | Inumaru & Yamada 1991 |
| punta toro phlebovirus N and NS-S proteins | Overton et al. 1987 |
| Puumala virus nucleocapsid protein | Vapalahti et al. 1996 |
| *Pyemotes tritici* toxin (Txp-1) | Tomalski et al. 1991 |
| *Pyrophorus plagiophthalamus* lucerifase | Kays et al. 1992 |
| Rab5 | Horiuchi et al. 1995 |
| Rap1 GTPase-activating protein | Rubinfeld & Polakis 1995 |
| Rap proteins | Porfiri et al. 1995 |
| p120Ras-GAP | Settleman & Foster 1995 |
| Ras proteins | Porfiri et al. 1995 |
| ras related rab6 protein | Schiedel et al. 1995 |
| Ras, Ras-related proteins | Khosravi-Far & Der 1995 |
| rabbit: | |
| cottontail papillomavirus virus-like particles | Christensen et al. 1996 |
| haemorrhagic disease virus capsid protein | Nagesha et al. 1995 |
| haemorrhagic disease virus structural protein VP60 | Marin et al. 1995 |
| hemorrhagic disease virus casid protein | Laurent et al. 1994 |
| 55 kDa 2P protein | Prasad et al. 1996 |
| 55-kilodalton zona pellucida protein | Prasad et al. 1995 |
| $Na^+$/glucose cotransporter protein | Smith et al. 1992 |
| papillomavirus L1 | Breitburd et al. 1995 |
| papillomavirus L2 | Breitburd et al. 1995 |
| prolactin receptor | Cahoreau et al. 1992 |
| prolactin receptor | Cahoreau et al. 1994 |
| skeletal muscle protein phosphatase 1 | Cohen and Berndt 1991 |
| UDP-GlcNac:a3-D-mannoside b-1, 2-N-acetylglucosaminyltransferase I catalytic domain | Sarkar 1994 |
| rabies virus: | |
| ERA strain - G protein | Fu et al. 1993 |
| glycoprotein | Prehaud et al. 1989 |
| | Tuchiya et al. 1992 |
| nucleoprotein | Fu et al. 1991 |
| M1; M2 | Prehaud et al. 1990 |
| N, M1, M2 antigens | Prehaud et al. 1992 |
| rat: | |
| 1, 25 dihydroxy vitamin $D_3$ receptor | Ross et al. 1991 |
| a subunit of g protein ($a_{i-1}$, $a_o$, $a_s$) | Lebierque et al. 1992 |
| $a_{iI}$ protein | Jones et al. 1993 |
| androgen receptor | Xie et al. 1992 |
| androgen receptor | Kallio et al. 1994 |
| androgen receptors | Kallio et al. 1994 |
| anion exchanger AE2 | He et al. 1993 |
| annexin 5 | Takehara et al. 1994 |
| bacterial dehydrase-domain mutant rat fatty acid synthase polyhydroxyalkanoate synthase | Williams et al. 1996 |
| brain Type II calmodulin - dependent protein kinase - a subunit | Takeuchi-Suzuki et al. 1992 |
| CTP:phosphocholine cytidylyltransferase | Luche et al. 1993 |
| calcineurin A | Perrino et al. 1992 |
| calmodulin-dependent protein kinase IV | Kitani et al. 1995 |
| cytochrome P450 | Asseffa et al. 1989 |
| $D_2$ dopamine receptors | Woodcock et al. 1995 |
| $D_2$ dopamine receptor isoform | Boundy et al. 1996 |
| $D_3$ dopamine receptors | Woodcock et al. 1995 |
| 10-formyltetrahydrofolate dehydrogenase | Krupenko et al. 1995 |
| a subunits FTase farnyl transferase | Moomaw et al. 1995 |
| b subunits FTase farnyl transferase | Moomaw et al. 1995 |

TABLE 9-continued

Heterologous Proteins for Use in the Present Invention

| Heterologous Protein | Reference |
| --- | --- |
| $GABA_A$ receptor subtypes | Im et al. 1994 |
| gastric H,K-ATPase a & b subunit | Klaassen et al. 1993 |
| glucocorticoid receptor | Alnemri et al. 1991 |
| glutamate receptor subunits GluR-B, GluR-D | Keinanen et al. 1994 |
| glycoprotein hormone a-subunit | Delahaye et al. 1996 |
| guanylate cyclase | Buechler et al. 1995 |
| hepatic microsomal epoxide hydrolase | Lacourciere et al. 1993 |
| hormone-sensitive lipase | Holm et al. 1994 |
| intrinsic factor | Gordon et al. 1992 |
| JAK2 (type 2 Janus tyrosine kinase) protein-tyrosine kinase | Duhe & Farrar 1995 |
| liver Ybi glutathione S-transferase | Hsieh et al. 1989 |
| liver CTP: phosphocholine cytidylyl transferase | MacDonald and Kent 1993 |
| liver phenylalanine hydroxylase | Gibbs et al. 1993 |
| lysyl hydroxylase | Armstrong & Last 1995 |
| m3 muscarinic acetylcholine receptor | Vasudevan et al. 1995 |
| $a_1$-microglobulin | Akerstrom et al. 1995 |
| $a_1$-microglobulin-bikunin | Bratt & Akerstrom 1995 |
| multifunctional animal fatty acid synthaes | Joshi & Smith 1993 |
| muscarinic acetylcholine receptor subtype m3 | Vasudevan et al. 1992 |
| Na, K-ATPase a2, a3, B1 isoforms | Blanco et al. 1993 |
| a4b2 neuronal nicotinic cholinergic receptor | Wang & Abood 1996 |
| neuronal nitric oxide synthase | Richards & Marletta 1994 |
| nitric oxide synthase | Harteneck et al. 1994 |
| nuclear pore protein p62 | Bailer et al. 1995 |
| p53 | Fuchs et al. 1995 |
| $p70^{56K}$ and $p85^{56K}$ kinases | Kozma et al. 1993 |
| pancreatic cholesteral esterase | di Persio et al. 1992 |
| pancreatic lithostathine | Bimmler et al. 1995 |
| papillomavirus L1 | Breitburd et al. 1995 |
| papillomavirus L2 | Breitburd et al. 1995 |
| peroxisomal Acyl-CoA oxidase | Chu et al. 1994 |
| phospholipase C-g1 | Horstman et al. 1995 |
| prostatic acid phosphatase | Vihko et al. 1993 |
| protein kinase C-d | McGlynn et al. 1992 |
| protein kinase C-x | McGlynn et al. 1992 |
| protein kinase C-y | Fiebich et al. 1990 |
| ram p25 | Suzuki et al. 1992 |
| recombinant liver carnitine palmitoyltransferase II | Johnson et al. 1995 |
| renal $Na/P_i$-cotransport ($NaP_i$-2) | Fucentese et al. 1995 |
| skeletal muscle chloride channel CIC-1 | Astill et al. 1996 |
| skeletal muscle phosphorylase kinase | Lee et al. 1992 |
| skeletal muscle phorylase kinase g subunit | Lee et al. 1992 |
| soluble, mutant G-protein a subunit | Jones et al. 1993 |
| substance receptor | Schreurs et al. 1995 |
| urate oxidase | Alvares et al. 1992 |
| receptor tyrosine kinase p180 | Guy et al. 1994 |
| respiratory syncytial virus F glycoprotein | Wathen et al. 1989 |
| retroviral gag precursors | Tobin et al. 1995 |
| rhesus rotavirus: | |
| VP5(1) | Dunn et al. 1995 |
| VP8 | Dunn et al. 1995 |
| ricin B | Ferrini et al. 1995 |
| *Rickettsia rickettsii* rOmpA protein | Sumner et al. 1995 |
| Rift valley fever virus: | |
| cDNA-complete | Takahara et al. 1990 |
| envelope glycoproteins G1 and G2 | Schmaljohn et al. 1989 |
| Rinderpest hemagglutinin and fusion proteins | Bassiri et al. 1993 |
| Rinderpest virus (kabete O strain) N protein | Ismail et al. 1994 |
| Rinderpest virus nucleocapsid gene | Kamata et al. 1993 |
| rodent Na,K-ATPase | DeTomaso et al. 1993 |

TABLE 9-continued

Heterologous Proteins for Use in the Present Invention

| Heterologous Protein | Reference |
| --- | --- |
| rotavirus: | |
| bovine VP1 | Cohen et al. 1989 |
| bovine VP2, VP6 | Labbe et al. 1991 |
| bovine VP6, VP7 | Sabara et al. 1991 |
| (Group C) - VP6 | Tosser et al. 1992 |
| (Group A) - VP2 | Tosser et al. 1992 |
| human adult diarrheal VP6 | Mackow et al. 1993 |
| -like particles | Zeng et al. 1996 |
| murine VP1; VP2; NS53; VP4; VP7; VP6; NS28; NS35 | Dharakul et al. 1991 |
| porcine VP4 gene product | Nishikawa et al. 1989 |
| rat (IDIR) group B, VP6 | Lindsay et al. 1993 |
| rhesus outer capsid protein VP4 | Mackow et al. 1990 |
| simian major capsid antigen | Estes et al. 1987 |
| simian nonstructural glycoprotein | Au et al. 1989 |
| simian SAII protein | Estes et al. 1987 |
| simian SAII - VP7 | McGonigal et al. 1992 |
| simian VP3 | Mattson & Estes 1992 |
| strain RF VP2 | Zeng et al. 1994 |
| VP2 | Labbe et al. 1991 |
| VP3 | Liu et al. 1992 |
| VP6 protein | Sabara et al. 1991 |
| VP7 protein | Sabara et al. 1991 |
| Rous sarcoma virus v-Src | Park et al. 1992 |
| Rubella virus: | |
| E2 glycoprotein | Seto et al. 1995 |
| p110 polyprotein precursor | Oker-Blom et al. 1995 |
| spike proteins | Oker-Blom et al. 1990 |
| SIV $Pr56^{gag}$ | Yamshchikov et al. 1995 |
| SV40 capsid proteins | |
| VP1 | Kosukegawa et al. 1996 |
| VP2 | Kosukegawa et al. 1996 |
| VP3 | Kosukegawa et al. 1996 |
| | Ayola et al. 1993 |
| *Saccharo myces* cerevisiae Kex2p endoprotease | Germain et al. 1992 |
| *Sarcophaga peregrina* sarcotoxin 1A | Yamada et al. 1990 |
| *Schistosoma mansoni* sarcotoxima protein Sm32 | Felleisen et al. 1990 |
| scorpion: | |
| a anti-insect neurotoxin (LqhaIT) | Chejanovsky et al. 1995 |
| *Buthus eupeus* insectotoxin-1 | Carbonell et al. 1988 |
| *Buthus occitaus tunetanus* a-toxin | Bouhaouah-Zahar et al. 1996 |
| secreted alkaline phosphatase | Davis et al. 1993 |
| Semliki forest virus: | |
| capsid protein | Favre et al. 1993 |
| membrane protein subunits | Barth et al. 1995 |
| Sendai Virus: | |
| fusion protein | Sato et al. 1993 |
| hemagglutinin-neuraminidase | Sato et al. 1993 |
| sheep choriogonadotropin-immunoglobulin G heavy-chain | Johnson et al. 1995 |
| silk moth chorion chromosomal gene product | Iatrou et al. 1989 |
| simian immunodeficiency virus gp160 | Hu et al. 1992 |
| simian rotavirus SA11 VP2, VP4, VP6, VP7 | Crawford et al. 1994 |
| simian sarcoma virus v-sis platlet derived growth factor B | Giese et al. 1989 |
| simian virus: | |
| 40 large and small T antigen | Lanford et al. 1988 |
| | Murphy et al. 1988 |
| 40 large T antigen | Hoss et al. 1990 |
| 40 T-antigen | Shearer et al. 1993 |
| 40 T and t antigen | Murphy et al. 1988 |
| 40 small t antigen | Jeang et al. 1987 |
| gag, pro, pol | Sommerfelt et al. 1993 |

TABLE 9-continued

Heterologous Proteins for Use in the Present Invention

| Heterologous Protein | Reference |
|---|---|
| Sindbis virus: | |
| 26S: 6 structural proteins | Oker-Blom et al. 1989 |
| nsP1, nsP2, nsP3, nsP4 | Buzan and Schlesinger 1992 |
| nsP3 | Lastarza et al. 1994 |
| snowshoe hare bunyavirus nucleoprotein and non structural protein NS-S | Urakawa et al. 1988 |
| soluble class I MHC heavy chain protein | Wang et al. 1996 |
| stromelysin | Peakman et al. 1992 |
| swine fever virus: | |
| glycoprotein E2 | Hulst et al. 1994 |
| protein E2 | Ruggli et al. 1995 |
| TMV movement protein | Atkins et al. 1991 |
| *Tenebrio molitor* desiccation stre gene | Graham et al. 1996 |
| *Theileria parva* sporozoite surface protein NS1-p67 | Nene et al. 1995 |
| Thogoto virus glycoprotein | Jones et al. 1995 |
| tobacco mosaic virus movement protein | Atkins et al. 1991 |
| tomato golden mosaic virus AL1 | Fontes et al. 1992 |
| Tonga virus NS1 | Qu et al. 1993 |
| Toronto virus capsid protein TV24 | Leite et al. 1996 |
| *Torpedo californica* acetylcholinesterase | Radic et al. 1992 |
| transmissible gastroenteritis virus S gene | Godet et al. 1991 |
| transmissible gastroenteritis virus spike protein | Tuboly et al. 1994 |
| Trypanosoma: | |
| *brucei* | |
| surface transferrin | Ligtenberg et al. 1994 |
| transferrin-binding protein complex | Chaudhri et al. 1994 |
| *congolense* variable surface glycoprotein (mVSGs) | Urakawa et al. 1995 |
| *cruzi* flagellar repetitive antigen | Duarte dos Santos et al. 1992 |
| *vivax* antigen | Masake et al. 1995 |
| turnip yellow mosaic virus 69K movement protein | Seron et al. 1996 |
| v-cath proteinase | Slack et al. 1995 |
| Vaccinia surface antigen | Morikawa & Ueda 1993 |
| Vaccinia virus Ag$^{35}$ | Mohandas et al. 1994 |
| varicella-zoster virus origin-binding protein | Webster et al. 1995 |
| vesicular stomatitis virus: | |
| glycoprotein | Bailey et al. 1989 |
| matrix protein | Li et al. 1993 |
| L protein | Mathur et al. 1996 |
| M protein | Li et al. 1993 |
| N protein | Ahamad et al. 1993 |
| viral haemorrhagic septicaemia glycoprotein | Lecocq-Zhonneux et al. 1994 |
| *Vibrio harveyi*: | |
| b-galactosidase | McIntosh & Grasela 1994 |
| luciferase | McIntosh & Grasela 1994 |
| Xenopus: | |
| bone morphogenetic protein | |
| (xBMP)-2 | Hazama et al. 1995 |
| (xBMP)-4 | Hazama et al. 1995 |
| (xBMP)-7 | Hazama et al. 1995 |
| fibroblast growth factor receptor-1 | Brown and Friesel 1993 |
| poly(A$^+$) binding protein | Stambuk and Moon 1992 |
| serine specific protein kinase pp90-rsk | Vik et al. 1990 |
| xlcaax-1 | Kloc et al. 1991 |
| yeast ARS and CEN | Patel et al. 1992 |
| yellow fever virus: | |
| 17D - envelope protein | Shiu et al. 1991 |
| E; NS1 | Despres et al. 1991 |

G. Marker Genes

In certain aspects of the present invention, specific cells are tagged with specific genetic markers to provide information about the infected, transduced or transformed cells. Therefore, the present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

1. Screening

Exemplary enzymes include esterases, phosphatases, proteases (tissue plasminogen activator or urokinase) and other enzymes capable of being detected by their activity, as will be known to those skilled in the art. Contemplated for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other particular examples are the enzyme chloramphenicol acetyltransferase (CAT) which may be employed with a radiolabelled substrate, firefly and bacterial luciferase, and the bacterial enzymes β-galactosidase and β-glucuronidase. Other marker genes within this class are well known to those of skill in the art, and are suitable for use in the present invention.

2. Selection

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U. S. Pat. No. 4,430,434), the gene conferring hygromycin B resistance (Santerre et al., 1984; U. S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

H. Homologous Recombination

An approach for incorporating specific constructs of the present invention into the genome of the host cell involves the use of homologous recombination, or "knock-out technology". Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, the target gene is selected within the host cell. Sequences homologous to the target gene are then included in a genetic construct, along with some mutation that will render the target gene inactive (stop codon, interruption, and the like). The homologous sequences flanking the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

Additionally, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

. . . vector•5'-flanking sequence•heterologous gene•selectable marker gene•flanking sequence-3'-vector . . .

Thus, using this kind of construct, it is possible, in a single recombinatorial event, to (i) "knock out" an endogenous gene, (ii) provide a selectable marker for identifying such an event and (iii) introduce a heterologous gene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

I. Cloning Cellular ODV-E66 Cognate and Membrane Targeting-Associated Gene(s)

The present invention contemplates cloning genes or cDNAs of cellular cognates of the ODV-E66 gene, as well as genes or cDNAs encoding proteins that associate with the membrane targeting sequences of the present invention. Candidate genes and/or cDNAs are contemplated for cloning from eukaryotic cells, and particularly, human cells.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, as exemplified by, a genomic library from baculovirus. The screening procedure may be an expression screening protocol employing antibodies directed against the protein, or activity assays. For example, antibody screening is very routinely employed. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, for example, in Sambrook et al. (I 989), incorporated herein by reference. Moreover, as the present invention encompasses the cloning of genomic segments as well as cDNA molecules, it is contemplated that suitable genomic cloning methods, as known to those in the art, may also be used.

J. Antibody Production

In certain aspects of the present invention, the preparation of polyclonal or monoclonal antibodies, for example to the baculovirus ODV-E66 protein, or to exemplary hydrophobic targeting constructs, is contemplated. Means for preparing and characterizing antibodies are well known in the art (See, e.g., Antibodies: A Laboratory Manual, Cold Spring Harbor Laboratory, 1988; incorporated herein by reference).

The invention also includes fragments (e.g., antigenic fragments) of the ODV-E66 polypeptide. As used herein, "fragment," as applied to a polypeptide, will ordinarily be at least 10 residues, more typically at least 20 residues in length. Fragments of the ODV-E66 polypeptide can be generated by methods known to those skilled in the art, e.g., by enzymatic digestion of naturally occurring or recombinant ODV-E66 polypeptide, by recombinant DNA techniques using an expression vector that encodes a defined fragment of ODV-E66, or by chemical synthesis.

The ability of a candidate fragment to exhibit a characteristic of ODV-E66 (e.g., binding to an antibody specific for ODV-E66) can be assessed by methods described herein. Purified ODV-E66 or antigenic fragments of ODV-E66 can be used to generate new antibodies or to test existing antibodies (e.g., as positive controls in a diagnostic assay) by employing standard protocols known to those skilled in the art. In one preferred embodiment, a monoclonal antibody is generated using a peptide comprising the hydrophobic domain which corresponds to a contiguous amino acid sequence of SEQ ID NO:2 to immunize an appropriate laboratory animal, such as a mouse.

Also included in this invention are polyclonal antisera generated by using ODV-E66 or a fragment of ODV-E66 as the immunogen in, e.g., rabbits. Standard protocols for monoclonal and polyclonal antibody production are detailed below.

Also included in the invention are ODV-E66 polypeptides which are encoded at least in part by portions of SEQ ID NO:1, e.g., products of alternative mRNA splicing or alternative protein processing events, or in which a portion of 23AA sequence has been deleted or altered. The fragment, or the intact ODV-E66 polypeptide, may be covalently linked to another polypeptide, e.g. which acts as a label, a ligand or a means to increase antigenicity.

The invention also includes a polyclonal or monoclonal antibody which specifically binds to ODV-E66 or a fragment thereof. Preferably, this antibody specifically binds to an epitope in the hydrophobic domain of ODV-E66 which corresponds to the sequence shown in SEQ ID NO:3. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In preferred embodiments, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin.

Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc.

Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415.

Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

1. Polyclonal Antibody Production

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention, either with or without prior immunotolerizing, depending on the antigen composition and protocol being employed, and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and Cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

2. Monoclonal Antibody Production

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified ODV-E66 or membrane targeting protein, polypeptide or peptide, or any hydrophobic membrane targeting composition, if used after tolerization to common antigens. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/ 5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonal antibodies. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

K. Mutagenesis

Mutagenesis may be performed in accordance with any of the techniques known in the art such as and not limited to synthesizing an oligonucleotide having one or more mutations within the sequence of a particular crystal protein. In particular, site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the point of the mutation. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents (see, e.g., a method described by Eichenlaub, 1979), such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

L. Pharmaceutical Compositions and Routes of Administration

Where clinical applications are contemplated, it will be necessary to prepare pharmaceutical compositions of the peptides, proteins, nucleic acids, viruses and cells in a form appropriate for the intended application. Generally, this will entail preparing compositions that are essentially free of pyrogens, as well as other impurities that could be harmful to humans or animals.

One will generally desire to employ appropriate salts and buffers to render peptides, proteins, nucleic acids, viruses or cells suitable for introduction into a patient. Aqueous compositions of the present invention comprise an effective amount of peptides, proteins, nucleic acids, viruses or cells, dissolved or dispersed in a pharmaceutically acceptable carrier or aqueous medium, and preferably encapsulated. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients, such as other anti-cancer agents, can also be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the peptides, proteins, nucleic acids, viruses or cells is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

A. Parenteral Administration

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

B. Other Routes of Administration

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. The injection can be general, regional, local or direct injection, for example, of a tumor. Also contemplated is injection of a resected tumor bed, and continuous perfusion via catheter. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

M. Kits

All the essential materials and reagents required for the various aspects of the present invention may be assembled together in a kit. When the components of the kit are provided in one or more liquid solutions, the liquid solution preferably is an aqueous solution, with a sterile aqueous solution being particularly preferred.

For in vivo use, the instant compositions may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the chemotherapeutic drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Additionally, instructions for use of the kit components is typically included.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

General Materials and Methods Used for this Invention

1. Insect Cells and Viruses

Wild type AcMNPV (E2 strain), β-gal mutant viruses, and viruses overexpressing 23GFP, 23URF-13 or ODV-E66 were used to infect *Spodoptera frugiperda* (*Sf*9) cells at a multiplicity of infection (m.o.i.) of 20 (Summers and Smith, 1987). One of the β-gal mutant virus, 23 β-gal (FIG. 2, Construct #4) was also used to infect *Trichoplusia ni* (*TN*368) cells (moi.=20). Time zero was defined as the time when cells were inoculated with the virus. The virus inoculum was removed after 1 hr absorption.

2. Virus Purification, Fractionation, ODV-E66 Band Isolation, and N-Terminal Amino Acid Sequencing To purify the virus, media and cells were collected 5 days postinfection and centrifuged at 9000 rpm in a Beckman JA14 rotor. BV was purified from the supernatant essentially as described by Summers and Smith (1987). The supernatant was centrifuged at 100,000×g, 4° C. (Beckman Type 35, 30,000 rpm) to pellet the virus. Virus derived from 500 ml of cell supernatant was resuspended in 1 ml 0.1×TE (1×TE= 10 mM Tris, 1.0 mM EDTA, pH 7.4) and overlaid onto an 11 ml 25–56% sucrose gradient in 0.1×TE. Gradients were centrifuged at 100,000×g for 90 min at 4° C. (Beckman SW41, 24,000 rpm). The virus band was removed, diluted 1:4 in 0.1×TE, and re-pelleted by centrifugation at 100, 000×g for 30 min at 4° C. (SW41, 24,000 rpm). The virus was resuspended in 0.1×TE (approximately 0.5 ml per liter of cell supernatant) and stored at 4° C.

Viral occlusions were isolated from infected cells by the method of Whitt and Manning (1987) with some modifications. Cells harvested above (approximately 5×10$^9$ cells) were resuspended in 15 ml of 0.2% Triton X-100 and lysed by sonication on ice (6×30 sec, output 5, duty cycle 50%; Model W-375 sonicator; Heat Systems Ultrasonics, Inc.). The sonicates were brought to 80 ml with 0.2% Triton X-100 and the lysate was laid over four 10 ml 30% sucrose (w/v)/0.2% Triton X-100 pads. Viral occlusions were pelleted by centrifugation at 9000 rpm for 20 min in Beckman JA-21 rotor. Each pellet of partially purified viral occlusions was resuspended in 3–4 ml of 0.2% Triton X-100, laid onto a 35 ml 35–60% (wt/wt) sucrose gradient made in water, and centrifuged at 100,000×g for 30 min at 4° C. (Beckman SW28, 24,000 rpm). The viral occlusion band was removed and washed twice by diluting in H$_2$O and low speed centrifugation. The viral occlusions were resuspended in a small volume of H$_2$O and stored at 4° C. Protein concentration was determined by absorbance at 550 nm (extinction coefficient=0.28; Summers and Smith, 1987).

ODV was purified from viral occlusions by the method of Tweeten et al., (1980) with some modifications. ODV was liberated from viral occlusions (40 mg/ml) by incubating at 37° C. for 2 hr in diluted alkaline solution (0.1 M NaCO$_2$, 0.5 M NaCl, pH 10.9). Approximately 1 ml of alkali-treated viral occlusions was laid onto an 11 ml 25–56% (w/v) sucrose/10 mM Tris (pH 7.5) gradient and centrifuged at 50,000×g for 30 min at 4° C. (SW41, 17,500 rpm). Multiple ODV bands were removed, washed by diluting in 10 mM Tris (pH 8.5), pelleted, and finally resuspended with 10 mM Tris (pH 8.5).

Purified viruses were fractionated into envelope and nucleocapsid preparations using modifications of the protocol of Whitt and Manning (1987). In a 250 µl reaction, 200 µg of BV or ODV were incubated in 1% NP40, 10 mM Tris, pH 8.5 at room temperature for 30 min with gentle agitation. The solution was then laid onto a 4 ml 30–70% (wt/vol) glycerol/10 mM Tris (pH 8.5) gradient and centrifuged at 150,000×g for 60 min at 4° C. (Beckman SW60, 34,000 rpm). The envelope fraction was then recovered from the top of the gradient, while the nucleocapsids formed a band approximately ⅔ into the gradient. Both fractions were dialyzed against 10 mM Tris (pH 7.4) overnight at 4° C. All fractions were concentrated using an Amicon Centricon-3 microconcentrator.

For N-terminal amino acid sequencing, purified viral envelope and nucleocapsid fractions were denatured in disruption buffer (2% SDS, 1% β-mercaptoethanol, 25 mM Tris, 7% glycerol, and 0.1% bromophenol blue, pH 6.8) and proteins were separated on a 3% stacking/12.5% separating gel that was pre-run for 30 min with 200 mM thioglycolic acid added to the upper buffer. The separated proteins were electrophoretically transferred to the PVDF membrane (Pro-Blott; Applied Biosystems). Following transfer, the membrane was stained (45% methanol, 5% acetic acid, 0.1% Coomassie blue R250), destained (45% methanol, 5% acetic acid), and washed with water. Two protein bands were excised and N-terminal sequence was determined. The sequence for a 66 kDa band unique to the ODV envelope was determined to be MSIVLIIVI (SEQ ID NO:4; Biotechnology Instrumentation Facility, Univ. of Calif., Riverside, Calif.). A degenerate oligonucleotide was predicted from these amino acids and used to screen AcMNPV genomic DNA digested with PstI by standard Southern-blot techniques (Sambrook et al., 1989).

3. Plasmid Cloning and DNA Sequencing

Plasmid cloning was described by Sambrook et al, (1989). Double-stranded DNA sequencing was done according to Sequenase 2.0 protocols (USB) using α-[$^{35}$]S-dATP (DuPont NEN Research Products). Oligonucleotides were synthesized on a Model 391 PCR-MATE DNA Synthesizer (Applied Biosystems Inc.). DNA was sequenced on both strands and each nucleotide was sequenced an average of six times. The nucleotide and predicted amino acid sequences were analyzed using the programs of genetics computer group (Devereux et al., 1984; UWGCG, version 8.0; Madison, Wis.). The completed gene sequence has been deposited with the GenBank Data Library under Accession No. M96360.

4. Heterologous Protein Expression and Antibody Production

The region from amino acid 24 to 705 of the ODV-E66 ORF was amplified by polymerase chain reaction (PCR; 1 min at 94° C., 1 min at 37° C., and 3 min at 72° C. with 5 sec extension after each cycle, 25 cycles) using two primers (forward (SEQ ID NO:5): 5'-AAAA AAGCTTGTTAACAATAAAAATGATGCC-3' and reverse (SEQ ID NO:6): 5'-AAAA GGATCCTTACACAATTTCAAA-3') and Taq polymerase (Promega).

The resultant PCR fragment was extracted with phenol/chloroform, precipitated with ethanol, digested with HindIII and BamHI, separated on a 1% agarose gel, purified (GeneClean II, BIOL101, Inc.), and ligated into the HindIII and BamHI sites of pUC18 to give rise to PCR-pUC18. The FLAG epitope (amino acid sequence: DYKDDDDK (SEQ D NO:7);VWR Scientific) was cloned in frame at the N-terminus of the amplified region amino acids 24–705) to allow affinity purification of the fusion protein when necessary. A linker containing HindIII sites on both ends (underlined below) was cloned into the HindIII site of the PCR-pUC18 clone. The forward sequence of the linker is 5'-AAGCTTCATATGGACTACAAAGACGACGACGAC AAGCT-3' (SEQ ID NO:8). Immediately following the HindIII site on the left, there is an NdeI site (italic) containing an ATG in frame with the ODV-E66 ORF. DNA sequencing confirmed that the final construct encodes the following N-terminal amino acid sequence (SEQ ID NO:9): MDYKDDDDKLVN (amino acid 24 of ODV-E66 ORF is underlined). The N-terminal eight amino acids (italic)

encode the FLAG epitope. Finally, the FLAG-E66 ORF was cloned into the NdeI and BamHI sites of pET-11a (Novagen, Inc.) and expressed. The recombinant protein was found in the inclusion fraction of *E. coli* Bacterial inclusion fraction was prepared as described by the manufacturer (Novagen).

Three New Zealand White female rabbits were injected intramuscularly with approximately 500 μg of the inclusion fraction in Freund's complete adjuvant (Pierce). The rabbits were then given two additional injections in Freund's incomplete (Pierce) at monthly intervals. One week after the final injection, sera were collected by exsanguination of the rabbits. To eliminate the background reaction, the polyclonal antiserum was preadsorbed with uninfected *Sf*9 cells. Uninfected *Sf*9 cells were pelleted, resuspended in 1×BLOTTO (1% non-fat dry milk, 50 mM Tris, 150 mM NaCl, 0.05% Tween-20, 0.02% NaN$_3$, pH 7.4), and sonicated until all cells were lysed. ODV-E66 antiserum or preimmune serum was added (1:500) and allowed to bind overnight at 4° C. The antibody was then clarified by centrifugation for 20 min at 15,000 rpm in a Beckman JA-21 rotor. Preadsorbed polyclonal antiserum and preimmune serum were stored at −20° C. until use.

To prepare a better antibody which does not require preabsorption to be monospecific for ODV-E66, induced crude *E. coli* lysate was separated on a 10% SDS-PAGE gel. Gel strips were cut from both sides of the gel, stained with Coomassie blue (Sambrook et at., 1989), aligned with an unstained part of the same gel, and the band containing the expressed protein was excised. Then, the unstained gel slice was forced through a gauge 22 needle before letting protein diffuse out of gel by shaking in 50 ml TBS (50 mM Tris, 150 mM NaCl, pH 7.4) overnight at 4° C. Diffused protein was concentrated in a Centriprep-30 (Amicon). The protein concentration was determined by Bradford assay (Bradford, 1976). Two New Zealand White female rabbits were injected subcutaneously four times with a total of 220 μg of protein per rabbit in RIBI adjuvant (RIBI ImmunoChem Research) as described by Harlow and Lane (1988). Nine days after the final injection, sera were collected by exsanguination. Preimmune sera were collected before the first injection. Western-blot analyses showed that the antiserum was monospecific for ODV-E66.

5. Immunoelectron Microscopy (IEM)

To prepare samples for IEM, infected *Sf*9 or *TN*368 cells, transfected *Sf*9 cells, and freshly purified viruses were pelleted and sequentially fixed using 1% paraformaldehyde, 0.5% glutaraldehyde, 0.05 M sodium cacodylate, pH 7.1, 10 min at 4° C.; 2% paraformaldehyde, 2.5% glutaraldehyde, 0.05 M sodium cacodylate, pH 7.1, 30 min at 4° C. (all EM chemicals except gold-conjugates were purchased from Electron Microscopy Science). Fixed pellets were washed (0.05 M sodium cacodylate, pH 7.1; 3×10 min at 4° C.), postfixed (1% osmium tetraoxide, 0.05 M sodium cacodylate, pH 7.1; 30 min at room temperature), and washed again. After fixation, samples were dehydrated and infiltrated following a protocol described by Vandenbosch (1991). Briefly, the pellets were dehydrated at 4° C. with 30% ethanol for 30 min and then at −20° C. with the following graded ethanol series: 50%; 70%; 90%; 100% (30 min/step). Samples were infiltrated with 50%, 75%, 100% LR White/ethanol series −20° C. (1 hr per step). Samples were then infiltrated with 100% LR White at −20° C. overnight, followed by another 8 hr infiltration. The resin was polymerized in gelatin capsules heated to 50° C. for approximately 48 hr.

Ultrathin sections were cut on a Reichert-Jung ultracut E microtome and collected on nickel grids (Electron Micros-copy Sciences), etched (0.56 M sodium meta-periodate, 1 hr; Sigma), washed (H$_2$O, 2 min), incubated in 0.1 N HCl (10 min), and washed (H$_2$O, 4×2 min). The sections were blocked with TTBS-BSA (1% BSA, 50 mM Tris-HCl, 150 mM NaCl., 0.05% Tween-20, pH 7.4) for 15 min, reacted with primary antibody (1:500 E66 preabsorbed antiserum, 1:1250 β-gal mouse ascitic fluid, or 1:1500 GFP antiserum; 16 hr at 4° C.), and washed (50 mM Tris, 150 mM NaCl, pH 7.4; 4×2 min). The bound primary antibody was detected using anti-rabbit IgG 15 nm or 30 nm gold conjugate or anti-mouse IgG 30 nm conjugate (Amersham). The sections were stained with uranyl acetate (Bozzola and Russell, 1992) and lead citrate (Venable and Coggeshall, 1965), and visualized with a Zeiss 10C transmission electron microscope (Electron Microscopy Center, Department of Biology, Texas A&M University, College Station, Tex.).

6. Deletion and Site-directed Mutagenesis

Figure 1A-1:
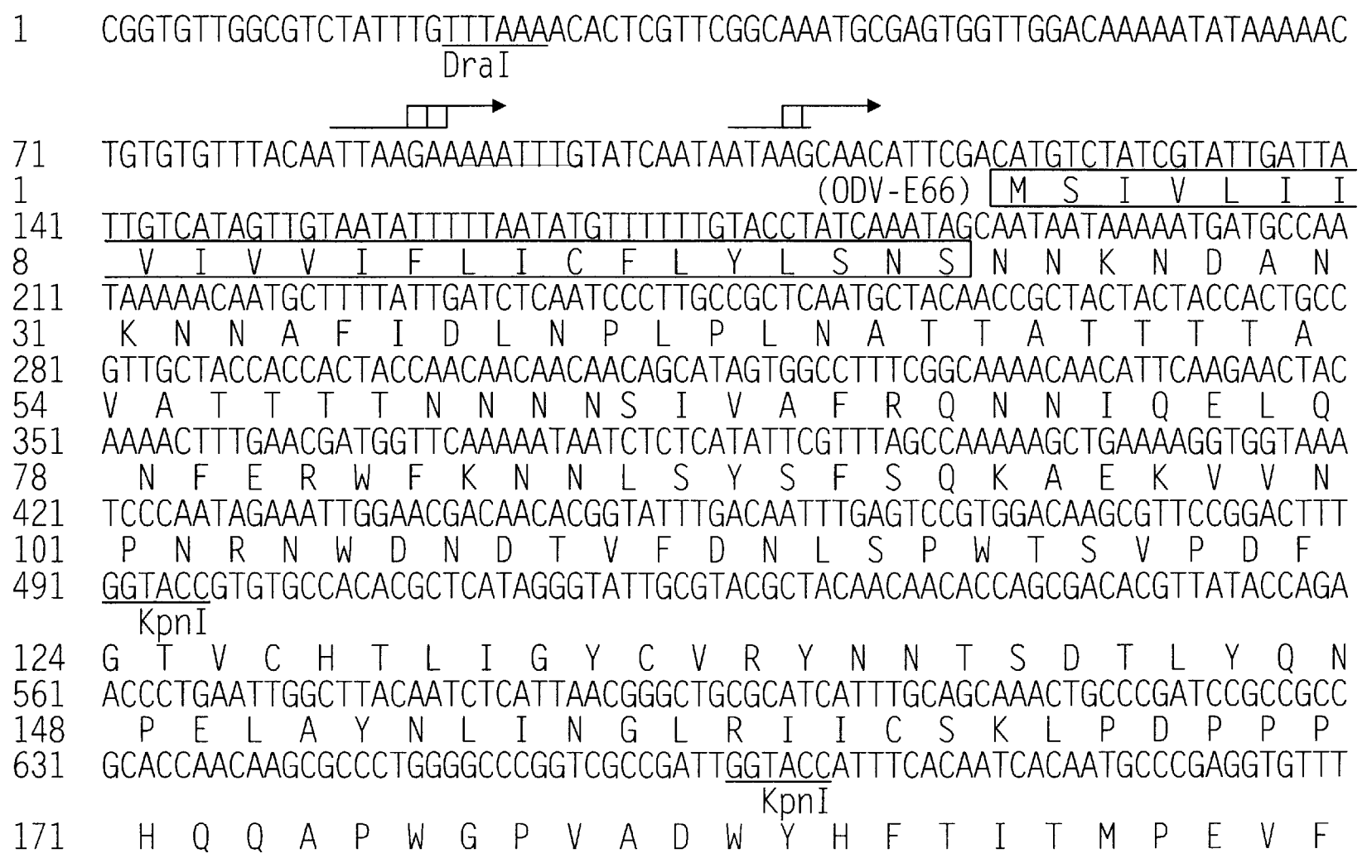

To construct the 125 β-gal plasmid, the KpnI-KpnI fragment (28.1–28.2 m.u., FIG. 1A-1, FIG. 1A-2 and FIG. 1A-3, Hong et al., 1994) within the PstI-F region (23.5–30.1 m.u.; cloned into pUC19) was replaced with a KpnI linker, 5'-GGTACCAAGGATCCTTGGTACC-3' (SEQ ID NO:10; BamHI site is underlined). A 3.1 kb BamHI fragment containing the lacZ gene from plasmid pAc360-β-gal (Luckow and Summers, 1989) was inserted into the BamHI site so that the region encoding N-terminal 125 amino acids of ODV-E66 was fused in frame with the lacZ gene.

To introduce partial deletions within the N-terminal 125 amino acids of 125 β-gal, the EcoRI-K region (25.0–29.2 m.u., FIG. 1A-1, FIG. 1A-2 and FIG. 1A-3, Hong et al., 1994) containing wild type ODV-E66 was cloned into the EcoRI site of pUC19 as the template for mutagenesis using transformer site-directed mutagenesis kit (ClonTech; See Construct #2, FIG. 2, "125 β-gal"). Both deletion and site-directed mutagenesis were done as instructed by the manufacturer. All mutants were confirmed by DNA sequencing (Sequenase 2.0; USB).

To obtain the construct Δ2–23 β-gal (See Construct #3, FIG. 2), amino acids 2–23 were deleted using the deletion oligonucleotide (SEQ ID NO:11) 5'-GCAACATTCGACATGAGCAATAATAAAAATGATG CC-3' and the selection oligonucleotide (SEQ ID NO:12) 5'-CTCTAGAGGAACCCCGGGAACCGAGCTCG-3'. After the introduction of deletion, the KpnI-KpnI fragment (28.1–28.2 m.u.) was replaced with the 3.1 kb KpnI fragment containing the LacZ gene from 125 β-gal. Construct #3 is the same as construct #2 except that the amino acids 2–23 (22 amino acids total) are deleted. The fusion protein Δ2–23 β-gal is cytoplasmic.

To obtain the construct 23 β-gal (See Construct #4, FIG. 2), nucleotide sequence encoding amino acids 24–25 were mutated to a KpnI site using the selection oligonucleotide (SEQ ID NO:12) 5'-CTCTAGAGGAACCCCGGGAACCGAGCTCG-5' and the site-mutation oligonucleotide (SEQ ID NO: 13; KpnI site is underlined) 5'-CCTATCAAATAGC GGTACCAAAAATGATGCCAAT-3'. The region from the new KpnI site at amino acids 24–25 to the KpnI site at 28.2 m.u. was replaced with the 3.1 kb KpnI fragment containing the LacZ gene from 125 β-gal.

7. Cloning Strategy for Overexpression of 23GFP

A DNA fragment encoding the N-terminal 23 amino acids of ODV-E66 (MSIVLIIVIVVIFLICFLYLSNS; SEQ ID NO:3) was amplified by PCR (30 sec at 94° C., 60 sec at 42° C., 90 sec at 72° C., 25 cycles) using the following oligonucleotides: 5'-TTTTTT AAGCTTATGTCTATCGTATTG-3' (SEQ ID NO:14; HindIII site is underlined) and 5'-TTTTTT GGATCCTTGCTATTTGATAGGTA-3' (SEQ ID NO:15; BamHI site is underlined). The PCR product was extracted with chloroform, precipitated with ethanol, digested with HindIII and BamHI, gel purified, and cloned into the HindIII and BamHI sites of pUC19. Amplified region was verified by DNA sequencing. The BamHI/EcoRI fragment from pGFP vector (ClonTech) which contains the complete GFP open reading frame (ORF) was cloned into the BamHI/EcoRI sites of the pUC19 PCR clone so that N-terminal 23 amino acids of ODV-E66 were fused in frame with GFP (pUC 19-23GFP).

The clone pVL1393-23GFP (See Construct #6, FIG. 2) was generated to overexpress 23GFP in insect cells. The HindIII site in pUC19-23GFP was filled by Klenow and the HindIII-EcoRI fragment was cloned into the SmaI/EcoRI sites of transfer vector pVL1393 (Webb and Summers, 1990). In this construct, expression of 23GFP was controlled by the polyhedrin promoter. Infected cells have an occlusion minus phenotype.

The 23GFP ORF was then cloned into the transfer vector pAcUW21 (PharMingen). The region from the BamHI site in the multiple cloning region of pVL1393-23GFP to the EcoRI site at the 3'-end was cloned into the BglII/EcoRI sites of pAcUW21 (ClonTech). In this construct (pAcUW21-23GFP; See Construct #5, FIG. 2) expression of 23GFP was under the control of the p10 promoter. Infected cells have an occlusion positive phenotype.

A recombinant virus containing GFP under the control of the polyhedrin promoter was provided by Dr. Christian Oker-Blom (VTT Biotechnology, Finland; Laukkanen et al., 1996; Oker-Blom et al., 1996) and was used as a control for immunofluorescence and immunogold labeling.

8. Cloning Strategy for Overexpression of ODV-E66

To express ODV-E66 at high levels under the polyhedrin promoter and in the polyhedrin locus, ODV-E66 was amplified by PCR (1 min at 94° C., I min at 37° C., and 3 min at 72° C. with 5 sec extension after each cycle, 25 cycles) using the following oligonucleotides: (SEQ ID NO:16; BamHI site underlined) 5'-TTTTT GGATCCACCATGTCTATCGTATTG-3' and (SEQ ID NO:17; PstI site underlined) 5'-TTTTT CTGCAGTTACTTGTCGTCGTCGTCTTTGTAGTCCAC AATTT CAAAAAT-3'. The second oligonucleotide contains the "FLAG" epitope (italic; amino acid sequence: DYKD-DDDK (SEQ ID NO:7; VWR Scientific) immediately upstream of the stop codon. The PCR product was cloned into the BamHI and PstI sites of pVL 1393 (Webb and Summers, 1990). The resultant construct (pVL1393-E66F; See Construct #7, FIG. 2) was sequenced to verify that PCR did not introduce errors in the nucleotide sequence.

9. Cloning Strategy for Overexpression of 23URF13

To overexpress a fusion gene encoding N-terminal 23 amino acids of ODV-E66 fused in frame with URF13 gene (Dewey et al., 1986) under the control of p10 promoter in the pAcUW21 transfer vector, recombinant PCR was used to amplify and combine the nucleotide sequence encoding the N-terminal 23 amino acids of ODV-E66 with the URF13 gene. A DNA fragment encoding the N-terminal 23 amino acids of ODV-E66 was amplified by PCR (60 sec at 94° C., 30 sec at 42° C., 60 sec at 72° C., 25 cycles) using the following oligonucleotides: (SEQ ID NO:18; BamHI underlined) 5'-TTTTCG GGATCCATGTCTATCGTATTG-3' and (SEQ ID NO:19) 5'-TAAGAAAGTAGTGATGCTATTTGATAGGTA-3'. The URF13 gene was amplified by PCR (60 sec at 94° C., 30 sec at 42° C., 60 sec at 72° C., 25 cycles) using the Turf-2b plasmid as template (Dewey et al., 1986) and the following oligonucleotides: 5'-TACCTATCAAATAGCATCACTACTTTCTTA-3' (SEQ ID NO:20) and 5'-AAAAAG GAATTCTCACGGTACTTGTAC-3' (SEQ ID NO:21; EcoRI site underlined). After the first round of PCR for the N-terminal 23 amino acids of ODV-E66 and the URF13 gene, 1 µl of PCR product from each PCR reaction was used as the templates for a second round of PCR (60 sec at 94° C., 30 sec at 42° C., 60 sec at 72° C., cycles) using two of the oligonucleotides used in the first PCR: 5'-TTTTCG GGATCCATGTCTATCGTATTG-3' (SEQ ID NO:18; BamHI underlined) and 5'-AAAAAG GAATTCTCACGGTACTTGTAC-3' (SEQ ID NO:21; EcoRI site underlined). Product from the second PCR was extracted with chloroform, precipitated with ethanol, digested with BamHI and EcoRI, and cloned into the BglII/EcoRI sites of pAcUW21 vector. Recombinant virus made using this construct (pAcUW21-23URF13; See Construct #8, FIG. 2) produces viral occlusions in infected cells.

10. Construction of Recombinant Viruses

Recombinant viruses 125 β-gal, Δ2–23 β-gal, and 23 β-gal, were constructed using the corresponding transfer plasmid and AcMNPV viral DNA (Summers and Smith, 1987). pVL1393-23GFP, pAcUW21-23GFP, pVL1393-E66F, and pAcUW21-23URF13 were constructed using the corresponding plasmid constructs and Bsu36I-digested Bak-Pak6 viral DNA (ClonTech). The locus of recombination was verified by Southern analyses and an appropriate probe. Protein expression was confirmed by Western-blot analyses of infected cell extracts using appropriate antibody: β-gal recombinant viruses (mouse anti-p-gal polyclonal antibody at 1:1250; Sigma); 23GFP recombinant viruses (rabbit anti-GFP polyclonal antibody at 1:1500; ClonTech). Southern and Western-blot analyses were done as described by Sambrook et al., (1989).

Figure 12:
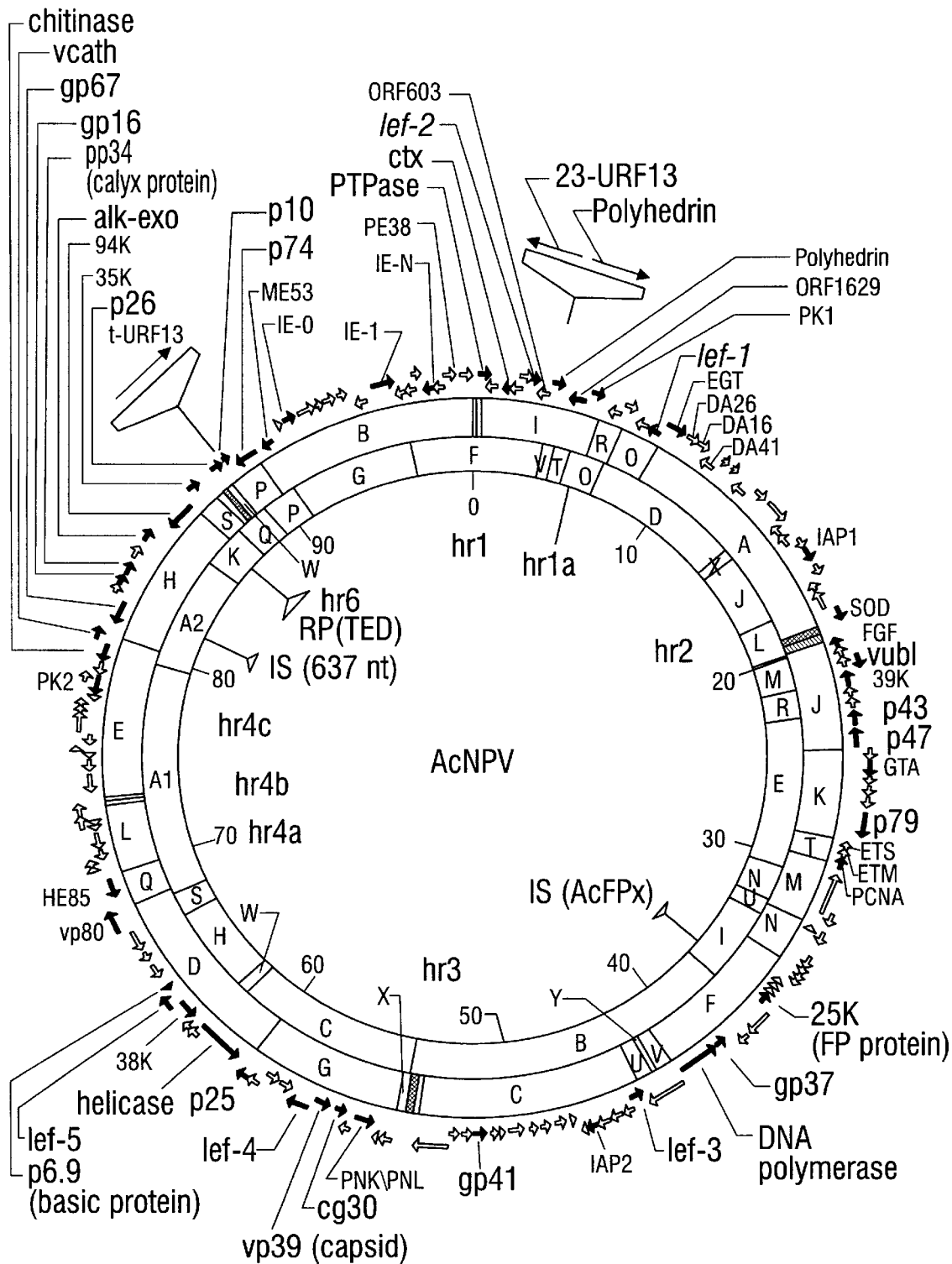
FIG. 12 is genomic map of *Autographa californica* NPV showing a construct containing dual promoters and which is occlusion positive and contains both NT-URF13 and WT t-URF13.
Figure 13A:
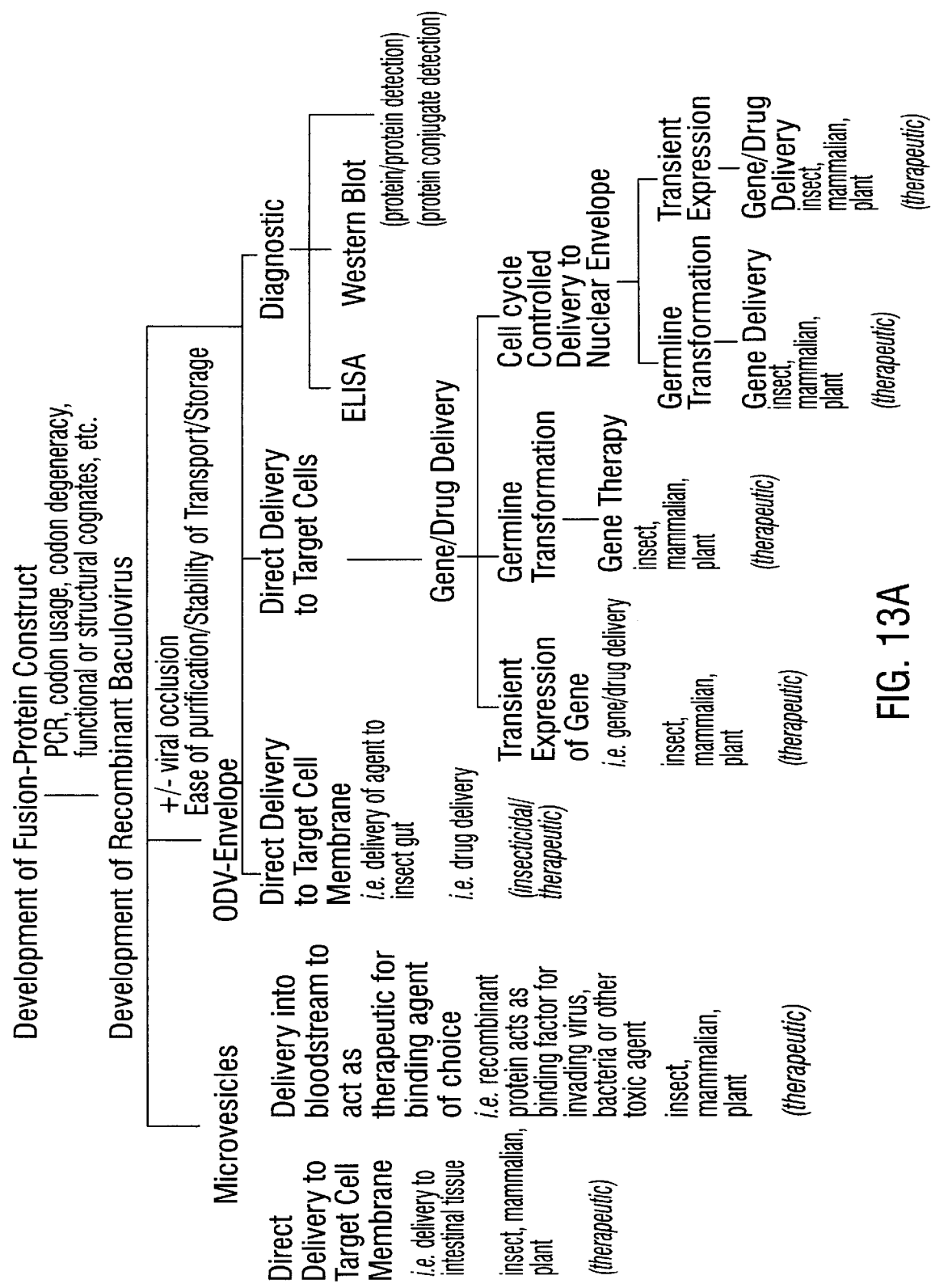
FIG. 13A and FIG. 13B are charts showing potential applications for the hydrophobic targeting sequences, as described in the Examples.
Figure 13B:
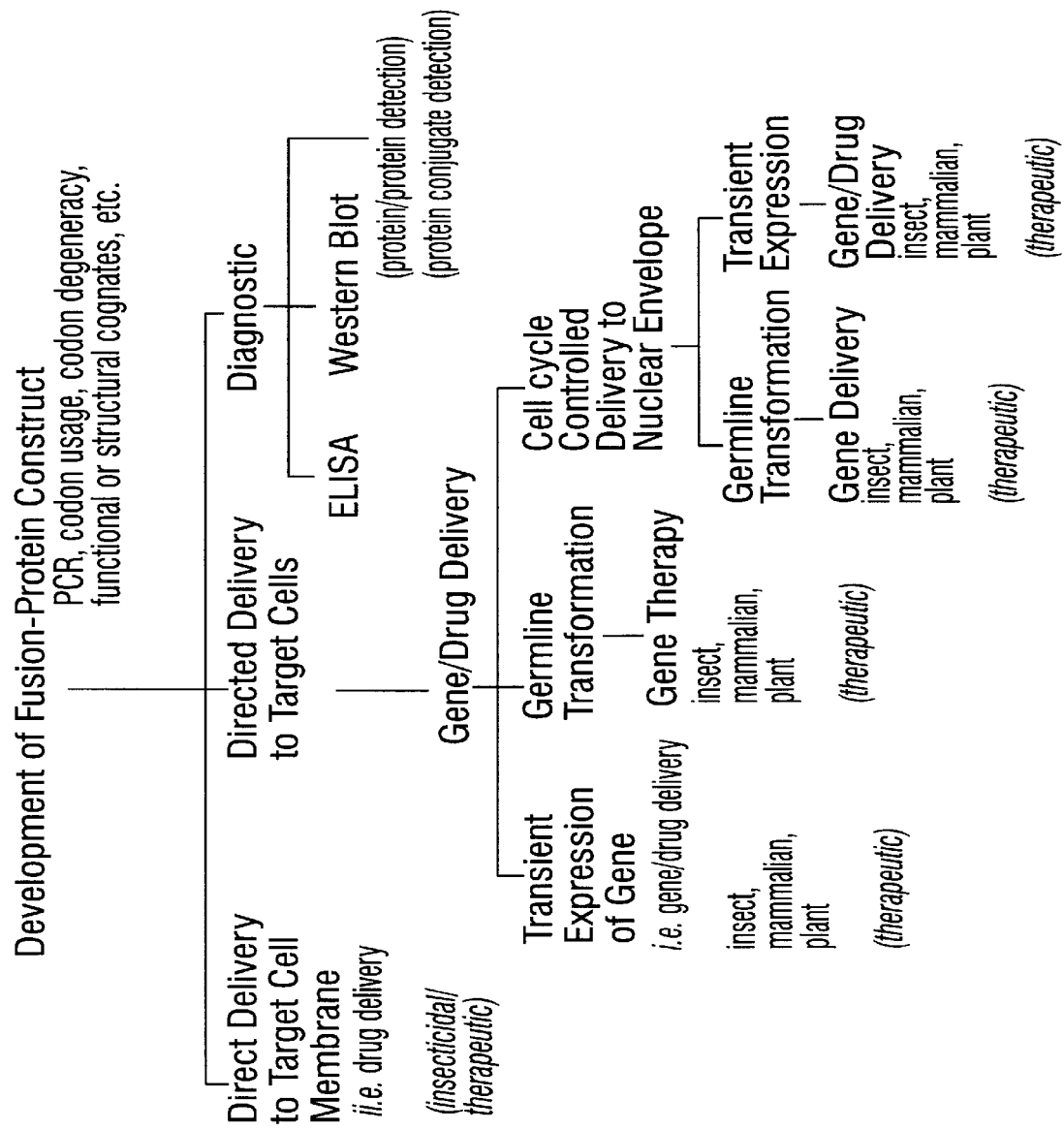

FIG. 12 is genomic map of *Autographa californica* NPV showing a construct containing dual promoters and which is occlusion positive and contain both 23URF13 and wild type t-URF13 (WT t-URF13). Multiple genes can be inserted at both the polyhedrin and p10 loci. In this manner, recombinant viruses can be constructed that are occlusion positive and contain multiple genes. Genomic map modified and reprinted from Ayres, et al. (1994). Construction of recombinants containing multiple genes is routine for the inventors using the techniques described by Belyaev and Roy (1993) and Summers and Smith (1987).

11. GFP Autofluorescence

Autofluorescence of GFP in cells expressing GFP or 23GFP was observed on a Zeiss Axiophot microscope (Electron Microscopy Center, Texas A&M University) equipped with a filter set for fluorescein isothiocyanate (FITC). Cells were photographed using phase contrast, fluorescence, or double exposure of phase contrast and fluorescence. Exposure time for cells at different time points postinfection was maintained constant and was set for proper exposure of the 72 h.p.i. time point for comparison of fluorescence intensity.

12. Transient Expression of 23GFP in Uninfected *Sf*9 Cells

To transiently express 23GFP under the control of the IE1 promoter, the HindIII/EcoRI fragment from 23GFP-pUC19 was filled with Klenow at both ends and cloned into the PmeI site of pIE1HR4 (Jarvis et al, 1996) so that the filled HindIII site was close to the BamHI site in pIE1 HR4. This construct was named pIE1HR4-23GFP (See Construct #9, FIG. 2).

Transfection of plasmid DNA into uninfected *Sf*9 cells was done using the CellFECTIN lipofection reagent as instructed by the manufacturer (Gibco BRL). For each transfection, 2 μg of plasmid DNA and 9 μl of CellFECTIN reagent were used. Cells were recovered at 24 or 48 hr post-transfection for fluorescence observation or EM fixation. The pattern of protein localization was indistinguishable between 24 and 48 hr post-transfection.

13. Transient Expression of 23GFP in Mammalian (COS-1) cells

The pUC19-23GFP construct (see Cloning Strategy for Overexpression of 23GFP) was digested with EcoRI, filled with Klenow (Sambrook et al., 1989), Klenow enzyme inactivated by heating at 75° C. for 15 min, and digested with HindIII. Then, the resulting HindIII/EcoRI fragment containing 23GFP was cloned into the HindIII/HpaI sites of pCMV Blue vector (PharMingen). In this construct (pCMV-23GFP; See Construct #10, FIG. 2) expression of 23GFP is under the control of the major immediate early promoter of cytomegalovirus which is active in the COS-1 cells.

COS-1 cells (Gluzman, 1981) were maintained at 37° C. in Dulbecco's modified Eagle's medium (Gibco BRL) supplemented with 10% fetal calf serum. Transfection of plasmid DNA into COS-1 cells was done in DMEM medium without serum and antibiotics using the CellFECTIN lipofection reagent as instructed by the manufacturer (Gibco BRL). For each transfection, 2 μg of plasmid DNA and 15 μl of CellFECTIN reagent were used. After transfection, cells were incubated at 37° C. for 24 hr for 23GFP to be expressed, then cells were transferred to 30° C. and incubated for another 48 hr for GFP autofluorescence to develop (Ogawa et al., 1995).

14. In Vitro Transcription, Translation, and Membrane Co-purification Assay

Genes encoding ODV-E66, Δ2–23β-gal and 23β-gal, were cloned into the pBS-vector (Stratagene). Plasmid DNA was linearized and transcribed (Hong et al., 1994). Co-translational membrane co-purification assay was done as described by Kabcenell and Atkinson (Kabcenell and Atkinson, 1985). Briefly, after translation membranes were diluted with a high salt buffer (20 mM Tris-HCl, 500 mM KCl, 2 mM CaCl$_2$, 5 mM MgCl$_2$, pH 7.4) and layered over a sucrose cushion (0.5M) made in the same buffer. Post-translational membrane co-purification was performed after translation for 1 hr at 30° C. in the absence of microsomal membranes, 2 mM cycloheximide was added to stop translation, and the reaction mixture was chilled on ice before addition of 1.8 μl of microsomal membranes. After 1 hr incubation at 4° C., the mixture was subject to the membrane co-purification assay briefly described (Kabcenell and Atkinson, 1985).

EXAMPLE 2

Identification, Sequence, and Analysis of ODV-E66 and the N-terminal 23 Amino Acid Hydrophobic Domain 1. Baculovirus Expression of AcMNPV ODV-E66 and Overexpression of ODV-E66 Under the Control of the Polyhedrin Gene Promoter in the Polyhedrin Locus To identify proteins unique to the ODV envelope, ODV and BV were purified and fractionated into envelope and nucleocapsid fractions. A comparison of the structural proteins of ODV, BV, and envelopes revealed a protein of 66 kDa unique to the ODV envelope (Braunagel and Summers, 1994, incorporated herein by reference). N-terminal amino acid sequencing of this protein determined the sequence of: MSIVLIIVI (SEQ ID NO:4). The gene was mapped to the EcoRI-PstI region (25.0–30.1 m.u., FIG. 1 of Hong et al., 1994, incorporated herein) of the AcMNPV genome and the nucleotide sequence (SEQ ID NO:1; 2530 nucleotides including 2115 nucleotides of open reading frame) of the gene encoding ODV-E66 predicts a protein of 704 amino acids (SEQ ID NO:2; FIG. 1).

ODV-E66 is an integral membrane protein of the ODV envelope. In the infected cell nucleus, ODV-E66 is present in the intranuclear viral-induced microvesicles and ODV envelope, providing evidence that the microvesicles function as an immediate precursor in the assembly of the ODV envelope. In infected cells, ODV-E66 also localizes to the membranes of the nuclear envelope, and cytoplasmic membranes in close juxtaposition to the nuclear envelope. A mutant virus in which the ODV-E66 gene was replaced with a fusion gene encoding the N-terminal 125 amino acids of ODV-E66 and E. coli β-galactosidase (β-gal) showed that the 125-amino acid N-terminal domain targeted the β-gal fusion protein to the intranuclear microvesicles and ODV envelope. This function localizes specifically to a unique N-terminal hydrophobic sequence of 23 amino acids which is derived from the N-terminal 125 amino acids of ODV-E66. In infected insect cells this 23-amino acid sequence targets β-gal, green fluorescent protein (GFP), and URF-13 to the membranes of the nuclear envelope which are further transported into the intranuclear microvesicles and ODV envelope.

In uninfected insect and mammalian (COS-1) cells, this sequence targets GFP to the membranes of the nuclear envelope. This amino acid sequence also inserted β-gal into microsomal membranes in the rabbit reticulocyte in vitro translation system. This is the first report of a unique sequence which can specifically target foreign proteins to the nuclear envelope, intranuclear microvesicles, and ODV envelope and has important applications in insecticide, human, and animal health.

Listed below is a summary of known hydrophobic protein sequences of inner nuclear membrane proteins reported in the literature (see Table 10 below). Except for HSV-1 gB (protein #2 below), all of the proteins listed in Table 10 below are non-viral proteins. Also, all of these proteins are located in either the nuclear envelope, the nuclear pore, and/or cytoplasmic membrane. Of interest, except for the rat gp210 protein, all of the other listed proteins localize to the inner nuclear membrane (INM).

Table 10 below outlines how the hydrophobic targeting sequence of this invention functions differently from the other reported non-baculovirus inner nuclear membrane proteins. Specifically, in infected cells, the hydrophobic targeting sequence of this invention targets proteins to intranuclear viral-induced membranes, in addition to protein targeting to nuclear envelope and cytoplasmic membranes.

Also, in uninfected Sf9 and COS-1 cells, the targeting of proteins to membranes of the nuclear envelope (NE) correlates with cell cycle-regulated movement of integral membrane proteins.

The following abbreviations are used in Table 1: LBR—Lamin B receptor; INM—Inner nuclear membrane; TM—Transmembrane domain; NE—Nuclear envelope; HSV—Herpes simplex virus; gB—Glycoprotein B; ER—Endoplasmic reticulum; LAP—Lamina associated protein; and NPC—Nuclear pore complex.

TABLE 10

Inner Nuclear Membrane Proteins

| Protein | Location | Summary |
|---|---|---|
| Chicken LBR (COS-7 cells) Smith and Blobel, 1993 and Soullam and Worman, 1993 | INM (not detected on ER, Golgi, and cell surface) | 1. Chicken LBR has 8 potential transmembrane segments. The first segment is from #206–226. TM: FGTFMLMFFLPATVLYLVLMC (SEQ ID NO:29)<br>2. Region from #205–246, including the first TM, when fused to the C-terminus of β-gal, is sufficient to target fusion protein to INM.<br>3. The nucleoplasmic domain (191 aa) of LBR, when fused to the TM and C-terminal domain of chicken heptic lectin (a type II protein with internal signal sequence-the TM), targets the fusion protein to INM. The nucleoplasmic domain of LBR, when expressed alone, is in the nucleoplasm. |
| HSV-1gB (COS-1 cells) Gilbert et al., 1994 | NE-INM (also ONM, ER, Golgi, and cell surface) | 1. gB is targeted to INM in the immature N-glycoform.<br>2. TM of gB is form aa.#727–795 and consists of three hydrophobic segments.<br>3. Segment 3 is sufficient to target VSV G protein to nuclear envelope when it replaces the TM of G protein in the fusion. Note that the fusion protein still has the signal peptide from G protein and also localizes to ER, Golgi, and cell surface. |
| Rat LAP2 (Hela cells) Furukawa et al., 1995 | INM (not detected on ER, Golgi, and cell surface) | 1. LAP2 has 452 amino acid; type II protein with 409 aa., nucleoplasmic domain; TM is between #410–433. TM: VPMWIKMLLFALVAGFLFLYQAM (SEQ ID NO:30)<br>2. TM is likely to function as membrane anchor and is not required or sufficient for INM targeting. Domain between #298–370 is essential, but not sufficient for Triton X-100 stable INM targeting. Domain #298–370 possibly functions to bind lamina and thus retain protein in INM. |
| Rat gp210 (Mouse Balb/c 3T3 cells) Wozniak and Blobel, 1992 | Membrane domain of NPC | 1. gp210 is an integral membrane N-glycoprotein.<br>2. 1886 aa in total; TM-#1806–1818; 58 aa. C-terminal domain. TM: SYQVMFFTFFALLAGTAVTIIAY (SEQ ID NO:31)<br>3. TM domain of gp210 is sufficient to target CD8-TM fusion to NPC (CD8 is a plasma membrane protein with an internal signal/stop transfer sequence; the TM and C-terminal domain of CD8 were deleted in the fusion).<br>4. The 58 aa. C-terminal domain of gp210 is a weak, but sufficient NPC targeting signal when fused after the TM domain of CD8 (the CD8 C-terminal domain was replaced). |
| Otefin (Drosophilia) Harel et al., 1989 Paden et al., 1990 | INM | 1. Targeting signal is unknown. |
| Turkey p18 (erythrocytes) Simos et al., 1996 | INM | 1. p18 is a component of a complex consisting of LBR, lamins, LBR kinase, p34, and p18.<br>2. Targeting sequence is unknown. |
| Rat LAPIC Senior and Gerace, 1988 Martin et al., 1995 | INM | 1. 506 aa in total; TM is between #311–333; type II protein with N-terminal nucleoplasmic domain.<br>2. Targeting signal is unknown. |

FIG. 1A-1, FIG. 1A-2 and FIG. 1A-3 is a diagram representing the nucleotide and amino acid sequences of the gene encoding ODV-E66. Nucleotide sequences upstream and downstream of ODV-E66 open reading frame are also included. The amino acid sequence of ODV-E66 is shown in single capital letters. The numbers to the left indicate positions of nucleotide and amino acid. The N-terminal 23 amino acid hydrophobic sequence is boxed thereby including nucleotide numbers 122 through 190 (sixty-nine (69) nucleotides). Restriction endonuclease sites (DraI, KpnI, and EcoRI) are underlined. Arrows above the nucleotide sequences (TTAAG and ATAAG) indicate the transcription initiation sites.

The nucleotide and amino acid sequences for the 23AA sequence of ODV-E66 are shown in FIG. 1B. The ODV-E66 23 AA sequence has the following amino acid sequence: MSIVLIIVIVVIFLICFLYLSNS (SEQ ID NO:3).

Studies of the gene encoding ODV-E66 demonstrated that it is a baculovirus late gene with transcription initiating from conserved TAAG motifs FIG. 1A-1, FIG. 1A-2 and FIG. 1A-3, arrows; for complete description of genetic analysis including Northern-blot, primer extension, 5' and 3' S1 nuclease analysis see Hong et al., 1994).

FIG. 2 is an outline summarizing some of the different constructs used in this invention and includes the construct name, gene promoter and locus, occlusion production, and protein location in cells. Numbers above the structures indicate locations of amino acids. In Construct #1, ODV-E66, the ODV-E66 expression is controlled by its native promoter in the native locus in wild type virus and infected cells produce viral occlusions.

FIG. 3A, FIG. 3B and FIG. 3C are photographs showing immunogold labeling of purified ODV and wild type AcMNPV infected Sf9 cells at 48 h.p.i. Rabbit ODV-E66 antiserum and anti-rabbit IgG 15 nm gold-conjugate were used. FIG. 3A shows the labeling of the viral envelope of purified ODV (arrowhead). FIG. 33B shows the labeling of the intranuclear viral-induced microvesicles. Note the microvesicles are surrounded by fibrillar structures and viral occlusions. FIG. 3C shows the labeling of the viral envelope of ODV being occluded into a viral occlusion (arrowhead). The following abbreviations are used in this figure: m, microvesicles; f, fibrillar structure; oc, viral occlusion.

Studies of the protein ODV-E66 show that it is a structural protein of the ODV envelope (FIG. 3A, arrowheads; Hong et al., 1994). During viral assembly, ODV-E66 locates to viral induced intranuclear microvesicles (FIG. 3B, m) and the ODV envelope that is maturing into the occluded form (FIG. 3C, arrowheads; Hong et al., 1994).

A recombinant virus was generated that places an additional copy of the gene encoding ODV-E66 into the baculovirus genome under the control of the polyhedrin promoter (FIG. 2, Construct #7). In construct #7, an extra copy of ODV-E66 gene replaces the polyhedrin gene in the polyhedrin locus in Construct #7. In this construct, (a) expression of the extra copy of ODV-E66 gene is under the control of polyhedrin promoter, (b) infected cells did not produce viral occlusions due to the absence of a functional polyhedrin gene, and (c) the ODV-E66 gene in the native locus is intact.

FIG. 4A, FIG. 4B, and FIG. 4C are photographs showing immunogold labeling of Sf9 cells infected with pVL1393-

E66F at 48 h.p.i. Rabbit ODV-E66 antiserum and anti-rabbit IgG 15 nm gold-conjugate were used. FIG. 4A shows labeling in the intranuclear microvesicles and cytoplasmic membranes close to the nuclear envelope (dual arrow). FIG. 4B shows labeling of the cytoplasmic membranes (dual arrow). FIG. 4C shows labeling of the outer (arrowhead) and inner (arrow) nuclear membranes. The following abbreviations are used in this figure: m, microvesicles; n, nucleus; c, cytoplasm.

Immunoelectron microscopy of the localization of ODV-E66 in this recombinant virus shows the same protein localization as wild type AcMNPV, however the amount of ODV-E66 is increased significantly (FIG. 4). By increasing the amount of ODV-E66 we could detect the same labeled structures as wild type, but additionally can visualize cellular locations of the protein that were indicated by wild type virus, but were observed at low levels. These locations include: ODV envelope (FIG. 4A and FIG. 4C), microvesicles and other intranuclear membranes (FIG. 4A and FIG. 4C; m), membranes closely associated with the nucleus (FIG. 4A and FIG. 4B, dual arrow), the nuclear envelope, including the inner and outer nuclear membrane (FIG. 4C, INM, arrow; ONM, arrowhead).

Overexpression of ODV-E66 by this recombinant virus confirms that ODV-E66 locates to the nuclear membrane, an observation that was indicated with wild type virus, but difficult to confirm due to decreased levels of proteins. Additionally, pVL1393-E66F generated virus confirms that when ODV-E66 (or derived fusion) is placed in the baculovirus genome at an alternative locus (i.e., polyhedrin locus) and under the control of an alternate promoter (i.e., polyhedrin or p10 or other classes of viral gene promoters), it locates to the same cellular organelles and structures as it would locate in wild type baculovirus infected cells.

2. Analysis of the N-terminal 23 Amino Acids of ODV-E66, Development of Recombinant Viruses Containing Fusion Proteins, and Localization of Fusion Proteins During Viral Infection a. Beta-Galactosidase Protein (β-gal) as a Marker A mutant virus was constructed in which a fusion gene encoding the N-terminal 125 amino acids of ODV-E66 was fused in frame with β-galactosidase (β-gal; FIG. 2; 125 β-gal, Construct #2) and replaced ODV-E66 in the native locus.

Construct #2 shows that the ODV-E66 gene, in the native locus, is replaced by a mutant gene 125 β-gal (in frame fusion of N-terminal 125 amino acids of ODV-E66 with β-galactosidase of E. coli) whose expression is still controlled by the native ODV-E66 promoter.

Because β-gal is cytoplasmic when expressed in infected Sf9 and Sf21 cells (Jarvis et al., 1991; Hershberger et al, 1994), it was expected that the fusion protein would also locate to the cytoplasm. However, immunofluorescence and immunogold labeling showed that the 125 β-gal fusion protein localized into the nucleus and to viral induced intranuclear microvesicles and ODV envelope (Hong, 1995). The conclusion was that the N-terminal 125 amino acids of ODV-E66 must contain the requisite signal(s) necessary to direct β-gal or potentially other proteins into the nucleus and intranuclear membranes.

Using computer-assisted analysis, an N-terminal hydrophobic region of 23 amino acids with a general hydrophobic character similar to the signal/anchor sequences in many membrane proteins (von Heijne, 1990) was identified: MSIVLIIVIVVIFLICFLYL SNS (SEQ ID NO:3).

Several additional constructs were made which included fusion mutants with or without the N-terminal hydrophobic domain (FIG. 2). After cloning the gene encoding each mutant protein, a recombinant virus was produced and expression of each gene, under a variety of baculovirus promoters, was studied. These recombinant gene constructs were then inserted at various loci within the baculovirus genome (FIG. 2).

When the hydrophobic 23 amino acid sequence was fused in frame with the normally cytosolic protein β-galactosidase (23 β-gal; FIG. 2, Construct #4), the fusion protein was transported into the nucleus and this was initially confirmed using fluorescent confocal microscopy (Hong, 1995). In construct #4, the ODV-E66 gene, in the native locus, is replaced by a mutant gene 23 β-gal (in frame fusion of N-terminal 23 amino acids of ODV-E66 with β-galactosidase of E. coli) whose expression is still controlled by the native ODV-E66 promoter.

Figure 5B:

FIG. 5A and FIG. 5B are photographs showing immunogold labeling of Spodoptera frugiperda (Sf9) and Trichoplusia ni (TN368) cells infected with 23 β-gal virus at 48 h.p.i. For these figures, mouse β-gal antiserum and anti-mouse IgG 30 nm gold-conjugate were used. FIG. 5A shows that 23 β-gal fusion protein was localized to the intranuclear microvesicles (arrowhead) and ODV envelope (arrow) in infected Sf9 cells. FIG. 5B shows that 23 β-gal fusion protein was localized to the intranuclear microvesicles (arrowhead) and ODV envelope (arrow) in infected TN368 cells. The following abbreviations are used in this figure: m, microvesicles; n, nucleus; c, cytoplasm.

Figures 15A, 15C, 15E:
FIG. 15A, FIG. 15B, FIG. 15C, FIG. 15D, FIG. 15E and FIG. 15F show immunogold localization of 23 β-gal, ODV-E25, 23GFP, 24GFP and ODV-E66. All data is presented from *Sf*9 infected cells at 48 h.p.i. and secondary antibody linked to gold.
Figures 15B, 15D, 15F:
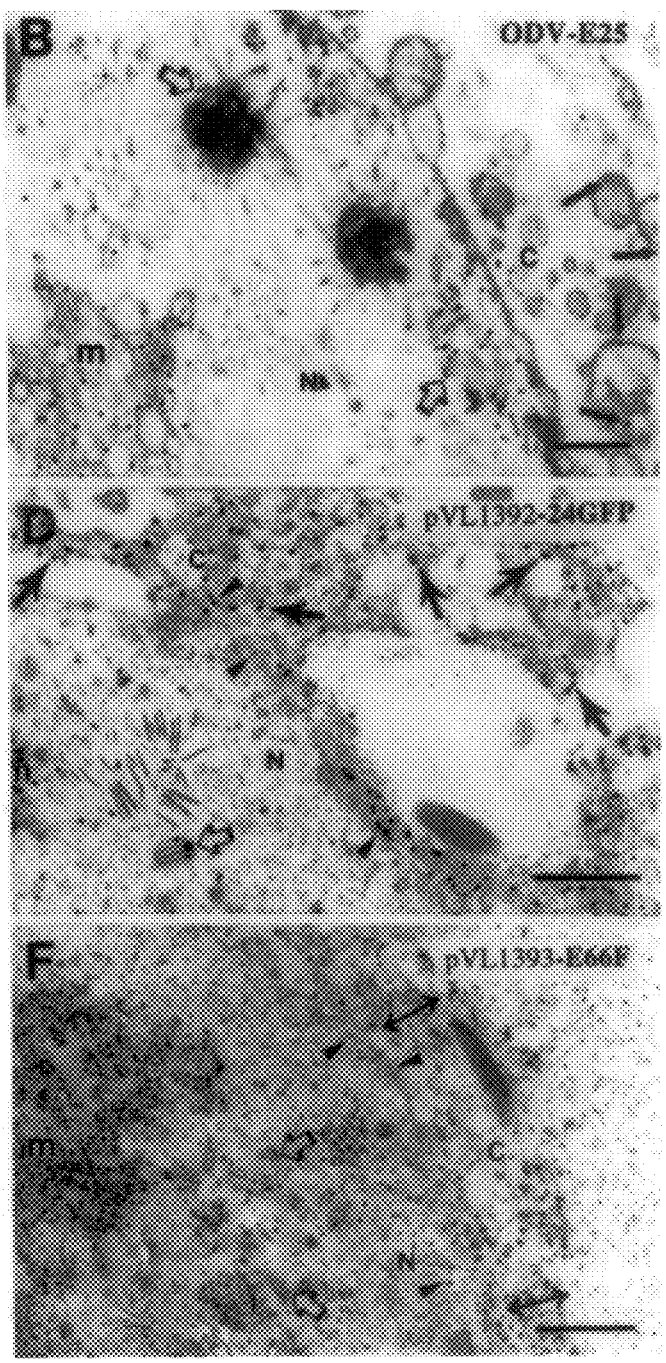

Immunoelectron microscopy of 23 β-gal infected Sf9 cells showed that the N-terminal 23 amino acids of ODV-E66 were sufficient to direct the fusion protein 23 β-gal to the viral induced intranuclear microvesicles and ODV envelope (FIG. 5A). This is also shown in FIG. 15A, with significant levels of label observed within the viral induced intranuclear microvesicles (FIG. 15A, m), ODV envelope (FIG. 15A, open arrows) and slight but discernible label along the nuclear membrane and associated with intracellular, cytoplasmic membranes (FIG. 15A, arrows). This labeling pattern is very similar to ODV-E25, another ODV envelope protein that contains an N-terminal hydrophobic domain (Russell and Rohrmann, 1993). FIG. 15B shows that ODV-E25 antibody also labels intranuclear microvesicles and the ODV envelope (FIG. 15B, m and open arrow) with limited but discernible labeling of the nuclear membrane and intracellular cytoplasmic membranes (FIG. 15B, arrows).

When compared to the labeling pattern of wild type or fusion proteins expressed under the ODV-E66 promoter, fusion proteins more highly expressed under the control of the polyhedrin promoter still label the viral induced microvesicles and ODV envelope, but significant amounts of label were visualized associated with intracellular cytoplasmic membranes located near the periphery of the nucleus (FIG. 15C through FIG. 15F). Increased amounts of label are also visualized in the microvesicles and ODV envelope (FIG. 15D through FIG. 15F, m and open arrow). However, label is enriched in the nuclear envelope, both outer and inner nuclear membrane (FIG. 15D through FIG. 15F, arrowheads) and in cytoplasmic membranes near the nucleus (FIG. 15F, dual arrows).

These results are not restricted to Sf9 cells, and these results were confirmed using another insect cell line, Trichoplusia ni (TN368; FIG. 5B).

Figure 14:
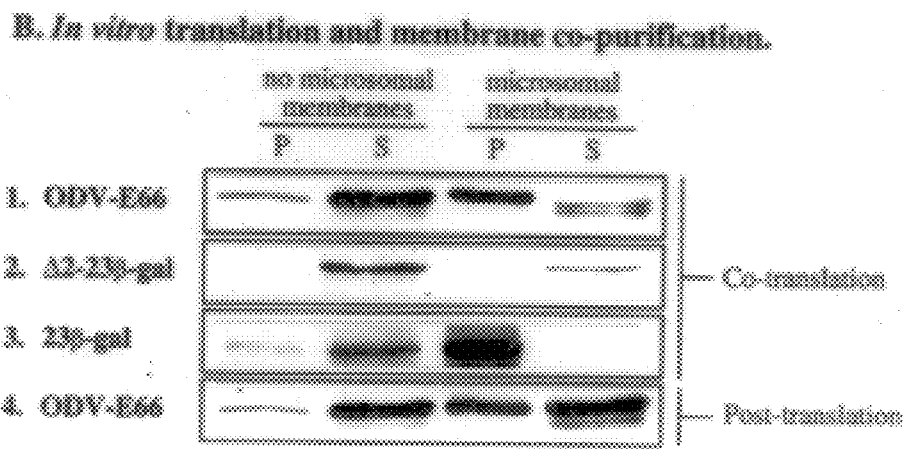
FIG. 14. shows the in vitro translation and membrane co-purification assay performed on the ODV-E66 (co- and post-translation), Δ2-23 β-gal and 23 β-gal constructs (co-translation only). P, microsomal membrane pellet fraction; S, supernatant fraction.

ODV-E66 and fusion proteins containing the ODV-E66 N-terminal hydrophobic domain were tested for their ability to stably integrate into microsomal membranes. ODV-E66, and 23β-gal proteins were able to incorporate into microsomal membranes (FIG. 14, #1 and #3), whereas Δ2–23,β-gal remained in the soluble fraction (FIG. 14, #2). Additionally, it was determined that ODV-E66 was capable of post-translational insertion into microsomal membranes, however at a lower efficiency (FIG. 14, #4). To determine if ODV-E66 was transported into the lumen of the microsomal membranes, protease digestion studies were performed and these studies indicated that after insertion into microsomal membranes, ODV-E66 was not protected from protease activity. These data are consistent with N-glycosylation studies of ODV-E66. Data obtained using tunicamycin, N-glycosidase F and incorporation of $^3$H-sugars; indicate that ODV-E66 is not N-glycosylated.

b. Green Fluorescent Protein (GFP) as a Marker

Green fluorescent protein (GFP) is a small protein that normally resides throughout the cells, including the cytoplasm and nucleus and is not normally membrane associated. It is known that if wild type GFP is expressed in baculovirus under the control of the polyhedrin promoter that it also uniformly distributes throughout the cell. GFP was chosen as an additional marker protein for several reasons: (a) because it normally is not excluded from the nucleus, the 23GFP fusion should also indicate specific controls or in the presence of specific localizations factors, for both the cytoplasmic and nuclear compartments; and (b) the autofluorescence of GFP should allow one to visually track and locate the fusion protein movement after viral infection. Thus, GFP should provide another example and an overview of specific localization and transport with a high degree of sensitivity and specificity for detection.

Two recombinant viruses were generated which contained the N-terminal 23 amino acids of ODV-E66 fused in frame with GFP (23GFP; FIG. 2, Constructs #5 and #6). In construct #5, a fusion gene of N-terminal 23 amino acids with green fluorescent protein (23GFP) was placed under the control of p10 promoter and inserted into the polyhedrin locus as an extra copy of transcriptional unit. The polyhedrin and p10 genes in their native loci are still intact, thus infected cells still produced viral occlusions. In construct #6, the 23GFP fusion gene replaced the polyhedrin gene in the polyhedrin locus. Expression of 23GFP was under the control of polyhedrin promoter. Infected cells did not produce viral occlusions due to the absence of a functional polyhedrin gene.

Cells infected by pAcUW21–23GFP (p10 promoter) or pVL1393-23GFP (polyhedrin promoter) were occlusion-positive or occlusion-negative, respectively. Cells infected by pAcUW21-23GFP produced normal amounts of viral occlusions and occluded virus as determined by immunogold labeling. The pattern of label of 23GFP fusion protein location was essentially the same for the occlusion positive and occlusion negative mutants. Because of the additional complexity of occlusion formation within the nucleus, the data using the occlusion-negative mutant has been chosen for the representative observation of GFP localization (FIG. 6).

Figure 6E:
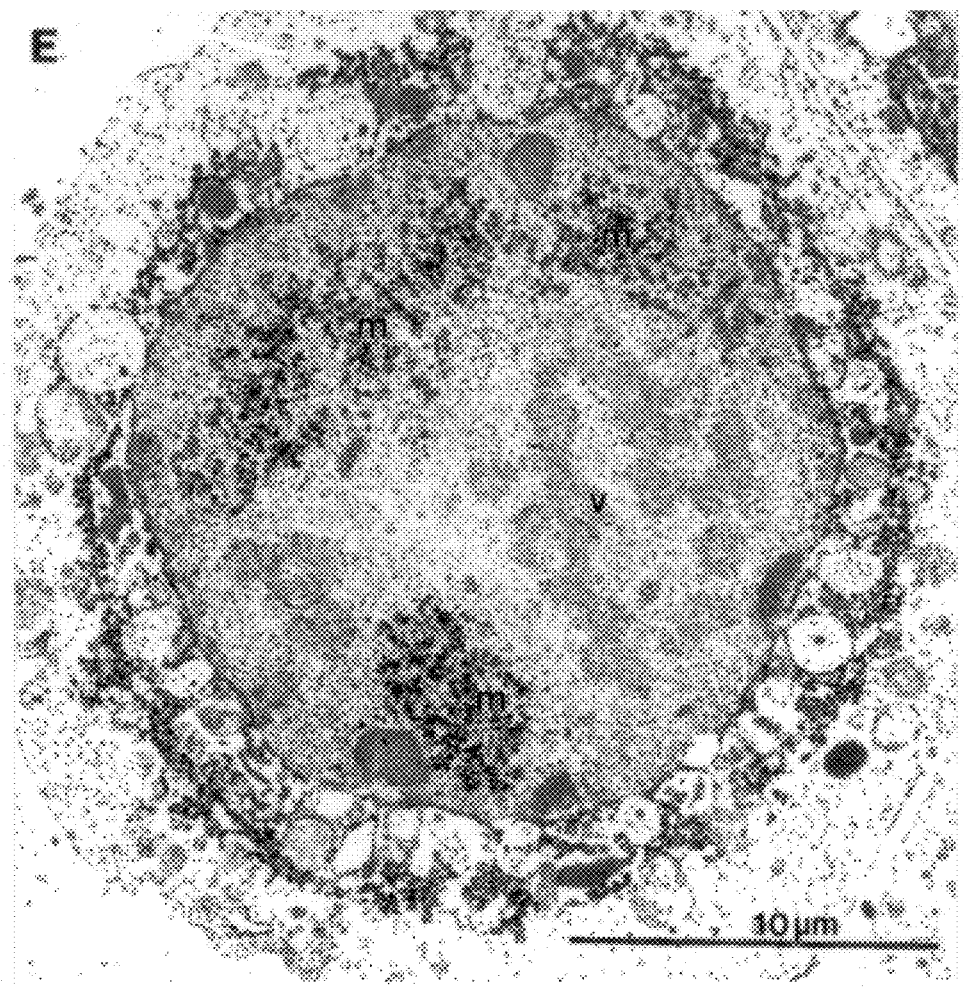
Figure 6F:
Figure 6G:
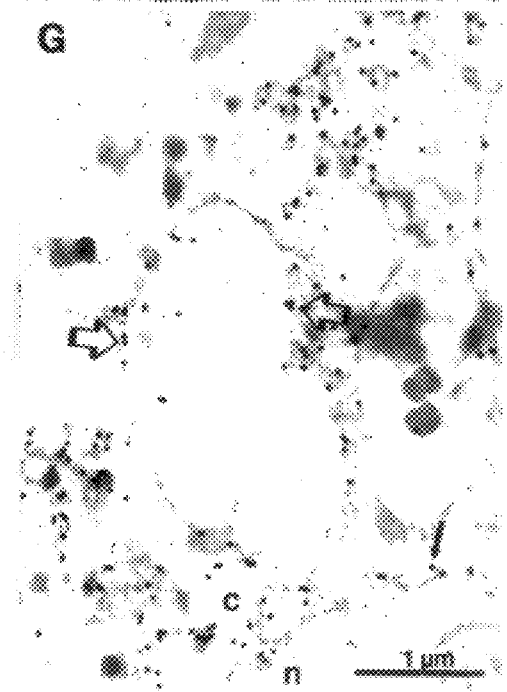
Figure 6H:
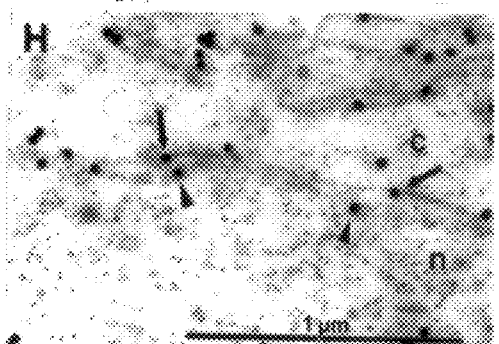
Figure 6I:

FIG. 6A through FIG. 6I are photographs showing localization of 23GFP in pVL1393-23GFP infected Sf9 cells. FIG. 6A shows the GFP autofluorescence at 48 h.p.i. FIG. 6B shows the GFP autofluorescence and phase contrast at 48 h.p.i. Arrows in FIG. 6A and FIG. 6B point to the fluorescence at the periphery of the nucleus, indicating that 23GFP accumulates at the cytoplasmic periphery of the nucleus at 48 h.p.i. FIG. 6C shows the GFP autofluorescence at 72 h.p.i. FIG. 6D shows the GFP autofluorescence and phase contrast at 72 h.p.i. Arrowheads in FIG. 6C and FIG. 6D point to the fluorescence in the interior of the nucleus, indicating that 23GFP becomes concentrated at interior regions of the nucleus in discrete foci as the infection progresses. FIG. 6E, FIG. 6F, FIG. 6G, FIG. 6H and FIG. 6I shows immunogold labeling of Sf9 cells infected with pVL1393-23GFP at 48 h.p.i. using rabbit GFP antiserum and anti-rabbit IgG 30 nm gold-conjugate. FIG. 6E shows that the cytoplasmic membranes condense around the periphery of the nucleus and are intensely labeled using antibody to GFP and gold particles linked to secondary antibody. The fusion protein also locates to intranuclear foci of viral-induced membranes. FIG. 6F shows labeling of cytoplasmic membranes (dual arrow), outer (arrow) and inner (arrowhead) nuclear membranes. FIG. 6G shows labeling of large cytoplasmic vesicles (open-arrow). FIG. 6H shows labeling of outer (arrow) and inner (arrowhead) nuclear membranes. FIG. 6I shows labeling of the ODV envelope (arrow). The following abbreviations are used in these figures: c, cytoplasm; n, nucleus; v, virogenic stroma; m, microvesicles.

Immunoelectron microscopy showed that 23GFP located to the same cellular membranes as the 125 β-gal and 23 β-gal fusion proteins and wild type ODV-E66 (FIG. 6). 23GFP initially locates to regions closely associated with the nuclear envelope (FIG. 6A and FIG. 6B; arrow) and as infection progresses, 23GFP moves into the nucleoplasm as discrete foci of microvesicles (FIG. 6C and FIG. 6D; arrowhead). Immunogold analysis shows that the 23GFP fusion protein locates to the same cellular membranes as wild type ODV-E66. These membranes include: cytoplasmic membranes juxtaposed to the periphery of the nucleus (FIG. 6E and FIG. 6F; dual arrows; FIG. 6G, open arrows); inner and outer nuclear membranes (INM and ONM) of the nuclear envelope (FIG. 6F and FIG. 6H; INM, arrowheads, ONM, arrows); Intranuclear foci of microvesicles (FIG. 6E, m); and, ODV envelope (FIG. 6I; arrows) and other intranuclear membranes.

The data demonstrated that proteins normally cytosolic (β-gal) or freely dispersed between the nucleus and cytoplasm (GFP) are specifically trafficked into defined membranes when fused to the 23 hydrophobic amino acid sequence of ODV-E66.

c. Plasma Membrane Protein URF13 as a Marker

To confirm that the 23 amino acid sequence was also capable of directing a protein that normally locates to the plasma membrane, the plasma membrane protein URF13 was chosen for additional study. The N-terminal 23 amino acid sequence was fused to wild type URF13 (23URF13; FIG. 2, Construct #8) and the recombinant virus generated. In construct #8, a fusion gene of N-terminal 23 amino acids with URF13 gene was placed under the control of p10 promoter and inserted into the polyhedrin locus as an extra copy of transcriptional unit. In this construct, the polyhedrin and p10 genes in their native loci are still intact, thus infected cells still produce viral occlusions.

Figure 7A:
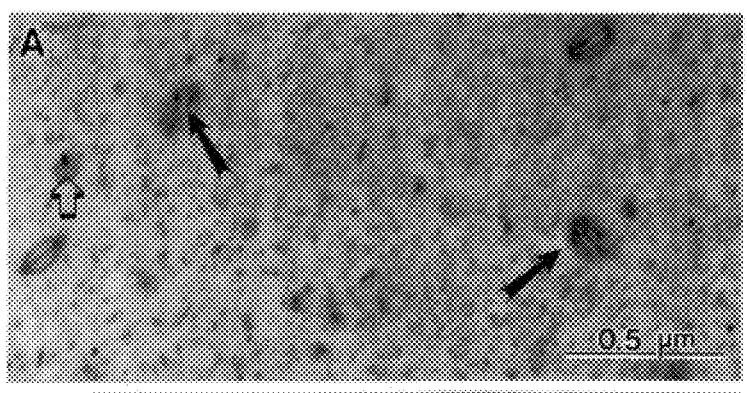
FIG. 7A and FIG. 7B are photographs showing immunogold labeling of Sf9 cells infected with pAcUW21-23URF13 virus at 48 h.p.i.
Figure 7B:
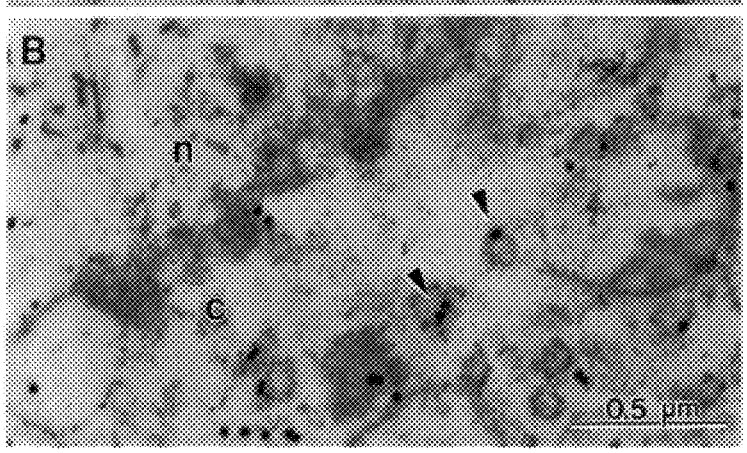
Figure 8A:
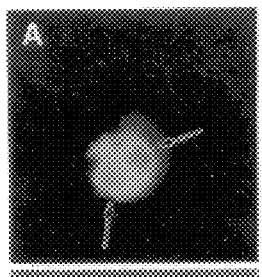
FIG. 8A, FIG. 8B, FIG. 8C, FIG. 8D, FIG. 8E, FIG. 8F, FIG. 8G and FIG. 8H are photographs showing transient transfection of uninfected Sf9 cells with pIE1HR4-23GFP.
Figure 8C:
Figure 8E:
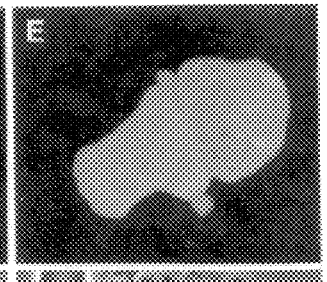
Figure 8B:
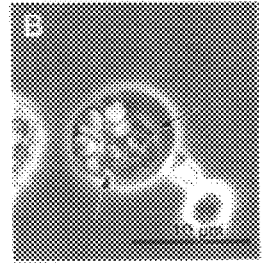
Figure 8D:
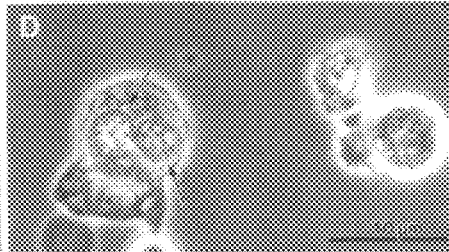
Figure 8F:
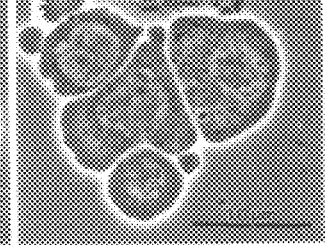
Figure 8G:
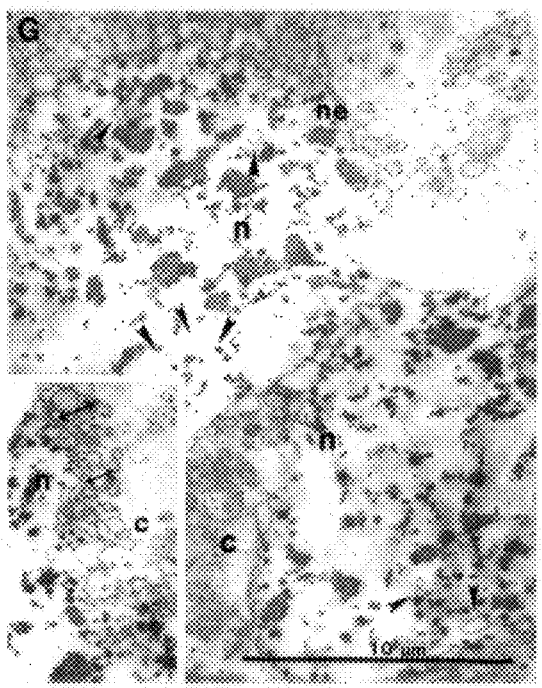
Figure 8H:
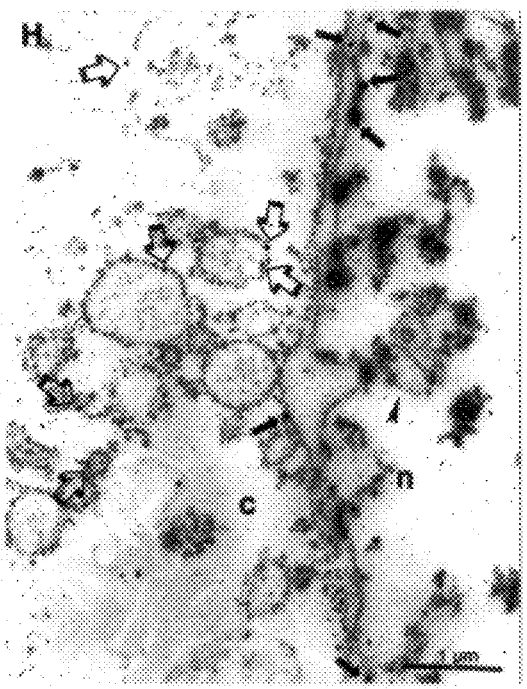
Figures 9A, 9B:
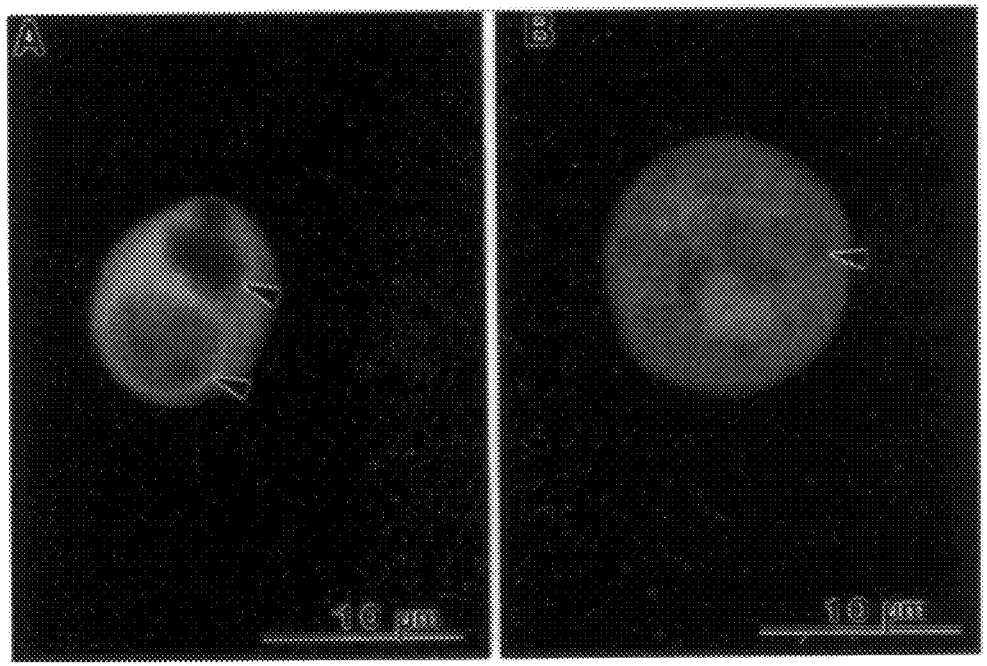
FIG. 9A and FIG. 9B are photographs showing fluorescence microscopy of mammalian COS-1 cells transiently transfected with pCMV-23GFP.

FIG. 7A and FIG. 7B are photographs showing immunogold labeling of Sf9 cells infected with pAcUW21-23URF13 virus at 48 h.p.i. Rabbit URF13 antiserum and anti-rabbit IgG 30 nm gold-conjugate were used in these experiments. FIG. 7A shows labeling of the ODV envelope (arrow) and intranuclear vesicles (open arrow). FIG. 7B shows labeling of cytoplasmic membranes (arrowhead). The following abbreviations are used in this figure: c, cytoplasm; n, nucleus.

The data showed that 23URF13 located to the same structures as the β-gal and GFP fusion proteins, i.e., the ODV envelope (FIG. 7A, arrow), intranuclear membranes (FIG. 7A, open arrow) and membranes closely associated with the nuclear envelope (FIG. 7B, arrowhead).

Thus, three marker proteins that normally locate to three different regions of the cell were used in this experiment: β-gal, which is normally cytosolic; GFP, which is normally both cytosolic and nuclear; and URF13, which is usually targeted to the plasma membrane.

This data demonstrates that when each of these three different proteins was fused to the N-terminal 23 amino acid sequence of ODV-E66, it was targeted to different cellular locations than their wild type counterparts. Specifically these locations were: cytoplasmic membranes juxtaposed to the nuclear envelope, both the outer and inner nuclear membranes of the nuclear envelope, foci of viral induced intranuclear microvesicles and the ODV viral envelope. These examples clearly showed that in baculovirus infected cells, the 23 amino acid sequence specifically located a protein to distinct membrane structures.

3. Localization of the Fusion Proteins in Uninfected Insect Cells and Mammalian Cells—Demonstrated Use of Alternate Promoters, and Potential Cell Cycle Regulation of Protein Location To determine where this 23 amino acid sequence targets a protein in uninfected cells would more specifically address the role of the 23 amino acids and eliminate the possible role of other viral encoded proteins for the specific localization of the fusion proteins.

Thus, these experiments were performed in both uninfected insect (*Sf*9) cells and uninfected mammalian (COS-1) cells. To perform these experiments, promoters were chosen that are recognized by the host cell RNA polymerase II. For the insect cells, the promoter from the immediate early gene IE1 of *Ac*MNPV was used (FIG. 2, Construct #9). For the mammalian cells, the promoter of the major immediate early gene of cytomegalovirus was chosen (CMV; FIG. 2, Construct #10).

In construct #9, the 23GFP fusion gene was placed under the control of IE1 promoter in the pIE1HR4 vector for transient expression in uninfected insect cells. This was different from previous constructs #1-#8, which were recombinant viruses expressing proteins in infected cells. For this construct, an IE1 promoter was used (IE1 is an *Ac*MNPV immediate early gene promoter that is active in uninfected insect cells). The fusion gene construct was transfected into *Sf*9 cells and transient expression was achieved without viral infection. Autofluorescence of GFP indicates that in uninfected *Sf*9 cells, 23GFP protein localized to the nuclear envelope in a cell cycle-dependent manner, as judged by the bi-nucleated cells.

It must be emphasized that a wide variety of promoters from many known genes could have been chosen for this study or any similar experiment with similar results.

FIG. 8A through FIG. 8H are photographs showing transient transfection of uninfected *Sf*9 cells with pIE1HR4-23GFP. FIG. 8A, FIG. 8C and FIG. 8E show fluorescence microscopy at 24 hr post-transfection. FIG. 8B, FIG. 8D and FIG. 8F show matched fluorescence and phase contrast image double exposure to fluorescence images in FIG. 8A, FIG. 8C and FIG. 8E, respectively. FIG. 8G and FIG. 8H show immunogold labeling of binucleated cells at 48 hr post-transfection using rabbit GFP antiserum and anti-rabbit IgG 30 nm gold-conjugate. Note small vesicles in the nucleoplasm (arrowhead) and cytoplasmic vesicles juxtaposed to the nuclear envelope (dual arrow in insert) in FIG. 8G. FIG. 8H shows labeling of cytoplasmic vesicles (open arrow), outer and inner nuclear membranes (arrow). Also note the invagination of the inner nuclear membrane into the nucleoplasm (arrowhead). The following abbreviations are used in this figure: c, cytoplasm; n, nucleus; ne, nuclear envelope.

Two general patterns of fluorescence were observed in insect *Sf*9 cells that were transiently transfected with IE1-23GFP: (1) some cells showed diffuse fluorescence indicating that 23GFP was located throughout the cell (FIG. 8C, FIG. 8D, FIG. 8E and FIG. 8F); and (2) dividing cells, as determined by the presence of two nuclei in the same cell, showed an enhancement of fluorescence around the periphery of the nucleus or in the nuclear envelope (FIG. 8A, FIG. 8B, FIG. 8C and FIG. 8D: arrows).

Immunogold labeling of cells harvested at 48 hr post transfection confirmed these observations. Many cells showed labeling throughout the cell, both the cytoplasm and nucleus (data not shown); however, in binucleated cells, 23GFP located to vesiculated cytoplasmic membranes adjacent to the nuclear envelope (FIG. 8H, open arrows), and the outer and inner nuclear membranes (FIG. 8H, arrows). These results indicate that proteins containing the 23 amino acid sequence are differentially regulated to the nuclear membrane during discrete stages of the cell cycle. Genetically transformed *Sf*9 cells have been developed containing the 23GFP fusion protein, and studies using time lapse exposures to closely evaluate protein movement relative to cell cycle are being performed. In mitotic cells, observations show that cytoplasmic membranes vesiculate and locate in close proximity to the nuclear envelope (FIG. 8G, ne, and insert; dual arrows) in a manner very analogous to the type of membrane localization observed in baculovirus infected cells. Thus, scientific discoveries of specific pathways of protein movement in baculovirus infection may extend significantly to currently unknown pathways of protein movement for nuclear membranes and membranes within the nucleus in other cell types that may be regulated by the cell cycle.

Next, a 23GFP fusion product under the control of a promoter which is optimized for mammalian cell expression was constructed (FIG. 2; Construct #10). In construct #10, the 23GFP fusion gene was placed under the control of the major immediate early gene promoter of cytomegalovirus (CMV-IE) in the pCMV vector for transient expression in uninfected mammalian COS-1 cells. The fusion gene construct was transfected into COS-1 cells and transient expression was achieved without viral infection.

In uninfected COS-1 cells, 23GFP protein localized to the nuclear envelope in a cell cycle-dependent manner. FIG. 9A and FIG. 9B are photographs showing fluorescence microscopy of mammalian COS-1 cells transiently transfected with pCMV-23GFP. Note the ring of fluorescence (arrowhead) in a cell with two nuclei that is likely in mitosis in FIG. 9A. The ring of fluorescence is not obvious in FIG. 9B. This cell is possibly not in the mitosis due to the presence of a single nucleus and intact nuclear envelope (arrowhead). Using the pCMV-23GFP construct the results demonstrate that autofluorescence of 23GFP is enriched along the nuclear membranes of bi-nucleated (i.e., mitotic) cells (FIG. 9A), while in non-mitotic cells the fluorescence is diffuse (FIG. 9B). This data predicts and supports that the fusion protein containing the ODV-E66 N-terminal 23 amino acids is specifically located to the membranes closely associated with the nucleus, including the inner nuclear membrane, at specific times during the cell cycle. This data also predicts that this sequence functions in a similar manner in both insect and mammalian cells.

EXAMPLE 3

Expression of 23 Green Fluorescent Protein in Plant Cells

This Example presents a method for constructing a plant vector containing the N-terminal 23 hydrophobic amino acids from ODV-E66 and was designed to study the localization of protein (green fluorescent protein) as a result of the 23 amino acid sequence.

To express 23 green fluorescent protein (23GFP) in plant cells, the 23GFP fusion gene was amplified by two rounds of PCR in order to be cloned into the plant expression vector pRTL2 (Carrington and Freed, 1990). The first round of PCR includes two PCR reactions (94° C., 30 sec; 42° C., 60 sec; 72° C., 60 sec; 25 cycles): The first reaction used the pAcUW21-23GFP construct as template and two oligonucleotides (5'-TTTTTT<u>CCATGG</u>CATCTATCGTATTGATT-3' SEQ ID NO:23; the NcoI site is underlined; and 5'-GACAAGTGTTGGCCAGGGAACAGGTAGTTTTCC-3'; SEQ ID NO:24); the second reaction used the pAcUW21-23GFP construct as template and two oligonucleotides (5'-GGAAAACTACCTGTTCCCTGGCCAACACTTGTC-3'; SEQ ID NO:25; and 5'-TTTTTT<u>TCTAGA</u>CTATTTGTATAGTTC-3'; SEQ ID NO:26, the XbaI site is underlined). The second round of PCR used 1% of each of the first round of PCR reactions and two oligonucleotides (5'-TTTTTT<u>CCATGG</u>CATCTATCGTATTGATT-3'; SEQ ID NO:23; and 5'-TTTTTT<u>TCTAGA</u>CTATTTGTATAGTTC-3'; SEQ ID NO:26; the NcoI and XbaI sites are underlined). PCR fragment from the second PCR was extracted with chloroform, precipitated with ethanol, digested with NcoI and XbaI, purified from 1% agarose gel using GeneClean kit (BIOL101), and cloned into the NcoI/XbaI sites of pRTL2 vector. This construct was named pRTL2-23GFP (FIG. 2., Construct #11). Thus, in this construct, the 23GFP fusion gene was placed under the control of the 35S promoter in the pRTL2 vector for expression in plant cells. 35S promoter is active in plant cells without viral infection.

23GFP autofluorescence in plant cells can be observed using a FITC filter in a Zeiss Axiophot microscope (Zeiss). Experiments are in progress to determine the location of 23GFP in plant cells.

EXAMPLE 4

Expression of a Fusion Gene of N-Terminal 24 Amino Acid Hydrophobic Sequence of ODV-E25 With GFP in Insect Sf9 Cells ODV-E25 is another ODV enevlope protein of baculovirus OpMNPV (Russell and Rohrmann, 1993), and AcMNPV (Ayres et al., 1994), is related to ODV E66. An antibody to ODV-E25 also labels intranuclear microvesicles and the ODV envelope (FIG. 15B, m and open arrow) with limited but discernible labeling of the nuclear membrane and intracellular cytoplasmic membranes (FIG. 15B, arrows). This Example presents a method for constructing a vector containing the 24 N-terminal amino acids from ODV-E25 and forming a fusion product. This construct will be used to identify the presence of a functional cognate of the ODV-E66 23 N-terminal amino acid sequence in these 24 amino acids.

AcMNPV ODV-E25 was localized to the microvesicles (FIG. 15B), and also contains an uncleaved N-terminal 24 amino acid hydrophobic sequence. To determine if this 24 amino acid sequence functions similarly to the 23 amino acid sequence of ODV-E66, a fusion construct (24GFP) was made in which the 24 amino acid sequence of ODV-E25 was fused in frame with GFP. The nucleotide sequence encoding the N-terminal 24 amino acids of ODV-E25 was amplified by PCR (94° C., 30 sec; 42° C., 60 sec; 72° C., 60 sec; 25 cycles) using purified AcMNPV viral DNA (Summers and Smith, 1987) as template and two oligonucleotides: (SEQ ID NO:27; PstI site underlined; 5'-TTTTTT<u>CTGCAG</u>ATGTGGGGAATCGTG-3'; and SEQ ID NO:28; BamHI site underlined; 5'-TTTTTT<u>GGATCC</u>TTGAAATTTAATGCATT-3'). The PCR product was extracted with chloroform, precipitated in ethanol, digested with PstI and BamHI, purified from 1% agarose gel using GeneClean kit (BIOL101), and cloned into PstI/BamHI sites of pUC19 vector. The PstI/BamHI PCR insert in pUC19 and the BamHI/EcoRI fragment from the pGFP vector (ClonTech) containing the GFP gene were cloned into the PstI/EcoRI sites of pVL1392 vector (Webb and Summers, 1990). This construct was named pVL1392-24GFP (FIG. 2, Construct #12). In this construct, the N-terminal 24 amino acid hydrophobic sequence from ODV-E25 was fused in frame with GFP. Recombinant virus expressing 24GFP was made using the construct pVL1392-24GFP and Bsu361 digested BakPak6 viral DNA (ClonTech.). In this virus, the 24GFP fusion gene replaces the polyhedrin gene in the polyhedrin locus. Infected cells do not produce viral occlusions due to the absence of a functional polyhedrin gene.

When compared to the labeling pattern of wild type or fusion proteins expressed under the ODV-E66 promoter, fusion proteins more highly expressed under the control of the polyhedrin promoter, in this case the 24GFP construct, still label the viral induced microvesicles and ODV envelope, but significant amounts of label are now visualized associated with intracellular cytoplasmic membranes located near the periphery of the nucleus (FIG. 15D). Increased amounts of label are also visualized in the microvesicles and ODV envelope (FIG. 15D, m and open arrow). However, label is enriched in the nuclear envelope, both outer and inner nuclear membrane (FIG. 15D, arrowheads). Thus, the ODV-E25 N-terminal hydrophobic sequence appears to perform the same function as the ODV-E66 N-terminal hydrophobic sequence.

EXAMPLE 5

Studies on the Biochemistry and Molecular Process of Transport of Proteins Containing the N-Terminal Hydrophobic Domain of ODV-E66

Additional studies are being performed to address the molecular basis and regulation of transport of proteins containing the N-terminal amino acid hydrophobic domain of ODV-E66. These studies demonstrate the effect on both baculovirus infected insect cells and in uninfected cells including insect, vertebrate and plant cell lines. Clonal isolates of Sf9 cells that have undergone genetic transformation and have a copy of the IE1-23GFP gene placed within its genome have been developed.

Additionally, wild type ODV-E66 and fusion proteins are being utilized to identify other protein factors or protein processing that may be involved in some function to assist, target, or transport proteins to membranes of the nuclear envelope.

These studies may suggest normal insect cells contain cellular cognates of several of the baculovirus ODV envelope proteins, and that these cognates may prove to be important in protein movement in uninfected cells. Sequencing of clones for two potential cellular cognates is being performed. Screening for accessory proteins that may play a role in protein transport of ODV-E66 and several other ODV envelope proteins is also being performed. Screening methods being utilized in this laboratory include: yeast two-hybrid methodology, covalent linkages of protein complexes, anti-idiotype identification of binding proteins, and identification of protein complexes using antibody isolation techniques.

EXAMPLE 6

Identification of Other Hydrophobic Sequences Found in Baculovirus ODV Envelope Proteins— Structural and Functional Cognates of 23AA of ODV E66

This Example is designed to identify potential cognates from other baculovirus genes with known hydrophobic sequences. The additional, known, hydrophobic sequences, found in baculovirus ODV envelope proteins, will be characterized as either structural or functional cognates of 23AA of ODV-E66.

The inventors compared the N-terminal amino acid sequence of ODV-E66 and ODV-E25 from the *Autographa californica* multinucleocapsid nuclear polyhedrosis virus with the sequence of these proteins from *Orgyia pseudotasugata* multinucleocapsid nuclear polyhedrosis virus and *Bombyx mori* multinucleocapsid nuclear polyhedrosis virus, as well as some of the fusion constructs generated in the Examples (FIG. 16). These sequences contain a hydrophobic domain (shaded box) composed primarily of isoleucine, leucine and valine followed by a asparagine-serine rich region and finally a region containing charged amino acids.

Listed in Table 11 below are hydrophobic sequences identified in baculovirus ODV envelope proteins. In order to identify structural or functional cognates of the 23AA of ODV E66, constructs are being made for each of these hydrophobic sequences with protocols and goes to those disclosed above. These protocols are very similar to those designed to produce the constructs shown in FIG. 2. The analyses as shown in Example 2 are being performed to determine if a transport, retention or signal sequence, similar to the 23AA of this invention, is contained within the tested hydrophobic ODV domains.

The following abbreviations are used in Table 11 below:

AcMNPV: *Autographa californica* multinucleocapsid nuclear polyhedrosis virus
OpMNPV: *Orgyia pseudotasugata* multinucleocapsid nuclear polyhedrosis virus
BmMNPV: *Bombyx mori* multinucleocapsid nuclear polyhedrosis virus
HzSNPV: *Helicoverpa zea* singlenucleocapsid nuclear polyhedrosis virus
CfMNPV: *Choristoneura fumiferana* multinucleocapsid nuclear polyhedrosis virus
CpGV: *Cydia pomonella* granulosis virus agents to insects (Martens, 1994). For successful results, the gene of interest must be expressed, secreted from infected cells or modified by the infected cell, and become active in the insect hemolymph or cells. These approaches have resulted in the insects dying faster than when infected with wild type baculovirus. Initial indications suggest that these recombinant viruses cause sufficiently rapid cessation of feeding and will be sufficiently cost-effective to make these viral constructs commercially viable insecticidal agents in the field.

Baculovirus ODV fuses with the insect gut cell to deliver their genetic components into the infected cell. The use of the hydrophobic targeting sequences of the present invention, or structural or functional cognate thereof, which may target proteins to the ODV envelope, provides an effective way to directly deliver a toxic agent to the cellular membranes of the insect gut.

FIG. 10A and FIG. 10B are diagrams showing an overview of directed delivery to target cell and subsequent gene delivery. FIG. 10A is a diagram showing targeting and delivery to target cell via membrane fusion with the purified microvesicles or ODV envelope (I-V). If the delivered protein has toxic activity after being incorporated into the cell membrane, then this protein may have an insecticidal application (VI). FIG. 10B is an extension of the delivery shown in FIG. 10A to include gene delivery and expression. This use is either insecticidal or therapeutic depending upon the function of the protein encoded by the recombinant gene. Thus, immediately upon infection, the direct delivery results in compromised cellular function and integrity, and cessation of eating. In addition, the direct delivery of toxic agent(s) to the insect gut cell membranes can be combined with the classical gene delivery approach (FIG. 10B). A number of different toxic agents are contemplated for use in the present invention. These agents can be grouped into four major classes: (i) hormones and hormone modifying enzymes; (ii) toxins; (iii) small peptides, and; (iv) miscellaneous compounds. The time course of delivery and concentration of any of these genes can be regulated by choice

TABLE 11

Summary of Hydrophobic Sequences in Baculovirus ODV Envelope Proteins
(Structural and Functional Cognates of 23AA of ODV-E66)

| Protein | Location | Sequence |
| --- | --- | --- |
| AcMNPV ODV-E66 (Hong et al., 1994) | N-terminus (23 amino acids) | MSIVLIIVIVVIFLICFLYLSNS (SEQ ID NO: 3) |
| AcMNPV ODV-E25 (Ayres et al., 1994) | N-terminus (24 amino acids) | MWGIVLLIVLLILFYLYWTNALNF (SEQ ID NO: 33) |
| AcMNPV ODV-E56 (Theilmann et al., 1996) | Internal (19 amino acids) | IILLIGAVLFLGLIFYFIY (SEQ ID NO: 34) |
| AcMNPV ODV-E18 (Braunagel et al., 1996b) | Internal (19 amino acids) | MFLTILAVVVIIALIIIFV (SEQ ID NO: 35) |
| OpMNPV ODV-E25 (Russell and Rohrmann, 1993) | N-terminus (19 amino acids) | MWGALILLILLVFLFYLWY (SEQ ID NO: 36) |
| OpMNPV ODV-E56 (Theilmann et al., 1996) | Internal (19 amino acids) | LIWLIGAVLFLALVVYLIY (SEQ ID NO: 37) |
| BmMNPV ODV-E66 (Maeda et al., 1996*; GenBank Access #L33180) * - not published, GenBank data | N-terminus (21 amino acids) | MSTVLIIVVVVIFLICFWCLL (SEQ ID NO: 38) |
| BmMNPV ODV-E25 (Maeda et al., 1996*; GenBank Access #L33180) * - not published, GenBank data | N-terminus (18 amino acids) | MWKIVLLIVLLVLIYLYW (SEQ ID NO: 39) |
| BmMNPV ODV-E56 (Theilmann et al., 1996) | Internal (19 amino acids) | IIMMIGAVLFLGLILYFIY (SEQ ID NO: 40) |
| BmMNPV ODV-E18 (Braunagel et al., 1996b) | Internal (19 amino acids) | MFLTILAVVVIIALIIMFV (SEQ ID NO: 41) |
| HzSNPV ODV-E56 (Theilmann et al., 1996) | Internal (19 amino acids) | IIVVLGIVLLIIFIGYIVI (SEQ ID NO: 42) |
| HzSNPV ODV-E18 (Braunagel et al., 1996b) | Internal (19 amino acids) | MLMTILIALVIIILLIMLF (SEQ ID NO: 43) |
| CfMNPV ODV-E56 (Theilmann et al., 1996) | Internal (19 amino acids) | LIWLIGAVLFLGLIIYLIY (SEQ ID NO: 44) |
| CpGV ODV-E56 (Theilmann et al., 1996) | Internal (19 amino acids) | ILLVIGGILLLTFIGFVIF (SEQ ID NO: 45) |

EXAMPLE 7

Application of Newly Identified 23 Amino Acid Targeting Sequence—Insecticides/Insecticidal Toxins Current approaches to genetically engineer baculoviruses to serve as insecticide delivery agent(s) utilize a recombinant baculovirus for delivery of a gene encoding toxic of promoter—both temporal expression, e.g., immediate early, delayed early, late or very late, and strength and activity levels of promote, as will also be understood by those skilled in this art.

1. Hormones and Hormone Modifying Enzymes

Most activities of larvae affecting homeostasis or development, such as water balance, feeding behavior, molting etc., are regulated by hormones. Thus it is possible that expression of any hormone, or hormone modifier would result in aberrant insect behavior and the result could be: cessation of eating, cessation of molting and death, improper water balance resulting in death etc. Selected examples are shown in Table 12 below.

TABLE 12

| Hormones | Hormone Modifying Enzymes |
| --- | --- |
| juvenile hormone esterase | juvenile hormone epoxide hydrolase |
| diuretic hormone | ecdysteroid UDP glucosyl transferase |
| prothoracicitropic hormone | ecdystone inactivating enzymes |
| allatostatin | |
| allatotropin | |
| eclosion hormone | |

2. Insecticidal Toxins

Insect specific toxins are a good choice to develop recombinant baculoviruses to serve as biocontrol agents. In general they are very potent and specific, and after delivery of the toxin to the hemolymph, paralytic action is rapid. Exemplary of this class of compounds are the insecticidal crystal proteins of *Bacillus thuringiensis* (B.T.), Scorpion toxins (*Buthus eupeus, Androctonus australis*), and mite toxins (*Pyemotes tritici*)

3. Peptides

Small peptides can mimic the action of selected hormones and/or toxins. Thus, such peptides could function in an insecticidal capacity. These peptides can be derived from biological sources or synthesized in the laboratory. Examples contemplated for use in the present invention include, but are not limited to, neuropeptide bombixin, neuropeptide sarcotoxin and peptides fashioned after the family of conotoxins.

4. Miscellaneous Toxic Agents

Other toxins, or agents that compromise cell health, ionic pore regulators, etc., can be utilized for insecticidal purposes using the hydrophobic targeting sequences of this invention and the protein or gene delivery approach as described in this example.

Because so little is known of insect molecular biology, it is contemplated that many proteins will function in ways that are not at first obvious. Two such examples include URF13 (maize mitochondrial protein) and hornet allergen (HA5). Delivery of the URF13 protein is described in more detail below.

a. Producing Insecticidal Toxin URF13 Protein and Direct Delivery to the Insect Midgut Maize exhibiting the Texas male-sterile cytoplasm (cms-T) trait was widely used in commercial hybrid maize production before, in 1970, severe disease outbreaks to fungal pathogens forced the industry to curtail its use. The URF13 protein (13 kDa) encoded by the mitochondrial gene T-urfl13, is responsible for cms-T trait and has received considerable scientific investigation because of the impact on commercial maize production (Dewey et al., 1986). Unexpectedly, researchers observed that baculoviruses expressing URF13 were lethal to *Trichoplusia ni* larva (*T. ni.*; cabbage looper; Korth and Levings, 1993). Additionally, when URF13 is expressed in baculovirus and is transported to the plasma membrane of the infected insect cells, it confers T-toxin or methomyl (fungicide) sensitivity to the cell.

The ODV form of baculoviruses is the primary infectious agent in the insect. The ODV envelope fuses with the plasma membrane of the gut cells, thus immediately upon infection, viral envelope proteins are incorporated into the gut cell plasma membrane. URF13 lethality in insects is independent of other factors and apparently only requires delivery to the plasma membrane for toxic activity.

Thus, in view of this background and discussion, the inventors contemplate direct delivery of URF13 to the plasma membrane of the insect gut by constructing a recombinant virus that contains URF13 in its ODV envelope (e.g., 23URF13). This direct delivery will cause damage to the insect gut cell, resulting in compromised insect health and a cessation of eating (FIG. 10A). Since URF13, when located in the plasma membrane of baculovirus infected cells, confers sensitivity to methomyl, adding trace amounts of the fungicide methomyl to the feeding formulation will increase the toxicity of the delivered protein, e.g., URF 13.

One advantage of this approach, is that it can be combined with the more traditional approaches to deliver gene(s) that encode additional copies of the same, or additional toxins. Thus, after the insect function is compromised, via direct delivery of a toxin to the gut, the insect will immediately be exposed to additional toxin activity, thus decreasing its ability to recover (FIG. 10B) and increasing the speed and efficacy of the insecticidal effects. To increase URF13 insecticidal activity, another mutant virus containing the 23URF13 and an additional copy of the wild type URF13 under the control of the early baculovirus promoter (IE1) may also be employed. Moreover, as will be appreciated by those skilled in this area, additional copies of either URF13 or other toxins, e.g., the scorpion toxin AaHIT, can also be used in the delivery system of this invention, although additional toxin delivery and reinforcement may be required.

EXAMPLE 8

Application of Newly Identified 23 Amino Acid Targeting Sequence—Protein Mediated Targeting and Virus-Like Particles Therapeutic Use Baculovirus infection results in a large number of small, intranuclear membrane vesicles. These have been named "microvesicles". These microvesicles serve as one source of the ODV envelope and it has been shown that the 23 amino acid sequence locates proteins to these structures at a high efficiency (Hong et al., 1994, Braunagel et al, 1996a, Braunagel et al., 1996b; Example 2 above). Techniques are currently being tested to purify these microvesicles. The inventors have identified at least one protein that results in a greatly enhanced production of intranuclear microvesicles, if expressed at high levels in an infected cell. Thus, purification of large quantities of microvesicles from infected cells in vitro appears possible. For the purposes presented here, purified microvesicles and "virus-like" particles are used interchangeably. Thus, by inserting proteins(s) that are of medical value into these vesicles, virus-like particles useful themselves as a therapeutic are created.

1. Virus-Like Particle Delivery of Protein to Gut Tissue

Baculovirus ODV fuses with insect gut cells (Kawanishi et al., 1972). There is no evidence that ODV randomly fuses with other membrane systems. Of interest, ODV is virtually non-infectious when delivered into the bloodstream or is used as an infectious agent in vitro (Volkman and Summers, 1977). The inventors have evidence that the baculovirus envelope contains at least one protein homolog in its viral envelope that resembles a protein of human rotavirus, a virus which infects humans through the gut (Braunagel et al., 1992). It was therefore predicted that ODV would fuse with mammalian gut membranes. The development of recombinant virus carrying defined fusion proteins, e.g., 23GFP, in the ODV envelope now provides the tools to confirm this prediction in vitro.

Specific therapeutic or regulatory proteins, and derivatives thereof, may now be incorporated directly into the microvesicles and directly delivered to the microvillar membranes of the gut tissue upon ingestion. Thus, generating 23AA-fusion products of integral membrane proteins selectivity incorporates the fusion proteins into the microvesicles. Upon ingestion, these proteins become transiently incorporated in gut microvillar membranes. Proteins and/or receptors that enhance or replace essential components for nutrient and/or drug absorption, are examples of this type of delivery.

Thus, it now appears feasible that suitable foodstuff or drug formulations can include microvesicles or artificially prepared structural or functional cognates containing the relevant accessory protein for proper absorption and/or delivery. This provides an effective direct delivery system to the intestinal microvillar membranes in a mammalian system.

2. Virus-Like Particle Delivery Into the Bloodstream

A number of approaches have been designed to expose certain antigens, and/or receptors or anti-receptors to infectious agents in the bloodstream. One well characterized example is delivery of CD4. CD4 is a receptor that resides on a subset of T cells and is a target for the anti-receptor gp120 of Human Immunodeficiency Virus (HIV). The recognition of CD4 by gp120 allows viral entry and subsequent viral infection (Maddon et al., 1986). If CD4 is presented to the HIV virus on another surface than T cells, it acts as a "negative sink" or scavenger of the virus, thus decreasing the amount of virus that successfully infects the target cells. This strategy has been studied and shows potential as an AIDS therapeutic (Nicolau et al., 1990; Arvinte et al., 1989 and Webb et al., 1989).

While the concept of this type of delivery system is straightforward, the methods of incorporating integral membrane proteins, i.e., receptors, with a defined secondary structure and orientation into artificial membrane systems (i.e. liposomes) or resealed ghosts can be very difficult. Usually only a small proportion of the total incorporated protein is exposed and conformationally correct. Thus, only a small percent of protein is functional. The advantage of using baculovirus derived microvesicles is that the orientation of the fusion protein can be designed and tested to determine functional authenticity. Once the construct is tested and confirmed to be biologically active, all copies of the protein should be inserted into the microvesicles in the same conformation. Additionally, multiple proteins or protein complexes can be inserted into the microvesicles. Use of different promoters of various strengths and temporal activities, allows for the regulation of the amount and timing of gene expression and protein production (Belyaev and Roy, 1993). Thus, this approach provides significant control and flexibility not only of conformation of protein insertion, but also with a way to engineer active protein complexes in membrane vesicles or virus-like particles for therapeutic use. This approach is feasible in both animal and human hosts.

Many different proteins can be genetically engineered to be inserted into intranuclear microvesicles. Since ODV is not the infectious form of baculovirus in cell culture and is not required for passage in vitro, then, presumably, any number of proteins could be incorporated into the ODV envelope for this purpose. Since the production of infectious ODV is not required, some non-essential ODV proteins could be deleted from the viral genome to generate additional space in the ODV envelope for recombinant fusion proteins. For example, it is already known that ODV-E66 and ODV-E56 are non-essential for viral propagation in vitro (Hong, 1995; Braunagel et al., 1996a).

EXAMPLE 9

Application of Newly Identified 23 Amino Acid Targeting Sequence—Protein Mediated Targeting and Gene or Drug Delivery 1. General Approach Using the observation that any protein could be targeted to the ODV envelope, and that baculovirus can be used to reconstruct membrane protein complexes, including specific fusion proteins, it becomes possible to insert a receptor, etc., into the ODV envelope that is specific for cell type recognition and fuses only with the target cell. A virus that contains such engineered protein(s) on its viral envelope could be used in several ways: (1) direct delivery to the target cells via specific recognition and fusion, thus direct delivery of the protein of interest to the target cell membrane; and (2) use of specific protein complexes to direct and fuse ODV envelope to the target cell with subsequent gene delivery using any promoter recognized by the host cell. In this manner, the baculovirus becomes a specific vector to target protein (i.e. receptor and/or drug) or gene delivery in both animal and human hosts (FIG. 10).

2. Delivery of Protein(s) to Cellular Plasma Membranes Using ODV as Agent

This example (i.e., using modified ODV to deliver proteins to the membranes of the target cell) is similar to the example using purified virus-like particles to deliver proteins, but has distinct advantages. In an occlusion positive baculovirus, mature ODV is incorporated into viral occlusions. Once ODV is embedded within the viral occlusion, it is very stable. This form of the virus remains viable for an extended period of time, several years under outdoor environmental conditions, and considerably longer if stored protected from UV light. Viral occlusions are easily purified from infected cell lysates. The occlusion can be dissolved using an alkaline treatment to release ODV.

Since refrigeration and drug storage is a major problem in many areas of the world, this invention can be used to transport therapeutic agent(s) in the stable form of viral occlusions. At the site of delivery, a premeasured via of occlusions is mixed with an aliquoted alkaline solution, allowed to incubate at room temperature for a specific period of time, thereby releasing the ODV, then neutralized with the appropriate solvent system and administered to the patient.

3. Gene and/or Drug Delivery to Target Cell Using ODV as Agent

This example utilizes the ability to direct ODV to the target cell by incorporating receptors, fusion proteins etc. into the ODV envelope. Upon fusion with the host cell membrane the viral nucleocapsid is released into the host cell. When genes encoding therapeutic agents are genetically engineered into the viral genome under the control of promoters that are recognized by the host cell (i.e. baculovirus IE1 gene promoter), then this system can be utilized for gene delivery purposes. The obvious example uses gp120 and the AIDS virus. Engineering ODV to have a 23-CD4 receptor located on the viral envelope, enables the targeting of that virus directly to HIV infected cells. After membrane fusion with the HIV infected cell, a gene that is under the control of an appropriate promoter encoding an anti-HIV toxic protein could be delivered and expressed.

The resultant protein production would mediate the killing of the HIV infected cell.

Baculovirus infection and DNA replication have been analyzed in a number of species. These included: intraperitoneal injection of virus into white mice (Ignoffo, 1971); feeding virus to rats, white mice and guinea pigs (Ignoffo et al., 1972; Ignoffo and Heimpel, 1965) and inoculating mammalian cell lines with virus (Ignoffo and Rafajko, 1972; Roder and Punter, 1977). Over the past 25 years, a large body of literature has been collected that confirms the safety of wild type baculoviruses. The overwhelming conclusion from this literature with inoculation of a large number of hosts with baculoviruses, is that exposure of non-host cells to baculoviruses does not result in cytopathic, or detrimental effects (Groner, 1986).

If baculoviruses are utilized as delivery agents to mammalian hosts, safety issues would need to be carefully addressed. Again, baculovirus offers unique advantages. If baculovirus is incorporated into some non-host cells, limited viral gene expression occurs (IE1 promoter) but the entry of the virus does not result in late gene expression or productive infection. The genome of *Autographa californica* and *Bombyx mori* nuclear polyhedrosis virus (AcMNPV; BmMNPV) has been sequenced (Ayres et al., 1994; GenBank accession number #L33180) and the genes essential for viral DNA replication have been identified (Kool et al., 1994). If viral DNA replication occurring in the non-host, target cell is identified as a safety issue, it should be possible to place one or more of the genes required for DNA replication under the control of an inducible promoter temperature sensitive, chemical induction, etc.). In this manner, the virus can be replicated in the laboratory using inducing conditions, and will not be capable of replication in the target cell.

EXAMPLE 10

Application of 23 Amino Acid Targeting Sequence—Genetic Germ Line Transformation or Delivery of Protein to Vertebrate and/or Invertebrate Cells This example takes into account several potential properties of this novel 23AA targeting sequence. Another use that combines many of the features already described and extends their application is to selectively deliver a gene that has been engineered to allow genetic transformation of the target cell genome. This approach would include: (a) proteins within the ODV envelope that serve to target the recombinant virus to the specific cell; (b) the gene of interest is modified within the baculovirus genome to contain flanking transposable elements, retroviral transposition elements, pantropic vectors, etc. such that after delivery, the engineered gene becomes incorporated into the cellular genome (Jarvis et al., 1996; Matsubara et al., 1996).

Another use for such targeting and gene delivery system might include precise delivery of a gene to a cell type lacking a normal function. By placing the gene of interest in the baculovirus genome using transposable elements according to this invention, the gene, upon transposition, becomes stably integrated into the genome of the target cell.

Signal targeting to the nuclear membrane into a vertebrate is also contemplated. This application takes into account several potential properties of the cell by any one of a number of viral vectors (adenovirus, herpesvirus, retrovirus adeno-associate virus, etc.) or cell transformation systems to transform the cell for the novel targeting sequence, including constitutive expression and insertion of 23AA-fusion protein for whatever function desired.

If the nuclear membrane insertion signal functions as the data shows, then the targeting sequence could be inserted into the nuclear envelope of any cell (vertebrate, invertebrate, or lower eukaryotes) by a variety of transformation or vector systems. An example might include a sindbis virus transformation vector carrying an insecticidal or lethal 23 AA-fusion protein into mosquito cells.

EXAMPLE 11

Application of The 23 Amino Acid Targeting Sequence—Protein Targeting

Data show that proteins containing the 23 amino acid sequence and functional cognates thereof locate to the nuclear envelope, both the outer and inner nuclear membrane, during defined times of the cell cycle. This location has been shown in both insect (*Sf*9) cell lines and mammalian (COS) cell lines during mitosis (as indicated by bi-nucleated cells). Thus, in actively dividing cells, the fusion protein is located in the nuclear membrane; while in non-dividing cells, the fusion protein is incorporated within a general, but undefined set of cytoplasmic membranes. By using targeted ODV gene delivery, it becomes possible to specifically deliver a gene using the modified ODV envelope containing targeting proteins, express a gene encoding a drug or toxin and deliver that drug or toxin to the nuclear membrane of actively dividing cells. This approach provides another level of molecular approaches to potentially control or modify the organization and function of the nuclear envelope.

1. Control of Cell Cycle

Using either gene delivery or genetic transformation approaches, it may be possible to target cells which are undergoing mitosis. An example might include selective targeting of a cancerous tissue growth. All of the cells of that tissue type contain the same defining surface receptor, so normal and non-cancerous cell would be targets for the modified ODV. All cells would receive the gene encoding the therapeutic or toxic agent, however the therapeutic effects would only be active in dividing cells, when the protein located to the nuclear membrane. In this manner, cancerous cells, which are dividing at an accelerated rate, would be primary recipients of the therapeutic agent or toxic agent.

A large number of genes/proteins have been identified that are involved in the progression of a cell through the cell cycle (Andrews and Mason, 1993). It is conceivable that delivery of a protein to the nuclear envelope could regulate any phase of the cell cycle, depending upon the protein and timing of delivery. An exemplary list of known cell cycle regulation proteins is shown in Table 13 below.

TABLE 13

| | | |
|---|---|---|
| Cyclin A | CLN1 | HCS26 |
| Cyclin B | CLN2 | ORFD |
| Cyclin C | CLN3 | Gl Cyclin |
| Cyclin D | Cyclin E | CDI3 |
| cdc5 | polo | Plk |
| cdc2 | Dmcdc2 | cdk2 |
| cdc28 | Snk | HCS26 |
| cdc25 | string | twine |
| $p34^{cdc2}$ | $p80^{cdc25}$ | CYL1 |
| Y15 | suc1 | PRAD1 |

TABLE 13-continued

| CDI1 | CDI2 | CDI4 |
| CDI5 | CDI6 | CDI7 |
| PP1 | PP2A | PP2B |
| PP2C | CSF-1 | cdc2B |
| cdc2/MPF | | |

In addition a range of additional protein are necessary for proper mitotic response. These include, but are not limited to, the tubulin gene family, the kinesin gene family, the actin gene family, the lamin gene family and actin binding proteins. Examples of places in the cell mitotic event that may lend itself to interruption include: not allowing nuclear membrane dissolution (i.e. through interrupting the lamin B phosphorylation pathway) or adding a copy of cyclin B that has been genetically modified so that it cannot be ubiquinated and thus freezing the cell in metaphase (Hunter, 1993). These are two such examples, however there are many processes and temporal activities within the cell cycle that potentially could be altered or modified by foreign protein localization to the nuclear envelope and specifically the inner nuclear membrane.

2. Delivery of Proteins to the Nuclear Membrane For Therapeutic Use

By using protein targeting, genetic transformation techniques and/or gene delivery approaches, proteins could be delivered to the inner nuclear membrane that may function to interfere with, or modify the effects or functions of, for example, known oncogenes. Both approaches outlined above are potential uses of this technology to deliver proteins to the nuclear membrane of cancerous cells for cancer therapy. However, this approach should not be limited to cancerous conditions. Any malfunction in a cell that could be corrected or treated with gene/protein delivery to the nuclear membrane would be a candidate for use of this technology. Exemplary of other nuclear proteins (Pante and Aebi, 1996) contemplated for use in the present invention are those listed in Table 14 below.

TABLE 14

| otefin | gp188 | |
| LAP1a | LAP1b | LAP1c |
| LAP2 | p54 | POM152 |
| lamin B receptor | cytochrome p450 | perichromin |
| Nup116 | p110 | gp190–gp210 |
| gp174 | gNPC | p62 |
| p28 | nup153 | gp210 |
| nup98/p97 | CAN/nup214/p250 | nup107 |
| RanBP2/nup358 | nup155 | trp/p265 |
| POM121 | NSP1 | Nup1 |
| Nup2 | Nup49 | Nup57 |
| Nup159/RAT7 | Nup100 | Nup145 |
| NIC96 | Nup82 | Nup120/RAT2 |
| Nup133/RAT3 | Nup157 | Nup170 |

EXAMPLE 12

Application of 23 Amino Acid Targeting Sequence—Diagnostics

The instant invention can be used to produce a variety of different proteins that locate to the ODV envelope. Using the 23 amino acid sequence, and functional cognates thereof as described in this invention, would be especially beneficial for producing diagnostics based on receptors or integral membrane protein or protein complexes. Briefly, the advantages of this system are: (a) proteins can be placed in the ODV envelope in a known orientation; (b) ODV can be generated in insect larva rather than the more expensive in vitro systems; and (c) the ability to incorporate ODV into viral occlusions at will allows ease of purification of viral occlusions and ODV, and ability to store the preparation for extended periods of time. Viral occlusions are easy to purify and allow for long-term storage in that form.

The ability to produce certain diagnostic reagents in insect larva allows the protein reagent(s) to be produced more efficiently, inexpensively and with less effort compared with producing proteins from tissue culture systems. FIG. 11 is a diagram comparing the levels of protein expression in vitro (tissue culture cells) with the levels in larva for several proteins (applicable to diagnostic applications). Protein can be produced in vitro and in insect larva utilizing recombinant baculovirus at high levels.

As can be seen for certain proteins, the expression level can be much higher in larva than in tissue culture cells. For example, one insect larvae can provide enough material for approximately 30,000 ELISA diagnostic tests. Another advantage of isolating viral occlusions from larva (and not from tissue culture cells) is that the virus and incorporated proteins are extremely stable in the occlusion form. Once viral occlusions have been purified, they can be stored for years before final purification of ODV and sample use.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,196,265
U.S. Pat. No. 4,237,224
U.S. Pat. No. 4,554,101
U.S. Pat. No. 4,745,051
U.S. Pat. No. 4,879,236
U.S. Pat. No. 5,077,214
U.S. Pat. No. 5,155,037
U.S. Pat. No. 5,162,222
U.S. Pat. No. 5,169,784
U.S. Pat. No. 5,278,050

Adams, J. R., and McClintock, J. T. (1991). Baculoviridae. Nuclear polyhedrosis virus, In "Atlas of invertebrate viruses" (J. R. Adams and J. R. Bonami, Eds.). CRC Press, Boca Raton, Fla.

Ahmad S., Bassiri M., Banerjee A K., Yilma T. (1993). Immunological characterization of the VSV nucleocapsid (N) protein expressed by recombinant baculovirus in *Spodoptera exigua* larva: use in differential diagnosis between vaccinated and infected animals. *Virology* 192, 207–216.

Alt, Kellems, Bertino and Schimke, *J. Biol. Chem.,* 253:1357, 1978

Andrews, F. J. and Mason, S. W. (1993) Gene expression and the cell cycle: a family affair. *Science* 261,1543–1544.

Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5' Flanking Region," *Mol. Cell. Biol.,* 7:2256, 1987a.

Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell,* 49:729, 1987b.

Arvinte T. Schulz B. Cudd A. Nicolau C. (1989). Low-pH association of proteins with the membranes of intact red blood cells. I. Exogenous glycophorin and the CD4 molecule. *Biochim. Biophys. Acta* 981, 51–60.

Atchison and Perry, "Tandem Kappa Immunoglobulin Promoters are Equally Active in the Presence of the Kappa Enhancer: Implications for Model of Enhancer Function," *Cell,* 46:253, 1986.

Atchison and Perry, "The Role of the Kappa Enhancer and its Binding Factor NF-kappa B in the Developmental Regulation of Kappa Gene Transcription," *Cell,* 48:121, 1987.

Ayres, M. D., Howard, S. C., Kuzio, J., Lopez-Ferber, and Possee, R. D. (1994). The complete DNA sequence of *Autographa californica* nuclear polyhedrosis virus. *Virology* 202, 586–605.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Banerji, Olson, and Schaffner, "A Lymphocyte-Specific Cellular Enhancer is Located Downstream of the Joining Region in Immunoglobulin Heavy-Chain Genes," *Cell,* 35:729, 1983.

Banerji, Rusconi, and Schaffner, "Expression of a Beta-Globin Gene is Enhanced by Remote SV40 DNA Sequences," *Cell,* 27:299, 1981.

Belyaev, A. S., and Roy, P. (1993). Development of baculovirus triple and quadruple expression vectors: co-expression of three or four bluetongue virus proteins and the synthesis of bluetongue virus-like particles in insect cells. *Nucleic Acids Res.* 21, 1219–1223.

Berkhout, Silverman, and Jeang, "Tat Trans-activates the Human Immunodeficiency Virus Through a Nascent RNA Target," *Cell,* 59:273, 1989.

Blanar, Baldwin, Flavell, and Sharp, "A Gamma-Interferon-Induced Factor That Binds the Interferon Response Sequence of the MHC Class I Gene, H-2Kb," *EMBO J.,* 8:1139, 1989.

Blissard, G. W., and Rohrmann, G. F. (1989). Location, sequence, transcriptional mapping, and temporal expression of the gp64 envelope glycoprotein gene of the *Orgyia pseudotsugata* multicapsid nuclear polyhedrosis virus. *Virology* 170, 537–555.

Blissard, G. W., and Rohrmann, G. F. (1990). Baculovirus diversity and molecular biology. *Annu. Rev. Entomol.* 35, 127–155.

Bodine and Ley, "An Enhancer Element Lies 3' to the Human A Gamma Globin Gene," *EMBO J.,* 6:2997, 1987.

Boshart, Weber, Jahn, Dorsch-Hasler, Fleckenstein, and Schaffner, "A Very Strong Enhancer is Located Upstream of an Immediate Early Gene of Human Cytomegalovirus," *Cell,* 41:521, 1985.

Bosze, Thiesen, and Charnay, "A Transcriptional Enhancer with Specificity for Erythroid Cells is Located in the Long Terminal Repeat of the Friend Murine Leukemia Virus," *EMBO J.,* 5:1615, 1986.

Bozzola, J. J., and Russell, L. D. (1992). Electron Microscopy. Jones and Bartlett Publishers, Boston, Mass.

Braddock, Chambers, Wilson, Esnouf, Adams, Kingsman, and Kingsman, "HIV-I Tat Activates Presynthesized RNA In the Nucleus," *Cell,* 58:269, 1989.

Bradford, M. B. (1976). A rapid and sensitive method for the quantitation of microgram quantities of protein utilizing the principle of protein-dye binding. *Anal Biochem.* 72, 248–254.

Braunagel, S. C., and Summers, M. D. (1994). *Autographa californica* nuclear polyhedrosis virus, PDV and ECV viral envelopes and nucleocapsids: Structural proteins; antigens; lipid and fatty acid profiles. *Virology* 202, 315–328.

Braunagel, S. C., Daniel, K. D., Reilly, L. M., Guarino, L. A., Hong, T., and Summers, M. D. (1992). Sequence, genomic organization of the EcoRI-A fragment of *Autographa californica* nuclear polyhedrosis virus, and identification of a viral-encoded protein resembling the outer capsid protein VP8 of rotavirus. *Virology* 191, 1003–1008.

Braunagel, S. C., Elton D. M., Ma, H., and Summers, M. D. (1996a). Identification and analysis of an *Autographa californica* nuclear polyhedrosis virus structural protein of the occlusion-derived virus envelope: ODV-E56. *Virology* 217, 97–110.

Braunagel, S. C., He, H., Ramamurthy, P., and Summers, M. D. (1996b). Transcription, translation, and cellular localization of three *Autographa californica* nuclear polyhedrosis virus structural proteins: ODV-E18, ODV-E35 and ODV-EC27. *Virology* 222, 100–114.

Bulla and Siddiqui, "The Hepatitis B Virus Enhancer Modulates Transcription of the Hepatitis B Virus Surface-Antigen Gene From an Internal Location," *J. Virol.,* 62:1437, 1986.

Campbell and Villarreal, "Functional Analysis of the Individual Enhancer Core Sequences of Polyoma Virus: Cell-Specific Uncoupling of DNA Replication From Transcription," *Mol. Cell. Biol.,* 8:1993, 1988.

Campbell, in: *Monoclonal Antibody Technology, Laboratory Techniques in Biochemistry and Molecular Biology,* Vol. 13, Burden and Von Knippenberg, Eds. pp. 75–83, Amsterdam, Elseview, 1984.

Campere and Tilghman, "Postnatal Repression of the α-fetoprotein Gene is Enhancer Independent," *Genes and Dev.,* 3:537, 1989.

Campo, Spandidos, Lang, and Wilkie, "Transcriptional Control Signals in the Genome of Bovine Papilloma Virus Type 1," *Nature,* 303:77, 1983.

Carrington, J. C., and Freed, D. D. (1990). Cap-independent enhancement of translation by a plant potyvirus 5' non-translated region. *J. Virol.* 64, 1590–1597.

Carson, D. D., Guarino, L. A., and Summers, M. D. (1988). Functional mapping of an AcMNPV immediate early gene which augments expression of the IE-1 transactivated 39K gene. *Virology* 162, 444–451.

Carson, D. D., Summers, M. D., and Guarino, L. A. (1991). Transient expression of the *Autographa californica* nuclear polyhedrosis virus immediate early gene, IE-N, is regulated by three viral elements. *J. Virol* 65, 945–951.

Celander and Haseltine, "Glucocorticoid Regulation of Murine Leukemia Virus Transcription Elements is Specified by Determinants Within the Viral Enhancer Region," *J. Virology,* 61:269, 1987.

Celander, Hsu, and Haseltine, "Regulatory Elements Within the Murine Leukemia Virus Enhancer Regions Mediate Glucocorticoid Responsiveness," *J. Virology,* 62:1314, 1988.

Chalfie et al., *Science*, 263:802–805, 1994.

Chandler, Maler, and Yamamoto, "DNA Sequences Bound Specifically by Glucocorticoid Receptor in vitro Render a Heterlogous Promoter Hormone Responsive in vivo," *Cell*, 33:489, 1983.

Chang et al., "Foreign gene delivery and expression in hepatocytes using a hepatitis B virus vector," *Hepatology*, 14:134A, 1991.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Charlton, C. A., and Volkman, L. E. (1993). Penetration of *Autographa californica* nuclear polyhedrosis virus nucleocapsids into IPLB Sf 21 cells induces actin cable formation. *Virology* 197, 245–254.

Chatterjee, Lee, Rentoumis, and Jameson, "Negative Regulation of the Thyroid-Stimulating Hormone Alpha Gene by Thyroid Hormone: Receptor Interaction Adjacent to the TATA Box," *Proc Natl. Acad Sci. U.S.A.*, 86:9114, 1989.

Chen and Okayama, "High-efficiency transformation of mammalian cells by plasmid DNA," *Mol. Cell. Biol.* 7:2745–2752, 1987

Choi, Chen, Kriegler, and Roninson, "An Altered Pattern of Cross-Resistance in Multi-Drug-Resistant Human Cells Results From Spontaneous Mutations in the Mdr-1 (P-glycoprotein) Gene," *Cell*, 53:519, 1988.

Choi, J., and Guarino, L. A. (1995a). A temperature-sensitive IE1 protein of *Autographa californica* nuclear polyhedrosis virus has altered transactivation and DNA binding activities. *Virology* 209, 90–98.

Choi, J., and Guarino, L. A. (1995b). Expression of the IE1 transactivator of *Autographa californica* nuclear polyhedrosis virus during viral infection. *Virology* 209, 99–107.

Choi, J., and Guarino, L. A. (1995c). The baculovirus trans-activator IE1 binds to viral enhancer elements in the absence of insect cell factors. *J. Virol* 69, 4548–4551.

Clark, Voulgaropoulou, Fraley, and Johnson, "Cell lines for the production of recombinant adeno-associated virus," *Human Gene Therapy*, 6:1329–1341, 1995.

Coffin, "Retroviridae and their replication," In: *Virology*, Fields et al. (eds.), New York: Raven Press, pp. 1437–1500, 1990.

Cohen, Walter, and Levinson, "A Repetitive Sequence Element 3' of the Human c-Ha-ras1 Gene Has Enhancer Activity," *J. Cell. Physiol.*, 5:75, 1987.

Colberre-Garapin et al., *J. Mol. Biol*, 150:1, 1981

Cory, J. S., and Bishop, D. H. L. (1995). Use of baculoviruses as biological insecticides, In "Methods in Molecular Biology", vol. 39, pp. 277–294, (C. D. Richardson, ed.). Humana Press, Inc., Totowa, N.J.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81, 1988.

Cotten, Wagner, Zatloukal, Phillips, and Curiel, "High efficiency receptor-mediated delivery of small and large (48 kilobase) gene constructs using the endosome disruption activity of defective or inactivated adenovirus particles," P.N.A.S. USA, 89:6094–6098, 1992.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Culotta and Hamer, "Fine Mapping of a Mouse Metallothionein Gene Metal-Response Element," *Mol. Cell. Biol.*, 9:1376, 1989.

Curiel, "Gene transfer mediated by adenovirus-polylysine DNA complexes," In: *Viruses in Human Gene Therapy*, J.-M. H. Vos (Ed.), Carolina Academic Press, Durham, N.C., pp. 179–212,1994.

Dandolo, Blangy, and Kamen, "Regulation of Polyma Virus Transcription in Murine Embryonal Carcinoma Cells," *J. Virology*, 47:55, 1983.

De Villiers, Schaffner, Tyndall, Lupton, and Kamen, "Polyoma Virus DNA Replication Requires an Enhancer," *Nature*, 312:242, 1984.

Deschamps, Meijlink, and Verma, "Identification of a Transcriptional Enhancer Element Upstream From the Proto-Oncogene Fos," *Science*, 230:1174, 1985.

Devereux, J., Haeberli, P., and Smithies, O. (1984). A comprehensive set of sequence analysis programs for the VAX. *Nucl. Acids Res.* 12, 389–395.

Dewey, R. E., Levings, C. S., III, and Timothy, D. H. (1986). Novel recombinations in the maize mitochondrial genome produce a unique transcriptional unit in the Texas male-sterile cytoplasm. *Cell* 44, 439–449.

Edbrooke, Burt, Cheshire, and Woo, "Identification of cis-Acting Sequences Responsible for Phorbol Ester Induction of Human Serum Amyloid A Gene Expression Via a Nuclear-Factor-κB-like Transcription Factor," *Mol. Cell. Biol.*, 9:1908, 1989.

Edlund, Walker, Barr, and Rutter, "Cell-Specific Expression of the Rat Insulin Gene: Evidence for Role of Two Distinct 5' Flanking Elements," *Science*, 230:912, 1985.

Eichenlaub, R., *J. Bacteriol* 138:559–566, 1979.

Fechheimer, Boylan, Parker, Sisken, Patel and Zimmer, "Transfection of mammalian cells with plasmid DNA by scrape loading and sonication loading," *Proc Nat'l. Acad. Sci. USA* 84:8463–8467, 1987

Feng and Holland, "HIV-I Tat Trans-Activation Requires the Loop Sequence Within Tar," *Nature*, 334:6178, 1988.

Firak and Subramanian, "Minimal Transcription Enhancer of Simian Virus 40 is a 74-Base-Pair Sequence that Has Interacting Domains," *Mol. Cell. Biol.*, 6:3667, 1986.

Flotte, Afione, Conrad, McGrath, Solow, Oka, Zeitlin, Guggino, and Carter, "Stable in vivo expression of the cystic fibrosis transmembrane conductance regulator with an adeno-associated virus vector," *Proc Natl. Acad. Sci. USA*, 90:10613–10617, 1993.

Flotte, Barraza-Ortiz, Solow, Afione, Carter, and Guggino, "An improved system for packaging recombinant adeno-associated virus vectors capable of in vivo transduction," *Gene Therapy*, 2:29–37, 1995.

Flotte, Solow, Owens, Afione, Zeitlin, and Carter, "Gene expression from adeno associated virus vector in airway epithelial cells," *Am. J. Respir. Cell Mol. Biol.*, 7:349–356, 1992.

Foecking and Hofstetter, "Powerful and Versatile Enhancer-Promoter Unit for Mammalian Expression Vectors," *Gene*, 45:101, 1986.

Fraley, Fornari and Kaplan, "Entrapment of a bacterial plasmid in phospholipid vesicles:potential for gene transfer," *Proc Nat'l. Acad. Sci. USA* 76:3348–3352, 1979

Friedmann, "Progress toward human gene therapy," *Science*, 244:1275–1281, 1989.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Funk, C. J., and Consigli, R. A. (1993). Temporal expression and immunogold localization of Plodia interpunctella granu-losis virus structural proteins. *Virus Res.* 28, 57–66.

Furukawa, K., Pante, N., Aebi, U., and Gerace, L. (1995). Cloning of a cDNA for lamina-associated polypeptide 2 (LAP2) and identification of regions that specify targeting to the nuclear envelope. *EMBO J.* 14, 1626–1636.

Gefter et al., *Somatic Cell Genet.* 3:231–236, 1977.

Ghosh-Choudhury et al., "Protein IX, a minor component of the human adenovirus capsid, is essential for the packaging of full-length genomes," *EMBO J.*, 6:1733–1739, 1987.

Ghosh and Bachhawat, "Targeting of liposomes to hepatocytes," In. Wu G. and C. Wu ed. Liver diseases, targeted diagnosis and therapy using specific receptors and ligands. New York: Marcel Dekker, pp. 87–104, 1991.

Gilbert, R., Ghosh, K., Rasile, L., and Ghosh, H. P. (1994). Membrane anchoring domain of herpes simplex virus glycoprotein gB is sufficient for nuclear envelope localization. *J. Virol.* 68, 2272–2285.

Gilles, Morris, Oi, and Tonegawa, "A Tissue-Specific Transcription Enhancer Element is Located in the Major Intron of a Rearranged Immunoglobulin Heavy-Chain Gene," *Cell*, 33:717, 1983.

Gius, Grossman, Bedell, and Laimins, "Inducible and Constitutive Enhancer Domains in the Noncoding Region of Human Papilloma Virus Type 18," *J. Virology*, 62:665, 1988.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Gluzman, Y. (1981). SV40-transformed Simian cells support the replication of early SV40 mutants. *Cell* 23, 175–182.

Godbout, Ingram, and Tilghman, "Fine-Structure Mapping of the Three Mouse Alpha-Fetoprotein Gene Enhancers," *Mol. Cell. Biol.*, 8:1169, 1988.

Goding, in: *Monoclonal Antibodies. Principles and Practice*, 2d ed., Orlando, Fla., Academic Press, 1986, pp. 60–61, 65–66, 71–74.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Goodbourn and Maniatis, "Overlapping Positive and Negative Regulatory Domains of the Human β-Interferon Gene," *Proc Natl. Acad. Sci. USA*, 85:1447, 1988.

Goodbourn, Burstein, and Maniatis, "The Human Beta-Interferon Gene Enhancer is Under Negative Control," *Cell*, 45:601, 1986.

Gopal, "Gene transfer method for transient gene expression, stable transformation, and cotransformation of suspension cell cultures," *Mol. Cell. Biol.* 5:1188–1190, 1985

Graham and Prevec, "Adenovirus-based expression vectors and recombinant vaccines," *Biotechnology*, 20:363–390, 1992.

Graham and Prevec, "Manipulation of adenovirus vectors," In. *Gene Transfer and Expression Protocols*, Murray, E. J., ed., Humana, New Jersey, vol. 7, 109–128, 1991.

Graham and Van Der Eb, "A new technique for the assay of infectivity of human adenovirus 5 DNA," *Virology* 52:456–467, 1973

Graham et al., "Characteristics of a human cell line transformed by DNA from human adenovirus type 5", *J. Gen. Virol.*, 36:59–72, 1977.

Greene, Böhnlein, and Ballard, "HIV-1, and Normal T-Cell Growth: Transcriptional Strategies and Surprises," *Immunology Today*, 10:272, 1989.

Groner, A. (1986). Specificity and safety of baculoviruses. In "The Biology of Baculoviruses", pp. 177–202, (R. R. Granados and B. A. Federici, eds.). CRC Press, Boca Raton, Fla.

Grosschedl and Baltimore, "Cell-Type Specificity of Immunoglobulin Gene Expression is Regulated by at Least Three DNA Sequence Elements," *Cell*, 41:885, 1985.

Grunhaus and Horwitz, "Adenovirus as cloning vector," *Seminar in Virology*, 3:237–252, 1992.

Guarino and Smith, "Nucleotide sequence of the 39K gene region of Autographa californica nuclear polyhedrosis virus," *Virology*, 179:1–8, 1991.

Guarino and Summers, "Nucleotide sequence and temporal expression of a baculovirus regulatory gene," *J. Virol*, 61:2091–2099, 1987.

Guarino, Gonzalez, and Summers, "Complete sequence and enhancer function of the homologous DNA regions of Autographa californica nuclear polyhedrosis virus," *J. Virol*, 60:224–229, 1986.

Guarino, L. A., Smith, G., and Dong, W. (1995). Ubiquitin is attached to membranes of baculovirus particles by a novel type of phospholipid anchor. *Cell* 80, 301–309.

Harel, A., Zlotkin, E., Nainudel-Epszteyn, S., Feinstein, N., Fisher, P. A., and Gruenbaum, Y. (1989). Persistence of major nuclear envelope antigens in an envelope-like structure during mitosis in Drosophila melanogaster embryos. *J. Cell Sci.* 94, 463–470.

Harland and Weintraub, "Translation of mRNA injected into Xenopus oocytes is specifically inhibited by antisense RNA," *J. Cell Biol.* 101:1094–1099, 1985

Harlow, E., and Lane, D. (1988). Antibodies: A laboratory manual. Cold Spring Harbor Laboratory Press, Cold Spring Harbor, N.Y.

Haslinger and Karin, "Upstream Promoter Element of the Human Metallothionein-II Gene Can Act Like an Enhancer Element," *Proc Natl. Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321:249, 1986.

Hensel, Meichle, Pfizenmaier, and Kronke, "PMA-Responsive 5' Flanking Sequences of the Human TNF Gene," *Lymphokine Res.*, 8:347, 1989.

Hermonat and Muzyczka, "Use of adeno-associated virus as a mammalian DNA cloning vector; transduction of neomycin resistance into mammalian tissue culture cells," *Proc Nat'l. Acad. Sci. USA*, 81:6466–6470, 1984.

Herr and Clarke, "The SV40 Enhancer is Composed of Multiple Functional Elements That Can Compensate for One Another," *Cell*, 45:461, 1986.

Hersdorffer et al., "Efficient gene transfer in live mice using a unique retroviral packaging line," *DNA Cell Biol.*, 9:713–723, 1990.

Hershberger, P. A., LaCount, D. J., and Friesen, P. D. (1994). The apoptotic suppressor P35 is required early during baculovirus replication and is targeted to the cytosol of infected cells. *J. Virol* 68, 3467–3477.

Herz and Gerard, "Adenovirus-mediated transfer of low density lipoprotein receptor gene acutely accelerates cholesterol clearance in normal mice," *Proc Nat'l. Acad. Sci. USA* 90:2812–2816, 1993.

Hill, J. E., and Faulkner, P. (1994). Identification of the gp67 gene of a baculovirus pathogenic to the spruce budworm, *Choristoneura fumiferana* multinucleocapsid nuclear polyhedrosis virus. *J. Gen Virol.* 75, 1811–1813.

Hirochika, Browker, and Chow, "Enhancers and Trans-Acting E2 Transcriptional Factors of Papilloma Viruses," *J. Virol.,* 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.,* 10:1959, 1990.

Holbrook, Gulino, and Ruscetti, "cis-Acting Transcriptional Regulatory Sequences in the Gibbon Ape Leukemia Virus (GALV) Long Terminal Repeat," *Virology,* 157:211, 1987.

Hong, T. (1995). Studies on a PDV envelope protein of *Autographa californica* nuclear polyhedrosis virus. Ph.D dissertation, Department of Biology, Texas A&M University, College Station, Tex.

Hong, T., Braunagel, S. C., and Summers, M. D. (1994). Transcription, translation, and cellular localization of PDV-E66: a structural protein of the PDV envelope of *Autographa californica* nuclear polyhedrosis virus. *Virology* 204, 210–222.

Hooft van Iddekinge, B. J. L., Smith, G. E., and Summers, M. D. (1983). Nucleotide sequence of the polyhedrin gene of *Autographa californica* nuclear polyhedrosis virus. *Virology* 131, 561–565.

Horlick and Benfield, "The Upstream Muscle-Specific Enhancer of the Rat Muscle Creatine Kinase Gene is Composed of Multiple Elements," *Mol. Cell. Biol.,* 9:2396, 1989.

Horwich et al. "Synthesis of hepadenovirus particles that contain replication-defective duck hepatitis B virus genomes in cultured HuH7 cells," *J. Virol,* 64:642–650, 1990.

Huang, Ostrowski, Berard, and Hagar, "Glucocorticoid Regulation of the Ha-MuSV p21 Gene Conferred by Sequences From Mouse Mammary Tumor Virus," *Cell,* 27:245, 1981.

Hug, Costas, Staeheli, Aebi, and Weissmann, "Organization of the Murine Mx Gene and Characterization of its Interferon- and Virus-Inducible Promoter," *Mol. Cell. Biol.,* 8:3065, 1988.

Hunter, T. (1993). Braking the cycle. *Cell* 75, 839–841.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.,* 10:585, 1990.

Ignoffo, C. M. (1971). Intraperitoneal injection of white mice with nucleopolyhedrosis virus of the beet armyworm, *Spodopteera exigua. J. Invert. Pathol.* 17, 453–454.

Ignoffo, C. M., and Heimpel, A. M. (1965). The nuclear-polyhedrosis virus of *Heliothis zea* (Boddie) and *Heliothis virescens* (Fabricius) V. Toxicity-pathogenicity of virus to white mice and guinea pigs. *J. Invert. Pathol.* 7, 329–340.

Ignoffo, C. M., and Rafajko, R. R. (1972). In vitro attempts to infect primate cells with the nucleopolyhedrosis virus of Heliothis. *J. Invert. Pathol.* 20, 321–325.

Ignoffo, C. M., Anderson, R. F., and Woodward, G. (1972). Teratogenic potential in rats fed the nuclear polyhedrosis virus of Heliothis. *Environmental Entomology* 2, 337–338.

Imagawa, Chiu, and Karin, "Transcription Factor AP-2 Mediates Induction by Two Different Signal-Transduction Pathways: Protein Kinase C and cAMP," *Cell,* 51:251, 1987.

Imbra and Karin, "Phorbol Ester Induces the Transcriptional Stimulatory Activity of the SV40 Enhancer," *Nature,* 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol,* 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.,* 4:875, 1984.

Ismail, T., Ahmad, S., D'Souza-Ault, M., Bassiri, M., Saliki, J., Mebus, C., Yilma, T. (1994). Cloning and expression of the nucleocapsid gene of virulent Kabete O strain of rinderpest virus in baculovirus: use in differential diagnosis between vaccinated and infected animals. *Virology* 198, 138–147.

Jackson, A. O., Francki, R. I. B., and Zuidema, D. (1987). Biology, structure and replication of plant rhabdoviruses. In "The Rhabdoviruses" (R. R. Wagner, Ed.). Plenum Press, New York.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.,* 8:2555, 1988.

Jameel and Siddiqui, "The Human Hepatitis B Virus Enhancer Requires Transacting Cellular Factor(s) for Activity," *Mol. Cell. Biol.,* 6:710, 1986.

Jarvis, D. L., Bohlmeyer, D. A., and Garcia, A., Jr. (1991). Requirements for nuclear localization and supramolecular assembly of a baculovirus polyhedrin protein. *Virology* 185, 795–810.

Jarvis, D. L., Weinkauf, C., and Guarino, L. A. (1996). Immediate early baculovirus vectors for foreign gene expression in transformed or infected insect cells. *Protein Expression and Purification* 8, 191–203.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.,* 8:62, 1988.

Jha, P. K., Nakhai, B., Sridhar, P., Talwar, G. P., Hasnain, S. E. (1990). Firefly luciferase, synthesized to very high levels in caterpillars infected with a recombinant baculovirus, can also be used as an efficient reporter enzyme in vivo. *FEBS Letters* 274, 23–26.

Johnson, Wold, and Hauschka, "Muscle Creatine Kinase Sequence Elements Regulating Skeletal and Cardiac Muscle Expression in Transgenic Mice," *Mol. Cell. Biol.,* 9:3393, 1989a.

Jones and Shenk, "Isolation of deletion and substitution mutants of adenovirus type 5," *Cell,* 13:181–188, 1978.

Kabcenell and Atkinson (1985) *J. Cell Biol.,* 101:1270–1280.

Kadesch and Berg, "Effects of the Position of the Simian Virus 40 Enhancer on Expression of Multiple Transcription Units in a Single Plasmid," *Mol. Cell. Biol.,* 6:2593, 1986.

Kaneda et al., "Increased expression of DNA cointroduced with nuclear protein in adult rat liver," *Science,* 243:375–378, 1989.

Kaplitt, Leone, Samulski, Siao, Pfaff, O'Malley, and During, "Long-term gene expression and phenotypic correction suing adeno-associated virus vectors in the mammalian brain," *Nature Genetics*, 8:148–154, 1994.

Karin, Haslinger, Heguy, Dietlin, and Cooke, "Metal-Responsive Elements Act as Positive Modulators of Human Metallothionein-IIA Enhancer Activity," *Mol. Cell. Biol.*, 7:606, 1987.

Karlsson et al., *EMBO J.*, 5:2377–2385, 1986.

Katinka, Vasseur, Montreau, Yaniv, and Blangy, "Polyoma DNA Sequences Involved in the Control of Viral Gene Expression in Murine Embryonal Carcinoma Cells," *Nature*, 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell*, 20:393, 1980.

Kato et al., "Expression of hepatitis β virus surface antigen in adult rat liver," *J. Biol. Chem.*, 266:3361–3364, 1991.

Kaufman, "Selection and Coamplification of Heterologous Genes in Mammalian Cells," *Methods in Enzymology*, 185:537–566, 1990.

Kawamoto, Makino, Niw, Sugiyama, Kimura, Anemura, Nakata, and Kakunaga, "Identification of the Human Beta-Actin Enhancer and its Binding Factor," *Mol. Cell. Biol.*, 8:267, 1988.

Kawanishi, C. Y., Summers, M. D., Stoltz, D. B., and Arnott, H. J. (1972). Entry of an insect virus in vivo by fusion of viral envelope and microvillus membrane. *J. Invert. Pathol.* 20, 104–108.

Keddie, B. A., and Volkman, L. E. (1985). Infectivity differences between the two phenotypes of *Autographa californica* nuclear polyhedrosis virus: importance of the 64K envelope glycoprotein. *J. Gen. Virol.* 66, 1195–1200.

Kelleher and Vos, "Long-term episomal gene delivery in human lymphoid cells using human and avian adenoviral-assisted transfection," *Biotechniques*, 17(6): 1110–1117, 1994.

Kiledjian, Su, and Kadesch, "Identification and Characterization of Two Functional Domains Within the Murine Heavy-Chain Enhancer," *Mol. Cell. Biol.*, 8:145, 1988.

Klamut, Gangopadyhay, Worton, and Ray, "Molecular and Functional Analysis of the Muscle-Specific Promoter Region of the Duchenne Muscular Dystrophy Gene," *Mol. Cell. Biol.*, 10:193, 1990.

Klein et al., "High-velocity microprojectiles for delivering nucleic acids into living cells," *Nature*, 327:70–73, 1987.

Koch, Benoist, and Mathis, "Anatomy of a New B-Cell-Specific Enhancer," *Mol. Cell. Biol.*, 9:303, 1989.

Kohler and Milstein, *Eur. J Immunol.*, 6:511–519, 1976.

Kohler and Milstein, *Nature*, 256:495–497, 1975.

Kool, M., Ahrens, C. H., Goldbach, R. W., Rohrmann, G. F., and Vlak, J. M. (1994). Identification of genes involved in DNA replication of the *Autographa californica* baculovirus. *Proc Natl. Acad. Sci. USA* 91, 11212–11216.

Korth, K. L., and Levings, C. S., III (1993). Baculovirus expression of the maize mitochondrial protein URF13 confers insecticidal activity in cell cultures and larvae. *Proc Natl. Acad. Sci. USA* 90, 3388–3392.

Kotin, Siniscalco, Samulski, Zhu, Hunter, McLaughlin, Muzyczka, and Bems, "Site-specific integration by adeno-associated virus," *Proc Natl Acad. Sci. USA*, 87:2211–2215, 1990.

Kovacs, G. R., Guarino, L. A., and Summers, M. D. (1991b). Novel regulatory properties of the IE1 and IE0 transactivators encoded by the baculovirus *Autographa californica* multi-capsid nuclear polyhedrosis virus. *J. Virol* 65, 5281–5288.

Kovacs, G. R., Guarino, L. A., Graham, B. L., and Summers, M. D. (1991a). Identification of spliced baculovirus RNAs expressed late in infection. *Virology* 185, 633–643.

Kozuma, K., and Hukuhara, T. (1994). Fusion characteristics of a nuclear polyhedrosis virus in cultured cells: time course and effect of a synergistic factor and pH. *J. Invert. Pathol.* 63, 63–67.

Krappa, R., Krappa, A. B., Jahnel, F., Doerfler, W., and Morsdorf, D. K. (1992). Differential factor binding at the promoter of early baculovirus gene PE38 during viral infection: GATA motif is recognized by an insect protein. *J. Virol* 66, 3494–3503.

Kriegler and Botchan, "A Retrovirus LTR Contains a New Type of Eukaryotic Regulatory Element," *In: Eukaryotic Viral Vectors*, ed. Y. Gluzman. Cold Spring Harbor: Cold Spring Harbor Laboratory, NY, 1982.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler, Perez, and Botchan, "Promoter Substitution and Enhancer Augmentation Increases the Penetrance of the SV40 A Gene to Levels Comparable to That of the Harvey Murine Sarcoma Virus Ras Gene in Morphologic Transformation," *In: Gene Expression*, eds. D. Hamer and M. Rosenberg. New York: Alan R. Liss, 1983.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell*, 53:45, 1988.

Kriegler, Perez, Hardy and Botchan, "Transformation Mediated by the SV40 T Antigens: Separation of the Overlapping SV40 Early Genes with a Retroviral Vector," *Cell*, 38:483, 1984a.

Kriegler, Perez, Hardy, and Botchan, "Viral Integration and Early Gene Expression Both Affect the Efficiency of SV40 Transformation of Murine Cells: Biochemical and Biological Characterization of an SV40 Retrovirus," *In: Cancer Cells 2/Oncogenes and Viral Genes*, G. F. Van de Woude, A. J. Levine, W. C. Topp, and J. D. Watson, Cold Spring Harbor: Cold Spring Harbor Laboratory, 1984b.

Kuhl, De La Fuenta, Chaturvedi, Parinool, Ryals, Meyer, and Weissman, "Reversible Silencing of Enhancers by Sequences Derived From the Human IFN-alpha Promoter," *Cell*, 50:1057, 1987.

Kunkel et al., Methods Enzymol., 154:367–382, 1987.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.*, 17:1121, 1989.

Kuzio, J., Jaques, R., and Faulkner, P. (1989). Identification of p74, a gene essential for virulence of baculovirus occlusion bodies. *Virology* 173, 759–763.

Kuzio, J., Rohel, D. Z., Curry, C. J., Krebs, A., Carstens, E. B., and Faulkner, P. (1984). Nucleotide sequence of the p10 polypeptide gene of *Autographa californica* nuclear poly-hedrosis virus. *Virology* 139, 414–418.

Kyte and Doolittle. (1982) A simple method for displaying the hydropathic character of a protein. *J. Mol. Biol.*, 157,105–132.

LaFace, Hermonat, Wakeland, and Peck, "Gene transfer into hematopoietic progenitor cells mediated by an adeno-associated virus vector," *Viology*, 162:483–486, 1988.

Larsen, Harney, and Moore, "Repression Medaites Cell-Type-Specific Expression of the Rat Growth Hormone Gene," *Proc Natl. Acad. Sci. USA.*, 83:8283, 1986.

Laspia, Rice, and Mathews, "HIV-1 Tat Protein Increases Transcriptional Initiation and Stabilizes Elongation," Cell, 59:283, 1989.

Latimer, Berger, and Baumann, "Highly Conserved Upstream Regions of the $\alpha_1$-Antitrypsin Gene in Two Mouse Species Govern Liver-Specific Expression by Different Mechanisms," Mol. Cell. Biol., 10:760, 1990.

Laughlin, Cardellichio, and Coon, "Latent Infection of KB Cells with Adeno-Associated Virus Type 2," J. Virol, 60:515–524, 1986.

Laukkanen, M-L., Oker-Blom, C., and Keinanen, K. (1996). Secretion of green fluorescent protein from baculovirus-infected insect cells. Biochem. Biophys. Res. Commun 226, 755–761.

Le Gal La Salle et al., "An adenovirus vector for gene transfer into neurons and glia in the brain," Science, 259:988–990, 1993.

Lebkowski, McNally, Okarma, and Lerch, "Adeno-associated virus: a vector system for efficient introduction and integration of DNA into a variety of mammalian cell types," Mol. Cell. Biol., 8:3988–3996, 1988.

Lee, Mulligan, Berg, and Ringold, "Glucocorticoids Regulate Expression of Dihydrofolate Reductase cDNA in Mouse Mammary Tumor Virus Chimaeric Plasmids," Nature, 294:228, 1981.

Levinson, Khoury, VanDeWoude, and Gruss, "Activation of SV40 Genome by 72-Base-Pair Tandem Repeats of Moloney Sarcoma Virus," Nature, 295:79, 1982.

Levrero et al., "Defective and nondefective adenovirus vectors for expressing foreign genes in vitro and in vivo," Gene, 101:195–202, 1991.

Lin, Cross, Halden, Dragos, Toledano, and Leonard, "Delineation of an Enhancerlike Positive Regulatory Element in the Interleukin-2 Receptor $\alpha$-Chain Gene," Mol. Cell. Biol., 10:850, 1990.

Lu, A., and Carstens, E. B. (1992). Nucleotide sequence and transcriptional analysis of the p80 gene of Autographa californica nuclear polyhedrosis virus: A homologue of the Orgyia pseudotsugata nuclear polyhedrosis virus capsid-associated protein. Virology 190, 201–209.

Luckow, V. A., and Summers, M. D. (1989). High level expression of nonfused foreign genes with Autographa californica nuclear polyhedrosis virus expression vectors. Virology 170, 31–39.

Luo, Zhou, Cooper, Munshi, Boswell, Broxmeyer, and Srivastava, "Adeno-associated virus 2 mediated transfer and functional expression of a gene encoding the human granulocyte-macrophage colony-stimulating factor," Blood,82 (Supp.): 1,303A, 1994.

Luria, Gross, Horowitz, and Givol, "Promoter Enhancer Elements in the Rearranged Alpha-Chain Gene of the Human T-Cell Receptor," EMBO J., 6:3307, 1987.

Lusky and Botchan, "Transient Replication of Bovine Papilloma Virus Type 1 Plasmids: cis and trans Requirements," Proc Natl. Acad. Sci. U.S.A., 83:3609, 1986.

Lusky, Berg, Weiher, and Botchan, "Bovine Papilloma Virus Contains an Activator of Gene Expression at the Distal End of the Early Transcription Unit," Mol. Cell. Biol. 3:1 108, 1983.

Maddon, P. J., Dalgleish, A. G., McDougal, J. S., Clapham, P. R., Weiss, R. A., and Axel, R. (1986). The T4 gene encodes the AIDS virus receptor and is expressed in the immune system and the brain. Cell 47, 333–348.

Maeda, S., Kawai, T., Obinata, M., Fujiwara, H., Horiuchi, T., Saeki, Y., Sato, Y., and Furusawa, M. (1985). Production of human alpha-interferon in silkworm using a baculovirus vector. Nature 315, 592–594.

Majors and Varmus, "A Small Region of the Mouse Mammary Tumor Virus Long Terminal Repeat Confers Glucocorticoid Hormone Regulation on a Linked Heterologous Gene," Proc Natl. Acad. Sci. U.S.A., 80:5866, 1983.

Mann et al., "Construction of a retrovirus packaging mutant and its use to produce helper-free defective retrovirus," Cell, 33:153–159, 1983.

Markowitz et al., "A safe packaging line for gene transfer: Separating viral genes on two different plasmids," J. Virol, 62:1120–1124, 1988.

Martens, J. (1994). Development of a baculovirus insecticide exploiting the Bacillus thuringiensis insecticidal crystal protein. Ph.D dissertation, Department of Virology, Agricultural University in Wageningen, Netherlands.

Martignoni, M. E., Stelzer, M. J., and Iwai, P. J. (1982). Baculovirus of Autographa californica (Lepidoptera: Noctuidae): a candidate biological control agent for Douglas-fir tussock moth (Lepidoptera: Lymantriidae). J. Econ. Entomol. 75, 1120–1124.

Martin, L., Crimaudo, C., and Gerace, L. (1995). cDNA cloning and characterization of lamina-associated polypeptide 1C (LAPIC), an integral protein of the inner nuclear membrane. J. Biol. Chem. 270, 8822–8828.

Marumoto, Y., Sato, Y., Fujiwara, H., Sakano, K., Saeki, Y., Agata, M., Furusawa, M., and Maeda, S. (1987). Hyperproduction of polyhedrin-IGF II fusion protein in silkworm larvae infected with recombinant Bombyx mori nuclear polyhedrosis virus. J. Gen. Virol. 68, 2599–2606.

Matsubara, T., Beeman, R. W., Shike, H., Besansky, N. J., Mukabayire, O., Higgs, S., James, A. A., and Burns, J. C. (1996). Pantropic retroviral vectors integrate and express in cells of the malaria mosquito, Anopheles gambiae. Proc Natl. Acad. Sci. USA 93,6181–6185.

McCarty, Christensen, and Muzyczka, "Sequences Required for Coordinate Induction of Adeno-Associated Virus p19 and p40 Promoters by Rep Protein," J. Virol, 65:2936–2945, 1991.

McLaughlin, Collis, Hermonat, and Muzyczka, "Adeno-Associated Virus General Transduction Vectors: Analysis of Proviral Structures," J. Virol., 62:1963–1973, 1988.

McNeall, Sanchez, Gray, Chesterman, and Sleigh, "Hyper-inducible Gene Expression From a Metallotionein Promoter Containing Additional Metal-Responsive Elements," Gene, 76:81, 1989.

Michael, Biotechniques, 16:410–412, 1994.

Miksicek, Heber, Schmid, Danesch, Posseckert, Beato, and Schutz, "Glucocorticoid Responsiveness of the Transcriptional Enhancer of Moloney Murine Sarcoma Virus," Cell, 46:203, 1986.

Mordacq and Linzer, "Co-localization of Elements Required for Phorbol Ester Stimulation and Glucocorticoid Repression of Proliferin Gene Expression," Genes and Dev., 3:760, 1989.

Moreau, Hen, Wasylyk, Everett, Gaub, and Chambon, "The SV40 Base-Repair Repeat Has a Striking Effect on Gene Expression Both in SV40 and Other Chimeric Recombinants," Nucl. Acids Res., 9:6047, 1981.

Morsdorf, D. K., Kremer, A, and Jahnel, F. (1993). Baculovirus gene ME53, which contains a putative Zinc finger motif, is one of the major early-transcribed genes. J. Virol 67, 753–758.

Murphy, F. A., Fauquet, C. M., Bishop, D. H. L., Ghabrial, S. A., Jarvis, A. W., Martelli, G. P., Mayo, M. A., and Summers, M. D. (1995). Virus taxonomy. Sixth report of the international committee on taxonomy of viruses. Springer-Verlag Wien, New York.

Musesing, Smith, and Capon, "Regulation of mRNA Accumulation by a Human Immunodeficiency Virus Trans-Activator Protein," *Cell*, 48:691, 1987.

Muzyczka, "Use of Adeno-Associated Virus as a General Transduction Vector for Mammalian Cells," *Curr. Top. Microbiol. Immunol.*, 158:97–129, 1992.

Ng, Gunning, Liu, Leavitt, and Kedes, "Regulation of the Human Beta-Actin Promoter by Upstream and Intron Domains," *Nuc. Acids Res.*, 17:601, 1989.

Nicolas and Rubinstein, "Retroviral vectors," *In: Vectors: A survey of molecular cloning vectors and their uses*, Rodriguez and Denhardt (eds.), Stoneham: Butterworth, pp. 494–513, 1988.

Nicolau and Sene, "Liposome-mediated DNA transfer in eukaryotic cells: dependence of the transfer efficiency upon the type of liposomes used and the host cell cycle stage," *Biochim. Biophys. Acta* 721:185–190, 1982

Nicolau et al., "Liposomes as carriers for in vivo gene transfer and expression," *Methods Enzymol.*, 149:157–176, 1987.

Nicolau, C., Tosi, P. F., Arvinte, T., Mouneimne, Y., Cudd A., Sneed, L., Madoulet, C., Schulz, B., Barhoumi, R. (1990). CD4 inserted in red blood cell membranes or reconstituted in liposome bilayers as a potential therapeutic agent against AIDS. *Progress in Clinical and Biological Research* 343, 147–177.

O'Reilly, Miller, and Luckow, *In Baculovirus expression vectors*, W. H. Freeman and Company, N.Y, 1992.

Ogawa, H., Inouye, S., Tsuji, F. I., Yasuda, K., and Umesono, K. (1995). Localization, trafficking, and temperature-dependence of the Aequorea green fluorescent protein in cultured vertebrate cells. *Proc Natl. Acad. Sci.* 92, 11899–11903.

Ohi, Dixit, Tillery, and Plonk, "Construction and replication of an adeno-associated virus expression vector that contains human λ-globin cDNA," *Gene*, 89L:279–282, 1990.

Oker-Blom, C., Orellana, A., and Keinanen, K. (1996). Highly efficient production of GFP and its derivatives in insect cells for visual in vitro applications.*FEBS Letters* 389, 238–243.

Ondek, Sheppard, and Herr, "Discrete Elements Within the SV40 Enhancer Region Display Different Cell-Specific Enhancer Activities," *EMBO J.*, 6:1017, 1987.

Ornitz, Hammer, Davison, Brinster, and Palmiter, "Promoter and Enhancer Elements From the Rat Elastase I Gene Function Independently of Each Other and of Heterologous Enhancers," *Mol. Cell. Biol.* 7:3466, 1987.

Padan, R., Nainudel-Epszteyn, S., Goitein, R., Fainsod, A., and Gruenbaum, Y. (1990). Isolation and characterization of the Drosophila nuclear envelope otefin cDNA. *J. Biol. Chem.* 265, 7808–7813.

Palmiter, Chen, and Brinster, "Differential Regulation of Metallothionein-Thymidine Kinase Fusion Genes in Transgenic Mice and Their Offspring," *Cell*, 29:701, 1982.

Pante, N. and Aebi, U. (1996) Molecular dissection of the nuclear pore complex. *Crit. Rev. Biochem. Molec. Biol.* 31,153–199.

Paskind et al., "Dependence of moloney murine leukemia virus production on cell growth," *Virology*, 67:242–248, 1975.

Pech, Rao, Robbins, and Aaronson, "Functional Identification of Regulatory Elements Within the Promoter Region of Platelet-Derived Growth Factor 2," *Mol. Cell. Biol.*, 9:396, 1989.

Perales et al., *Proc Natl. Acad. Sci. USA*, 91:4086–4090, 1994.

Perez-Stable and Constantini, "Roles of Fetal γ-globin Promoter Elements and the Adult β-globin 3' Enhancer in the Stage-Specific Expression of Globin Genes," *Mol. Cell. Biol.*, 10:1116, 1990.

Picard and Schaffner, "A Lymphocyte-Specific Enhancer in the Mouse Immunoglobulin Kappa Gene," *Nature*, 307:83, 1984.

Pinkert, Ornitz, Brinster, and Palmiter, "An Albumin Enhancer Located 10 kb Upstream Functions Along With its Promoter to Direct Efficient, Liver-Specific Expression in Transgenic Mice," *Genes and Dev.*, 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.*, 82:1020, 1985.

Porton, Zaller, Lieberson, and Eckhardt, "Immunoglobulin Heavy-Chain Enhancer is Required to Maintain Transfected γ2A Gene Expression in a pre-B-cell Line," *Mol. Cell. Biol.*, 10:1076, 1990.

Potter et al., "Enhancer-dependent expression of human k immunoglobulin genes introduced into mouse pre-B lymphocytes by electroporation," *Proc Nat'l Acad. Sci. USA*, 81:7161–7165, 1984.

Queen and Baltimore, "Immunoglobulin Gene Transcription is Activated by Downstream Sequence Elements," *Cell*, 35:741, 1983.

Quinn, Farina, Gardner, Krutzsch, and Levens, "Multiple Components are Required for Sequence Recognition of the AP1 Site in the Gibbon Ape Leukemia Virus Enhancer," *Mol. Cell. Biol.*, 9:4713, 1989.

Racher et al., Biotechnology Techniques, 9:169–174, 1995.

Ragot et al., "Efficient adenovirus-mediated transfer of a human minidystrophin gene to skeletal muscle of mdx mice," *Nature*, 361:647–650, 1993.

Redondo, Hata, Brocklehurst, and Krangel, "A T-Cell-Specific Transcriptional Enhancer Within the Human T-Cell Receptor δ Locus," *Science*, 247:1225, 1990.

Reis, U., Blum, B., von Specht, B. U., Domdey, H.,and Collins, J. (1992). Antibody production in silkworm cells and silkworm larvae infected with a dual recombinant *Bombyx mori* nuclear polyhedrosis virus. *Bio/Technology* 10, 910–912.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.*, 9:3571, 1989.

Renan, "Cancer genes: current status, future prospects, and applicants in radiotherapy/oncology," *Radiother. Oncol.*, 19:197–218, 1990.

Resendez Jr., Wooden, and Lee, "Identification of Highly Conserved Regulatory Domains and Protein-Binding Sites in the Promoters of the Rat and Human Genes Encoding the Stress-Inducible 78-kilodalton Glucose-Regulated Protein," *Mol. Cell. Biol.*, 8:4579, 1988.

Rich et al., "Development and analysis of recombinant adenoviruses for gene therapy of cystic fibrosis," *Hum. Gene Ther.*, 4:461–476, 1993.

Richardson, C. D., Banville, M., Lalumiere, M., Vialard, J., Meighen, E. A. (1992). Bacterial luciferase produced with rapid-screening baculovirus vectors is a sensitive reporter for infection of insect cells and larvae. *Intervirology* 34, 213–227.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Ripe, Lorenzen, Brenner, and Breindl, "Regulatory Elements in the 5' Flanking Region and the First Intron Contribute to Transcriptional Control of the Mouse alpha-1-type Collagen Gene," *Mol. Cell. Biol.,* 9:2224, 1989.

Rippe, Brenner and Leffert, "DNA-mediated gene transfer into adult rat hepatocytes in primary culture," *Mol. Cell Biol.,* 10:689–695, 1990.

Rittling, Coutinho, Amarm, and Kolbe, "AP-1/jun-binding Sites Mediate Serum Inducibility of the Human Vimentin Promoter," *Nuc. Acids Res.,* 17:1619, 1989.

Roder, A., and Punter, J. (1977). Interactions between nuclear polyhedrosis viruses and vertebrate cells. *Zbl. Bakt. Hyg. I. Abt. Orig. A.* 239, 459–464.

Rohrmann, G. F. (1992). Baculovirus structural proteins. *J. Gen. Virol.* 73, 749–761.

Roizman, B., and Sears, A. E. (1990). Herpes simplex viruses and their replication. In "Virology" (B. N. Fields and D. M. Knipe, Eds.), pp. 1795–1841, vol. 2. Raven Press, New York.

Rosen, Sodroski, and Haseltine, "The Location of cis-acting Regulatory Sequences in the Human T-Cell Lymphotropic Virus Type III (HTLV-111/LAV) Long Terminal Repeat," *Cell,* 41:813, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant α 1-antitrypsin gene to the lung epithelium in vivo," *Science,* 252:431–434,1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell,* 68:143–155,1992.

Ross, T. K., Prahl, J. M., Herzberg, I. M., and DeLuca, H. F. (1992). Baculovirus-mediated expression of retinoic acid receptor type gamma in cultured insect cells reveals a difference in specific DNA-binding behavior with the 1,25-dihydroxyvitamin D3 receptor. *Proc Natl. Acad. Sci. USA* 89, 10282–10286.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc Natl. Acad. Sci. USA,* 86:9079–9083, 1989.

Russell, R. L. Q., and Rohrmann, G. F. (1993). A 25-kDa protein is associated with the envelopes of occluded baculovirus virions. *Virology* 195, 532–540.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.,* 2:1144, 1988.

Sambrook, J., Fritsch, E. F., and Maniatis, T. (1989). Molecular cloning: a laboratory manual. Cold Spring Harbor Laboratory Press, Cold Spring Harbor, New York.

Samulski, Chang, and Shenk, "Helper-free stocks of recombinant adeno-associated viruses: Normal integration does not require viral gene expression," *J. Virol,* 63:3822–3828, 1989.

Samulski, Zhu, Xiao, Brook, Housman, Epstein, and Hunter, "Targeted integration of adeno-associated virus (AAV) into human chromosome 19," *EMBO J,* 10:3941–3950, 1991.

Santerre, et al, *Gene,* 30:147, 1984

Satake, Furukawa, and Ito, "Biological Activities of Oligonucleotides Spanning the F9 Point Mutation Within the Enhancer Region of Polyoma Virus DNA," *J. Virology,* 62:970, 1988.

Schaffner, Schirm, Muller-Baden, Wever, and Schaffner, "Redundancy of Information in Enhancers as a Principle of Mammalian Transcription Control," *J. Mol. Biol.,* 201:81, 1988.

Searle, Stuart, and Palmiter, "Building a Metal-Responsive Promoter With Synthetic Regulatory Elements," *Mol. Cell. Biol.,* 5:1480, 1985.

Senior, A., and Gerace, L. (1988). Integral membrane proteins specific to the inner nuclear membrane and associated with the nuclear lamina. *J. Cell Biol.* 107, 2029–2036.

Sharp and Marciniak, "HIV Tar: an RNA Enhancer?," *Cell,* 59:229, 1989.

Shaul and Ben-Levy, "Multiple Nuclear Proteins in Liver Cells are Bound to Hepatitis B Virus Enhancer Element and its Upstream Sequences," *EMBO J.,* 6:1913, 1987.

Sherman, Basta, Moore, Brown, and Ting, "Class II Box Consensus Sequences in the HLA-DRα Gene: Transcriptional Function and Interaction with Nuclear Proteins," *Mol. Cell. Biol.,* 9:50, 1989.

Simos, G., Maison, C., and Georgatos, S. D. (1996). Characterization of p18, a component of the lamin B receptor complex and a new integral membrane protein of the avian erythrocyte nuclear envelope. *J. Biol. Chem.* 271, 12617–12625.

Sleigh and Lockett, "SV40 Enhancer Activation During Retinoic-Acid-Induced Differentiation of F9 Embryonal Carcinoma Cells," *J. EMBO,* 4:3831, 1985.

Smith, S., and Blobel, G. (1993). The first membrane spanning region of the lamin B receptor is sufficient for sorting to the inner nuclear membrane. *J. Cell Biol.* 120, 631–637.

Soullman, B., and Worman, H. J. (1993). The amino-terminal domain of the lamin B receptor is a nuclear envelope targeting signal. *J. Cell Biol.* 120, 1093–1100.

Spalholz, Yang, and Howley, "Transactivation of a Bovine Papilloma Virus Transcriptional Regulatory Element by the E2 Gene Product," *Cell,* 42:183, 1985.

Spandau and Lee, "Trans-Activation of Viral Enhancers by the Hepatitis B Virus X Protein," *J. Virology,* 62:427, 1988.

Spandidos and Wilkie, "Host-Specificities of Papilloma Virus, Moloney Murine Sarcoma Virus and Simian Virus 40 Enhancer Sequences," *EMBO J.,* 2:1193, 1983.

Stephens and Hentschel, "The Bovine Papilloma Virus Genome and its Uses as a Eukaryotic Vector," *Biochem. J.,* 248:1, 1987.

Stratford-Perricaudet and Perricaudetp. 51–61, *In: Human Gene Transfer,* Eds, O. Cohen-Haguenauer and M. Boiron, Editions John Libbey Eurotext, France, 1991.

Stratford-Perricaudet et al., *Hum. Gene. Ther.* 1:241–256, 1991.

Stuart, Searle, and Palmiter, "Identification of Multiple Metal Regulatory Elements in Mouse Metallothionein-I Promoter by Assaying Synthetic Sequences," *Nature,* 317:828, 1985.

Sullivan and Peterlin, "Transcriptional Enhancers in the HLA-DQ Subregion," *Mol. Cell. Biol.,* 7:3315, 1987.

Summers, M. D., and Smith, G. E. (1987). A manual of methods for baculovirus vectors and insect cell culture procedures. *Tex. Agric. Exp. Stn. Bull. No.*1555.

Swartzendruber and Lehman, "Neoplastic Differentiation: Interaction of Simian Virus 40 and Polyoma Virus with Murine Teratocarcinoma Cells," *J. Cell. Physiology,* 85:179, 1975.

Takebe, Seiki, Fujisawa, Hoy, Yokota, Arai, Yoshida, and Arai, "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.,* 8:466, 1988.

Tavernier, Gheysen, Duerinck, Can Der Heyden, and Fiers, "Deletion Mapping of the Inducible Promoter of Human IFN-beta Gene," *Nature,* 301:634, 1983.

Taylor and Kingston, "Ela Trans-Activation of Human HSP70 Gene Promoter Substitution Mutants is Independent of the Composition of Upstream and TATA Elements," *Mol. Cell. Biol.,* 10:176, 1990b.

Taylor and Kingston, "Factor Substitution in a Human HSP70 Gene Promoter: TATA-Dependent and TATA-Independent Interactions," *Mol. Cell. Biol.,* 10:165, 1990a.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.,* 264:15160, 1989.

Temin, "Retrovirus vectors for gene transfer: Efficient integration into and expression of exogenous DNA in vertebrate cell genome," *In: Gene Transfer,* Kucherlapati (ed.), New York: Plenum Press, pp. 149–188, 1986.

Theilmann, D. A., Chantler, J. K., Stewart, S., Flipsen, H. T. M., Vlak, J. M., Crook, N. E. (1996). Characterization of a highly conserved baculovirus structural protein that is specific for occlusion-derived virus. *Virology* 218, 148–158.

Thiem, S. M., and Miller, L. K. (1989). Identification, sequence, and transcriptional mapping of the capsid protein gene of the baculovirus, *Autographa californica* nuclear polyhedrosis virus. *J. Virol.* 63, 2008–2018.

Thiesen, Bosze, Henry, and Charnay, "A DNA Element Responsible for the Different Tissue Specificities of Friend and Moloney Retroviral Enhancers," *J. Virology,* 62:614.

Tomic et al., *Nucl. Acids Res.,* 12:1656, 1990.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Tratschin, Miller, Smith, and Carter, "Adeno-associated virus vector for high-frequency integration, expression and rescue of genes in mammalian cells," *Mol. Cell. Biol.,* 5:32581–3260, 1985.

Tratschin, West, Sandbank, and Carter, "A human parvovirus, adeno-associated virus, as a eucaryotic vector: transient expression and encapsidation of the procaryotic gene for chloramphenicol acetyltransferase," *Mol. Cell. Biol.,* 4:2072–2081, 1984.

Treisman, "Transient Accumulation of c-fos RNA Following Serum Stimulation Requires a Conserved 5' Element and c-fos 3' Sequences," *Cell,* 42:889, 1985.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," *Mol. Cell. Biol.,* 9:4759, 1989.

Tronche, Rollier, Herbomel, Bach, Cereghini, Weiss, and Yaniv, "Anatomy of the Rat Albumin Promoter," *Mol. Biol. Med.,* 7:173, 1990.

Trudel and Constantini, "A 3' Enhancer Contributes to the Stage-Specific Expression of the Human Beta-Globin Gene," *Genes and Dev.,* 6:954, 1987.

Tur-Kaspa, Teicher, Levine, Skoultchi and Shafritz, "Use of electroporation to introduce biologically active foreign genes into primary rat hepatocytes," *Mol. Cell Biol.,* 6:716–718, 1986.

Tweeten, K. A., Bulla, L. A., and Consigli, R. A. (1980). Characterization of an extremely basic protein derived from granulosis virus nucleocapsids. *J. Virol* 33, 866–876.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Upender et al., *Biotechniques,* 18:29–31, 1995.

Vandenbosch, K. A. (1991). Immunogold labeling. In "Electron Microscopy of Plant Cells" (J. L. Hall and C. Hawes, Eds.), pp. 181–218. Academic Press, New York.

Vannice and Levinson, "Properties of the Human Hepatitis B Virus Enhancer: Position Effects and Cell-Type Nonspecificity," *J. Virology,* 62:1305, 1988.

Vasseur, Kress, Montreau, and Blangy, "Isolation and Characterization of Polyoma Virus Mutants Able to Develop in Multipotential Murine Embryonal Carcinoma Cells," *Proc Natl. Acad. Sci. U.S.A.,* 77:1068, 1980.

Venable, J. H., and Coggeshall, R. (1965). A simplified lead citrate stain for use in electron microscopy. *J. Cell Biol.* 25, 407–408.

Volkman, L. E. (1986). The 64K envelope protein of budded *Autographa californica* nuclear polyhedrosis virus. *Curr. Top. Microbiol. Immunol.* 131, 103–118.

Volkman, L. E., and Summers, M. D. (1977). *Autographa californica* nuclear polyhedrosis virus: Comparative infectivity of the occluded, alkali-liberated, and nonoccluded forms. *J. Invert. Pathol.* 30, 102–103.

Volkman, L. E., Goldsmith, P. A., and Hess, R. T. (1986). Alternate pathway of entry of budded *Autographa californica* nuclear polyhedrosis virus: fusion at the plasma membrane. *Virology* 148, 288–297.

Volkman, L. E., Summers, M. D., and Hsieh, C. H. (1976). Occluded and nonoccluded nuclear polyhedrosis virus grown in *Trichoplusia ni*: comparative neutralization, comparative infectivity, and in vitro growth studies. *J. Virol* 19, 820–832.

von Heijne, G. (1990). The signal peptide. *J. Membr. Biol.* 115, 195–201.

Wada, K-n., Aota, S-i., Tsuchiya, R., Ishibashi, F., Gojobori, T. and Ikemura, T. (1990) Codon usage tabulated from the GenBank genetic sequence data. *Nucleic Acids Res.* 18,2367–2411.

Wagner et al., *Science,* 260:1510–1513, 1990.

Walsh, Nienhuis, Samulski, Brown, Miller, Young, and Liu, "Phenotypic correction of Fanconi anemia in human hematopoietic cells with a recombinant adeno-associated virus vector," *J. Clin. Invest,* 94:1440–1448, 1994.

Wang and Calame, "SV40 Enhancer-Binding Factors are Required at the Establishment but not the Maintenance Step of Enhancer-Dependent Transcriptional Activation," *Cell,* 47:241, 1986.

Watson, J. D. et al., *Molecular Biology of the Gene,* 4th Ed., W. A. Benjamin, Inc., Menlo Park, Calif., 1987.

Webb, N. R., and Summers, M. D. (1990). Expression of proteins using recombinant baculoviruses. *Technique* 2, 173–188.

Webb, N. R., Madoulet, C., Tosi, P. F., Broussard, D. R., Sneed, L., Nicolau, C., and Summers, M. D. (1989). Cell-surface expression and purification of human CD4 produced in baculovirus-infected cells. *Proc Natl. Acad. Sci. USA* 86, 7731–7735.

Weber, De Villiers, and Schaffner, "An SV40 'Enhancer Trap' Incorporates Exogenous Enhancers or Generates Enhancers From its Own Sequences," *Cell,* 36:983, 1984.

Wei, Wei, Samulski, and Barranger, "Expression of the human glucocerebrosidase and arylsulfatase A genes in murine and patient primary fibroblasts transduced by an adeno-associated virus vector," *Gene Therapy*, 1:261–268, 1994.

Weinberger, Jat, and Sharp, "Localization of a Repressive Sequence Contributing to B-cell Specificity in the Immunoglobulin Heavy-Chain Enhancer," *Mol. Cell. Biol.*, 8:988, 1984.

White, J. M. (1990). Viral and cellular membrane fusion proteins. *Annu. Rev. Physiol.* 52, 675–698.

Whitford, M., and Faulkner, P. (1992a). A structural polypeptide of the baculovirus *Autographa californica* nuclear polyhedrosis virus contains O-linked N-Acetylglucosamine. *J. Virol.* 66, 3324–3329.

Whitford, M., and Faulkner, P. (1992b). Nucleotide sequence and transcriptional analysis of a gene encoding gp41, a structural glycoprotein of the baculovirus *Autographa californica* nuclear polyhedrosis virus. J. Virol. 66, 4763–4768. [Authors' correction (1993) *J. Virol.* 67: 2427].

Whitford, M., Stewart, S., Kuzio, J., and Faulkner, P. (1989). Identification and sequence analysis of a gene encoding gp67, an abundant envelope glycoprotein of the baculovirus *Autographa californica* nuclear polyhedrosis virus. *J. Virol* 63, 1393–1399.

Whitt, M. A., and Manning, J. S. (1987). Role of chelating agents, monovalent anion and cation in the dissociation of *Autographa californica* nuclear polyhedrosis virus occlusion body. *J. Invert. Pathol.* 49, 61–69.

Williams, McClanahan, and Morimoto, "Ela Transactivation of the Human HSP70 Promoter is Mediated Through the Basal Transcriptional Complex," *Mol. Cell. Biol,* 9:2574, 1989.

Wilson, M. E. (1988). A synthetic peptide to the predicted 6.9K translation product of the HindIII-H/EcoRI-D region of the AcNPV genome induces antibodies to the basic DNA-binding protein. *Virus Res.* 9, 21–31.

Wilson, M. E., Mainprize, T. H., Friesen, P. D., and Miller, L. K. (1987). Location, transcription, and sequence of a baculovirus gene encoding a small arginine-rich polypeptide. *J. Virol* 61, 661–666.

Winoto and Baltimore, αβ-lineage-specific Expression of the α T-Cell Receptor Gene by Nearby Silencers," *Cell,* 59:649, 1989.

Wolgamot, G. M., Gross, C. H., Russell, R. L. Q., and Rohrmann, G. F. (1993). Immunocytochemical characterization of p24, a baculovirus capsid-associated protein. *J. Gen. Virol.* 74, 103–107.

Wong et al., "Appearance of β-lactamase activity in animal cells upon liposome mediated gene transfer," *Gene,* 10:87–94, 1980.

Wozniak, R. W., and Blobel, G. (1992). The single transmembrane segment of gp210 is sufficient for sorting to the pore membrane domain of the nuclear envelope. *J. Cell Biol.* 119, 1441–1449.

Wu and Wu, "Receptor-mediated in vitro gene transfections by a soluble DNA carrier system," *J. Biol. Chem.,* 262:4429–4432, 1987.

Wu and Wu, *Adv. Drug Delivery Rev.,* 12:159–167, 1993.

Yang, Burkholder, Roberts, Martinell and McCabe, "In vivo and in vitro gene transfer to mammalian somatic cells by particle bombardment," *Proc Nat'l Acad Sci. USA,* 87:9568–9572, 1990.

Yang, Chen, Trempe, "Characterization of cell lines that inducibly express the adeno-associated virus Rep proteins," *J. Virol,* 68:4847–4856, 1994.

Yoder, Kang, Zhou, Luo, and Srivastava, "In vivo gene transfer in murine hematopoietic reconstituting stem cells mediated by the adeno-associated virus 2-based vectors," *Blood,* 82 (Supp.): 1:347A, 1994.

Yutzey, Kline, and Konieczny, "An Internal Regulatory Element Controls Troponin I Gene Expression," *Mol. Cell. Biol.,* 9:1397, 1989.

Zhou, Broxmyer, Cooper, Harrington, and Srivastava "Adeno-associated virus 2 mediated gene transfer in murine hematopoietic cells, *Exp. Hematol (N.Y.),* 21:928–933, 1993.

Zhou, Cooper, Kang, Ruggieri, Heimfeld, Srivastava, and Broxmeyer, "Adeno-associated virus 2-mediated high efficiency gene transfer into immature and mature subsets of hematopoietic progenitor cells in human umbilical cord blood," *J.Exp.Med.,* 179:1867–1875, 1994.

What is claimed is:

1. A nucleic acid segment comprising at least a first sequence region that encodes a targeting polypeptide of between 12 and about 24 amino acids in length, wherein said first sequence region is separated from sequences that naturally flank said sequence region, said polypeptide comprising a twelve amino acid targeting sequence comprising:

a) a first amino acid selected from the group consisting of valine, leucine and isoleucine;

b) a second amino acid selected from the group consisting of leucine, isoleucine, valine and glycine;

c) a third amino acid selected from the group consisting of isoleucine, leucine, alanine and glycine;

d) a fourth amino acid selected from the group consisting of isoleucine, alanine, leucine and valine;

e) a fifth amino acid selected from the group consisting of valine, leucine and isoleucine;

f) a sixth amino acid selected from the group consisting of isoleucine, valine, leucine and phenylalanine;

g) a seventh amino acid selected from the group consisting of valine, leucine and isoleucine;

h) an eighth amino acid selected from the group consisting of valine, leucine, alanine, glycine, isoleucine and threonine;

i) a ninth amino acid selected from the group consisting of isoleucine, leucine, phenylalanine, valine and alanine;

j) a tenth amino acid selected from the group consisting of phenylalanine, leucine, valine and isoleucine;

k) an eleventh amino acid selected from the group consisting of leucine, valine, phenylalanine, isoleucine and glycine; and l) a twelfth amino acid selected from the group consisting of isoleucine, phenylalanine and tyrosine.

2. The nucleic acid segment of claim 1, wherein the encoded polypeptide comprises the contiguous amino acid sequence from amino acid 4 to amino acid 15 of SEQ ID NO:3, SEQ ID NO:33, SEQ ID NO:38, or SEQ ID NO:39; from amino acid 5 to amino acid 16 of SEQ ID NO:34, SEQ ID NO:35, SEQ ID NO:36, SEQ ID NO:37, SEQ ID NO:40, SEQ ID NO:41, SEQ ID NO:42, SEQ ID NO:43, SEQ ID NO:44, or SEQ ID NO:45; or from amino acid 6 to amino acid 17 of SEQ ID NO:46.

3. The nucleic acid segment of claim 2, wherein the encoded polypeptide comprises the contiguous amino acid sequence from amino acid 4 to amino acid 15 of SEQ ID NO:3.

4. The nucleic acid segment of claim 2, wherein the encoded polypeptide comprises the contiguous amino acid sequence from amino acid 4 to amino acid 15 of SEQ ID NO:33.

5. The nucleic acid segment of claim 2, wherein the encoded polypeptide comprises the contiguous amino acid sequence from amino acid 4 to amino acid 15 of SEQ ID NO:38.

6. The nucleic acid segment of claim 2, wherein the encoded polypeptide comprises the contiguous amino acid sequence from amino acid 4 to amino acid 15 of SEQ ID NO:39.

7. The nucleic acid segment of claim 2, wherein the encoded polypeptide comprises the contiguous amino acid sequence from amino acid 5 to amino acid 16 of SEQ ID NO:34.

8. The nucleic acid segment of claim 2, wherein the encoded polypeptide comprises the contiguous amino acid sequence from amino acid 5 to amino acid 16 of SEQ ID NO:35.

9. The nucleic acid segment of claim 2, wherein the encoded polypeptide comprises the contiguous amino acid sequence from amino acid 5 to amino acid 16 of SEQ ID NO:36.

10. The nucleic acid segment of claim 2, wherein the encoded polypeptide comprises the contiguous amino acid sequence from amino acid 5 to amino acid 16 of SEQ ID NO:37.

11. The nucleic acid segment of claim 2, wherein the encoded polypeptide comprises the contiguous amino acid sequence from amino acid 5 to amino acid 16 of SEQ ID NO:40.

12. The nucleic acid segment of claim 2, wherein the encoded polypeptide comprises the contiguous amino acid sequence from amino acid 5 to amino acid 16 of SEQ ID NO:42.

13. The nucleic acid segment of claim 2, wherein the encoded polypeptide comprises the contiguous amino acid sequence from amino acid 5 to amino acid 16 of SEQ ID NO:43.

14. The nucleic acid segment of claim 2, wherein the encoded polypeptide comprises the contiguous amino acid sequence from amino acid 5 to amino acid 16 of SEQ ID NO:44.

15. The nucleic acid segment of claim 2, wherein the encoded polypeptide comprises the contiguous amino acid sequence from amino acid 5 to amino acid 16 of SEQ ID NO:45.

16. The nucleic acid segment of claim 2, wherein the encoded polypeptide comprises the contiguous amino acid sequence from amino acid 6 to amino acid 17 of SEQ ID NO:46.

17. The nucleic acid segment of claim 1, wherein the encoded polypeptide further comprises at least three additional amino acids immediately preceding said targeting sequence, said additional amino acids comprising:

a) a first amino acid selected from the group consisting of methionine, leucine, tryptophan, isoleucine and phenylalanine;

b) a second amino acid selected from the group consisting of serine, isoleucine, tryptophan, glycine, methionine, valine and leucine; and c) a third amino acid selected from the group consisting of isoleucine, threonine, glycine, alanine, lysine, leucine, methionine and valine.

18. The nucleic acid segment of claim 1, wherein the encoded polypeptide further comprises at least three additional amino acids immediately following said targeting sequence, said additional amino acids comprising:

a) a first amino acid selected from the group consisting of cysteine, alanine, leucine, isoleucine, phenylalanine, valine and methionine;

b) a second amino acid selected from the group consisting of phenylalanine, serine, tyrosine, tryptophan, isoleucine, valine and leucine; and c) a third amino acid selected from the group consisting of leucine, asparagine, tryptophan, tyrosine, isoleucine, phenylalanine and valine.

19. The nucleic acid segment of claim 2, wherein said first sequence region encodes a targeting polypeptide that has the contiguous amino acid sequence of SEQ ID NO:3, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 or SEQ ID NO:46.

20. The nucleic acid segment of claim 19, wherein said first sequence region encodes a targeting polypeptide that has the contiguous amino acid sequence of SEQ ID NO:3.

21. The nucleic acid segment of claim 20, wherein said first sequence region has the contiguous nucleic acid sequence from position 122 to position 190 of SEQ ID NO:1.

22. The nucleic acid segment of claim 19, wherein said first sequence region encodes a targeting polypeptide that has the contiguous amino acid sequence of SEQ ID NO:33.

23. The nucleic acid segment of claim 22, wherein said first sequence region has the contiguous nucleic acid sequence from position 1 to position 72 of SEQ ID NO:47.

24. The nucleic acid segment of claim 19, wherein said first sequence region encodes a targeting polypeptide that has the contiguous amino acid sequence of SEQ ID NO:34.

25. The nucleic acid segment of claim 19, wherein said first sequence region encodes a targeting polypeptide that has the contiguous amino acid sequence of SEQ ID NO:35.

26. The nucleic acid segment of claim 19, wherein said first sequence region encodes a targeting polypeptide that has the contiguous amino acid sequence of SEQ ID NO:36.

27. The nucleic acid segment of claim 19, wherein said first sequence region encodes a targeting polypeptide that has the contiguous amino acid sequence of SEQ ID NO:37.

28. The nucleic acid segment of claim 19, wherein said first sequence region encodes a targeting polypeptide that has the contiguous amino acid sequence of SEQ ID NO:38.

29. The nucleic acid segment of claim 19, wherein said first sequence region encodes a targeting polypeptide that has the contiguous amino acid sequence of SEQ ID NO:39.

30. The nucleic acid segment of claim 19, wherein said first sequence region encodes a targeting polypeptide that has the contiguous amino acid sequence of SEQ ID NO:40.

31. The nucleic acid segment of claim 19, wherein said first sequence region encodes a targeting polypeptide that has the contiguous amino acid sequence of SEQ ID NO:41.

32. The nucleic acid segment of claim 19, wherein said first sequence region encodes a targeting polypeptide that has the contiguous amino acid sequence of SEQ ID NO:42.

33. The nucleic acid segment of claim 19, wherein said first sequence region encodes a targeting polypeptide that has the contiguous amino acid sequence of SEQ ID NO:43.

34. The nucleic acid segment of claim 19, wherein said first sequence region encodes a targeting polypeptide that has the contiguous amino acid sequence of SEQ ID NO:44.

35. The nucleic acid segment of claim 19, wherein said first sequence region encodes a targeting polypeptide that has the contiguous amino acid sequence of SEQ ID NO:45.

36. The nucleic acid segment of claim 19, wherein said first sequence region encodes a targeting polypeptide that has the contiguous amino acid sequence of SEQ ID NO:46.

37. The nucleic acid segment of claim 1, positioned under the control of a promoter.

38. The nucleic acid segment of claim 1, further comprising a cloning site or a multiple cloning site.

39. The nucleic acid segment of claim 38, wherein said cloning site or multiple cloning site is operationally positioned downstream from said first sequence region.

40. The nucleic acid segment of claim 1, further comprising at least a second sequence region encoding a selected protein or polypeptide heterologous to said targeting polypeptide, said second sequence region operably linked, in frame, to said first sequence region, the nucleic acid segment encoding a fusion protein that comprises said targeting polypeptide operably attached to said selected protein or polypeptide.

41. The nucleic acid segment of claim 1, comprised within a host cell.

42. The nucleic acid segment of claim 41, comprised within a eukaryotic host cell.

43. A recombinant nucleic acid vector comprising a nucleic acid segment in accordance with claim 37.

44. The recombinant nucleic acid vector of claim 43, wherein said vector is a mammalian expression vector.

45. The recombinant nucleic acid vector of claim 43, wherein said vector is a viral vector.

46. The recombinant nucleic acid vector of claim 45, wherein said vector is a baculoviral vector.

47. The recombinant nucleic acid vector of claim 45, comprised within a virus.

48. The recombinant nucleic acid vector of claim 43, further comprising at least a second sequence region encoding a selected protein or polypeptide heterologous to said targeting polypeptide, said second sequence region operably linked to said first sequence region to form a fusion protein coding region that encodes a fusion protein comprising said targeting polypeptide operably attached to said selected protein or polypeptide.

49. A method for preparing a recombinant nucleic acid vector, comprising the steps of:
   a) obtaining an nucleic acid segment in accordance with claim 1, the nucleic acid segment comprising at least a first sequence region that encodes a targeting polypeptide;
   b) operatively linking said first sequence region to a second sequence region that encodes a selected protein or polypeptide heterologous to said targeting polypeptide to prepare a fusion protein coding region; and
   c) positioning said fusion protein coding region under the control of a promoter, thereby preparing said recombinant nucleic acid vector.

50. A recombinant host cell comprising a recombinant nucleic acid vector in accordance with claim 43.

51. The host cell of claim 50, comprising a recombinant nucleic acid vector in accordance with claim 48.

52. A method of preparing a fusion protein, comprising expressing the recombinant nucleic acid vector of claim 48 in a cell, thereby preparing said fusion protein.

53. A nucleic acid segment comprising an isolated ODV-E66 gene.

54. The nucleic acid segment of claim 53, comprising an isolated ODV-E66 gene that encodes an ODV-E66 protein that comprises a contiguous amino acid sequence of at least about 8 amino acids from SEQ ID NO:2.

55. The nucleic acid segment of claim 54, comprising an isolated ODV-E66 gene that encodes an ODV-E66 protein that comprises the contiguous amino acid sequence of SEQ ID NO:2.

56. The nucleic acid segment of claim 55, comprising an isolated ODV-E66 gene that comprises the contiguous nucleic acid sequence from position 122 to position 2233 of SEQ ID NO:1.

* * * * *